US007947873B2

(12) United States Patent
Li et al.

(10) Patent No.: US 7,947,873 B2
(45) Date of Patent: May 24, 2011

(54) COMPOSITIONS AND METHODS FOR REGULATION OF PLANT GAMMA-TOCOPHEROL METHYLTRANSFERASE

(75) Inventors: Guofu Li, Johnston, IA (US); Qiang Liu, Foster City, CA (US); Andrew Jamieson, San Francisco, CA (US); Edward Rebar, El Cerrito, CA (US); Mylavarapu Venkatramesh, Ballwin, MO (US)

(73) Assignee: Sangamo Biosciences, Inc., Richmond, CA (US)

( * ) Notice: Subject to any disclaimer, the term of this patent is extended or adjusted under 35 U.S.C. 154(b) by 1498 days.

(21) Appl. No.: 10/418,552

(22) Filed: Apr. 17, 2003

(65) Prior Publication Data
US 2003/0233672 A1    Dec. 18, 2003

Related U.S. Application Data

(60) Provisional application No. 60/373,488, filed on Apr. 17, 2002, provisional application No. 60/385,992, filed on Jun. 4, 2002, provisional application No. 60/442,470, filed on Jan. 24, 2003.

(51) Int. Cl.
*A01H 1/00* (2006.01)
*C12N 15/82* (2006.01)
*C12N 15/87* (2006.01)

(52) U.S. Cl. ..... 800/288; 800/278; 435/69.7; 435/320.1; 435/69.1; 530/300

(58) Field of Classification Search .......... None
See application file for complete search history.

(56) References Cited

FOREIGN PATENT DOCUMENTS

| WO | WO 02/057293 A2 | 7/2002 |
| WO | WO 02/057294 A2 | 7/2002 |
| WO | WO 02/063022 A2 | 8/2002 |

OTHER PUBLICATIONS

Greisman et al. 1997, Science 275:657-661.*
Beerli et al. 2000, PNAS, 97:1495-1500.*
Nedved et al. 1994, Nucleic Acids Research 22:4705-4711.*
Abel et al., "Transient transformation of *Arabidopsis* leaf protoplasts: a versatile experimental system to study gene expression," *Plant J.* 5, 421-427 (1994).
Bartsevich et al., "Regulation of the MDRI gene by transcriptional repressors selected using peptide combinatorial libraries," *Mol Pharmacol* 58, 1-10. (2000).
Beerli et al., "Engineering polydactyl zinc-finger transcription factors," *Nat. Biotech.* 20, 135-141 (2002).
Beerli et al., "Positive and negative regulation of endogenous genes by designed transcription factors," *Proc. Natl. Acad. Sci. USA* 97, 1495-1500 (2000).
Bramley et al., "Vitamin E," *J Sci Food Agr* 80, 913-938 (2000).
Clough et al., "Floral dip: a simplified method for Agrobacterium-mediated transformation of *Arabidopsis thaliana*," *Plant J.* 16, 735-743 (1998).
Cook et al., "Sp1 and its likes: biochemical and functional predictions for a growing family of zinc finger transcription factors," *Ann N Y Acad Sci* 880, 94-102. (1999).
Desjarlais et al., "Use of a Zinc-Finger Consensus Sequence Framework and Specificity Rules to Design Specific DNA Binding Proteins," *Proc. Natl. Acad. Sci. USA* 90, 2256-2260. (1993).
Dreier et al., "Development of zinc finger domains for recognition of the 5'-ANN-3'0 family of DNA sequences and their use in the construction of artificial transcription factors," *J. Biol. Chem.* 276, 29466-29478 (2001).
Goff et al., "Identification of functional domains in the maize transcriptional activator C1: comparison of wild-type and dominant inhibitor proteins," *Genes Dev.* 5, 298-309 (1991).
Guan et al., "Heritable endogenous gene regulation in plants with designed polydactyl zinc finger transcription factors," *Proc Natl Acad Sci USA* 99, 13296-13301 (2002).
Guyer et al., "Activation of latent transgenes in *Arabidopsis* using a hybrid transcription factor," *Genet.* 149, 633-639 (1998).
Huala et al., "The *Arabidopsis* Information Resource (TAIR): A comprehensive database and web-based information retrieval, analysis, and visualization system for a model plant," *Nucleic Acids Res.* 29, 102-105 (2001).
Kridl et al. "Isolation and characterization of an expressed napin gene from *Brassica napus*," *Seed Sci. Res.* 1, 209-219 (1991).
Li et al., "Chromatin structure and phaseolin gene regulation,"*Plant Mol. Biol.* 46, 121-129 (2001).
Li et al., "Architectural specificity in chromatin structure at the TATA box in vivo: nucleosome displacement upon beta-phaseolin gene activation," *Proc Natl Acad Sci USA* 95, 4772-4777 (1998).
Liu et al., "Regulation of an endogenous locus using a panel of designed zinc finger proteins targeted to accessible chromatin regions,"*J. Biol. Chem.* 276, 11323-11334 (2001).
McBride et al., "Controlled expression of plastid transgenes in plants based on a nuclear DNA-encoded and plastid-targeted T7 RNA polymerase," *Proc. Natl. Acad. Sci. USA* 91, 7301-7305 (1994).
Ordiz et al., "Regulation of transgene expression in plants with polydactyl zinc finger transcription factors," *Proc Natl Acad Sci USA* 99, 13290-13295 (2002). Pabo et al., "Design and selection of novel $Cys_2His_2$ zinc finger proteins," *Annu. Rev. Biochem.* 70, 313-340 (2001).
PE__Applied__Biosystems. User Bulletin #2. Relative quantitation of gene expression. ABI prism 7700 sequence detections system. (The Perkin-Elmer Corporation, Chicago, IL, 1997).
Ren et al., "PPARgamma knockdown by engineered transcription factors: exogenous PPARgamma 2 but not PPARgamma 1 reactivates adipogenesis," *Genes Dev.* 16, 27-32 (2002).
Savidge et al., "Isolation and characterization of homogentisate phytyltransferase genes from *Synechocystis* PCC 6803 and *Arabidopsis,*" *Plant Phys.* 129, 321-332 (2002).
Segal et al., "Custom DNA-binding proteins come of age: polydactyl zinc-finger proteins," *Curr. Opin. Biotechnol.* 12, 632-637 (2001).

(Continued)

*Primary Examiner* — Medina A Ibrahim
*Assistant Examiner* — Li Zheng
(74) *Attorney, Agent, or Firm* — Dahna S. Pasternak; Robins & Pasternak LLP

(57) ABSTRACT

Disclosed herein are zinc finger proteins that bind to target sites in a plant gamma-tocopherol methyl transferase (GMT) gene; compositions comprising these GMT-targeted zinc finger proteins and methods of making and using such zinc finger proteins. Also disclosed are methods for modulating the alpha-tocopherol content in various plant organs, particularly seeds, in transgenic plants.

29 Claims, 23 Drawing Sheets

OTHER PUBLICATIONS

Sheppard, A.J., Pennington, J.A.; Weihrauch, J.L. in Vitamin E in health and disease. (ed. Packer, J.F.L.) 9-31 (Marcel Dekker, New York, 1993).

Shigeoka et al., "Isolation and properties of γ-tocopherol methyltransferase in Euglena gracilis," *Biochim Biophys Acta.* 1128(2-3):220-6 (1992).

Shintani et al., "Elevating the vitamin E content of plants through metabolic engineering," *Science* 282, 2098-2100 (1998).

Traber et al., *Annu. Rev. Nutr.* 16:321-347 (1996).

Utley et al., "SWI/SNF stimulates the formation of disparate activator-nucleosome complexes but is partially redundant with cooperative binding," *J. Biol. Chem.* 272, 12642-12649 (1997).

Zhang et al., "Synthetic zinc finger transcription factor action at an endogenous chromosomal site," *J. Biol. Chem.* 275, 33850-33860(2000).

* cited by examiner

FIGURE 6A

GB_AT:AC006193 AC006193 Arabidopsis thaliana chromosome I BAC F13O11
genomic sequence, complete sequence. 5/2000
Length = Reverse complement of bases from 97758 - 101414

```
GAAAGATCCCACCACGCAGCCTAAAGCGGTGCATTATACTCGTGGAGGGCCTTGGTTTGATGCTTGGAAGG
ATTGCGAGTTTGCGGATCTTTGGCTTAATGAGATGGAAGAGTACAACAAAGAGAACAAGAAGGAAGCTGAT
AACGCAAAGTAGAAAGAAAGAAGTAAGAGGTATGTTGTTACTTACCAACACGAGTAGTGAACTTCCTTTAC
ATAGTGTTGGCTTTGTAGAGCCAGGGATCATTAGTCTTGTGGAGGGCTATGGAGTTTTTTTTAATTTCATT
GAATTCGTTAAATCATTCGCAAACACTATTAGTACCTATATTGAGGTCATATGGTATAATAACCCTATTCG
TTTGTTTATTTGTTGTGTTTTGTACCTTTGATGGTATTTTATTTGTATAATTGATATGTGAATTTATGTAG
CATTTCTTTTTAATTGATCTATAATGAGCAGTAGCTCAACATATTTAAAACATGGATGGATGAGTAATGAT
CATTAGCTAGCAACCTTCCAGATGATCAGCGGCTGTAACAAGGTAGACTCGCCTTCGTGGACGAGTAACTA
CCGTTGTAATGGGACTTGTACATGTACTTACTGATAATTACCTAACTAAACGAGACTCAGTGCTAGAATAT
GAGCATAAATCCTCATATTGAGGAATCACTAATCATTTTTATACTATTTACCTTTCACATCGTATTCTTAT
TCATTTTGATCCTTTTTTGGTATCAAACTAACAATGTTGAGTTATTCAGTTTTTCATTCTGATTATCTCTT
TTCTTCATCTTCTAATCTAGTACTGATCAATAGAAAGCCTTTCTCATTTTGATTTGTTACTCTATCCTGCG
AATATCTTACCCCTAAATGTTACCCATCCCGATAAAAAAAATTACATTGATACGGACTTTATATATTCAC
ACCCACCATCACTATGCATCATATTAACTCATAATAAATGTTGTCGAAATCCTCTTCTGTGAGTTTGTAAT
GCACAACTACAAATCTTCAAGTGGATAAAAACACGTTACTATGTTTGTATGTGATTTCAAATATTATAAAT
TAGTAGGTGATACAATTATTACTTTATCTTACAACATTAATAATAGGTATCTATGTTTATTTTTATTTTCT
TAAAACTTGTAATTTATATAGTTTTTATAAAGTATTAGGCCGCAGATTGGTCTTTTTCTAAATGGATTCAA
CCATTTGAAATTGATGCGTGTGATATGCTAATCCACAATATCCAAAAAAAATTCCTTCTAAAATTGTGACT
TTAAAATTTTGACTGGTTTTGTTAAGAGTAACGTTGAAGAGGAAGGGGAAGGAAAAGTCAATAATGAAAGA
AAATAGTTTCTTCATTTTTGGATTTAAATGGTGAGCATGGTTAGAAGAAAAGAAAATTATCAAAGGAAACA
ATATCTATATATTACCCAACTATTTATCAGTCAAAAAAAAGAATTGTTTCCACCCTACCAAAAAAAAAAA
AAAATATTGTTTCCAACATATTTTTTCTTTTTTCTGAATAATCCATTTTTGACCGGACAAACAGTTGGGTA
GTCAGATTAACTTTTGTACTTTACCATTTTAATCTTTCTCTAACCTACTCATCCGTAATAGAACGGTGTCC
ACGAGGCTCATAGTCCTACAAGCATGTGATAGTTGTCACAATTACCATATTAAGCTCTCTTTGCTTACTTC
ACTTCTTCTATCAATATTTGTTTGCCACTGACTTTTCACTAAATTACAAAACTAAAATGATGGAAGAAAAA
GAAAAGTTAAACAAAAAAAAGGAGAAAAATCAAAGTGATAAGTGGATGTAGACGATTGGCCCTTTCCCCA
AGACCTGTGGCAACAGAAAGTTTTGTGGCTCTAAAGTTAAGAAAAATGGTCCAATGTTATATATCCAAAGT
TTGATCTCACACAGTCACACTGTAACAATAATCAAATAATCCCTGACTTCGTCACGTTTCTTTGTATCTCC
AACGTCCAATAAATGAAAGCAACTCTAGCAGCACCCTCTTCTCTCACAAGCCTCCCTTATCGAACCAACTC
TTCTTTCGGCTCAAAGTCATCGCTTCTCTTTCGGTCTCCATCCTCCTCCTCCTCAGTCTCTATGACGACAA
CGCGTGGAAACGTGGCTGTGGCGGCTGCTGCTACATCCACTGAGGCGCTAAGAAAAGGAATAGCGGAGTTC
TACAATGAAACTTCGGGTTTGTGGGAAGAGATTTGGGGAGATCATATGCATCATGGCTTTTATGACCCTGA
TTCTTCTGTTCAACTTTCTGATTCTGGTCACAAGGAAGCTCAGATCCGTATGATTGAAGAGTCTCTCCGTT
TTGCCGGTGTTACTGGTTAGCTTCCTCAATCTTTTGCTCTGATATTATCACTTGAGTTAAATACGCTGTTT
GATATATGGTTAACGAACAAATAAAGAGTTAATAATACAACAAAATGACTCTTAAAATCTTTTAAACCAC
AGAAAAAAAACTTATTGTCTACAGAAATGACTAGGGATAATTGTCTTTTTGTTGTACTCTGTTACCCCAT
GAAAGGTGGTTTATTAGCCACAAGCCATCTCTAACCTTTTATTTTTAAGAACAATACTTTTTCTTGCATTT
GAATTAAGAGATGATTGTAAGCTTAATGAATACATAATTTTAAACTCAAAAAGTAAATATAGTTTAGAAAT
ATATATTTTATTTTTTATCTTTGGTTTGTTATTCAGTTATTGTTACCTTTTAATTATTATACATATGAA
GTTGAGTTGATGCCATGTAAATGATTGTGATTGAAAAAAGATGAAGAGGAGGAGAAAAAGATAAAGAAAGT
AGTGGATGTTGGGTGTGGGATTGGAGGAAGCTCAAGATATCTTGCCTCTAAATTTGGAGCTGAATGCATTC
GCATTACTCTCAGCCCTGTTCAGGCCAAGAGAGCCAATGATCTCGCGGCTGCTCAATCACTCGCTCATAAG
GTAGCTTTGGATAAAACATAACCTTTCATTTTGTGAAAATTTCATCTAACGTATGGACATTGGACTTCTAG
GCTTCCTTCCAAGTTGCGGATGCGTTGGATCAGCCATTCGAAGATGGAAAATTCGATCTAGTGTGGTCGAT
GGAGAGTGGTGAGCATATGCCTGACAAGGCCAAGTTTGTAAAAGAGTTGGTACGTGTGGCGGCTCCAGGAG
GTAGGATAATAATAGTGACATGGTGCCATAGAAATCTATCTGCGGGGGAGGAAGCTTTGCAGCCGTGGGAG
CAAAACATCTTGGACAAAATCTGTAAGACGTTCTATCTCCCGGCTT
```

FIGURE 6B

```
GGTGCTCCACCGATGATTATGTCAACTTGCTTCAATCCCATTCTCTCCAGGTTATTATATTCCCTACCCTT
TGCTGCCGAAAACATTACTTAACTAGAGTTTTTTTACTAAACTAGAATCTGAAATATGTGTTTTTAGGATA
TTAAGTGTGCGGATTGGTCAGAGAACGTAGCTCCTTTCTGGCCTGCGGTTATACGGACTGCATTAACATGG
AAGGGCCTTGTGTCTCTGCTTCGTAGTGGTATGAAAAGTATTAAAGGAGCATTGACAATGCCATTGATGAT
TGAAGGTTACAAGAAAGGTGTCATTAAGTTTGGTATCATCACTTGCCAGAAGCCACTCTAA
```

SEQ ID NO: 150

FIGURE 7

TCCAGCGGACTACATGCAAAGTGGTAGTTGTCACAATGACGTTGTTTTAGCTCTCATTACCTTTTTTTTTG
AGCTCTCATTGCTTACTTCACGTCTTCTAACAATATTTGTTTGCTACCGACGTTCTACTAAATCACAAAAA
TAAACTTAACTGAACCTATTTTGACCATATCCACTTGAAAAAACTGTGAACAAAAAAAGAAGATAACCAAA
GTAAGATATGGATGTACATGATTGGCCCTTATCCCAATACATATGGTATCAGAAAAGTTTGTGGCAGTTAA
AGTTCATCAGACTGCTGTACTAACATCATAATTTCAGACGCAGTCACGTTTCTCGTCTCTCCAACCTCCAT
TGCACCGTCCATCCTAAAAGAGATAATACTAATTTTTTTATAAAAAATATGATAATATATTAATTTAGAAT
TACTCTATTTTAAAATAAAAAAATAGAGAACCATTGGAAATGGTATAAGACGGAACCACTGATCACTCATA
TAAAGCTACCGACCATCAAGAATGATATGCGAAAGAGAACAACCACGTAAGTGAAGCAGGAGAAGTTTATC
AAAATTTTGAAGGAGAAGTATCACAGCTAAGAGATGCTGGTTCTTAATCTATTGGAGAGGAAGATGAAGAA
GAGTTTTGTGTTGAAGAGACCATGGTATACCATACTCTGATCAACATGATGAAAACCAACAAAAAACTC
ATTATCAAGTCGACTAAAAAATTATAGAGGAGAACAAGAATGCCAACATATATTTGTTTGAAGAAAGTCT
TCAATGAGGTTGGAAGAGATGATGATAAGTTCAGATACATCCATTTTGCAGACCATCATCAAGAACCATAA
AGATACTTATACGGGAGAGAAGCATAAAACAACCAGTTTAGATGTTTTTAGATTTTTATGAATTTTATGA
TTTTCTAAAACTTTATATCTATGGAAATTTATTATTTTATGAAATATTCAATTTTTTGGAAAAAGAACAAC
TGTTTTTTTGCAAGAGCTGTTGTTAATTGAGAACATTCATAAAATTGATGTACTAAGTTGACAAAACAGTT
AATGGAATTATTATATTAAATAACAGAAAGGTTAAGTATTAAATGGCTTATAATTTTTTACTTTCTTGTC
AAAGTTCTTATAAAAATTTAGTTGGAATACTGTTATAAAAAAAATTAAATACATGTTGATATAAATATTTG
GTTTATCGATTACATTTTAGATATTTACTAATTTTAAAACTAAATATATATAAAATATTAAGAGTAAAAGA
CGTATTTCAATATATTCATGAATACATTCAATTTTCAGTTTGATTCGTGTCCAATTTTTAGATATTGAAAG
CAGAAACTATTTAGATATTTTTGATTATTCAGTTAAGTTTGGACTGTTTGGTTTGATTTGTCGGTCCTAAA
TAAAACATCCTTACCTAAAAATTAATATAAAGATAAATAAAAAGTAGAGGACTGTAGCAATAAAGAATACA
TAATCCCCCTCCATACACAGAGCCACTTTCTTGTTCCGCCAACCTCTCATTATAAATGAAAGCGACTCTCG
CACCCTCCTCTCTCATAAGCCTCCCCAGGCACAAAGTATCTTCTCTCCGTTCACCGTCGCTTCTCCTTCAG
TCCCAACGGCCATCCTCAGCCTTAATGACGACGACGACGGCATCACGTGGAAGCGTGGCTGTGACGGCTGC
TGCTACCTCCTCCGTTGAGGCGCTGCGGGAAGGAATAGCGGAATTCTACAACGAGACGTCGGGATTATGGG
AGGAGATTTGGGGAGATCATATGCATCACGGCTTCTACGATCCTGATTCCTCTGTTCAACTTTCAGATTCC
GGTCACCGGGAAGCTCAGATCCGGATGATCGAAGAGTCTCTACGTTTCGCCGGCGTTACTGAAGAGGAGAA
AAAGATAAAGAGAGTAGTGGATGTTGGGTGTGGATCGGCGGAAGCTCAAGGTATATTGCCTCTAAATTTG
GTGCCGAATGCATTGGCATCACACTCAGTCCCGTTCAAGCCAAGAGAGCCAATGATCTCGCCGCCGCTCAA
TCACTCTCTCATAAGGTTTCCTTCCAAGTTGCAGATGCACTGGAGCAACCATTTGAACATGGTATATTCGA
TCTTGTGTGGTCAATGGAAAGCGGTGAGCATATGCCTGACAAGGCCAAGTTCGTGAAGGAATTGGTACGTG
TGGCGGCTCCAGGAGGAAGGATAATAATAGTGACATGGTGCCACAGAAATCTATCTCCAGGGGAAGAGGCT
TTGCAGCCATGGGAGCAGAACCTCTTGGACAGAATCTGCAAAACATTTTATCTCCCAGCCTGGTGCTCCAC
CTCGGATTATGTCGATTTGCTTCAGTCCCTCTCGCTCCAGGATATTAAGTGTGCAGATTGGTCAGAGAACG
TAGCTCCTTTCTGGCCGGCGGTTATACGAACCGCATTAACGTGGAAGGGCCTTGTGTCTCTGCTTCGTAGT
GGTATGAAGAGTATAAAAGGAGCATTGACAATGCCATTGATGATTGAAGGGTACAAGAAAGGTGTCATTAA
GTTTGGCATCATCACTTGCCAGAAGCCTCTCTAA

SEQ ID NO: 151

FIGURE 8
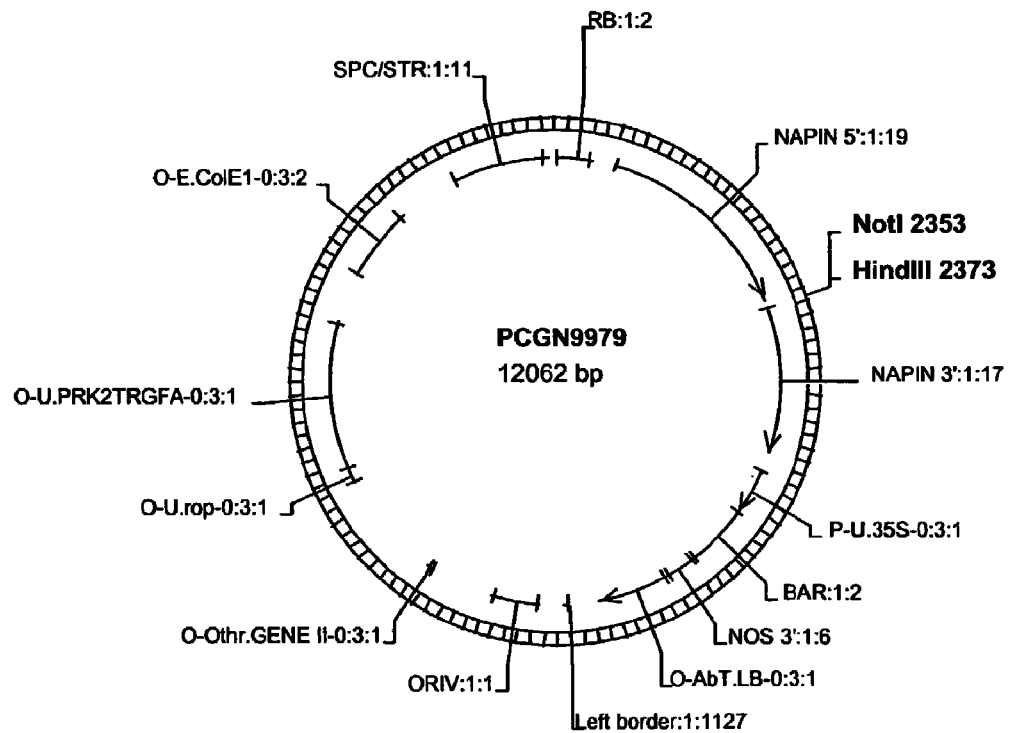
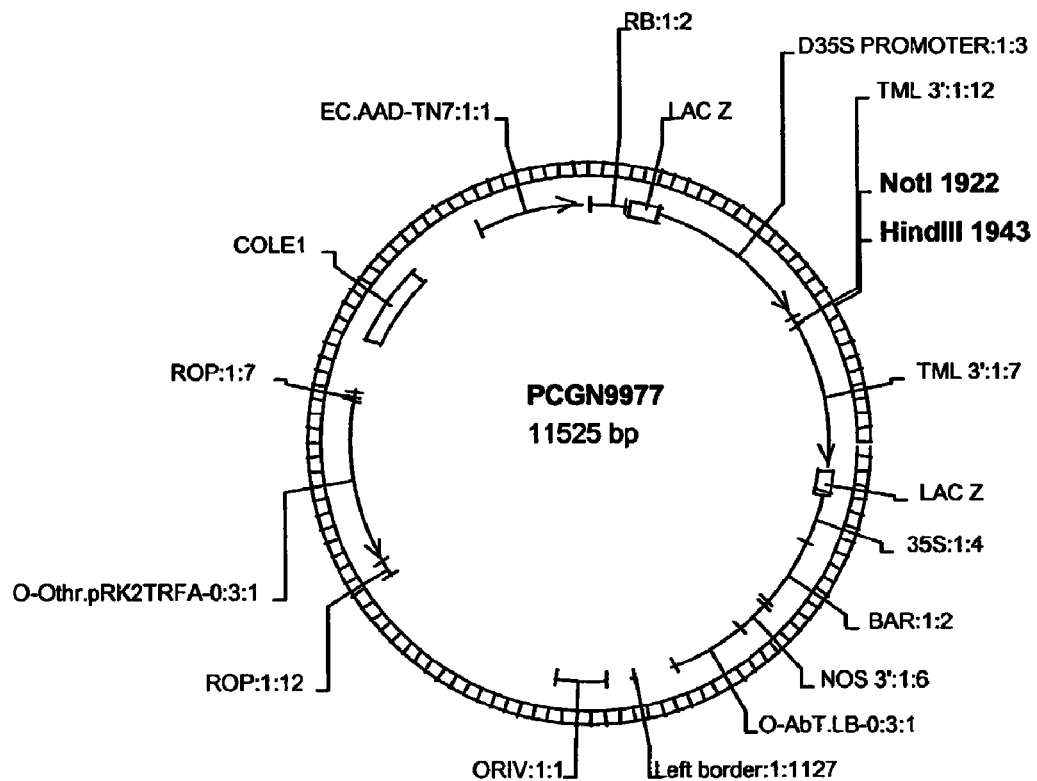

Figure 18

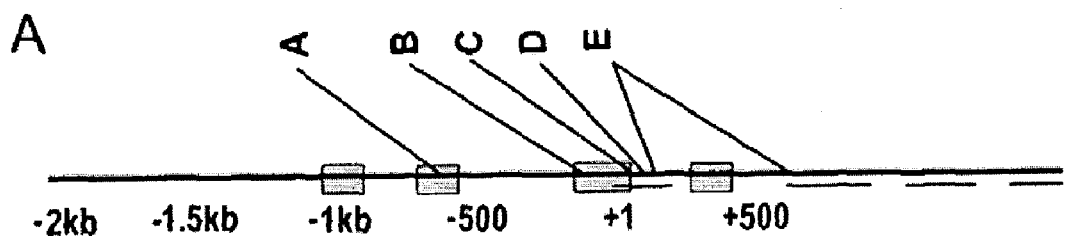

B

| ZFP | Target (5' to 3') Sequence | Target (5' to 3') Subsites | Finger designs (-1 to +6) | Gel Shift | | Kd (nM) |
|---|---|---|---|---|---|---|
| A | GAGGAAGGGg | GGGg<br>GAAg<br>GAGg | RSDHLAR<br>QSGNLAR<br>RSDNLTR | | Bound<br>Free | 0.001 |
| B | GGGGAAAGGg | AGGg<br>GAAa<br>GGGg | RSDHLTQ<br>QSGNLAR<br>RSDHLSR | | Bound<br>Free | 0.0036 |
| C | GAAGAGGGTg | GGTg<br>GAGg<br>GAAg | QSSHLAR<br>RSDNLAR<br>QSGNLAR | | Bound<br>Free | 0.0036 |
| D | GAGGAGGATg | GATg<br>GAGg<br>GAGg | QSSNLQR<br>RSDNLAR<br>RSDNLQR | | Bound<br>Free | 0.0003 |
| E | GAGGAGGAGg | GAGg<br>GAGg<br>GAGg | RSDNLAR<br>RSDNLAR<br>RSDNLTR | | Bound<br>Free | 0.0008 |
| SP1 | GGGGCGGGGg | GGGg<br>GCGg<br>GGGg | KTSHLRA<br>RSDELQR<br>RSDHLSK | | Bound<br>Free | 0.055 |

SEQUENCE LISTING

```
<160> NUMBER OF SEQ ID NOS: 172

<210> SEQ ID NO 1
<211> LENGTH: 25
<212> TYPE: PRT
<213> ORGANISM: Artificial
<220> FEATURE:
<223> OTHER INFORMATION: first class of ZFPs
<220> FEATURE:
<221> NAME/KEY: MISC_FEATURE
<222> LOCATION: (2)..(5)
<223> OTHER INFORMATION: Xaa = any amino acid
<220> FEATURE:
<221> NAME/KEY: MISC_FEATURE
<222> LOCATION: (4)..(5)
<223> OTHER INFORMATION: Xaa may be present or absent
<220> FEATURE:
<221> NAME/KEY: MISC_FEATURE
<222> LOCATION: (7)..(18)
<223> OTHER INFORMATION: Xaa = any amino acid
<220> FEATURE:
<221> NAME/KEY: MISC_FEATURE
<222> LOCATION: (20)..(24)
<223> OTHER INFORMATION: Xaa = any amino acid
<220> FEATURE:
<221> NAME/KEY: MISC_FEATURE
<222> LOCATION: (23)..(24)
<223> OTHER INFORMATION: Xaa may be present or absent

<400> SEQUENCE: 1

Cys Xaa Xaa Xaa Xaa Cys Xaa Xaa Xaa Xaa Xaa Xaa Xaa Xaa Xaa Xaa
1               5                   10                  15

Xaa Xaa His Xaa Xaa Xaa Xaa Xaa His
            20                  25
```

```
<210> SEQ ID NO 2
<211> LENGTH: 9
<212> TYPE: DNA
<213> ORGANISM: Artificial
<220> FEATURE:
<223> OTHER INFORMATION: target sequence

<400> SEQUENCE: 2 ggcgtagac                                                                 9

<210> SEQ ID NO 3
<211> LENGTH: 9
<212> TYPE: DNA
<213> ORGANISM: Artificial
<220> FEATURE:
<223> OTHER INFORMATION: target sequence

<400> SEQUENCE: 3 ggcgacgta                                                                 9

<210> SEQ ID NO 4
<211> LENGTH: 5
<212> TYPE: PRT
<213> ORGANISM: Artificial
<220> FEATURE:
<223> OTHER INFORMATION: linker

<400> SEQUENCE: 4

Thr Gly Glu Lys Pro
1               5

<210> SEQ ID NO 5
<211> LENGTH: 5
<212> TYPE: PRT
<213> ORGANISM: Artificial
<220> FEATURE:
<223> OTHER INFORMATION: linker

<400> SEQUENCE: 5

Gly Gly Gly Gly Ser
1               5

<210> SEQ ID NO 6
<211> LENGTH: 8
<212> TYPE: PRT
<213> ORGANISM: Artificial
<220> FEATURE:
<223> OTHER INFORMATION: linker

<400> SEQUENCE: 6

Gly Gly Arg Arg Gly Gly Gly Ser
1               5

<210> SEQ ID NO 7
<211> LENGTH: 9
<212> TYPE: PRT
<213> ORGANISM: Artificial
<220> FEATURE:
<223> OTHER INFORMATION: linker

<400> SEQUENCE: 7

Leu Arg Gln Arg Asp Gly Glu Arg Pro
1               5

<210> SEQ ID NO 8
<211> LENGTH: 12
<212> TYPE: PRT
<213> ORGANISM: Artificial
```

```
<220> FEATURE:
<223> OTHER INFORMATION: linker

<400> SEQUENCE: 8

Leu Arg Gln Lys Asp Gly Gly Gly Ser Glu Arg Pro
1               5                   10

<210> SEQ ID NO 9
<211> LENGTH: 16
<212> TYPE: PRT
<213> ORGANISM: Artificial
<220> FEATURE:
<223> OTHER INFORMATION: linker

<400> SEQUENCE: 9

Leu Arg Gln Lys Asp Gly Gly Gly Ser Gly Gly Gly Ser Glu Arg Pro
1               5                   10                  15

<210> SEQ ID NO 10
<211> LENGTH: 28
<212> TYPE: PRT
<213> ORGANISM: Artificial
<220> FEATURE:
<223> OTHER INFORMATION: SP-1 consensus
<220> FEATURE:
<221> NAME/KEY: misc_feature
<222> LOCATION: (12)..(18)
<223> OTHER INFORMATION: Xaa can be any naturally occurring amino acid

<400> SEQUENCE: 10

Tyr Lys Cys Pro Glu Cys Gly Lys Ser Phe Ser Xaa Xaa Xaa Xaa Xaa
1               5                   10                  15

Xaa Xaa His Gln Arg Thr His Thr Gly Glu Lys Pro
            20                  25

<210> SEQ ID NO 11
<211> LENGTH: 34
<212> TYPE: PRT
<213> ORGANISM: Artificial
<220> FEATURE:
<223> OTHER INFORMATION: F1
<220> FEATURE:
<221> NAME/KEY: misc_feature
<222> LOCATION: (18)..(24)
<223> OTHER INFORMATION: Xaa can be any naturally occurring amino acid

<400> SEQUENCE: 11

Lys Lys Lys Ser Lys Gly His Glu Cys Pro Ile Cys Phe Arg Val Phe
1               5                   10                  15

Lys Xaa Xaa Xaa Xaa Xaa Xaa Xaa His Lys Arg Ser His Thr Gly Glu
            20                  25                  30

Lys Pro

<210> SEQ ID NO 12
<211> LENGTH: 28
<212> TYPE: PRT
<213> ORGANISM: Artificial
<220> FEATURE:
<223> OTHER INFORMATION: F2
<220> FEATURE:
<221> NAME/KEY: misc_feature
<222> LOCATION: (12)..(18)
<223> OTHER INFORMATION: Xaa can be any naturally occurring amino acid

<400> SEQUENCE: 12

Tyr Lys Cys Thr Val Cys Gly Lys Ser Phe Ser Xaa Xaa Xaa Xaa Xaa
1               5                   10                  15
```

```
Xaa Xaa His Lys Arg Leu His Thr Gly Glu Lys Pro
            20                  25
```

```
<210> SEQ ID NO 13
<211> LENGTH: 23
<212> TYPE: PRT
<213> ORGANISM: Artificial
<220> FEATURE:
<223> OTHER INFORMATION: F3
<220> FEATURE:
<221> NAME/KEY: misc_feature
<222> LOCATION: (12)..(18)
<223> OTHER INFORMATION: Xaa can be any naturally occurring amino acid

<400> SEQUENCE: 13

Phe Ser Cys Asn Tyr Cys Gln Arg Lys Phe Tyr Xaa Xaa Xaa Xaa Xaa
1               5                   10                  15

Xaa Xaa His Val Arg Ile His
            20
```

```
<210> SEQ ID NO 14
<211> LENGTH: 4
<212> TYPE: PRT
<213> ORGANISM: Artificial
<220> FEATURE:
<223> OTHER INFORMATION: sequence added to the C-terminus of F3

<400> SEQUENCE: 14

Gln Asn Lys Lys
1
```

```
<210> SEQ ID NO 15
<211> LENGTH: 5
<212> TYPE: PRT
<213> ORGANISM: Artificial
<220> FEATURE:
<223> OTHER INFORMATION: helix capping sequence
<220> FEATURE:
<221> NAME/KEY: MISC_FEATURE
<222> LOCATION: (4)..(4)
<223> OTHER INFORMATION: Xaa = Lys or Arg
<220> FEATURE:
<221> NAME/KEY: MISC_FEATURE
<222> LOCATION: (5)..(5)
<223> OTHER INFORMATION: Xaa = Lys or Pro

<400> SEQUENCE: 15

Thr Gly Glu Xaa Xaa
1               5
```

```
<210> SEQ ID NO 16
<211> LENGTH: 32
<212> TYPE: PRT
<213> ORGANISM: Artificial
<220> FEATURE:
<223> OTHER INFORMATION: zinc finger backbone
<220> FEATURE:
<221> NAME/KEY: MISC_FEATURE
<222> LOCATION: (16)..(22)
<223> OTHER INFORMATION: Xaa = any amino acid

<400> SEQUENCE: 16

Lys Ser Lys Gly His Glu Cys Pro Ile Cys Phe Arg Val Phe Lys Xaa
1               5                   10                  15

Xaa Xaa Xaa Xaa Xaa Xaa His Lys Arg Ser His Thr Gly Glu Lys Pro
            20                  25                  30
```

```
<210> SEQ ID NO 17
<211> LENGTH: 28
```

```
<212> TYPE: PRT
<213> ORGANISM: Artificial
<220> FEATURE:
<223> OTHER INFORMATION: zinc finger backbone
<220> FEATURE:
<221> NAME/KEY: MISC_FEATURE
<222> LOCATION: (12)..(18)
<223> OTHER INFORMATION: Xaa = any amino acid

<400> SEQUENCE: 17

Tyr Lys Cys Thr Val Cys Gly Lys Ser Phe Ser Xaa Xaa Xaa Xaa Xaa
1               5                   10                  15

Xaa Xaa His Lys Arg Leu His Thr Gly Glu Lys Pro
            20                  25

<210> SEQ ID NO 18
<211> LENGTH: 27
<212> TYPE: PRT
<213> ORGANISM: Artificial
<220> FEATURE:
<223> OTHER INFORMATION: zinc finger backbone
<220> FEATURE:
<221> NAME/KEY: MISC_FEATURE
<222> LOCATION: (12)..(18)
<223> OTHER INFORMATION: Xaa =  any amino acid

<400> SEQUENCE: 18

Phe Ser Cys Asn Tyr Cys Gln Arg Lys Phe Gly Xaa Xaa Xaa Xaa Xaa
1               5                   10                  15

Xaa Xaa His Val Arg Ile His Gln Asn Lys Lys
            20                  25

<210> SEQ ID NO 19
<211> LENGTH: 60
<212> TYPE: DNA
<213> ORGANISM: Artificial
<220> FEATURE:
<223> OTHER INFORMATION: H1
<220> FEATURE:
<221> NAME/KEY: misc_feature
<222> LOCATION: (25)..(45)
<223> OTHER INFORMATION: n is a, c, g, or t

<400> SEQUENCE: 19
ctcaccggtg tgagaacgct tgtgnnnnnn nnnnnnnnnn nnnncttga aaacacggaa      60

<210> SEQ ID NO 20
<211> LENGTH: 60
<212> TYPE: DNA
<213> ORGANISM: Artificial
<220> FEATURE:
<223> OTHER INFORMATION: H2
<220> FEATURE:
<221> NAME/KEY: misc_feature
<222> LOCATION: (25)..(45)
<223> OTHER INFORMATION: n is a, c, g, or t

<400> SEQUENCE: 20
ttcaccagta tgaagacgct tatgnnnnnn nnnnnnnnnn nnnnagaaa aagacttacc      60

<210> SEQ ID NO 21
<211> LENGTH: 63
<212> TYPE: DNA
<213> ORGANISM: Artificial
<220> FEATURE:
<223> OTHER INFORMATION: H3
<220> FEATURE:
<221> NAME/KEY: misc_feature
<222> LOCATION: (28)..(48)
<223> OTHER INFORMATION: n is a, c, g, or t
```

-continued

```
<400> SEQUENCE: 21
cttcttgttc tggtggatac gcacgtgnnn nnnnnnnnn nnnnnnnnac cgaacttacg      60
ctg                                                                  63

<210> SEQ ID NO 22
<211> LENGTH: 45
<212> TYPE: DNA
<213> ORGANISM: Artificial
<220> FEATURE:
<223> OTHER INFORMATION: PB1

<400> SEQUENCE: 22
aagtctaagg gtcacgagtg cccaatctgc ttccgtgttt tcaag                    45

<210> SEQ ID NO 23
<211> LENGTH: 54
<212> TYPE: DNA
<213> ORGANISM: Artificial
<220> FEATURE:
<223> OTHER INFORMATION: PB2

<400> SEQUENCE: 23
tctcacaccg gtgagaagcc atacaagtgc actgtttgtg gtaagtcttt ttct          54

<210> SEQ ID NO 24
<211> LENGTH: 54
<212> TYPE: DNA
<213> ORGANISM: Artificial
<220> FEATURE:
<223> OTHER INFORMATION: PB3

<400> SEQUENCE: 24
cttcatactg gtgaaaagcc attctcttgc aactactgcc agcgtaagtt cggt          54

<210> SEQ ID NO 25
<211> LENGTH: 10
<212> TYPE: DNA
<213> ORGANISM: Artificial
<220> FEATURE:
<223> OTHER INFORMATION: AGMT1 target

<400> SEQUENCE: 25
gtggacgagt                                                           10

<210> SEQ ID NO 26
<211> LENGTH: 7
<212> TYPE: PRT
<213> ORGANISM: Artificial
<220> FEATURE:
<223> OTHER INFORMATION: AGMT1 F1

<400> SEQUENCE: 26

Arg Ser Asp Asn Leu Ala Arg
1               5

<210> SEQ ID NO 27
<211> LENGTH: 7
<212> TYPE: PRT
<213> ORGANISM: Artificial
<220> FEATURE:
<223> OTHER INFORMATION: AGMT1 F2

<400> SEQUENCE: 27

Asp Arg Ser Asn Leu Thr Arg
1               5
```

```
<210> SEQ ID NO 28
<211> LENGTH: 7
<212> TYPE: PRT
<213> ORGANISM: Artificial
<220> FEATURE:
<223> OTHER INFORMATION: AGMT1 F3

<400> SEQUENCE: 28

Arg Ser Asp Ala Leu Thr Arg
1               5

<210> SEQ ID NO 29
<211> LENGTH: 10
<212> TYPE: DNA
<213> ORGANISM: Artificial
<220> FEATURE:
<223> OTHER INFORMATION: AGMT3 target

<400> SEQUENCE: 29
tggtgggtgt                                                          10

<210> SEQ ID NO 30
<211> LENGTH: 7
<212> TYPE: PRT
<213> ORGANISM: Artificial
<220> FEATURE:
<223> OTHER INFORMATION: AGMT3 F1

<400> SEQUENCE: 30

Arg Ser Asp Ala Leu Thr Arg
1               5

<210> SEQ ID NO 31
<211> LENGTH: 7
<212> TYPE: PRT
<213> ORGANISM: Artificial
<220> FEATURE:
<223> OTHER INFORMATION: AGMT3 F2

<400> SEQUENCE: 31

Arg Ser Asp His Leu Thr Thr
1               5

<210> SEQ ID NO 32
<211> LENGTH: 7
<212> TYPE: PRT
<213> ORGANISM: Artificial
<220> FEATURE:
<223> OTHER INFORMATION: AGMT3 F3

<400> SEQUENCE: 32

Arg Ser Asp His Leu Thr Thr
1               5

<210> SEQ ID NO 33
<211> LENGTH: 10
<212> TYPE: DNA
<213> ORGANISM: Artificial
<220> FEATURE:
<223> OTHER INFORMATION: AGMT4 target

<400> SEQUENCE: 33
gaagaggatt                                                          10

<210> SEQ ID NO 34
<211> LENGTH: 7
```

```
<212> TYPE: PRT
<213> ORGANISM: Artificial
<220> FEATURE:
<223> OTHER INFORMATION: AGMT4 F1

<400> SEQUENCE: 34

Gln Ser Ser Asn Leu Ala Arg
1               5

<210> SEQ ID NO 35
<211> LENGTH: 7
<212> TYPE: PRT
<213> ORGANISM: Artificial
<220> FEATURE:
<223> OTHER INFORMATION: AGMT4 F2

<400> SEQUENCE: 35

Arg Ser Asp Asn Leu Ala Arg
1               5

<210> SEQ ID NO 36
<211> LENGTH: 7
<212> TYPE: PRT
<213> ORGANISM: Artificial
<220> FEATURE:
<223> OTHER INFORMATION: AGMT4 F3

<400> SEQUENCE: 36

Gln Ser Gly Asn Leu Thr Arg
1               5

<210> SEQ ID NO 37
<211> LENGTH: 10
<212> TYPE: DNA
<213> ORGANISM: Artificial
<220> FEATURE:
<223> OTHER INFORMATION: AGMT5 target

<400> SEQUENCE: 37
gaggaagggg                                                          10

<210> SEQ ID NO 38
<211> LENGTH: 7
<212> TYPE: PRT
<213> ORGANISM: Artificial
<220> FEATURE:
<223> OTHER INFORMATION: AGMT5 F1

<400> SEQUENCE: 38

Arg Ser Asp His Leu Ala Arg
1               5

<210> SEQ ID NO 39
<211> LENGTH: 7
<212> TYPE: PRT
<213> ORGANISM: Artificial
<220> FEATURE:
<223> OTHER INFORMATION: AGMT5 F2

<400> SEQUENCE: 39

Gln Ser Gly Asn Leu Ala Arg
1               5

<210> SEQ ID NO 40
<211> LENGTH: 7
<212> TYPE: PRT
<213> ORGANISM: Artificial
<220> FEATURE:
```

```
<223> OTHER INFORMATION: AGMT5 F3

<400> SEQUENCE: 40

Arg Ser Asp Asn Leu Thr Arg
1               5

<210> SEQ ID NO 41
<211> LENGTH: 9
<212> TYPE: DNA
<213> ORGANISM: Artificial
<220> FEATURE:
<223> OTHER INFORMATION: AGMT6 target

<400> SEQUENCE: 41 tgggtagtc                                                                 9

<210> SEQ ID NO 42
<211> LENGTH: 7
<212> TYPE: PRT
<213> ORGANISM: Artificial
<220> FEATURE:
<223> OTHER INFORMATION: AGMT6 F1

<400> SEQUENCE: 42

Glu Arg Gly Thr Leu Ala Arg
1               5

<210> SEQ ID NO 43
<211> LENGTH: 7
<212> TYPE: PRT
<213> ORGANISM: Artificial
<220> FEATURE:
<223> OTHER INFORMATION: AGMT6 F2

<400> SEQUENCE: 43

Gln Ser Gly Ser Leu Thr Arg
1               5

<210> SEQ ID NO 44
<211> LENGTH: 7
<212> TYPE: PRT
<213> ORGANISM: Artificial
<220> FEATURE:
<223> OTHER INFORMATION: AGMT6 F3

<400> SEQUENCE: 44

Arg Ser Asp His Leu Thr Thr
1               5

<210> SEQ ID NO 45
<211> LENGTH: 10
<212> TYPE: DNA
<213> ORGANISM: Artificial
<220> FEATURE:
<223> OTHER INFORMATION: AGMT7 target

<400> SEQUENCE: 45
ggggaaaggg                                                               10

<210> SEQ ID NO 46
<211> LENGTH: 7
<212> TYPE: PRT
<213> ORGANISM: Artificial
<220> FEATURE:
<223> OTHER INFORMATION: AGMT7 F1

<400> SEQUENCE: 46
```

Arg Ser Asp His Leu Thr Gln
1               5

<210> SEQ ID NO 47
<211> LENGTH: 7
<212> TYPE: PRT
<213> ORGANISM: Artificial
<220> FEATURE:
<223> OTHER INFORMATION: AGMT7 F2

<400> SEQUENCE: 47

Gln Ser Gly Asn Leu Ala Arg
1               5

<210> SEQ ID NO 48
<211> LENGTH: 7
<212> TYPE: PRT
<213> ORGANISM: Artificial
<220> FEATURE:
<223> OTHER INFORMATION: AGMT7 F3

<400> SEQUENCE: 48

Arg Ser Asp His Leu Ser Arg
1               5

<210> SEQ ID NO 49
<211> LENGTH: 10
<212> TYPE: DNA
<213> ORGANISM: Artificial
<220> FEATURE:
<223> OTHER INFORMATION: AGMT8 target

<400> SEQUENCE: 49
gaagagggtg                                                           10

<210> SEQ ID NO 50
<211> LENGTH: 7
<212> TYPE: PRT
<213> ORGANISM: Artificial
<220> FEATURE:
<223> OTHER INFORMATION: AGMT8 F1

<400> SEQUENCE: 50

Gln Ser Ser His Leu Ala Arg
1               5

<210> SEQ ID NO 51
<211> LENGTH: 7
<212> TYPE: PRT
<213> ORGANISM: Artificial
<220> FEATURE:
<223> OTHER INFORMATION: AGMT8 F2

<400> SEQUENCE: 51

Arg Ser Asp Asn Leu Ala Arg
1               5

<210> SEQ ID NO 52
<211> LENGTH: 7
<212> TYPE: PRT
<213> ORGANISM: Artificial
<220> FEATURE:
<223> OTHER INFORMATION: AGMT8 F3

<400> SEQUENCE: 52

Gln Ser Gly Asn Leu Ala Arg
1               5

```
<210> SEQ ID NO 53
<211> LENGTH: 10
<212> TYPE: DNA
<213> ORGANISM: Artificial
<220> FEATURE:
<223> OTHER INFORMATION: AGMT9 target

<400> SEQUENCE: 53
gaggaggatg                                                              10

<210> SEQ ID NO 54
<211> LENGTH: 7
<212> TYPE: PRT
<213> ORGANISM: Artificial
<220> FEATURE:
<223> OTHER INFORMATION: AGMT9 F1

<400> SEQUENCE: 54

Gln Ser Ser Asn Leu Gln Arg
1               5

<210> SEQ ID NO 55
<211> LENGTH: 7
<212> TYPE: PRT
<213> ORGANISM: Artificial
<220> FEATURE:
<223> OTHER INFORMATION: AGMT9 F2

<400> SEQUENCE: 55

Arg Ser Asp Asn Ala Leu Arg
1               5

<210> SEQ ID NO 56
<211> LENGTH: 7
<212> TYPE: PRT
<213> ORGANISM: Artificial
<220> FEATURE:
<223> OTHER INFORMATION: AGMT9 F3

<400> SEQUENCE: 56

Arg Ser Asp Asn Leu Gln Arg
1               5

<210> SEQ ID NO 57
<211> LENGTH: 10
<212> TYPE: DNA
<213> ORGANISM: Artificial
<220> FEATURE:
<223> OTHER INFORMATION: AGMT10 target

<400> SEQUENCE: 57
gaggaggagg                                                              10

<210> SEQ ID NO 58
<211> LENGTH: 7
<212> TYPE: PRT
<213> ORGANISM: Artificial
<220> FEATURE:
<223> OTHER INFORMATION: AGMT10 F1

<400> SEQUENCE: 58

Arg Ser Asp Asn Ala Leu Arg
1               5

<210> SEQ ID NO 59
<211> LENGTH: 7
<212> TYPE: PRT
```

```
<213> ORGANISM: Artificial
<220> FEATURE:
<223> OTHER INFORMATION: AGMT10 F2

<400> SEQUENCE: 59

Arg Ser Asp Asn Leu Ala Arg
1               5

<210> SEQ ID NO 60
<211> LENGTH: 7
<212> TYPE: PRT
<213> ORGANISM: Artificial
<220> FEATURE:
<223> OTHER INFORMATION: AGMT10 F3

<400> SEQUENCE: 60

Arg Ser Asp Asn Leu Thr Arg
1               5

<210> SEQ ID NO 61
<211> LENGTH: 10
<212> TYPE: DNA
<213> ORGANISM: Artificial
<220> FEATURE:
<223> OTHER INFORMATION: AGMT11 target

<400> SEQUENCE: 61
gtggcggctg                                                              10

<210> SEQ ID NO 62
<211> LENGTH: 7
<212> TYPE: PRT
<213> ORGANISM: Artificial
<220> FEATURE:
<223> OTHER INFORMATION: AGMT11 F1

<400> SEQUENCE: 62

Gln Ser Ser Asp Leu Arg Arg
1               5

<210> SEQ ID NO 63
<211> LENGTH: 7
<212> TYPE: PRT
<213> ORGANISM: Artificial
<220> FEATURE:
<223> OTHER INFORMATION: AGMT11 F2

<400> SEQUENCE: 63

Arg Ser Asp Glu Leu Gln Arg
1               5

<210> SEQ ID NO 64
<211> LENGTH: 7
<212> TYPE: PRT
<213> ORGANISM: Artificial
<220> FEATURE:
<223> OTHER INFORMATION: AGMT11 F3

<400> SEQUENCE: 64

Arg Ser Asp Ala Leu Thr Arg
1               5

<210> SEQ ID NO 65
<211> LENGTH: 9
<212> TYPE: DNA
<213> ORGANISM: Artificial
<220> FEATURE:
<223> OTHER INFORMATION: AGMT12 target
```

```
<400> SEQUENCE: 65 tggggagat                                                              9

<210> SEQ ID NO 66
<211> LENGTH: 7
<212> TYPE: PRT
<213> ORGANISM: Artificial
<220> FEATURE:
<223> OTHER INFORMATION: AGMT12 F1

<400> SEQUENCE: 66

Gln Ser Ser Asn Leu Ala Arg
1               5

<210> SEQ ID NO 67
<211> LENGTH: 7
<212> TYPE: PRT
<213> ORGANISM: Artificial
<220> FEATURE:
<223> OTHER INFORMATION: AGMT12 F2

<400> SEQUENCE: 67

Gln Ser Gly His Leu Gln Arg
1               5

<210> SEQ ID NO 68
<211> LENGTH: 7
<212> TYPE: PRT
<213> ORGANISM: Artificial
<220> FEATURE:
<223> OTHER INFORMATION: AGMT12 F3

<400> SEQUENCE: 68

Arg Ser Asp His Leu Thr Thr
1               5

<210> SEQ ID NO 69
<211> LENGTH: 9
<212> TYPE: DNA
<213> ORGANISM: Artificial
<220> FEATURE:
<223> OTHER INFORMATION: AGMT13 target

<400> SEQUENCE: 69 gaggaagct                                                              9

<210> SEQ ID NO 70
<211> LENGTH: 7
<212> TYPE: PRT
<213> ORGANISM: Artificial
<220> FEATURE:
<223> OTHER INFORMATION: AGMT13 F1

<400> SEQUENCE: 70

Gln Ser Ser Asp Leu Arg Arg
1               5

<210> SEQ ID NO 71
<211> LENGTH: 7
<212> TYPE: PRT
<213> ORGANISM: Artificial
<220> FEATURE:
<223> OTHER INFORMATION: AGMT13 F2

<400> SEQUENCE: 71

Gln Ser Gly Asn Leu Ala Arg
```

```
<210> SEQ ID NO 72
<211> LENGTH: 7
<212> TYPE: PRT
<213> ORGANISM: Artificial
<220> FEATURE:
<223> OTHER INFORMATION: AGMT13 F3

<400> SEQUENCE: 72

Arg Ser Asp Asn Leu Thr Arg
1               5

<210> SEQ ID NO 73
<211> LENGTH: 10
<212> TYPE: DNA
<213> ORGANISM: Artificial
<220> FEATURE:
<223> OTHER INFORMATION: AGMT14 target

<400> SEQUENCE: 73
gcttgtggct                                                          10

<210> SEQ ID NO 74
<211> LENGTH: 7
<212> TYPE: PRT
<213> ORGANISM: Artificial
<220> FEATURE:
<223> OTHER INFORMATION: AGMT14 F1

<400> SEQUENCE: 74

Asp Arg Ser His Leu Thr Arg
1               5

<210> SEQ ID NO 75
<211> LENGTH: 7
<212> TYPE: PRT
<213> ORGANISM: Artificial
<220> FEATURE:
<223> OTHER INFORMATION: AGMT14 F2

<400> SEQUENCE: 75

Thr Ser Gly His Leu Thr Thr
1               5

<210> SEQ ID NO 76
<211> LENGTH: 7
<212> TYPE: PRT
<213> ORGANISM: Artificial
<220> FEATURE:
<223> OTHER INFORMATION: AGMT14 F3

<400> SEQUENCE: 76

Gln Ser Ser Asp Leu Thr Arg
1               5

<210> SEQ ID NO 77
<211> LENGTH: 10
<212> TYPE: DNA
<213> ORGANISM: Artificial
<220> FEATURE:
<223> OTHER INFORMATION: AGMT15 target

<400> SEQUENCE: 77
gtagtggatg                                                          10

<210> SEQ ID NO 78
```

```
<211> LENGTH: 7
<212> TYPE: PRT
<213> ORGANISM: Artificial
<220> FEATURE:
<223> OTHER INFORMATION: AGMT15 F1

<400> SEQUENCE: 78

Gln Ser Ser Asn Leu Ala Arg
1               5

<210> SEQ ID NO 79
<211> LENGTH: 7
<212> TYPE: PRT
<213> ORGANISM: Artificial
<220> FEATURE:
<223> OTHER INFORMATION: AGMT15 F2

<400> SEQUENCE: 79

Arg Ser Asp Ala Leu Ser Arg
1               5

<210> SEQ ID NO 80
<211> LENGTH: 7
<212> TYPE: PRT
<213> ORGANISM: Artificial
<220> FEATURE:
<223> OTHER INFORMATION: AGMT15 F3

<400> SEQUENCE: 80

Gln Ser Gly Ser Leu Thr Arg
1               5

<210> SEQ ID NO 81
<211> LENGTH: 10
<212> TYPE: DNA
<213> ORGANISM: Artificial
<220> FEATURE:
<223> OTHER INFORMATION: AGMT16 target

<400> SEQUENCE: 81
gtgtgggatt                                                         10

<210> SEQ ID NO 82
<211> LENGTH: 7
<212> TYPE: PRT
<213> ORGANISM: Artificial
<220> FEATURE:
<223> OTHER INFORMATION: AGMT16 F1

<400> SEQUENCE: 82

Gln Ser Ser Asn Leu Ala Arg
1               5

<210> SEQ ID NO 83
<211> LENGTH: 7
<212> TYPE: PRT
<213> ORGANISM: Artificial
<220> FEATURE:
<223> OTHER INFORMATION: AGMT16 F2

<400> SEQUENCE: 83

Arg Ser Asp His Leu Thr Thr
1               5

<210> SEQ ID NO 84
<211> LENGTH: 7
<212> TYPE: PRT
<213> ORGANISM: Artificial
```

```
<220> FEATURE:
<223> OTHER INFORMATION: AGMT16 F3

<400> SEQUENCE: 84

Arg Ser Asp Ala Leu Thr Arg
1               5

<210> SEQ ID NO 85
<211> LENGTH: 18
<212> TYPE: DNA
<213> ORGANISM: Artificial
<220> FEATURE:
<223> OTHER INFORMATION: GMT forward primer

<400> SEQUENCE: 85
aatgatctcg cggctgct                                                 18

<210> SEQ ID NO 86
<211> LENGTH: 20
<212> TYPE: DNA
<213> ORGANISM: Artificial
<220> FEATURE:
<223> OTHER INFORMATION: GMT reverse primer

<400> SEQUENCE: 86
gaatggctga tccaacgcat                                               20

<210> SEQ ID NO 87
<211> LENGTH: 29
<212> TYPE: DNA
<213> ORGANISM: Artificial
<220> FEATURE:
<223> OTHER INFORMATION: GMT probe

<400> SEQUENCE: 87
tcactcgctc ataaggcttc cttccaagt                                     29

<210> SEQ ID NO 88
<211> LENGTH: 21
<212> TYPE: DNA
<213> ORGANISM: Artificial
<220> FEATURE:
<223> OTHER INFORMATION: 18S forward primer

<400> SEQUENCE: 88
tgcaacaaac cccgacttat g                                             21

<210> SEQ ID NO 89
<211> LENGTH: 19
<212> TYPE: DNA
<213> ORGANISM: Artificial
<220> FEATURE:
<223> OTHER INFORMATION: 18S reverse primer

<400> SEQUENCE: 89
cccgcgtcga cctttatc                                                 19

<210> SEQ ID NO 90
<211> LENGTH: 16
<212> TYPE: DNA
<213> ORGANISM: Artificial
<220> FEATURE:
<223> OTHER INFORMATION: 18S probe

<400> SEQUENCE: 90
aataaatgcg tcccctt                                                  16
```

```
<210> SEQ ID NO 91
<211> LENGTH: 9
<212> TYPE: DNA
<213> ORGANISM: Artificial
<220> FEATURE:
<223> OTHER INFORMATION: CGMT3 target

<400> SEQUENCE: 91 gatgctggt                                                               9

<210> SEQ ID NO 92
<211> LENGTH: 7
<212> TYPE: PRT
<213> ORGANISM: Artificial
<220> FEATURE:
<223> OTHER INFORMATION: CGMT3 F1

<400> SEQUENCE: 92

Gln Ser Ser His Leu Ala Arg
1               5

<210> SEQ ID NO 93
<211> LENGTH: 7
<212> TYPE: PRT
<213> ORGANISM: Artificial
<220> FEATURE:
<223> OTHER INFORMATION: CGMT3 F2

<400> SEQUENCE: 93

Gln Ser Ser Asp Leu Thr Arg
1               5

<210> SEQ ID NO 94
<211> LENGTH: 7
<212> TYPE: PRT
<213> ORGANISM: Artificial
<220> FEATURE:
<223> OTHER INFORMATION: CGMT3 F3

<400> SEQUENCE: 94

Thr Ser Gly Asn Leu Thr Arg
1               5

<210> SEQ ID NO 95
<211> LENGTH: 9
<212> TYPE: DNA
<213> ORGANISM: Artificial
<220> FEATURE:
<223> OTHER INFORMATION: CGMT4 target

<400> SEQUENCE: 95 gaggaagat                                                               9

<210> SEQ ID NO 96
<211> LENGTH: 7
<212> TYPE: PRT
<213> ORGANISM: Artificial
<220> FEATURE:
<223> OTHER INFORMATION: CGMT4 F1

<400> SEQUENCE: 96

Gln Ser Ser Asn Leu Ala Arg
1               5

<210> SEQ ID NO 97
<211> LENGTH: 7
<212> TYPE: PRT
```

```
<213> ORGANISM: Artificial
<220> FEATURE:
<223> OTHER INFORMATION: CGMT4 F2

<400> SEQUENCE: 97

Gln Ser Gly Asn Leu Ala Arg
1               5

<210> SEQ ID NO 98
<211> LENGTH: 7
<212> TYPE: PRT
<213> ORGANISM: Artificial
<220> FEATURE:
<223> OTHER INFORMATION: CGMT4 F3

<400> SEQUENCE: 98

Arg Ser Asp Asn Leu Thr Arg
1               5

<210> SEQ ID NO 99
<211> LENGTH: 9
<212> TYPE: DNA
<213> ORGANISM: Artificial
<220> FEATURE:
<223> OTHER INFORMATION: CGMT5 target

<400> SEQUENCE: 99 gaagaagag                                                                 9

<210> SEQ ID NO 100
<211> LENGTH: 7
<212> TYPE: PRT
<213> ORGANISM: Artificial
<220> FEATURE:
<223> OTHER INFORMATION: CGMT5 F1

<400> SEQUENCE: 100

Arg Ser Asp Asn Leu Ala Arg
1               5

<210> SEQ ID NO 101
<211> LENGTH: 7
<212> TYPE: PRT
<213> ORGANISM: Artificial
<220> FEATURE:
<223> OTHER INFORMATION: CGMT5 F2

<400> SEQUENCE: 101

Gln Ser Gly Asn Leu Ala Arg
1               5

<210> SEQ ID NO 102
<211> LENGTH: 7
<212> TYPE: PRT
<213> ORGANISM: Artificial
<220> FEATURE:
<223> OTHER INFORMATION: CGMT5 F3

<400> SEQUENCE: 102

Gln Ser Gly Asn Leu Ala Arg
1               5

<210> SEQ ID NO 103
<211> LENGTH: 9
<212> TYPE: DNA
<213> ORGANISM: Artificial
<220> FEATURE:
<223> OTHER INFORMATION: CGMT6 target
```

-continued

```
<400> SEQUENCE: 103 gaggttgga                                                                 9

<210> SEQ ID NO 104
<211> LENGTH: 7
<212> TYPE: PRT
<213> ORGANISM: Artificial
<220> FEATURE:
<223> OTHER INFORMATION: CGMT6 F1

<400> SEQUENCE: 104

Gln Ser Gly His Leu Ala Arg
1               5

<210> SEQ ID NO 105
<211> LENGTH: 7
<212> TYPE: PRT
<213> ORGANISM: Artificial
<220> FEATURE:
<223> OTHER INFORMATION: CGMT6 F2

<400> SEQUENCE: 105

Thr Ser Gly Ala Leu Thr Arg
1               5

<210> SEQ ID NO 106
<211> LENGTH: 7
<212> TYPE: PRT
<213> ORGANISM: Artificial
<220> FEATURE:
<223> OTHER INFORMATION: CGMT6 F3

<400> SEQUENCE: 106

Arg Ser Asp Asn Leu Thr Arg
1               5

<210> SEQ ID NO 107
<211> LENGTH: 9
<212> TYPE: DNA
<213> ORGANISM: Artificial
<220> FEATURE:
<223> OTHER INFORMATION: CGMT7 target

<400> SEQUENCE: 107 gatgatgat                                                                 9

<210> SEQ ID NO 108
<211> LENGTH: 7
<212> TYPE: PRT
<213> ORGANISM: Artificial
<220> FEATURE:
<223> OTHER INFORMATION: CGMT7 F1

<400> SEQUENCE: 108

Gln Ser Ser Asn Leu Ala Arg
1               5

<210> SEQ ID NO 109
<211> LENGTH: 7
<212> TYPE: PRT
<213> ORGANISM: Artificial
<220> FEATURE:
<223> OTHER INFORMATION: CGMT7 F2

<400> SEQUENCE: 109

Thr Ser Gly Asn Leu Thr Arg
```

<210> SEQ ID NO 110
<211> LENGTH: 7
<212> TYPE: PRT
<213> ORGANISM: Artificial
<220> FEATURE:
<223> OTHER INFORMATION: CGMT7 F3

<400> SEQUENCE: 110

Thr Ser Gly Asn Leu Thr Arg
1               5

<210> SEQ ID NO 111
<211> LENGTH: 9
<212> TYPE: DNA
<213> ORGANISM: Artificial
<220> FEATURE:
<223> OTHER INFORMATION: CGMT8 target

<400> SEQUENCE: 111 cggggagag                                                                 9

<210> SEQ ID NO 112
<211> LENGTH: 7
<212> TYPE: PRT
<213> ORGANISM: Artificial
<220> FEATURE:
<223> OTHER INFORMATION: CGMT8 F1

<400> SEQUENCE: 112

Arg Ser Ser Asn Leu Ala Arg
1               5

<210> SEQ ID NO 113
<211> LENGTH: 7
<212> TYPE: PRT
<213> ORGANISM: Artificial
<220> FEATURE:
<223> OTHER INFORMATION: CGMT8 F2

<400> SEQUENCE: 113

Gln Ser Gly His Leu Gln Arg
1               5

<210> SEQ ID NO 114
<211> LENGTH: 7
<212> TYPE: PRT
<213> ORGANISM: Artificial
<220> FEATURE:
<223> OTHER INFORMATION: CGMT8 F3

<400> SEQUENCE: 114

Arg Ser Asp His Leu Arg Glu
1               5

<210> SEQ ID NO 115
<211> LENGTH: 9
<212> TYPE: DNA
<213> ORGANISM: Artificial
<220> FEATURE:
<223> OTHER INFORMATION: CGMT9 target

<400> SEQUENCE: 115 tagttggaa                                                                 9

<210> SEQ ID NO 116

```
<211> LENGTH: 7
<212> TYPE: PRT
<213> ORGANISM: Artificial
<220> FEATURE:
<223> OTHER INFORMATION: CGMT9 F1

<400> SEQUENCE: 116

Gln Ser Gly Asn Leu Ala Arg
1               5

<210> SEQ ID NO 117
<211> LENGTH: 7
<212> TYPE: PRT
<213> ORGANISM: Artificial
<220> FEATURE:
<223> OTHER INFORMATION: CGMT9 F2

<400> SEQUENCE: 117

Arg Ser Asp Ala Leu Thr Thr
1               5

<210> SEQ ID NO 118
<211> LENGTH: 7
<212> TYPE: PRT
<213> ORGANISM: Artificial
<220> FEATURE:
<223> OTHER INFORMATION: CGMT9 118

<400> SEQUENCE: 118

Arg Ser Asp Asn Leu Thr Thr
1               5

<210> SEQ ID NO 119
<211> LENGTH: 9
<212> TYPE: DNA
<213> ORGANISM: Artificial
<220> FEATURE:
<223> OTHER INFORMATION: CGMT10 target

<400> SEQUENCE: 119 gtagaggac                                                                 9

<210> SEQ ID NO 120
<211> LENGTH: 7
<212> TYPE: PRT
<213> ORGANISM: Artificial
<220> FEATURE:
<223> OTHER INFORMATION: CGMT10 F1

<400> SEQUENCE: 120

Asp Arg Ser Asn Leu Thr Arg
1               5

<210> SEQ ID NO 121
<211> LENGTH: 7
<212> TYPE: PRT
<213> ORGANISM: Artificial
<220> FEATURE:
<223> OTHER INFORMATION: CGMT10 F2

<400> SEQUENCE: 121

Arg Ser Asp Asn Leu Ala Arg
1               5

<210> SEQ ID NO 122
<211> LENGTH: 7
<212> TYPE: PRT
<213> ORGANISM: Artificial
```

<220> FEATURE:
<223> OTHER INFORMATION: CGMT10 F3

<400> SEQUENCE: 122

Gln Ser Gly Ser Leu Thr Arg
1               5

<210> SEQ ID NO 123
<211> LENGTH: 9
<212> TYPE: DNA
<213> ORGANISM: Artificial
<220> FEATURE:
<223> OTHER INFORMATION: CGMT12  target

<400> SEQUENCE: 123 gaggttggc                                                              9

<210> SEQ ID NO 124
<211> LENGTH: 7
<212> TYPE: PRT
<213> ORGANISM: Artificial
<220> FEATURE:
<223> OTHER INFORMATION: CGMT12 F1

<400> SEQUENCE: 124

Asp Arg Ser His Leu Thr Arg
1               5

<210> SEQ ID NO 125
<211> LENGTH: 7
<212> TYPE: PRT
<213> ORGANISM: Artificial
<220> FEATURE:
<223> OTHER INFORMATION: CGMT12 F2

<400> SEQUENCE: 125

Thr Ser Gly Ala Leu Thr Arg
1               5

<210> SEQ ID NO 126
<211> LENGTH: 7
<212> TYPE: PRT
<213> ORGANISM: Artificial
<220> FEATURE:
<223> OTHER INFORMATION: CGMT12 F3

<400> SEQUENCE: 126

Arg Ser Asp Asn Leu Thr Arg
1               5

<210> SEQ ID NO 127
<211> LENGTH: 22
<212> TYPE: DNA
<213> ORGANISM: Artificial
<220> FEATURE:
<223> OTHER INFORMATION: cGMT forward primer

<400> SEQUENCE: 127
caatggaaag cggtgagcat at                                              22

<210> SEQ ID NO 128
<211> LENGTH: 18
<212> TYPE: DNA
<213> ORGANISM: Artificial
<220> FEATURE:
<223> OTHER INFORMATION: cGMT reverse primer

<400> SEQUENCE: 128

```
tccttcctcc tggagccg                                                  18

<210> SEQ ID NO 129
<211> LENGTH: 29
<212> TYPE: DNA
<213> ORGANISM: Artificial
<220> FEATURE:
<223> OTHER INFORMATION: cGMT probe

<400> SEQUENCE: 129
ctgacaaggc caagttcgtg aaggaattg                                      29

<210> SEQ ID NO 130
<211> LENGTH: 23
<212> TYPE: DNA
<213> ORGANISM: Artificial
<220> FEATURE:
<223> OTHER INFORMATION: GAPDH forward primer

<400> SEQUENCE: 130
gatcatcaag attgtatctg atc                                            23

<210> SEQ ID NO 131
<211> LENGTH: 22
<212> TYPE: DNA
<213> ORGANISM: Artificial
<220> FEATURE:
<223> OTHER INFORMATION: GAPDH reverse primer

<400> SEQUENCE: 131
cggttccttc gataactaag tc                                             22

<210> SEQ ID NO 132
<211> LENGTH: 22
<212> TYPE: DNA
<213> ORGANISM: Artificial
<220> FEATURE:
<223> OTHER INFORMATION: GAPDH probe

<400> SEQUENCE: 132
cggttccttc gataactaag tc                                             22

<210> SEQ ID NO 133
<211> LENGTH: 29
<212> TYPE: DNA
<213> ORGANISM: Artificial
<220> FEATURE:
<223> OTHER INFORMATION: YCF4 primer

<400> SEQUENCE: 133
gggacttgac tagtgcggcc gccaccatg                                      29

<210> SEQ ID NO 134
<211> LENGTH: 26
<212> TYPE: DNA
<213> ORGANISM: Artificial
<220> FEATURE:
<223> OTHER INFORMATION: NVF1879rev primer

<400> SEQUENCE: 134
cgggtttaaa cgggccctct agactc                                         26

<210> SEQ ID NO 135
<211> LENGTH: 23
<212> TYPE: PRT
<213> ORGANISM: Artificial
```

```
<220> FEATURE:
<223> OTHER INFORMATION: maize opaque-2 nuclear localization signal

<400> SEQUENCE: 135

Arg Lys Arg Lys Glu Ser Asn Arg Glu Ser Ala Arg Arg Ser Arg Arg
1               5                   10                  15

Ser Arg Tyr Arg Lys Lys Val
            20

<210> SEQ ID NO 136
<211> LENGTH: 60
<212> TYPE: PRT
<213> ORGANISM: Artificial
<220> FEATURE:
<223> OTHER INFORMATION: maize C1 activation domain

<400> SEQUENCE: 136

Ala Gly Ser Ser Asp Asp Cys Ser Ser Ala Ala Ser Val Ser Leu Arg
1               5                   10                  15

Val Gly Ser His Asp Glu Pro Cys Phe Ser Gly Asp Gly Asp Gly Asp
            20                  25                  30

Trp Met Asp Asp Val Arg Ala Leu Ala Ser Phe Leu Glu Ser Asp Glu
        35                  40                  45

Asp Trp Leu Arg Cys Gln Thr Ala Gly Gln Leu Ala
    50                  55                  60

<210> SEQ ID NO 137
<211> LENGTH: 25
<212> TYPE: DNA
<213> ORGANISM: Artificial
<220> FEATURE:
<223> OTHER INFORMATION: GAPDH probe

<400> SEQUENCE: 137
caatgcctag ttcccccag gggag                                       25

<210> SEQ ID NO 138
<211> LENGTH: 18
<212> TYPE: DNA
<213> ORGANISM: Artificial
<220> FEATURE:
<223> OTHER INFORMATION: primer

<400> SEQUENCE: 138
aatgatctcg cggctgct                                              18

<210> SEQ ID NO 139
<211> LENGTH: 20
<212> TYPE: DNA
<213> ORGANISM: Artificial
<220> FEATURE:
<223> OTHER INFORMATION: primer

<400> SEQUENCE: 139
gaatggctga tccaacgcat                                            20

<210> SEQ ID NO 140
<211> LENGTH: 29
<212> TYPE: DNA
<213> ORGANISM: Artificial
<220> FEATURE:
<223> OTHER INFORMATION: probe

<400> SEQUENCE: 140
tcactcgctc ataaggcttc cttccaagt                                  29
```

<210> SEQ ID NO 141
<211> LENGTH: 20
<212> TYPE: DNA
<213> ORGANISM: Artificial
<220> FEATURE:
<223> OTHER INFORMATION: primer

<400> SEQUENCE: 141
tgccagaaca agaagggtgg                                              20

<210> SEQ ID NO 142
<211> LENGTH: 15
<212> TYPE: DNA
<213> ORGANISM: Artificial
<220> FEATURE:
<223> OTHER INFORMATION: primer

<400> SEQUENCE: 142
ataccgacgc cgccg                                                   15

<210> SEQ ID NO 143
<211> LENGTH: 19
<212> TYPE: DNA
<213> ORGANISM: Artificial
<220> FEATURE:
<223> OTHER INFORMATION: probe

<400> SEQUENCE: 143
tcgtccgacg accctgcgg                                               19

<210> SEQ ID NO 144
<211> LENGTH: 20
<212> TYPE: DNA
<213> ORGANISM: Artificial
<220> FEATURE:
<223> OTHER INFORMATION: primer

<400> SEQUENCE: 144
cgtccctgcc ctttgtacac                                              20

<210> SEQ ID NO 145
<211> LENGTH: 21
<212> TYPE: DNA
<213> ORGANISM: Artificial
<220> FEATURE:
<223> OTHER INFORMATION: primer

<400> SEQUENCE: 145
cgaacacttc accggatcat t                                            21

<210> SEQ ID NO 146
<211> LENGTH: 21
<212> TYPE: DNA
<213> ORGANISM: Artificial
<220> FEATURE:
<223> OTHER INFORMATION: probe

<400> SEQUENCE: 146
ccgcccgtcg ctcctaccga t                                            21

<210> SEQ ID NO 147
<211> LENGTH: 19
<212> TYPE: DNA
<213> ORGANISM: Artificial
<220> FEATURE:
<223> OTHER INFORMATION: primer

<400> SEQUENCE: 147
tgccccacct tgagacaag                                               19

<210> SEQ ID NO 148
<211> LENGTH: 21
<212> TYPE: DNA
<213> ORGANISM: Artificial
<220> FEATURE:
<223> OTHER INFORMATION: primer

<400> SEQUENCE: 148
cttgctctgg ttggtgttgc t                                            21

<210> SEQ ID NO 149
<211> LENGTH: 24
<212> TYPE: DNA
<213> ORGANISM: Artificial
<220> FEATURE:
<223> OTHER INFORMATION: probe

<400> SEQUENCE: 149
ccctggaatc taacggcctt ggca                                         24

<210> SEQ ID NO 150
<211> LENGTH: 3657
<212> TYPE: DNA
<213> ORGANISM: Arabidopsis thaliana

<400> SEQUENCE: 150
gaaagatccc accacgcagc ctaaagcggt gcattatact cgtggagggc cttggtttga     60
tgcttggaag gattgcgagt ttgcggatct ttggcttaat gagatggaag agtacaacaa    120
agagaacaag aaggaagctg ataacgcaaa gtagaaagaa agaagtaaga ggtatgttgt    180
tacttaccaa cacgagtagt gaacttcctt tacatagtgt tggctttgta gagccaggga    240
tcattagtct tgtggagggc tatggagttt tttttaattt cattgaattc gttaaatcat    300
tcgcaaacac tattagtacc tatattgagg tcatatggta taataaccct attcgtttgt    360
ttatttgttg tgttttgtac ctttgatggt attttatttg tataattgat atgtgaattt    420
atgtagcatt tcttttttaat tgatctataa tgagcagtag ctcaacatat ttaaaacatg    480
gatggatgag taatgatcat tagctagcaa ccttccagat gatcagcggc tgtaacaagg    540
tagactcgcc ttcgtggacg agtaactacc gttgtaatgg gacttgtaca tgtacttact    600
gataattacc taactaaacg agactcagtg ctagaatatg agcataaatc ctcatattga    660
ggaatcacta atcattttta tactatttac ctttcacatc gtattcttat tcattttgat    720
cctttttggg tatcaaacta acaatgttga gttattcagt ttttcattct gattatctct    780
tttcttcatc ttctaatcta gtactgatca atagaaagcc tttctcattt tgatttgtta    840
ctctatcctg cgaatatctt acccctaaat gttacccatc ccgataaaaa aaaattacat    900
tgatacggac tttatatatt cacacccacc atcactatgc atcatattaa ctcataataa    960
atgttgtcga atcctcttc tgtgagtttg taatgcacaa ctacaaatct tcaagtggat   1020
aaaaacacgt tactatgttt gtatgtgatt tcaaatatta taaattagta ggtgatacaa   1080
ttattacttt atcttacaac attaataata ggtatctatg tttattttta ttttcttaaa   1140
acttgtaatt tatatagttt ttataaagta ttaggccgca gattggtctt tttctaaatg   1200
gattcaacca tttgaaattg atgcgtgtga tatgctaatc cacaatatcc aaaaaaaatt   1260
ccttctaaaa ttgtgacttt aaaatttga ctggttttgt taagagtaac gttgaagagg   1320

```
aaggggaagg aaaagtcaat aatgaaagaa aatagtttct tcattttggg atttaaatgg    1380
tgagcatggt tagaagaaaa gaaaattatc aaaggaaaca atatctatat attacccaac    1440
tatttatcag tcaaaaaaaa agaattgttt ccaccctacc aaaaaaaaaa aaaaatattg    1500
tttccaacat atttttctt tttctgaat aatccatttt tgaccggaca aacagttggg      1560
tagtcagatt aacttttgta ctttaccatt ttaatctttc tctaacctac tcatccgtaa    1620
tagaacggtg tccacgaggc tcatagtcct acaagcatgt gatagttgtc acaattacca    1680
tattaagctc tctttgctta cttcacttct tctatcaata tttgtttgcc actgactttt    1740
cactaaatta caaaactaaa atgatggaag aaaagaaaa gttaaacaaa aaaaaggag      1800 aaaaatcaaa gtgataagtg gatgtagacg attggcccct tccccaagac ctgtggcaac    1860
agaaagtttt gtggctctaa agttaagaaa aatggtccaa tgttatatat ccaaagtttg    1920
atctcacaca gtcacactgt aacaataatc aaataatccc tgacttcgtc acgtttcttt    1980
gtatctccaa cgtccaataa atgaaagcaa ctctagcagc ccctcttct ctcacaagcc     2040 tcccttatcg aaccaactct tctttcggct caaagtcatc gcttctcttt cggtctccat    2100
cctcctcctc ctcagtctct atgacgcaca cgcgtggaaa cgtggctgtg gcggctgctg    2160
ctacatccac tgaggcgcta agaaaaggaa tagcggagtt ctacaatgaa acttcgggtt    2220
tgtgggaaga gatttgggga gatcatatgc atcatggctt ttatgaccct gattcttctg    2280
ttcaactttc tgattctggt cacaaggaag ctcagatccg tatgattgaa gagtctctcc    2340
gttttgccgg tgttactggt tagcttcctc aatcttttgc tctgatatta tcacttgagt    2400
taaatacgct gtttgatata tggttaacga acaaataaaa gagttaataa tacaacaaaa    2460
tgactcttaa aatcttttaa accacagaaa aaaaaactta ttgtctacag aaatgactag    2520
ggataattgt cttttttgttg tactctgtta ccccatgaaa ggtggtttat tagccacaag    2580
ccatctctaa ccttttattt ttaagaacaa tacttttct tgcatttgaa ttaagagatg      2640
attgtaagct taatgaatac ataattttaa actcaaaaag taaatatagt ttagaaatat    2700
atattttatt tttttatctt tggtttgtta ttcagttatt gttacctttt taattattat    2760
acatatgaag ttgagttgat gccatgtaaa tgattgtgat tgaaaaaga tgaagaggag     2820 gagaaaaaga taaagaaagt agtggatgtt gggtgtggga ttggaggaag ctcaagatat    2880
cttgcctcta aatttggagc tgaatgcatt ggcattactc tcagccctgt tcaggccaag    2940
agagccaatg atctcgcggc tgctcaatca ctcgctcata aggtagcttt ggataaaaca    3000
taacctttca ttttgtgaaa atttcatcta acgtatggac attggacttc taggcttcct    3060
tccaagttgc ggatgcgttg gatcagccat tcgaagatgg aaaattcgat ctagtgtggt    3120
cgatggagag tggtgagcat atgcctgaca aggccaagtt tgtaaaagag ttggtacgtg    3180
tggcggctcc aggaggtagg ataataatag tgacatggtg ccatagaaat ctatctgcgg    3240
gggaggaagc tttgcagccg tgggagcaaa acatcttgga caaaatctgt aagacgttct    3300
atctcccggc ttggtgctcc accgatgatt atgtcaactt gcttcaatcc cattctctcc    3360
aggttattat attccctacc ctttgctgcc gaaaacatta cttaactaga gttttttac     3420 taaactagaa tctgaaatat gtgttttag gatattaagt gtgcggattg gtcagagaac     3480
gtagctcctt tctggcctgc ggttatacgg actgcattaa catggaaggg ccttgtgtct    3540
ctgcttcgta gtggtatgaa aagtattaaa ggagcattga caatgccatt gatgattgaa    3600
ggttacaaga aaggtgtcat taagtttggt atcatcactt gccagaagcc actctaa       3657
```

<210> SEQ ID NO 151
<211> LENGTH: 2590
<212> TYPE: DNA
<213> ORGANISM: Brassica napus

<400> SEQUENCE: 151

```
tccagcggac tacatgcaaa gtggtagttg tcacaatgac gttgttttag ctctcattac        60
cttttttttt gagctctcat tgcttacttc acgtcttcta acaatatttg tttgctaccg       120
acgttctact aaatcacaaa aataaactta actgaaccta ttttgaccat atccacttga       180
aaaaactgtg aacaaaaaaa gaagataacc aaagtaagat atggatgtac atgattggcc       240
cttatcccaa tacatatggt atcagaaaag tttgtggcag ttaaagttca tcagactgct       300
gtactaacat cataatttca gacgcagtca cgtttctcgt ctctccaacc tccattgcac       360
cgtccatcct aaaagagata atactaattt ttttataaaa aatatgataa tatattaatt       420
tagaattact ctattttaaa ataaaaaaat agagaaccat tggaaatggt ataagacgga       480
accactgatc actcatataa agctaccgac catcaagaat gatatgcgaa agagaacaac       540
cacgtaagtg aagcaggaga agtttatcaa aatttttgaag gagaagtatc acagctaaga       600
gatgctggtt cttaatctat tggagaggaa gatgaagaag agttttgtgt tgaagagaga       660
ccatggtata ccatactctg atcaacatga tgaaaaccaa caaaaaactc attatcaagt       720
cgactaaaaa attatagagg agaacaagaa tgccaacata tatttgtttg aagaaaagtc       780
ttcaatgagg ttggaagaga tgatgataag ttcagataca tccatttttgc agaccatcat       840 caagaaccat aaagatactt atacggggag agaagcataa aacaaccagt ttagatgttt       900 ttagatttttt atgaattttta tgattttcta aaactttata tctatggaaa tttattattt       960
tatgaaatat tcaattttttt ggaaaaagaa caactgttttt tttgcaagag ctgttgttaa      1020
ttgagaacat tcataaaatt gatgtactaa gttgacaaaa cagttaatgg aattattata      1080
ttaaataaca gaaaggttaa gtattaaatg gcttataatt tttttacttt cttgtcaaag      1140
ttcttataaa aatttagttg gaatactgtt ataaaaaaaa ttaaatacat gttgatataa      1200
atatttggtt tatcgattac attttagata tttactaatt ttaaaactaa atatatataa      1260
aatattaaga gtaaaagacg tatttcaata tattcatgaa tacattcaat tttcagtttg      1320
attcgtgtcc aatttttaga tattgaaagc agaaactatt tagatatttt tgattattca      1380
gttaagtttg gactgtttgg tttgatttgt cggtcctaaa taaaacatcc ttacctaaaa      1440
attaatataa agataaataa aaagtagagg actgtagcaa taagaatac ataatccccc       1500 tccatacaca gagccacttt cttgttccgc caacctctca ttataaatga aagcgactct      1560
cgcaccctcc tctctcataa gcctccccag gcacaaagta tcttctctcc gttcaccgtc      1620
gcttctcctt cagtcccaac ggccatcctc agccttaatg acgacgacga cggcatcacg      1680
tggaagcgtg gctgtgacgg ctgctgctac ctcctccgtt gaggcgctgc gggaaggaat      1740
agcggaattc tacaacgaga cgtcgggatt atggaggag atttggggag atcatatgca      1800
tcacggcttc tacgatcctg attcctctgt tcaactttca gattccggtc accgggaagc      1860
tcagatccgg atgatcgaag agtctctacg tttcgccggc gttactgaag aggagaaaaa      1920
gataaagaga gtagtggatg ttgggtgtgg gatcggcgga agctcaaggt atattgcctc      1980
taaatttggt gccgaatgca ttggcatcac actcagtccc gttcaagcca agagagccaa      2040
tgatctcgcc gccgctcaat cactctctca taaggttttcc ttccaagttg cagatgcact      2100
ggagcaacca tttgaagatg gtatattcga tcttgtgtgg tcaatggaaa gcggtgagca      2160
tatgcctgac aaggccaagt tcgtgaagga attggtacgt gtggcggctc caggaggaag      2220
```

```
gataataata gtgacatggt gccacagaaa tctatctcca ggggaagagg ctttgcagcc    2280
atgggagcag aacctcttgg acagaatctg caaaacattt tatctcccag cctggtgctc    2340
cacctcggat tatgtcgatt tgcttcagtc cctctcgctc caggatatta agtgtgcaga    2400
ttggtcagag aacgtagctc cttttctggcc ggcggttata cgaaccgcat taacgtggaa    2460
gggccttgtg tctctgcttc gtagtggtat gaagagtata aaaggagcat tgacaatgcc    2520
attgatgatt gaagggtaca agaaaggtgt cattaagttt ggcatcatca cttgccagaa    2580
gcctctctaa                                                            2590
```

```
<210> SEQ ID NO 152
<211> LENGTH: 34
<212> TYPE: PRT
<213> ORGANISM: Artificial
<220> FEATURE:
<223> OTHER INFORMATION: zinc finger
<220> FEATURE:
<221> NAME/KEY: MISC_FEATURE
<222> LOCATION: (1)..(3)
<223> OTHER INFORMATION: Xaa = any amino acid
<220> FEATURE:
<221> NAME/KEY: MISC_FEATURE
<222> LOCATION: (5)..(8)
<223> OTHER INFORMATION: Xaa = any amino acid
<220> FEATURE:
<221> NAME/KEY: MISC_FEATURE
<222> LOCATION: (7)..(8)
<223> OTHER INFORMATION: Xaa may be present or absent
<220> FEATURE:
<221> NAME/KEY: MISC_FEATURE
<222> LOCATION: (10)..(21)
<223> OTHER INFORMATION: Xaa = any amino acid
<220> FEATURE:
<221> NAME/KEY: MISC_FEATURE
<222> LOCATION: (23)..(29)
<223> OTHER INFORMATION: Xaa = any amino acid
<220> FEATURE:
<221> NAME/KEY: MISC_FEATURE
<222> LOCATION: (24)..(29)
<223> OTHER INFORMATION: Xaa may be present or absent
<220> FEATURE:
<221> NAME/KEY: MISC_FEATURE
<222> LOCATION: (31)..(34)
<223> OTHER INFORMATION: Xaa = any amino acid

<400> SEQUENCE: 152

Xaa Xaa Xaa Cys Xaa Xaa Xaa Xaa Cys Xaa Xaa Xaa Xaa Xaa Xaa Xaa
1               5                   10                  15

Xaa Xaa Xaa Xaa Xaa His Xaa Xaa Xaa Xaa Xaa Xaa Xaa His Xaa Xaa
            20                  25                  30

Xaa Xaa

<210> SEQ ID NO 153
<211> LENGTH: 4
<212> TYPE: PRT
<213> ORGANISM: Artificial
<220> FEATURE:
<223> OTHER INFORMATION: second class of ZFPs

<400> SEQUENCE: 153

Cys Cys His Cys
1

<210> SEQ ID NO 154
<211> LENGTH: 34
<212> TYPE: PRT
<213> ORGANISM: Artificial
<220> FEATURE:
```

```
<223> OTHER INFORMATION: zinc finger
<220> FEATURE:
<221> NAME/KEY: MISC_FEATURE
<222> LOCATION: (1)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except Cys
<220> FEATURE:
<221> NAME/KEY: MISC_FEATURE
<222> LOCATION: (5)..(8)
<223> OTHER INFORMATION: Xaa = any amino acid
<220> FEATURE:
<221> NAME/KEY: MISC_FEATURE
<222> LOCATION: (7)..(8)
<223> OTHER INFORMATION: Xaa may be present or absent
<220> FEATURE:
<221> NAME/KEY: MISC_FEATURE
<222> LOCATION: (10)..(21)
<223> OTHER INFORMATION: Xaa = any amino acid
<220> FEATURE:
<221> NAME/KEY: MISC_FEATURE
<222> LOCATION: (23)..(29)
<223> OTHER INFORMATION: Xaa = any amino acid
<220> FEATURE:
<221> NAME/KEY: MISC_FEATURE
<222> LOCATION: (24)..(29)
<223> OTHER INFORMATION: Xaa may be present or absent
<220> FEATURE:
<221> NAME/KEY: MISC_FEATURE
<222> LOCATION: (31)..(34)
<223> OTHER INFORMATION: Xaa = any amino acid

<400> SEQUENCE: 154

Xaa Xaa Xaa Xaa Xaa Xaa Xaa Xaa Cys Xaa Xaa Xaa Xaa Xaa Xaa
1               5                   10                  15

Xaa Xaa Xaa Xaa Xaa His Xaa Xaa Xaa Xaa Xaa Xaa Xaa His Xaa Xaa
            20                  25                  30

Xaa Xaa

<210> SEQ ID NO 155
<211> LENGTH: 34
<212> TYPE: PRT
<213> ORGANISM: Artificial
<220> FEATURE:
<223> OTHER INFORMATION: zinc finger
<220> FEATURE:
<221> NAME/KEY: MISC_FEATURE
<222> LOCATION: (1)..(3)
<223> OTHER INFORMATION: Xaa = any amino acid
<220> FEATURE:
<221> NAME/KEY: MISC_FEATURE
<222> LOCATION: (5)..(8)
<223> OTHER INFORMATION: Xaa = any amino acid
<220> FEATURE:
<221> NAME/KEY: MISC_FEATURE
<222> LOCATION: (7)..(8)
<223> OTHER INFORMATION: Xaa may be present or absent
<220> FEATURE:
<221> NAME/KEY: MISC_FEATURE
<222> LOCATION: (9)..(9)
<223> OTHER INFORMATION: Xaa = any amino acid except Cys
<220> FEATURE:
<221> NAME/KEY: MISC_FEATURE
<222> LOCATION: (10)..(21)
<223> OTHER INFORMATION: Xaa = any amino acid
<220> FEATURE:
<221> NAME/KEY: MISC_FEATURE
<222> LOCATION: (23)..(29)
<223> OTHER INFORMATION: Xaa = any amino acid
<220> FEATURE:
<221> NAME/KEY: MISC_FEATURE
<222> LOCATION: (24)..(29)
<223> OTHER INFORMATION: Xaa may be present or absent
<220> FEATURE:
```

```
<221> NAME/KEY: MISC_FEATURE
<222> LOCATION: (31)..(34)
<223> OTHER INFORMATION: Xaa = any amino acid

<400> SEQUENCE: 155

Xaa Xaa Xaa Cys Xaa Xaa Xaa Xaa Xaa Xaa Xaa Xaa Xaa Xaa Xaa
1               5                   10                  15

Xaa Xaa Xaa Xaa Xaa His Xaa Xaa Xaa Xaa Xaa Xaa Xaa His Xaa Xaa
            20                  25                  30

Xaa Xaa

<210> SEQ ID NO 156
<211> LENGTH: 34
<212> TYPE: PRT
<213> ORGANISM: Artificial
<220> FEATURE:
<223> OTHER INFORMATION: zinc finger
<220> FEATURE:
<221> NAME/KEY: MISC_FEATURE
<222> LOCATION: (1)..(3)
<223> OTHER INFORMATION: Xaa = any amino acid
<220> FEATURE:
<221> NAME/KEY: MISC_FEATURE
<222> LOCATION: (5)..(8)
<223> OTHER INFORMATION: Xaa = any amino acid
<220> FEATURE:
<221> NAME/KEY: MISC_FEATURE
<222> LOCATION: (7)..(8)
<223> OTHER INFORMATION: Xaa may be present or absent
<220> FEATURE:
<221> NAME/KEY: MISC_FEATURE
<222> LOCATION: (10)..(21)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = any amino acid except His
<220> FEATURE:
<221> NAME/KEY: MISC_FEATURE
<222> LOCATION: (23)..(29)
<223> OTHER INFORMATION: Xaa = any amino acid
<220> FEATURE:
<221> NAME/KEY: MISC_FEATURE
<222> LOCATION: (24)..(29)
<223> OTHER INFORMATION: Xaa may be present or absent
<220> FEATURE:
<221> NAME/KEY: MISC_FEATURE
<222> LOCATION: (31)..(34)
<223> OTHER INFORMATION: Xaa = any amino acid

<400> SEQUENCE: 156

Xaa Xaa Xaa Cys Xaa Xaa Xaa Xaa Cys Xaa Xaa Xaa Xaa Xaa Xaa
1               5                   10                  15

Xaa Xaa Xaa Xaa Xaa Xaa Xaa Xaa Xaa Xaa Xaa Xaa Xaa His Xaa Xaa
            20                  25                  30

Xaa Xaa

<210> SEQ ID NO 157
<211> LENGTH: 34
<212> TYPE: PRT
<213> ORGANISM: Artificial
<220> FEATURE:
<223> OTHER INFORMATION: zinc finger
<220> FEATURE:
<221> NAME/KEY: MISC_FEATURE
<222> LOCATION: (1)..(3)
<223> OTHER INFORMATION: Xaa = any amino acid
<220> FEATURE:
<221> NAME/KEY: MISC_FEATURE
<222> LOCATION: (5)..(8)
<223> OTHER INFORMATION: Xaa = any amino acid
<220> FEATURE:
```

```
<221> NAME/KEY: MISC_FEATURE
<222> LOCATION: (7)..(8)
<223> OTHER INFORMATION: Xaa may be present or absent
<220> FEATURE:
<221> NAME/KEY: MISC_FEATURE
<222> LOCATION: (10)..(21)
<223> OTHER INFORMATION: Xaa = any amino acid
<220> FEATURE:
<221> NAME/KEY: MISC_FEATURE
<222> LOCATION: (23)..(29)
<223> OTHER INFORMATION: Xaa = any amino acid
<220> FEATURE:
<221> NAME/KEY: MISC_FEATURE
<222> LOCATION: (24)..(29)
<223> OTHER INFORMATION: Xaa may be present or absent
<220> FEATURE:
<221> NAME/KEY: MISC_FEATURE
<222> LOCATION: (30)..(30)
<223> OTHER INFORMATION: Xaa = any amino acid except His
<220> FEATURE:
<221> NAME/KEY: MISC_FEATURE
<222> LOCATION: (31)..(34)
<223> OTHER INFORMATION: Xaa = any amino acid

<400> SEQUENCE: 157

Xaa Xaa Xaa Cys Xaa Xaa Xaa Xaa Cys Xaa Xaa Xaa Xaa Xaa Xaa Xaa
 1               5                  10                  15

Xaa Xaa Xaa Xaa Xaa His Xaa Xaa Xaa Xaa Xaa Xaa Xaa Xaa
            20                  25                  30

Xaa Xaa

<210> SEQ ID NO 158
<211> LENGTH: 34
<212> TYPE: PRT
<213> ORGANISM: Artificial
<220> FEATURE:
<223> OTHER INFORMATION: zinc finger
<220> FEATURE:
<221> NAME/KEY: MISC_FEATURE
<222> LOCATION: (1)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except Cys
<220> FEATURE:
<221> NAME/KEY: MISC_FEATURE
<222> LOCATION: (5)..(8)
<223> OTHER INFORMATION: Xaa = any amino acid
<220> FEATURE:
<221> NAME/KEY: MISC_FEATURE
<222> LOCATION: (7)..(8)
<223> OTHER INFORMATION: Xaa may be present or absent
<220> FEATURE:
<221> NAME/KEY: MISC_FEATURE
<222> LOCATION: (9)..(9)
<223> OTHER INFORMATION: Xaa = any amino acid except Cys
<220> FEATURE:
<221> NAME/KEY: MISC_FEATURE
<222> LOCATION: (10)..(21)
<223> OTHER INFORMATION: Xaa = any amino acid
<220> FEATURE:
<221> NAME/KEY: MISC_FEATURE
<222> LOCATION: (23)..(29)
<223> OTHER INFORMATION: Xaa = any amino acid
<220> FEATURE:
<221> NAME/KEY: MISC_FEATURE
<222> LOCATION: (24)..(29)
<223> OTHER INFORMATION: Xaa may be present or absent
<220> FEATURE:
<221> NAME/KEY: MISC_FEATURE
<222> LOCATION: (31)..(34)
<223> OTHER INFORMATION: Xaa = any amino acid

<400> SEQUENCE: 158
```

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa His Xaa Xaa Xaa Xaa Xaa Xaa His Xaa Xaa
            20                  25                  30

Xaa Xaa

<210> SEQ ID NO 159
<211> LENGTH: 34
<212> TYPE: PRT
<213> ORGANISM: Artificial
<220> FEATURE:
<223> OTHER INFORMATION: zinc finger
<220> FEATURE:
<221> NAME/KEY: MISC_FEATURE
<222> LOCATION: (1)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except Cys
<220> FEATURE:
<221> NAME/KEY: MISC_FEATURE
<222> LOCATION: (5)..(8)
<223> OTHER INFORMATION: Xaa = any amino acid
<220> FEATURE:
<221> NAME/KEY: MISC_FEATURE
<222> LOCATION: (7)..(8)
<223> OTHER INFORMATION: Xaa may be present or absent
<220> FEATURE:
<221> NAME/KEY: MISC_FEATURE
<222> LOCATION: (10)..(21)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = any amino acid except His
<220> FEATURE:
<221> NAME/KEY: MISC_FEATURE
<222> LOCATION: (23)..(29)
<223> OTHER INFORMATION: Xaa = any amino acid
<220> FEATURE:
<221> NAME/KEY: MISC_FEATURE
<222> LOCATION: (24)..(29)
<223> OTHER INFORMATION: Xaa may be present or absent
<220> FEATURE:
<221> NAME/KEY: MISC_FEATURE
<222> LOCATION: (31)..(34)
<223> OTHER INFORMATION: Xaa = any amino acid

<400> SEQUENCE: 159

Xaa Xaa Xaa Xaa Xaa Xaa Xaa Xaa Cys Xaa Xaa Xaa Xaa Xaa Xaa
1               5                   10                  15

Xaa Xaa Xaa Xaa Xaa Xaa Xaa Xaa Xaa Xaa Xaa His Xaa Xaa
            20                  25                  30

Xaa Xaa

<210> SEQ ID NO 160
<211> LENGTH: 34
<212> TYPE: PRT
<213> ORGANISM: Artificial
<220> FEATURE:
<223> OTHER INFORMATION: zinc finger
<220> FEATURE:
<221> NAME/KEY: MISC_FEATURE
<222> LOCATION: (1)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except Cys
<220> FEATURE:
<221> NAME/KEY: MISC_FEATURE
<222> LOCATION: (5)..(8)
```

```
<223> OTHER INFORMATION: Xaa = any amino acid
<220> FEATURE:
<221> NAME/KEY: MISC_FEATURE
<222> LOCATION: (7)..(8)
<223> OTHER INFORMATION: Xaa may be present or absent
<220> FEATURE:
<221> NAME/KEY: MISC_FEATURE
<222> LOCATION: (10)..(21)
<223> OTHER INFORMATION: Xaa = any amino acid
<220> FEATURE:
<221> NAME/KEY: MISC_FEATURE
<222> LOCATION: (23)..(29)
<223> OTHER INFORMATION: Xaa = any amino acid
<220> FEATURE:
<221> NAME/KEY: MISC_FEATURE
<222> LOCATION: (24)..(29)
<223> OTHER INFORMATION: Xaa may be present or absent
<220> FEATURE:
<221> NAME/KEY: MISC_FEATURE
<222> LOCATION: (30)..(30)
<223> OTHER INFORMATION: Xaa = any amino acid except His
<220> FEATURE:
<221> NAME/KEY: MISC_FEATURE
<222> LOCATION: (31)..(34)
<223> OTHER INFORMATION: Xaa = any amino acid

<400> SEQUENCE: 160

Xaa Xaa Xaa Xaa Xaa Xaa Xaa Xaa Cys Xaa Xaa Xaa Xaa Xaa Xaa Xaa
 1               5                  10                  15

Xaa Xaa Xaa Xaa Xaa His Xaa Xaa Xaa Xaa Xaa Xaa Xaa Xaa Xaa
            20                  25                  30

Xaa Xaa

<210> SEQ ID NO 161
<211> LENGTH: 34
<212> TYPE: PRT
<213> ORGANISM: Artificial
<220> FEATURE:
<223> OTHER INFORMATION: zinc finger
<220> FEATURE:
<221> NAME/KEY: MISC_FEATURE
<222> LOCATION: (1)..(3)
<223> OTHER INFORMATION: Xaa = any amino acid
<220> FEATURE:
<221> NAME/KEY: MISC_FEATURE
<222> LOCATION: (5)..(8)
<223> OTHER INFORMATION: Xaa = any amino acid
<220> FEATURE:
<221> NAME/KEY: MISC_FEATURE
<222> LOCATION: (7)..(8)
<223> OTHER INFORMATION: Xaa may be present or absent
<220> FEATURE:
<221> NAME/KEY: MISC_FEATURE
<222> LOCATION: (9)..(9)
<223> OTHER INFORMATION: Xaa = any amino acid except Cys
<220> FEATURE:
<221> NAME/KEY: MISC_FEATURE
<222> LOCATION: (10)..(21)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = any amino acid except His
<220> FEATURE:
<221> NAME/KEY: MISC_FEATURE
<222> LOCATION: (23)..(29)
<223> OTHER INFORMATION: Xaa = any amino acid
<220> FEATURE:
<221> NAME/KEY: MISC_FEATURE
<222> LOCATION: (24)..(29)
<223> OTHER INFORMATION: Xaa may be present or absent
<220> FEATURE:
<221> NAME/KEY: MISC_FEATURE
<222> LOCATION: (31)..(34)
<223> OTHER INFORMATION: Xaa = any amino acid
```

-continued

<400> SEQUENCE: 161

Xaa Xaa Xaa Cys Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa His Xaa Xaa
            20                  25                  30

Xaa Xaa

<210> SEQ ID NO 162
<211> LENGTH: 34
<212> TYPE: PRT
<213> ORGANISM: Artificial
<220> FEATURE:
<223> OTHER INFORMATION: zinc finger
<220> FEATURE:
<221> NAME/KEY: MISC_FEATURE
<222> LOCATION: (1)..(3)
<223> OTHER INFORMATION: Xaa = any amino acid
<220> FEATURE:
<221> NAME/KEY: MISC_FEATURE
<222> LOCATION: (5)..(8)
<223> OTHER INFORMATION: Xaa = any amino acid
<220> FEATURE:
<221> NAME/KEY: MISC_FEATURE
<222> LOCATION: (7)..(8)
<223> OTHER INFORMATION: Xaa may be present or absent
<220> FEATURE:
<221> NAME/KEY: MISC_FEATURE
<222> LOCATION: (9)..(9)
<223> OTHER INFORMATION: Xaa = any amino acid except Cys
<220> FEATURE:
<221> NAME/KEY: MISC_FEATURE
<222> LOCATION: (10)..(21)
<223> OTHER INFORMATION: Xaa = any amino acid
<220> FEATURE:
<221> NAME/KEY: MISC_FEATURE
<222> LOCATION: (23)..(29)
<223> OTHER INFORMATION: Xaa = any amino acid
<220> FEATURE:
<221> NAME/KEY: MISC_FEATURE
<222> LOCATION: (24)..(29)
<223> OTHER INFORMATION: Xaa may be present or absent
<220> FEATURE:
<221> NAME/KEY: MISC_FEATURE
<222> LOCATION: (30)..(30)
<223> OTHER INFORMATION: Xaa = any amino acid except His
<220> FEATURE:
<221> NAME/KEY: MISC_FEATURE
<222> LOCATION: (31)..(34)
<223> OTHER INFORMATION: Xaa = any amino acid

<400> SEQUENCE: 162

Xaa Xaa Xaa Cys Xaa Xaa Xaa Xaa Xaa Xaa Xaa Xaa Xaa Xaa Xaa
1               5                   10                  15

Xaa Xaa Xaa Xaa Xaa His Xaa Xaa Xaa Xaa Xaa Xaa Xaa Xaa Xaa Xaa
            20                  25                  30

Xaa Xaa

<210> SEQ ID NO 163
<211> LENGTH: 34
<212> TYPE: PRT
<213> ORGANISM: Artificial
<220> FEATURE:
<223> OTHER INFORMATION: zinc finger
<220> FEATURE:
<221> NAME/KEY: MISC_FEATURE
<222> LOCATION: (1)..(3)
<223> OTHER INFORMATION: Xaa = any amino acid
<220> FEATURE:
<221> NAME/KEY: MISC_FEATURE
<222> LOCATION: (5)..(8)
<223> OTHER INFORMATION: Xaa = any amino acid
<220> FEATURE:

```
<221> NAME/KEY: MISC_FEATURE
<222> LOCATION: (7)..(8)
<223> OTHER INFORMATION: Xaa may be present or absent
<220> FEATURE:
<221> NAME/KEY: MISC_FEATURE
<222> LOCATION: (10)..(21)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = any amino acid except His
<220> FEATURE:
<221> NAME/KEY: MISC_FEATURE
<222> LOCATION: (23)..(29)
<223> OTHER INFORMATION: Xaa = any amino acid
<220> FEATURE:
<221> NAME/KEY: MISC_FEATURE
<222> LOCATION: (24)..(29)
<223> OTHER INFORMATION: Xaa may be present or absent
<220> FEATURE:
<221> NAME/KEY: MISC_FEATURE
<222> LOCATION: (30)..(30)
<223> OTHER INFORMATION: Xaa = any amino acid except His
<220> FEATURE:
<221> NAME/KEY: MISC_FEATURE
<222> LOCATION: (31)..(34)
<223> OTHER INFORMATION: Xaa = any amino acid

<400> SEQUENCE: 163

Xaa Xaa Xaa Cys Xaa Xaa Xaa Xaa Cys Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa

<210> SEQ ID NO 164
<211> LENGTH: 34
<212> TYPE: PRT
<213> ORGANISM: Artificial
<220> FEATURE:
<223> OTHER INFORMATION: zinc finger
<220> FEATURE:
<221> NAME/KEY: MISC_FEATURE
<222> LOCATION: (1)..(3)
<223> OTHER INFORMATION: Xaa = any amino acid
<220> FEATURE:
<221> NAME/KEY: MISC_FEATURE
<222> LOCATION: (5)..(8)
<223> OTHER INFORMATION: Xaa = any amino acid
<220> FEATURE:
<221> NAME/KEY: MISC_FEATURE
<222> LOCATION: (7)..(8)
<223> OTHER INFORMATION: Xaa may be present or absent
<220> FEATURE:
<221> NAME/KEY: MISC_FEATURE
<222> LOCATION: (9)..(9)
<223> OTHER INFORMATION: Xaa = any amino acid except Cys
<220> FEATURE:
<221> NAME/KEY: MISC_FEATURE
<222> LOCATION: (10)..(21)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = any amino acid except His
<220> FEATURE:
<221> NAME/KEY: MISC_FEATURE
<222> LOCATION: (23)..(29)
<223> OTHER INFORMATION: Xaa = any amino acid
<220> FEATURE:
<221> NAME/KEY: MISC_FEATURE
<222> LOCATION: (24)..(29)
<223> OTHER INFORMATION: Xaa may be present or absent
<220> FEATURE:
<221> NAME/KEY: MISC_FEATURE
<222> LOCATION: (30)..(30)
```

```
<223> OTHER INFORMATION: Xaa = any amino acid except His
<220> FEATURE:
<221> NAME/KEY: MISC_FEATURE
<222> LOCATION: (31)..(34)
<223> OTHER INFORMATION: Xaa = any amino acid

<400> SEQUENCE: 164

Xaa Xaa Xaa Cys Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa

<210> SEQ ID NO 165
<211> LENGTH: 34
<212> TYPE: PRT
<213> ORGANISM: Artificial
<220> FEATURE:
<223> OTHER INFORMATION: zinc finger
<220> FEATURE:
<221> NAME/KEY: MISC_FEATURE
<222> LOCATION: (1)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except Cys
<220> FEATURE:
<221> NAME/KEY: MISC_FEATURE
<222> LOCATION: (5)..(8)
<223> OTHER INFORMATION: Xaa = any amino acid
<220> FEATURE:
<221> NAME/KEY: MISC_FEATURE
<222> LOCATION: (7)..(8)
<223> OTHER INFORMATION: Xaa may be present or absent
<220> FEATURE:
<221> NAME/KEY: MISC_FEATURE
<222> LOCATION: (10)..(21)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = any amino acid except His
<220> FEATURE:
<221> NAME/KEY: MISC_FEATURE
<222> LOCATION: (23)..(29)
<223> OTHER INFORMATION: Xaa = any amino acid
<220> FEATURE:
<221> NAME/KEY: MISC_FEATURE
<222> LOCATION: (24)..(29)
<223> OTHER INFORMATION: Xaa may be present or absent
<220> FEATURE:
<221> NAME/KEY: MISC_FEATURE
<222> LOCATION: (30)..(30)
<223> OTHER INFORMATION: Xaa = any amino acid except His
<220> FEATURE:
<221> NAME/KEY: MISC_FEATURE
<222> LOCATION: (31)..(34)
<223> OTHER INFORMATION: Xaa = any amino acid

<400> SEQUENCE: 165

Xaa Xaa Xaa Xaa Xaa Xaa Xaa Xaa Cys Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa

<210> SEQ ID NO 166
<211> LENGTH: 34
<212> TYPE: PRT
<213> ORGANISM: Artificial
<220> FEATURE:
```

-continued

```
<223> OTHER INFORMATION: zinc finger
<220> FEATURE:
<221> NAME/KEY: MISC_FEATURE
<222> LOCATION: (1)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except Cys
<220> FEATURE:
<221> NAME/KEY: MISC_FEATURE
<222> LOCATION: (5)..(8)
<223> OTHER INFORMATION: Xaa = any amino acid
<220> FEATURE:
<221> NAME/KEY: MISC_FEATURE
<222> LOCATION: (7)..(8)
<223> OTHER INFORMATION: Xaa may be present or absent
<220> FEATURE:
<221> NAME/KEY: MISC_FEATURE
<222> LOCATION: (9)..(9)
<223> OTHER INFORMATION: Xaa = any amino acid except Cys
<220> FEATURE:
<221> NAME/KEY: MISC_FEATURE
<222> LOCATION: (10)..(21)
<223> OTHER INFORMATION: Xaa = any amino acid
<220> FEATURE:
<221> NAME/KEY: MISC_FEATURE
<222> LOCATION: (23)..(29)
<223> OTHER INFORMATION: Xaa = any amino acid
<220> FEATURE:
<221> NAME/KEY: MISC_FEATURE
<222> LOCATION: (24)..(29)
<223> OTHER INFORMATION: Xaa may be present or absent
<220> FEATURE:
<221> NAME/KEY: MISC_FEATURE
<222> LOCATION: (30)..(30)
<223> OTHER INFORMATION: Xaa = any amino acid except His
<220> FEATURE:
<221> NAME/KEY: MISC_FEATURE
<222> LOCATION: (31)..(34)
<223> OTHER INFORMATION: Xaa = any amino acid

<400> SEQUENCE: 166

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa His Xaa Xaa Xaa Xaa Xaa Xaa Xaa Xaa Xaa Xaa
            20                  25                  30

Xaa Xaa

<210> SEQ ID NO 167
<211> LENGTH: 34
<212> TYPE: PRT
<213> ORGANISM: Artificial
<220> FEATURE:
<223> OTHER INFORMATION: zinc finger
<220> FEATURE:
<221> NAME/KEY: MISC_FEATURE
<222> LOCATION: (1)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except Cys
<220> FEATURE:
<221> NAME/KEY: MISC_FEATURE
<222> LOCATION: (5)..(8)
<223> OTHER INFORMATION: Xaa = any amino acid
<220> FEATURE:
<221> NAME/KEY: MISC_FEATURE
<222> LOCATION: (7)..(8)
<223> OTHER INFORMATION: Xaa may be present or absent
<220> FEATURE:
<221> NAME/KEY: MISC_FEATURE
<222> LOCATION: (9)..(9)
<223> OTHER INFORMATION: Xaa = any amino acid except Cys
<220> FEATURE:
```

-continued

```
<221> NAME/KEY: MISC_FEATURE
<222> LOCATION: (10)..(21)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = any amino acid except His
<220> FEATURE:
<221> NAME/KEY: MISC_FEATURE
<222> LOCATION: (23)..(29)
<223> OTHER INFORMATION: Xaa = any amino acid
<220> FEATURE:
<221> NAME/KEY: MISC_FEATURE
<222> LOCATION: (24)..(29)
<223> OTHER INFORMATION: Xaa may be present or absent
<220> FEATURE:
<221> NAME/KEY: MISC_FEATURE
<222> LOCATION: (31)..(34)
<223> OTHER INFORMATION: Xaa = any amino acid

<400> SEQUENCE: 167

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa His Xaa Xaa
            20                  25                  30

Xaa Xaa

<210> SEQ ID NO 168
<211> LENGTH: 34
<212> TYPE: PRT
<213> ORGANISM: Artificial
<220> FEATURE:
<223> OTHER INFORMATION: zinc finger
<220> FEATURE:
<221> NAME/KEY: MISC_FEATURE
<222> LOCATION: (1)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid except Cys
<220> FEATURE:
<221> NAME/KEY: MISC_FEATURE
<222> LOCATION: (5)..(8)
<223> OTHER INFORMATION: Xaa = any amino acid
<220> FEATURE:
<221> NAME/KEY: MISC_FEATURE
<222> LOCATION: (7)..(8)
<223> OTHER INFORMATION: Xaa may be present or absent
<220> FEATURE:
<221> NAME/KEY: MISC_FEATURE
<222> LOCATION: (9)..(9)
<223> OTHER INFORMATION: Xaa = any amino acid except Cys
<220> FEATURE:
<221> NAME/KEY: MISC_FEATURE
<222> LOCATION: (10)..(21)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = any amino acid except His
<220> FEATURE:
<221> NAME/KEY: MISC_FEATURE
<222> LOCATION: (23)..(29)
<223> OTHER INFORMATION: Xaa = any amino acid
<220> FEATURE:
<221> NAME/KEY: MISC_FEATURE
<222> LOCATION: (24)..(29)
<223> OTHER INFORMATION: Xaa may be present or absent
<220> FEATURE:
<221> NAME/KEY: MISC_FEATURE
<222> LOCATION: (30)..(30)
<223> OTHER INFORMATION: Xaa = any amino acid except His
<220> FEATURE:
<221> NAME/KEY: MISC_FEATURE
<222> LOCATION: (31)..(34)
```

```
<223> OTHER INFORMATION: Xaa = any amino acid

<400> SEQUENCE: 168

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa

<210> SEQ ID NO 169
<211> LENGTH: 10
<212> TYPE: DNA
<213> ORGANISM: Artificial
<220> FEATURE:
<223> OTHER INFORMATION: SP1 target sequence

<400> SEQUENCE: 169
ggggcggggg                                                              10

<210> SEQ ID NO 170
<211> LENGTH: 7
<212> TYPE: PRT
<213> ORGANISM: Artificial
<220> FEATURE:
<223> OTHER INFORMATION: SP1 finger design

<400> SEQUENCE: 170

Lys Thr Ser His Leu Arg Ala
1               5

<210> SEQ ID NO 171
<211> LENGTH: 7
<212> TYPE: PRT
<213> ORGANISM: Artificial
<220> FEATURE:
<223> OTHER INFORMATION: SP1 finger design

<400> SEQUENCE: 171

Arg Ser Asp Glu Leu Gln Arg
1               5

<210> SEQ ID NO 172
<211> LENGTH: 7
<212> TYPE: PRT
<213> ORGANISM: Artificial
<220> FEATURE:
<223> OTHER INFORMATION: SP1 finger design

<400> SEQUENCE: 172

Arg Ser Asp His Leu Ser Lys
1               5
```

COMPOSITIONS AND METHODS FOR REGULATION OF PLANT GAMMA-TOCOPHEROL METHYLTRANSFERASE

CROSS-REFERENCE TO RELATED APPLICATIONS

This application claims the benefit of U.S. provisional patent applications Ser. No. 60/373,488, filed Apr. 17, 2002; Ser. No. 60/385,992, filed Jun. 4, 2002; and Ser. No. 60/442,470, filed Jan. 24, 2003; all of which disclosures are hereby incorporated by reference in their entireties.

TECHNICAL FIELD

The methods and compositions disclosed herein relate generally to the field of regulation of gene expression and specifically to methods of modulating expression of plant gamma-tocopherol methyltransferase (GMT) expression utilizing polypeptides derived from plant zinc finger-nucleotide binding proteins.

BACKGROUND

Vitamin E (tocopherol) is a fat-soluble vitamin found in many vegetable seed oils and leafy green vegetables. Vitamin E has many functions including acting as an antioxidant of lipids, protecting of cell membranes and prevention of damage to membrane associated enzymes. α-Tocopherol, often referred to as vitamin E, belongs to a class of lipid-soluble antioxidants that includes α, β, γ, and δ-tocopherols and α, β, γ, and δ-tocotrienols. Although α, β, γ, and δ-tocopherols and α, β, γ, and δ-tocotrienols are sometimes referred to collectively as "vitamin E," vitamin E is more appropriately defined chemically as (α-tocopherol. α-Tocopherol is significant for human health, in part because it is readily absorbed and retained by the body, and therefore has a higher degree of bioactivity than other tocopherol species (Traber and Sies, *Annu. Rev. Nutr.* 16:321-347 (1996)). However, other tocopherols, such as β, γ, and δ-tocopherols, also have significant health and nutritional benefits.

Supplements may contain the alpha tocopherol that is either in the "d" form or a combination of the "d" and "l" forms. The "d" form is more active than the "l" form but when comparing supplements, an equivalent number of international units (IU) indicate equivalent activity. Less information is available about the action of the beta, gamma and delta tocopherols, but they appear to have different antioxidant effects. Vitamin E supplementation in humans may have a variety of beneficial effects including slowing the progression of Alzheimer's disease, preventing heart disease, improving immune function in the elderly, reducing the risk of cataracts and decreasing the pain associated with arthritis.

Photosynthetic bacteria and higher plants share a common set of enzymatic reactions for tocopherol synthesis, in which gamma-tocopherol methyltransferase (GMT) catalyzes the conversion of gamma-tocopherol to alpha-tocopherol in the final step of Vitamin E synthesis. The gene encoding GMT has been isolated and characterized from a variety of plant species including, pepper, soybean, Euglena, spinach and *Arabidopsis*. See, e.g., Shigeoka et al. (1992) *Biochim Biophys Acta.* 1128(2-3):220-6; GenBank Accession Nos. BM890961, AAD 38271, AF213481 and AF104220). In many plant oils (the main dietary source of tocopherols), alpha-tocopherol is typically present in small amounts while high levels of its biosynthetic precursor, gamma-tocopherol are generally present. Attempts to overexpress GMT in order to produce crops with higher alpha tocopherol content have shown that GMT overexpression can result in higher alpha tocopherol levels. See, e.g., Shintani et al. (1998) *Science* 282:2098-2100. However, such attempts have been hampered in view of the lack of efficient and stable methods of gene regulation in a variety of crops and plants.

Thus, there remains a need for compositions and methods for targeted regulation of the gamma-tocopherol methyltransferase (GMT) gene in plants to facilitate numerous applications such as, for example, the optimization of crop traits affecting nutritional value. In addition, such targeted regulation of GMT can be used to study biosynthetic pathways and gene function in plants.

SUMMARY

In one aspect, the present disclosure relates to a zinc finger protein that binds to a target site in a plant gamma-tocopherol methyl transferase (GMT) gene. Also disclosed is a zinc finger protein that modulates expression of a plant GMT gene as well as a zinc finger protein that, when present in a plant cell, increases the amounts of alpha tocopherol in the plant cell. Any of the zinc finger proteins described herein can be, for example, engineered (e.g., designed, selected and/or rearranged) and/or tandem arrays of plant sequences. Furthermore, the plant can be either a dicotyledenous plant (e.g., *Brassica* or *Arabidopsis*) or a monocotyledenous plant. Furthermore, any of the zinc finger proteins described herein can comprise three component fingers, for example as shown in Table 1 and Table 3.

In another aspect, the disclosure relates to fusion polypeptides comprising any of the zinc finger proteins disclosed herein and at least one regulatory domain, for example an activation domain such as VP16 or C1, for example.

In yet another aspect, the disclosure relates to isolated polynucleotides encoding any of the zinc finger proteins described herein. Expression vectors comprising these isolated polynucleotides are also described including, for example, expression vectors comprising plant promoters such as tissue-specific (e.g., seed- and/or leaf-specific) plant promoters.

In still further aspects, plant cells comprising any of the zinc finger proteins, isolated polynucleotides and/or expression vectors described herein are also provided.

In still further aspects, transgenic plants comprising any of the isolated polynucleotides and/or expression vectors described herein are provided.

Also provided is a seed derived from a transgenic plant as described above.

In yet another aspect, the disclosure relates to methods for modulating expression of GMT in a plant cell, for example by contacting the cell with any of the zinc finger proteins; isolated polynucleotides or expression vectors as described herein, such that a zinc finger protein binds to a target site in a plant GMT gene.

In another aspect, the disclosure relates to methods for increasing the amount of vitamin E and/or the amount of alpha tocopherol present in a plant cell by contacting the cell with any of the zinc finger proteins; isolated polynucleotides or expression vectors as described herein. In certain embodiments, the plant cell is a seed.

A further embodiment is a method of generating grain having a desired a-tocopherol content, wherein the method comprises: (a) identifying a transcription factor that modulates expression of a gamma-methyltransferase (GMT) gene in a plant, (b) generating a transgenic plant comprising an isolated polynucleotide or expression vector which encodes the transcription factor, and (c) growing and harvesting the transgenic plant. The desired α-tocopherol content can be 2% or greater, 5% or greater, 10% or greater, 25% or greater, 50% or greater, 75% or greater or 90% or greater (all percentages with respect to total tocopherol content). All procedures needed to practice this embodiment are set forth herein or are well-known in the art.

Yet another embodiment is a method of generating oil from seed, wherein the oil has a desired α-tocopherol content, wherein the method comprises: (a) identifying a transcription factor that modulates expression of a gamma-methyltransferase (GMT) gene in a plant, (b) generating a transgenic plant comprising an isolated polynucleotide or expression vector which encodes the transcription factor, (c) growing and harvesting the transgenic plant and (d) obtaining seeds from the plant. The desired α-tocopherol content can be 2% or greater, 5% or greater, 10% or greater, 25% or greater, 50% or greater, 75% or greater or 90% or greater (all percentages with respect to total tocopherol content). All procedures needed to practice this embodiment are set forth herein or are well known in the art.

Also provided is a meal comprising plant material manufactured from a transgenic plant, wherein the tocopherol component in said plant has a desired α-tocopherol content, wherein the method comprises: (a) identifying a transcription factor that modulates expression of a gamma-methyltransferase (GMT) gene in a plant, (b) generating a transgenic plant comprising an isolated polynucleotide or expression vector which encodes the transcription factor, (c) growing and harvesting the transgenic plant and (d) using all or part of the plant for the production of meal. The desired α-tocopherol content can be 2% or greater, 5% or greater, 10% or greater, 25% or greater, 50% or greater, 75% or greater or 90% or greater (all percentages with respect to total tocopherol content). All procedures needed to practice this embodiment are set forth herein or are well known in the art.

These and other embodiments will readily occur to those of skill in the art in light of the disclosure herein.

BRIEF DESCRIPTION OF THE DRAWINGS

FIG. 6A and FIG. 6B show the Sequence of the *Arabidopsis thaliana* (Columbia) GMT gene (SEQ ID NO: 150). ZFP target sites are underlined and the translation initiation codon is shown in bold.

FIG. 7 shows the Sequence of the *Brassica napus* GMT gene (S8 homolog) (SEQ ID NO: 151). ZFP target sites are underlined and the translation initiation codon is shown in bold.

FIG. 8 shows diagrams of vectors used for the transformation of *Arabidopsis thaliana* plants. Sequences encoding GMT-targeted ZFPs were cloned between the NotI and HindIII sites in the napin (pCGN9979) or 35S (pCGN9977) expression cassettes.

FIGS. 18A and 18B show properties of zinc finger proteins (ZFPs) targeted to the *Arabidopsis* γ-tocopherol methyltransferase (GMT) gene.

FIG. 18A shows the location of the target sites of five ZFP DNA binding domains (A-E) designed to bind to 9 bp sequences in the *Arabidopsis* GMT gene. Numbering is relative to the start site of transcription (which is designated +1). Hypersensitive sites inferred from the data presented in FIG. 17 (shown in this figure as gray rectangles) and the first four exons of the GMT gene (black horizontal lines) are indicated.

FIG. 18B shows the DNA target sequences for each ZFP (ZFP A: SEQ ID NO: 37; ZFP B: SEQ ID NO: 45; ZFP C: SEQ ID NO: 49; ZFP D: SEQ ID NO: 53; ZFP E: SEQ ID NO: 57; SP1: SEQ ID NO: 169), the amino acid sequence of positions "−1" through "+6" of the α-helix of the component zinc fingers of each ZFP (ZFP A: SEQ ID NO: 38, SEQ ID NO: 39, SEQ ID NO: 40; ZFP B: SEQ ID NO: 46, SEQ ID NO: 47, SEQ ID NO: 48; ZFP C: SEQ ID NO: 50, SEQ ID NO: 51, SEQ ID NO: 52; ZFP D: SEQ ID NO: 54, SEQ ID NO: 59, SEQ ID NO: 56; ZFP E: SEQ ID NO: 59, SEQ ID NO: 59, SEQ ID NO: 40; SP1: SEQ ID NO: 170, SEQ ID NO: 171, SEQ ID NO: 172), and results of gel shift assays used to determine the apparent Kd of the designed zinc finger proteins. The apparent Kd of each designed ZFP for its target site, as determined by the gel-shift assay, is also given. The naturally-occurring ZFP SP1 was used as a control.

FIG. 19A is a schematic representation of the protoplast ZFP-TF expression cassette. The cauliflower mosaic virus 35S (CaMV35S) constitutive promoter was used to drive the expression of sequences encoding ZFP-TF fusion proteins comprising a maize opaque-2 nuclear localization signal (NLS), a plant-derived zinc finger protein DNA binding domain (ZFP), and a maize C1 activation domain.

FIG. 19B shows RNA analyses of transformed leaf protoplasts. Protoplasts were transformed with vectors having different ZFP binding domains, but otherwise having the structure shown in the upper portion of this figure. GMT mRNA levels were determined and were normalized to GAPDH mRNA and the transformation efficiency. The normalized GMT mRNA level for each sample was compared GMT RNA levels in leaf protoplasts that were transformed with a control vector containing only the CaMV35S driven C1 activation domain. Letters along the abscissa indicate the ZFP binding domain that was present in the transforming vector, and correspond to the designations given in FIG. 18.

DETAILED DESCRIPTION

General

Figure 1A:
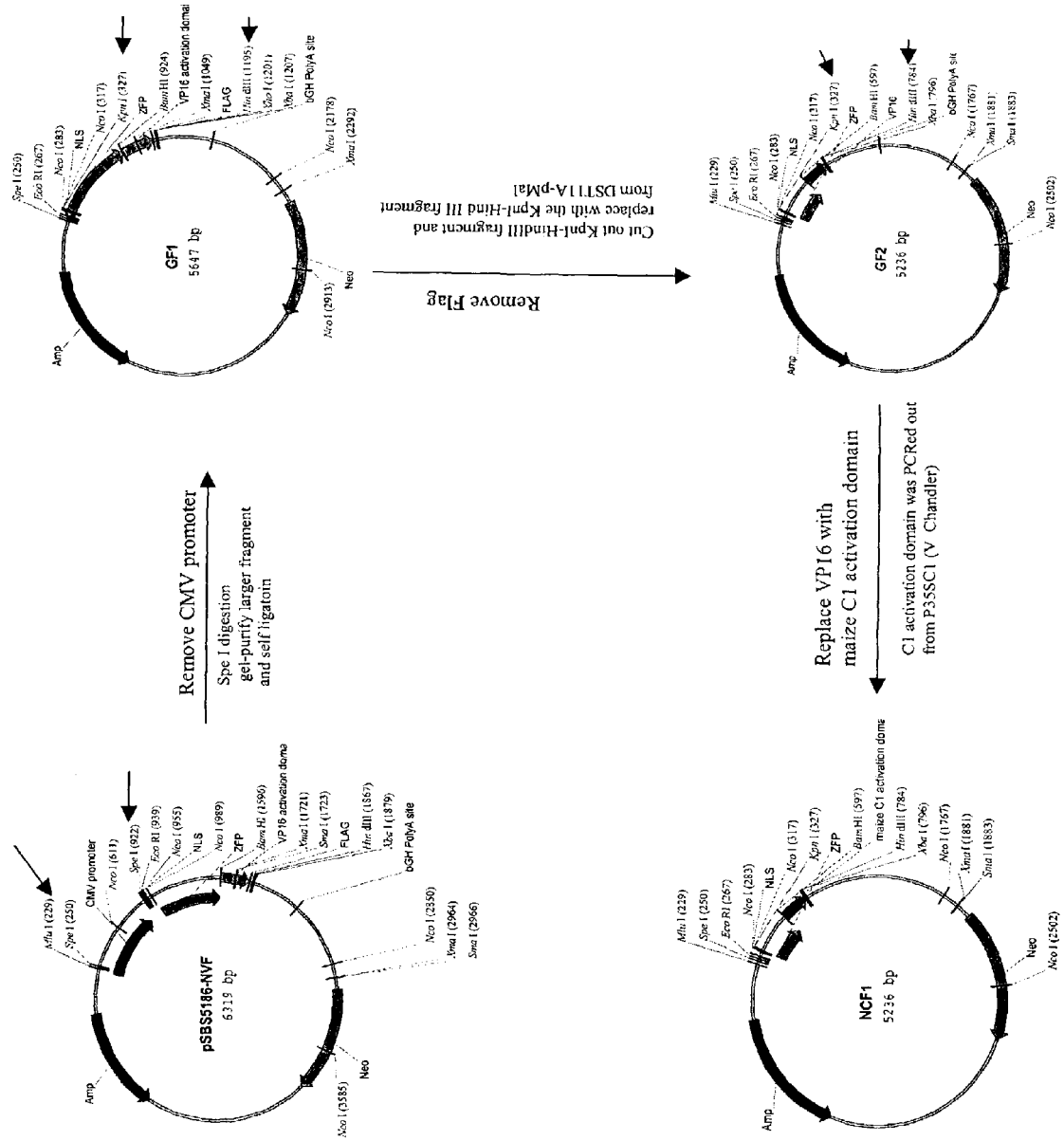
FIG. 1A and FIG. 1B are schematics depicting construction of the YCF3 expression vector useful in expressing GMT-targeted plant ZFPs.

The present disclosure provides ZFPs that bind to target sites in plant gamma-tocopherol methyltransferase (GMT) genes, for example *Arabidopsis* and *Brassica* GMT genes. The GMT enzyme, when generated by a plant in sufficient concentration, catalyzes the conversion of gamma-tocopherol (present in a seed, for example) into alpha-tocopherol, resulting in, for example, a seed in which the predominant tocopherol is of the alpha form. Conversely, in a plant part (such as, for example, a seed) in which GMT enzyme is absent or present in insufficient concentration, the tocopherol content is predominantly of the gamma form.

Also provided are methods of using these ZFPs along with host cells and transgenic plants comprising these ZFPs. The GMT-targeted ZFP can be a fusion polypeptide and, either by itself or as part of such a fusion, can enhance or suppress expression of GMT (i.e., modulate GMT gene expression). Polynucleotides encoding these ZFPs, and polynucleotides encoding fusion proteins comprising one or more of these ZFPs, are also provided. Additionally provided are compositions comprising, in combination with an acceptable carrier, any of the zinc finger binding polypeptides described herein or functional fragments thereof, and compositions comprising a nucleotide sequence that encodes a GMT-binding zinc finger binding polypeptide or functional fragment thereof, wherein the GMT-targeted zinc finger polypeptide or functional fragment thereof binds to a cellular nucleotide sequence to modulate the function of GMT. Also provided are plant cells and transgenic plants comprising the GMT-targeted ZFPs, as well as plant cells and transgenic plants comprising polynucleotide encoding GMT-targeted ZFPs.

In additional embodiments, methods for modulating expression of GMT in plant cells, using ZFPs described herein, are provided. For example, a GMT-targeted ZFP as described herein can be fused to an activation domain such that, in plant cells comprising such a fusion molecule, GMT is overexpressed (as compared to a control cell not containing the GMT-targeted ZFP). GMT overexpression can result in increased alpha-tocopherol (i.e., Vitamin E) production by a plant, plant cell or plant organ (e.g., a seed). Thus, the methods and compositions described herein allow for the production of plant cells and whole plants in which the amount (or concentration) of Vitamin E (in particular, alpha tocopherol) in the cells or plants is increased as compared to a cell or plant not comprising a GMT-targeted ZFP. It will be clear to those of skill in the art that increased Vitamin E levels (and, in particular, increased alpha tocopherol levels) can also result from modulation of expression of genes other than GMT. For example, up-regulation of any gene in a pathway leading to alpha-tocopherol synthesis can result in increased Vitamin E levels in plants in which the gene is up-regulated.

The practice of the disclosed methods employs, unless otherwise indicated, conventional techniques in molecular biology, biochemistry, genetics, computational chemistry, cell culture, recombinant DNA and related fields as are within the skill of the art. These techniques are fully explained in the literature. See, for example, Sambrook et al. MOLECULAR CLONING: A LABORATORY MANUAL, Third Edition, Cold Spring Harbor Laboratory Press, 2001; Ausubel et al., CURRENT PROTOCOLS IN MOLECULAR BIOLOGY, John Wiley & Sons, New York, 1987 and periodic updates; and the series METHODS IN ENZYMOLOGY, Academic Press, San Diego.

The disclosures of all patents, patent applications and publications mentioned herein are hereby incorporated by reference in their entireties.

Definitions

The terms "nucleic acid," "polynucleotide," and "oligonucleotide" are used interchangeably and refer to a deoxyribonucleotide or ribonucleotide polymer in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties. In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally occurring amino acid, for example selenocysteine (Bock et al. (1991) *Trends Biochem. Sci.* 16:463-467; Nasim et al. (2000) *J. Biol. Chem.* 275:14, 846-14,852) and the like.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger binding protein" is a protein or segment within a larger protein that binds DNA, RNA and/or protein in a sequence-specific manner as a result of stabilization of protein structure through coordination of a zinc ion. The term zinc finger binding protein is often abbreviated as zinc finger protein or ZFP. A "canonical" zinc finger refers to a zinc-coordinating component (e.g., zinc finger) of a zinc finger protein having the general amino acid sequence: $X_3$-Cys-$X_{2-4}$-Cys-$X_{12}$-His-$X_{1-7}$-His-$X_4$ (SEQ ID NO: 152) where X is any amino acid (also known as a C2H2 zinc finger). A "non-canonical" zinc finger refers to any type of finger other than a C2H2 zinc finger. Examples of non-canonical zinc fingers are described in International Patent Publication WO 02/52793.

An "engineered" zinc finger protein is a zinc finger protein, not occurring in nature, which has been designed or selected to bind to a particular target sequence. A "designed" zinc finger protein is a protein not occurring in nature whose structure and composition results principally from rational criteria. Criteria for rational design include application of substitution rules and computerized algorithms for processing information in a database storing information of existing ZFP designs and binding data, for example as described in PCT publications WO 98/53058, WO 98/53059, WO 98/53060 and WO 00/42219. A "selected" zinc finger protein is a protein not found in nature whose production results primarily from an empirical process such as phage display, two-hybrid systems and/or interaction trap assays. See e.g., U.S. Pat. Nos. 5,789,538; 6,007,988; 6,013,453; WO 95/19431; WO 96/06166; WO 98/54311, WO 01/88197 and Joung et al. (2000) *Proc. Natl. Acad. Sci. USA* 97:7382-7387. Selection methods also include ribosome display systems (e.g., PCT WO 00/27878) and mRNA-peptide fusion systems (e.g., U.S. Pat. No. 6,207,446; PCT WO 00/47775). Amino acid sequences of polypeptides (e.g., zinc fingers) obtained by selection or design can be referred to as "adapted" amino acid sequences. Designed and/or selected ZFPs are modified according to the methods and compositions disclosed herein and may also be referred to as "engineered" ZFPs. Engineered zinc finger proteins can also comprise non-naturally-occurring combinations of naturally-occurring zinc fingers.

The term "naturally-occurring" is used to describe an object that can be found in nature, as distinct from being artificially produced by a human. For example, naturally occurring plant ZFPs are characterized by long spacers of diverse lengths between adjacent zinc finger components.

A "target site" or "target sequence" is a nucleotide sequence that is bound by a binding molecule (e.g., a binding protein) such as, for example, a ZFP. Target sequences can be nucleotide sequences (either DNA or RNA) or amino acid sequences. By way of example, a DNA target sequence for a three-finger ZFP is generally either 9 or 10 nucleotides in length, depending upon the presence and/or nature of cross-strand interactions between the ZFP and the target sequence. A target sequence can be present in any DNA or RNA sequence, including but not limited to regulatory sequences, exons, introns and non-coding sequences.

A "target subsite" or "subsite" is the portion of a DNA target site that is bound by a single zinc finger, excluding cross-strand interactions. Thus, in the absence of cross-strand interactions, a subsite is generally three nucleotides in length. In cases in which a cross-strand interaction occurs (e.g., a "D-able subsite," as described for example in U.S. Pat. No. 6,453,242 and PCT WO 00/42219, incorporated by reference in their entireties herein) a subsite is four nucleotides in length and overlaps with another 3- or 4-nucleotide subsite.

Nucleic acid or amino acid sequences are "operably linked" (or "operatively linked") when placed into a functional relationship with one another. For instance, a promoter or enhancer is operably linked to a coding sequence if it regulates, or contributes to the modulation of, the transcription of the coding sequence. Operably linked DNA sequences are typically contiguous, and operably linked amino acid sequences are typically contiguous and in the same reading frame. However, since enhancers generally function when separated from the promoter by up to several kilobases or more and intronic sequences may be of variable lengths, some polynucleotide elements may be operably linked but not contiguous. Similarly, certain amino acid sequences that are non-contiguous in a primary polypeptide sequence may nonetheless be operably linked due to, for example folding of a polypeptide chain.

With respect to fusion polypeptides, the term "operatively linked" can refer to the fact that each of the components performs the same function in linkage to the other component as it would if it were not so linked. For example, with respect to a fusion polypeptide in which a GMT-targeted ZFP DNA-binding domain is fused to a functional domain (or functional fragment thereof), the ZFP DNA-binding domain and the functional domain (or functional fragment thereof) are in operative linkage if, in the fusion polypeptide, the GMT-targeted ZFP DNA-binding domain portion is able to bind its target site and/or its binding site, while the functional domain (or functional fragment thereof) is able to modulate (e.g., activate or repress) transcription.

"Specific binding" between, for example, a ZFP and a specific target site means a binding affinity of at least $1\times10^6$ $M^{-1}$.

A "fusion molecule" is a molecule in which two or more subunit molecules are linked, preferably covalently. The subunit molecules can be the same chemical type of molecule, or can be different chemical types of molecules. Examples of the first type of fusion molecule include, but are not limited to, fusion polypeptides (for example, a fusion between a GMT-targeted ZFP DNA-binding domain and a functional domain) and fusion nucleic acids (for example, a nucleic acid encoding a fusion polypeptide). Examples of the second type of fusion molecule include, but are not limited to, a fusion between a triplex-forming nucleic acid and a polypeptide, and a fusion between a minor groove binder and a nucleic acid.

A "gene," for the purposes of the present disclosure, includes a DNA region encoding a gene product (see below), as well as all DNA regions that regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. Further, a promoter can be a normal cellular promoter or, for example, a promoter of an infecting microorganism such as, for example, a bacterium or a virus.

"Gene expression" refers to the conversion of the information, contained in a gene, into a gene product. A "gene product" can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Gene activation" and "augmentation of gene expression" refer to any process that results in an increase in production of a gene product. A gene product can be either RNA (including, but not limited to, mRNA, rRNA, tRNA, and structural RNA) or protein. Accordingly, gene activation includes those processes that increase transcription of a gene and/or translation of an mRNA. Examples of gene activation processes which increase transcription include, but are not limited to, those which facilitate formation of a transcription initiation complex, those which increase transcription initiation rate, those which increase transcription elongation rate, those which increase processivity of transcription and those which relieve transcriptional repression (by, for example, blocking the binding of a transcriptional repressor). Gene activation can constitute, for example, inhibition of repression as well as stimulation of expression above an existing level. Examples of gene activation processes that increase translation include those that increase translational initiation, those that increase translational elongation and those that increase mRNA stability. In general, gene activation comprises any detectable increase in the production of a gene product, preferably an increase in production of a gene product by about 2-fold, more preferably from about 2- to about 5-fold or any integral value therebetween, more preferably between about 5- and about 10-fold or any integral value therebetween, more preferably between about 10- and about 20-fold or any integral value therebetween, still more preferably between about 20- and about 50-fold or any integral value therebetween, more preferably between about 50- and about 100-fold or any integral value therebetween, more preferably 100-fold or more.

"Gene repression" and "inhibition of gene expression" refer to any process that results in a decrease in production of a gene product. A gene product can be either RNA (including, but not limited to, mRNA, rRNA, tRNA, and structural RNA) or protein. Accordingly, gene repression includes those processes that decrease transcription of a gene and/or translation of an mRNA. Examples of gene repression processes which decrease transcription include, but are not limited to, those which inhibit formation of a transcription initiation complex, those which decrease transcription initiation rate, those which decrease transcription elongation rate, those which decrease processivity of transcription and those which antagonize transcriptional activation (by, for example, blocking the binding of a transcriptional activator). Gene repression can constitute, for example, prevention of activation as well as inhibition of expression below an existing level. Examples of gene repression processes that decrease translation include those that decrease translational initiation, those that decrease translational elongation and those that decrease mRNA stability. Transcriptional repression includes both reversible and irreversible inactivation of gene transcription. In general, gene repression comprises any detectable decrease in the production of a gene product, preferably a decrease in production of a gene product by about 2-fold, more preferably from about 2- to about 5-fold or any integral value therebetween, more preferably between about 5- and about 10-fold or any integral value therebetween, more preferably between about 10- and about 20-fold or any integral value therebetween, still more preferably between about 20- and about 50-fold or any integral value therebetween, more preferably between about 50- and about 100-fold or any integral value therebetween, more preferably 100-fold or more. Most preferably, gene repression results in complete inhibition of gene expression, such that no gene product is detectable.

The term "modulate" refers to a change in the quantity, degree or extent of a function. For example, the GMT-targeted zinc finger-nucleotide binding polypeptides disclosed herein can modulate the activity of a promoter sequence by binding to a motif within the promoter, thereby inducing, enhancing or suppressing transcription of a gene operatively linked to the promoter sequence (and thereby modulating expression of the gene, as well). Alternatively, modulation may include inhibition of transcription of a gene wherein a GMT-targeted zinc finger-nucleotide binding polypeptide binds to a structural gene and blocks the progression of DNA dependent RNA polymerase along the gene, thus inhibiting transcription of the gene. The structural gene may be a normal cellular gene or a gene of an infecting organism, such as a bacterium or virus, for example. In addition, modulation may include activation or inhibition of translation of a transcript. Thus, "modulation" of gene expression includes both gene activation and gene repression.

Modulation can be assayed by determining any parameter that is indirectly or directly affected by the expression of the target gene. Such parameters include, e.g., changes in RNA or protein levels; changes in protein activity; changes in product levels (e.g., gene product, product of a metabolic pathway); changes in downstream gene expression; changes in transcription or activity of reporter genes such as, for example, luciferase, CAT, beta-galactosidase, or GFP (see, e.g., Mistili & Spector, (1997) *Nature Biotechnology* 15:961-964); changes in signal transduction; changes in phosphorylation and dephosphorylation; changes in receptor-ligand interactions; changes in concentrations of second messengers such as, for example, cGMP, ☐xte, $IP_3$, and $Ca^{2+}$; changes in cell growth, changes in chemical composition (e.g., nutritional value), and/or changes in any functional effect of gene expression. Measurements can be made in vitro, in vivo, and/or ex vivo. Such functional effects can be measured by conventional methods, e.g., measurement of RNA or protein levels, measurement of RNA stability, and/or identification of downstream or reporter gene expression. Readout can be by way of, for example, chemiluminescence, fluorescence, colorimetric reactions, antibody binding, inducible markers, ligand binding assays; changes in intracellular second messengers such as cGMP and inositol triphosphate ($IP_3$); changes in intracellular calcium levels; cytokine release, and the like.

"Eucaryotic cells" include, but are not limited to, fungal cells (such as yeast), plant cells, animal cells, mammalian cells and human cells. Similarly, "prokaryotic cells" include, but are not limited to, bacteria.

A "regulatory domain" or "functional domain" refers to a protein or a polypeptide sequence that has transcriptional modulation activity, or that is capable of interacting with proteins and/or protein domains that have transcriptional modulation activity. Typically, a functional domain is covalently or non-covalently linked to a ZFP to modulate transcription of a gene of interest. Alternatively, a ZFP can act, in the absence of a functional domain, to modulate transcription. Furthermore, transcription of a gene of interest can be modulated by a ZFP linked to multiple functional domains.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well known in the art. Similarly, methods for determining protein function are well known. For example, the DNA-binding function of a polypeptide can be determined, for example, by filter-binding, electrophoretic mobility-shift, or immunoprecipitation assays. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340: 245-246; U.S. Pat. No. 5,585,245 and PCT WO 98/44350. The function of a protein, in terms of its ability to modulate gene expression, can be tested as described supra in connection with the definition of modulation and the description of exemplary assays for modulation.

The term "effective amount" includes that amount which results in the desired result, for example, deactivation of a previously activated gene, activation of a previously repressed gene, modulation of transcription of a structural gene or modulation of translation of a mRNA.

As used herein, "genetically modified" or "transgenic" means a plant cell, plant part, plant tissue or plant which comprises one or more polynucleotide sequences which are introduced into the genome of a plant cell, plant part, plant tissue or plant by transformation or other suitable methods. The term "wild type" refers to an untransformed plant cell, plant part, plant tissue or plant, i.e., one whose genome does not include introduced polynucleotide sequences.

As used herein, "plant" refers to either a whole plant, a plant tissue, a plant part (such as, for example, pollen, seed or an embryo), a plant cell, or a group of plant cells. The class of plants that can be used is generally as broad as the class of seed-bearing higher plants amenable to transformation techniques, including both monocotyledonous and dicotyledonous plants. Seeds derived from plants regenerated from transformed plant cells, plant parts or plant tissues, or progeny derived from the regenerated transformed plants, may be used directly as feed or food, or can be altered by further processing. In the practice of the present disclosure, exemplary plant seeds are those of *Arabidopsis* and *Brassica*. Transformation of plants can be carried out in essentially any of the various ways known to those skilled in the art of plant molecular biology. These include, but are not limited to, microprojectile bombardment, microinjection, vacuum infiltration, electroporation of protoplasts or cells comprising partial cell walls, and *Agrobacterium*-mediated DNA transfer.

Tocopherol Biosynthesis

The plastids of higher plants exhibit interconnected biochemical pathways leading to secondary metabolites including tocopherols. The tocopherol biosynthetic pathway in higher plants involves condensation of homogentisic acid and phytylpyrophosphate to form 2-methyl-6 phytylplastoquinol (Fiedler et al., *Planta* 155: 511-515 (1982); Soll et al., *Arch. Biochem. Biophys.* 204: 544-550 (1980); Marshall et al., *Phytochem.* 24: 1705-1711 (1985)). This plant tocopherol pathway can be divided into four parts: 1) synthesis of homogentisic acid, which contributes to the aromatic ring of tocopherol; 2) synthesis of phytylpyrophosphate, which contributes to the side chain of tocopherol; 3) cyclization, which plays a role in chirality and chromanol substructure of the vitamin E family; 4) and S-adenosyl methionine dependent methylation of an aromatic ring, which affects the relative abundance of each of the tocopherol species.

Homogentisic acid is the common precursor to both tocopherols and plastoquinones. In at least some bacteria the synthesis of homogentisic acid is reported to occur via the conversion of chorismate to prephenate and then to p-hydroxyphenylpyruvate via a bifunctional prephenate dehydrogenase. Examples of bifunctional bacterial prephenate dehydrogenase enzymes include the proteins encoded by the tyrA genes of *Erwinia herbicola* and *Escherichia coli*. The tyrA gene product catalyzes the production of prephenate from chorismate, as well as the subsequent dehydrogenation of prephenate to form p-hydroxyphenylpyruvate (p-HPP), the immediate precursor to homogentisic acid. p-HPP is then converted to homogentisic acid by hydroxyphenylpyruvate dioxygenase (HPPD). In contrast, plants are believed to lack prephenate dehydrogenase activity, and it is generally believed that the synthesis of homogentisic acid from chorismate occurs via the synthesis and conversion of the intermediate arogenate. Since pathways involved in homogentisic acid synthesis are also responsible for tyrosine formation, any alterations in these pathways can also result in the alteration in tyrosine synthesis and the synthesis of other aromatic amino acids.

Tocopherols are a member of the class of compounds referred to as the isoprenoids. Other isoprenoids include carotenoids, gibberellins, terpenes, chlorophyll and abscisic acid. A central intermediate in the production of isoprenoids is isopentenyl diphosphate (IPP). Cytoplasmic and plastid-based pathways to generate IPP have been reported. The cytoplasmic based pathway involves the enzymes acetoacetyl CoA thiolase, HMGCoA synthase, HMGCoA reductase, mevalonate kinase, phosphomevalonate kinase, and mevalonate pyrophosphate decarboxylase.

Recently, evidence for the existence of an alternative, plastid based, isoprenoid biosynthetic pathway emerged from studies in the research groups of Rohmer and Arigoni (Eisenreich et al., *Chem. Bio.*, 5:R221-R233 (1998); Rohmer, *Prog. Drug. Res.*, 50:135-154 (1998); Rohmer, *Comprehensive Natural Products Chemistry*, Vol. 2, pp. 45-68, Barton and Nakanishi (eds.), Pergamon Press, Oxford, England (1999)), who found that the isotope labeling patterns observed in studies on certain eubacterial and plant terpenoids could not be explained in terms of the mevalonate pathway. Arigoni and coworkers subsequently showed that 1-deoxyxylulose, or a derivative thereof, serves as an intermediate of the novel pathway, now referred to as the MEP pathway (Rohmer et al., *Biochem. J.*, 295:517-524 (1993); Schwarz, Ph.D. thesis, Eidgenössiche Technische Hochschule, Zurich, Switzerland (1994)). Recent studies showed the formation of 1-deoxyxylulose 5-phosphate (Broers, Ph.D. thesis (Eidgenössiche Technische Hochschule, Zurich, Switzerland) (1994)) from one molecule each of glyceraldehyde 3-phosphate (Rohmer, *Comprehensive Natural Products Chemistry*, Vol. 2, pp. 45-68, Barton and Nakanishi, eds., Pergamon Press, Oxford, England (1999)) and pyruvate (Eisenreich et al., *Chem. Biol.*, 5:R223-R233 (1998); Schwarz supra; Rohmer et al., *J. Am. Chem. Soc.*, 118:2564-2566 (1996); and Sprenger et al., *Proc. Natl. Acad. Sci. USA*, 94:12857-12862 (1997)) by an enzyme encoded by the dxs gene (Lois et al., *Proc. Natl. Acad. Sci. USA*, 95:2105-2110 (1997); and Lange et al., *Proc. Natl. Acad. Sci. USA*, 95:2100-2104 (1998)). 1-Deoxyxylulose 5-phosphate can be further converted into 2-C-methylerythritol 4-phosphate (Arigoni et al., *Proc. Natl. Acad. Sci. USA*, 94:10600-10605 (1997)) by a reductoisomerase encoded by the dxr gene (Bouvier et al., *Plant Physiol*, 11 7:1421-1431 (1998); and Rohdich et al., *Proc. Natl. Acad. Sci. USA*, 96:11758-11763 (1999)).

Reported genes in the MEP pathway also include ygbP, which catalyzes the conversion of 2-C-methylerythritol 4-phosphate into its respective cytidyl pyrophosphate derivative and ygbB, which catalyzes the conversion of 4-phosphocytidyl-2C-methyl-D-erythritol into 2C-methyl-D-erythritol, 3, 4-cyclophosphate. These genes are tightly linked on the *E. coli* genome (Herz et al., *Proc. Natl. Acad. Sci. U.S.A.*, 97(6): 2485-2490 (2000)).

Once IPP is formed by the MEP pathway, it is converted to GGDP by GGDP synthase, and then to phytylpyrophosphate, which is the central constituent of the tocopherol side chain.

Homogentisic acid is combined with either phytyl-pyrophosphate or solanyl-pyrophosphate by phytyl/prenyl transferase forming 2-methyl-6-phytyl plastoquinol or 2-methyl-6-solanyl plastoquinol, respectively. 2-methyl-6-solanyl plastoquinol is a precursor to the biosynthesis of plastoquinones, while 2-methyl-6-phytyl plastoquinol is ultimately converted to tocopherol.

The major structural difference between each of the tocopherol subtypes is the position of the methyl groups around the phenyl ring. Both 2-methyl-6-phytyl plastoquinol and 2-methyl-6-solanyl plastoquinol serve as substrates for 2-methyl-6-phytylplatoquinol/2-methyl-6-solanylplastoquinol-9 methyltransferase (Methyl Transferase 1; MT1), which catalyzes the formation of plastoquinol-9 and γ-tocopherol respectively, by methylation of the 7 position. Subsequent methylation at the 5 position of γ-tocopherol by γ-tocopherol methyl-transferase (GMT) generates the biologically active α-tocopherol. However, in seeds where alpha-tocopherol levels are low the expression of the GMT gene is also low.

Accordingly, levels of α-tocopherol in plants can be optimized using the methods and compositions disclosed herein. In certain embodiments, α-tocopherol levels are modulated by modulating the activity of GMT; however, it is clear that the activity of many other genes instead of or in addition to GMT, whose products catalyze reactions in the tocopherol pathways (see above), can be modulated using similar methods and compositions, so as to modulate tocopherol and/or Vitamin E levels.

Zinc Finger Proteins

Zinc finger proteins (ZFPs) are proteins that bind to DNA, RNA and/or protein, in a sequence-specific manner, by virtue of a metal stabilized domain known as a zinc finger. See, for example, Miller et al. (1985) *EMBO J.* 4:1609-1614; Rhodes et al. (1993) *Sci. Amer.* Feb:56-65; and Klug (1999) *J. Mol. Biol.* 293:215-218. There are at least 2 classes of ZFPs which coordinate zinc to form a compact DNA-binding domain. The first class includes the $C_2H_2$ ZFPs, that are composed of zinc fingers that contain two conserved cysteine residues and two conserved histidine residues in the following arrangement: -Cys-$(X)_{2-4}$-Cys-$(X)_{12}$-His-$(X)_{3-5}$-His (SEQ ID NO: 1). C2H2 recognition regions are also referred to as "canonical." A second class of ZFPs, referred to as Cys-Cys-His-Cys (SEQ ID NO: 153) ($C_3H$) ZFPs, have also been described, for example in Jiang et al. (1996) *J Biol. Chem.* 271:10723-10730. $C_3H$ ZFPS are a member of the family of non-canonical ZFPs, which include all non-$C_2H_2$ ZFPs. ZFPs including canonical, non-canonical and combinations of non-canonical and canonical zinc fingers can be utilized in the practice of the present disclosure.

Thus, zinc finger proteins are polypeptides that comprise zinc finger components. For example, zinc finger proteins can have one to thirty-seven or more fingers, commonly having 2, 3, 4, 5 or 6 fingers. Zinc finger DNA-binding proteins are described, for example, in Miller et al. (1985) *EMBO J.* 4:1609-1614; Rhodes et al. (1993) *Scientific American* February:56-65; and Klug (1999) *J. Mol. Biol.* 293:215-218. A zinc finger protein recognizes and binds to a target site (sometimes referred to as a target sequence or target segment) that represents a relatively small portion of sequence within a target gene. Each component finger of a zinc finger protein typically binds to a subsite within the target site. The subsite includes a triplet of three contiguous bases on the same strand (sometimes referred to as the target strand). The three bases in the subsite can be individually denoted the 5' base, the mid base, and the 3' base of the triplet, respectively. The subsite may or may not also include a fourth base on the non-target strand that is the complement of the base immediately 3' of the three contiguous bases on the target strand. The base immediately 3' of the three contiguous bases on the target strand is sometimes referred to as the 3' of the 3' base. Alternatively, the four bases of the target strand in a four base subsite can be numbered 4, 3, 2, and 1, respectively, starting from the 5' base.

The relative order of fingers in a zinc finger protein, from N-terminal to C-terminal, determines the relative order of triplets in the target sequence, in the 3' to 5' direction that will be recognized by the fingers. For example, if a zinc finger protein comprises, from N-terminal to C-terminal, first, second and third fingers that individually bind to the triplets 5'-GAC-3', 5'-GTA-3' and 5'-GGC-3', respectively, then the zinc finger protein binds to the target sequence 5'-GGCGTA-GAC-3' (SEQ ID NO: 2). If the zinc finger protein comprises the fingers in another order, for example, second finger, first finger, third finger, then the zinc finger protein binds to a target segment comprising a different permutation of triplets, in this example, 5'-GGCGACGTA-3' (SEQ ID NO: 3). See Berg et al. (1996) Science 271:1081 -1086. The first amino acid of the alpha helical portion of the finger is assigned the number +1 and succeeding amino acids (proceeding toward the C-terminus) are assigned successively increasing numbers. The alpha helix generally extends to the residue following the second conserved histidine. The entire helix can therefore be of variable length, e.g., between 11 and 13 residues. The numbering convention used above is standard in the field for the region of a zinc finger conferring binding specificity, otherwise known as the recognition region.

A. ZFPs Targeted to Plant GMT Genes

In general, GMT-targeted ZFPs are produced by first analyzing plant GMT sequences in order to select one or more target sites in or around a GMT gene, and engineering one or more ZFPs that bind to the target site(s). GMT gene sequences are disclosed herein and are publicly available on any number of databases. Three-dimensional modeling for design of ZFPs can be used, but is not required.

In certain embodiments, the target site is present in an accessible region of cellular chromatin. Accessible regions can be determined as described in International Publications WO 01/83751 and WO 01/83732. If the target site is not present in an accessible region of cellular chromatin, one or more accessible regions can be generated as described in International Publication WO 01/83793. In additional embodiments, one or more GMT-targeted zinc finger binding components (or fusion molecules comprising these components) are capable of binding to cellular chromatin regardless of whether its target site is in an accessible region or not. For example, a ZFP as disclosed herein can be capable of binding to linker DNA and/or to nucleosomal DNA. Examples of this type of "pioneer" DNA binding domain are found in certain steroid receptors and in hepatocyte nuclear factor 3 (HNF3). Cordingley et al. (1987) *Cell* 48:261-270; Pina et al. (1990) *Cell* 60:719-731; and Cirillo et al. (1998) *EMBO J.* 17:244-254.

Exemplary methods for selecting target sites are described in WO 00/42219.

For each target site that is selected, one or more ZFPs are engineered, e.g., by design or selection, to bind the target site. Preferably, the ZFPs disclosed herein are composed wholly or partly of plant sequences, but have a non-plant structure. Methods of engineering such ZFPs are described, for example, in International patent application publications WO 02/57293 and WO 02/57294. As described in these documents, the non-plant structure of the GMT-targeted ZFP can be similar to that of any class of non-plant ZFP, for instance the $C_2H_2$ canonical class of ZFPs as exemplified by TFIIIA, Zif268 and Sp-1 or, a non-C2H2 structure, for example, a zinc finger protein in which one or more zinc coordinating fingers making up the zinc finger protein has any of the following sequences:

$X_3$-B-$X_{2-4}$-Cys-$X_{12}$-His-$X_{1-7}$-His-$X_4$    (SEQ ID NO: 154)

$X_3$-Cys-$X_{2-4}$-B-$X_{12}$-His-$X_{1-7}$-His-$X_4$    (SEQ ID NO: 155)

$X_3$-Cys-$X_{2-4}$-Cys-$X_{12}$-Z-$X_{1-7}$-His-$X_4$    (SEQ ID NO: 156)

$X_3$-Cys-$X_{2-4}$-Cys-$X_{12}$-His-$X_{1-7}$-Z-$X_4$    (SEQ ID NO: 157)

$X_3$-B-$X_{2-4}$-B-$X_{12}$-His-$X_{1-7}$-His-$X_4$    (SEQ ID NO: 158)

$X_3$-B-$X_{2-4}$-Cys-$X_{12}$-Z-$X_{1-7}$-His-$X_4$    (SEQ ID NO: 159)

$X_3$-B-$X_{2-4}$-Cys-$X_{12}$-His-$X_{1-7}$-Z-$X_4$    (SEQ ID NO: 160)

$X_3$-Cys-$X_{2-4}$-B-$X_{12}$-Z-$X_{1-7}$-His-$X_4$    (SEQ ID NO: 161)

$X_3$-Cys-$X_{2-4}$-B-$X_{12}$-His-$X_{1-7}$-Z-$X_4$    (SEQ ID NO: 162)

$X_3$-Cys-$X_{2-4}$-Cys-$X_{12}$-Z-$X_{1-7}$-Z-$X_4$    (SEQ ID NO: 163)

$X_3$-Cys-$X_{2-4}$-B-$X_{12}$-Z-$X_{1-7}$-Z-$X_4$    (SEQ ID NO: 164)

$X_3$-B-$X_{2-4}$-Cys-$X_{12}$-Z-$X_{1-7}$-Z-$X_4$    (SEQ ID NO: 165)

$X_3$-B-$X_{2-4}$-B-$X_{12}$-His-$X_{1-7}$-Z-$X_4$    (SEQ ID NO: 166)

$X_3$-B-$X_{2-4}$-B-$X_{12}$-Z-$X_{1-7}$-His-$X_4$    (SEQ ID NO: 167)

$X_3$-B-$X_{2-4}$-B-$X_{12}$-Z-$X_{1-7}$-Z-$X_4$    (SEQ ID NO: 168)

where
X = any amino acid
B = any amino acid axcept cysteine
Z = any amino acid except histidine.

Furthermore, the ZFP can comprise sequences (e.g., recognition regions and/or backbones) from more than one class of ZFP. For example, a GMT-targeted ZFP can include a combination of canonical and non-canonical recognition regions inserted into a plant or other backbone. Selecting particular plant backbone residues to achieve the desired effector functions is disclosed herein and in International patent application publication WO 02/57294. Fungal ZFPs can also be used as models for design and/or as sources of zinc finger sequences for GMT-targeted ZFPs. See, e.g., WO 96/32475. The documents cited herein also disclose methods of assessing binding affinity and/or specificity of ZFPs.

Sequences from any ZFP described herein can be altered by mutagenesis, substitution, insertion and/or deletion of one or more residues so that the non-recognition plant-derived residues do not correspond exactly to the zinc finger protein from which they are derived.

Alterations in the recognition residues (i.e., positions –1 to +6 of a zinc finger) of any ZFP can be made so as to confer a desired binding specificity as described, for example, in WO 00/42219; WO 00/41566; as well as U.S. Pat. Nos. 5,789,538; 6,007,408; 6,013,453; 6,140,081; 6,140,466; 6,242,568 and 6,453,242; as well as PCT publications WO 95/19431, WO 98/54311, WO 00/23464; WO 00/27878; WO98/53057; WO98/53058; WO98/53059; and WO98/53060.

Furthermore, in certain embodiments, ZFPs, as disclosed herein, contain additional modifications in their zinc fingers including, for example, non-canonical zinc fingers, in which a zinc-coordinating amino acid residue (i.e., cysteine and/or histidine) is substituted with a different amino acid. A GMT-targeted ZFP of this type can include any number of zinc finger components, and, in one embodiment, contains three zinc fingers. Any or all of the fingers can be a non-canonical finger(s). One or more of the component fingers of the protein can be naturally occurring zinc finger components, GMT-targeted plant components, canonical $C_2H_2$ fingers or combinations of these components.

As described in further detail below, the GMT-targeted ZFPs described herein (and compositions comprising these ZFPs) can be provided to a plant or a plant cell as polypeptides or polynucleotides.

B. Linkage

Two or more GMT-targeted zinc finger proteins can be linked to have a target site specificity that is, to a first approximation, the aggregate of that of the component zinc finger proteins. For example, a first GMT-targeted zinc finger protein having first, second and third component fingers that respectively bind to sequences represented by XXX, YYY and ZZZ can be linked to a second GMT-targeted zinc finger protein having first, second and third component fingers with binding specificities, AAA, BBB and CCC. The binding specificity of the combined first and second proteins is thus 5'-CCCBBBAAANZZZYYYXXX-3', where N indicates a short intervening region (typically 0-5 bases of any type). In this situation, the target site can be viewed as comprising two target segments separated by an intervening segment.

Linkage of zinc fingers and zinc finger proteins can be accomplished using any of the following peptide linkers:

```
       TGEKP                     (SEQ ID NO: 4)
Liu et al. (1997) Proc. Natl. Acad. Sci. USA 94:
5525-5530.

(G4S)n                    (SEQ ID NO; 5)
Kim et al. (1996) Proc. Natl. Acad. Sci. USA 93:
1156-1160.

GGRRGGGS                  (SEQ ID NO: 6)

LRQRDGERP                 (SEQ ID NO: 7)

LRQKDGGGSERP              (SEQ ID NO: 8)

LRQKD(G3S)2ERP.           (SEQ ID NO: 9)
```

Alternatively, flexible linkers can be rationally designed using computer programs capable of modeling both DNA-binding sites and the peptides themselves, or by phage display methods. See, e.g., WO 99/45132 and WO 01/53480. In a further variation, non-covalent linkage can be achieved by fusing two zinc finger proteins with domains promoting heterodimer formation of the two zinc finger proteins. For example, one zinc finger protein can be fused with fos and the other with jun (see Barbas et al., WO 95/119431). Alternatively, dimerization interfaces can be obtained by selection. See, for example, Wang et al. (1999) *Proc. Natl. Acad. Sci. USA* 96:9568-9573. Structured linkers, such as those described in WO 01/53480, can also be used.

C. Fusion Molecules

The GMT-targeted zinc finger proteins described herein can also be used in the design of fusion molecules that facilitate regulation of GMT expression in plants. Thus, in certain embodiments, the compositions and methods disclosed herein involve fusions between at least one of the zinc finger proteins described herein (or functional fragments thereof) and one or more functional domains (or functional fragments thereof), or a polynucleotide encoding such a fusion. The presence of such a fusion molecule in a cell allows a functional domain to be brought into proximity with a sequence in a gene that is bound by the zinc finger portion of the fusion molecule. The transcriptional regulatory function of the functional domain is then able to act on the gene, by, for example, modulating expression of the gene.

In certain embodiments, fusion proteins comprising a GMT-targeted zinc finger DNA-binding domain and a functional domain are used for modulation of endogenous GMT expression. Modulation includes repression and activation of gene expression; the nature of the modulation generally depending on the type of functional domain present in the fusion protein. Any polypeptide sequence or domain capable of influencing gene expression (or functional fragment thereof) that can be fused to a DNA-binding domain, is suitable for use.

Suitable domains for achieving activation include the HSV VP 16 activation domain (see, e.g., Hagmann et al., J. Virol. 71, 5952-5962 (1997)) nuclear hormone receptors (see, e.g., Torchia et al., Curr. Opin. Cell. Biol. 10:373-383 (1998)); the p65 subunit of nuclear factor kappa B (Bitko & Barik, J. Virol. 72:5610-5618 (1998) and Doyle & Hunt, Neuroreport 8:2937-2942 (1997)); Liu et al., Cancer Gene Ther. 5:3-28 (1998)), or artificial chimeric functional domains such as VP64 (Seifpal et al., EMBO J. 11, 4961-4968 (1992)).

Additional exemplary activation domains include, but are not limited to, p300, CBP, PCAF, SRC1 PvALF, and ERF-2. See, for example, Robyr et al. (2000) *Mol. Endocrinol.* 14:329-347; Collingwood et al. (1999) *J. Mol. Endocrinol.* 23:255-275; Leo et al. (2000) *Gene* 245:1 -11; Manteuffel-Cymborowska (1999) *Acta Biochim. Pol.* 46:77-89; McKenna et al. (1999) *J. Steroid Biochem. Mol. Biol.* 69:3-12; Malik et al. (2000) *Trends Biochem. Sci.* 25:277-283; and Lemon et al. (1999) *Curr. Opin. Genet. Dev.* 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) *Gene* 245:21-29; Okanami et al. (1996) *Genes Cells* 1:87-99; Goffet al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J.* 22:1-8; Gong et al. (1999) *Plant Mol. Biol.* 41:33-44; and Hobo et al. (1999) *Proc. Natl. Acad. Sci. USA* 96:15,348-15,353.

A preferred activation domain is the maize C1 activation domain. Goff et al. (1991) *Genes & Devel* 5:298-309.

An exemplary functional domain for fusing with a ZFP DNA-binding domain, to be used for repressing gene expression, is a KRAB repression domain from the human KOX-1 protein (see, e.g., Thiesen et al., New Biologist 2, 363-374 (1990); Margolin et al., Proc. Natl. Acad. Sci. USA 91, 4509-4513 (1994); Pengue et al., Nucl. Acids Res. 22:2908-2914 (1994); Witzgall et al., Proc. Natl. Acad. Sci. USA 91, 4514-4518 (1994). Another suitable repression domain is methyl binding domain protein 2B (MBD-2B) (see, also Hendrich et al. (1999) *Mamm Genome* 10:906-912 for description of MBD proteins). Another useful repression domain is that associated with the v-ErbA protein. See, for example, Damm, et al. (1989) *Nature* 339:593-597; Evans (1989) *Int. J. Cancer Suppl.* 4:26-28; Pain et al. (1990) *New Biol.* 2:284-294; Sap et al. (1989) *Nature* 340:242-244; Zenkeetal. (1988) *Cell* 52:107-119; and Zenkeetal. (1990) *Cell* 61:1035-1049. Additional exemplary repression domains include, but are not limited to, thyroid hormone receptor (TR), SID, MBD1, MBD2, MBD3, MBD4, MBD-like proteins, members of the DNMT family (e.g., DNMT1, DNMT3A, DNMT3B), Rb, MeCP1 and MeCP2. See, for example, Zhang et al. (2000) *Ann Rev Physiol* 62:439-466; Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A.

See, for example, Chern et al. (1996) *Plant Cell* 8:305-321; and Wu et al. (2000) *Plant J.* 22:19-27.

Additional functional domains are disclosed, for example, in WO 00/41566. Further, insulator domains, chromatin remodeling proteins such as ISWI-containing domains, localization domains and/or methyl binding domain proteins suitable for use in fusion molecules are described, for example, in International Publications WO 01/83793, WO 02/26960 and WO 02/44376.

In additional embodiments, targeted remodeling of chromatin, as disclosed, for example, in International Publication WO 01/83793, can be used to generate one or more sites in plant cell chromatin that are accessible to the binding of a functional domain/GMT-targeted ZFP fusion molecule.

Fusion molecules are constructed by methods of cloning and biochemical conjugation that are well known to those of skill in the art. Fusion molecules comprise a GMT-targeted ZFP binding domain and, for example, a transcriptional activation domain, a transcriptional repression domain, a component of a chromatin remodeling complex, an insulator domain or a functional fragment of any of these domains. In certain embodiments, fusion molecules comprise a GMT-targeted zinc finger protein and at least two functional domains (e.g., an insulator domain or a methyl binding protein domain and, additionally, a transcriptional activation or repression domain). Fusion molecules also optionally comprise a nuclear localization signal (such as, for example, that from the SV40 T-antigen or the maize Opaque-2 NLS) and an epitope tag (such as, for example, myc, his, FLAG or hemagglutinin). Fusion proteins (and nucleic acids encoding them) are designed such that the translational reading frame is preserved among the components of the fusion.

Methods of gene regulation using a functional domain, targeted to a specific sequence by virtue of a fused DNA binding domain, can achieve modulation of gene expression. Genes so modulated can be endogenous genes or exogenous genes. Modulation of gene expression can be in the form of activation (e.g., activating expression of GMT to increase levels of alpha tocopherol in plant oils). As described herein, activation of GMT can be achieved by using a fusion molecule comprising a GMT-targeted zinc finger protein and a functional domain. The functional domain (e.g., insulator domain, activation domain, etc.) enables increased and/or sustained expression of the target gene. Alternatively, modulation can be in the form of repression. For any such applications, the fusion molecule(s) and/or nucleic acids encoding one or more fusion molecules can be formulated with an acceptable carrier, to facilitate introduction into and/or expression in plant cells, as is known to those of skill in the art.

Polynucleotide and Polypeptide Delivery

The compositions described herein can be provided to the target cell in vitro or in vivo. In addition, the compositions can be provided as polypeptides, polynucleotides or combination thereof.

A. Delivery of Polynucleotides

In certain embodiments, the compositions are provided as one or more polynucleotides. Further, as noted above, a GMT-targeted zinc finger protein-containing composition can be designed as a fusion between a zinc finger polypeptide and a functional domain that is encoded by a fusion nucleic acid. In both fusion and non-fusion cases, the nucleic acid can be cloned into intermediate vectors for transformation into prokaryotic or eukaryotic (e.g., plant) cells for replication and/or expression. Intermediate vectors for storage or manipulation of the nucleic acid or production of protein can be prokaryotic vectors, (e.g., plasmids), shuttle vectors, insect vectors, or viral vectors for example. A nucleic acid encoding a GMT-targeted zinc finger protein can also cloned into an expression vector, for administration to a bacterial cell, fungal cell, protozoal cell, plant cell, or animal cell, preferably a plant cell.

To obtain expression of a cloned nucleic acid, it is typically subcloned into an expression vector that contains a promoter to direct transcription. Suitable bacterial and eukaryotic promoters are well known in the art and described, e.g., in Sambrook et al., supra; Ausubel et al., supra; and Kriegler, *Gene Transfer and Expression: A Laboratory Manual* (1990). Bacterial expression systems are available in, e.g., *E. coli*, *Bacillus* sp., and *Salmonella*. Palva et al. (1983) *Gene* 22:229-235. Kits for such expression systems are commercially available. Eukaryotic expression systems for mammalian cells, yeast, and insect cells are well known in the art and are also commercially available, for example, from Invitrogen, Carlsbad, Calif. and Clontech, Palo Alto, Calif.

Plant expression vectors and reporter genes are also generally known in the art. (See, e.g., Gruber et al. (1993) in *Methods of Plant Molecular Biology and Biotechnology*, CRC Press.) The construction and use of such plant expression systems can include in vitro and in vivo recombinant DNA techniques, and any other synthetic or natural recombination. (See, e.g., *Transgenic Plants: A Production System for Industrial and Pharmaceutical Proteins*, Owen and Pen eds., John Wiley & Sons, 1996; *Transgenic Plants*, Galun and Breiman eds, Imperial College Press, 1997; *Applied Plant Biotechnology*, Chopra, Malik, and Bhat eds., Science Publishers, Inc., 1999.)

A construct or vector can include a plant promoter to express a polypeptide of choice. Any nucleic acid molecule described herein can be operably linked to a promoter region which functions in a plant cell to cause the production of an mRNA molecule. For example, any promoter that functions in a plant cell to cause the production of an mRNA molecule, such as those promoters described herein, without limitation, can be used. In a preferred embodiment, the promoter is a plant promoter.

A number of promoters that are active in plant cells have been described in the literature. These include the nopaline synthase (NOS) promoter (Ebert et al., *Proc. Natl. Acad. Sci.* (U.S.A.) 84:5745-5749 (1987)), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324 (1987)) and the CaMV 35S promoter (Odell et al., *Nature* 313:810-812 (1985)), the figwort mosaic virus 35S-promoter, the light-inducible promoter from the small subunit of ribulose-1,5-bis-phosphate carboxylase (ssRUBISCO), the Adh promoter (Walker et al., *Proc. Natl. Acad. Sci.* (U.S.A.) 84:6624-6628 (1987)), the sucrose synthase promoter (Yang et al., *Proc. Natl. Acad. Sci.* (U.S.A.) 87:4144-4148 (1990)), the R gene complex promoter (Chandler et al., *The Plant Cell* 1:1175-1183 (1989)) and the chlorophyll a/b binding protein gene promoter, etc. These promoters have been used to create DNA constructs that have been expressed in plants; see, e.g., PCT publication WO 84/02913. The aforementioned promoters, as well as any promoter known or found to cause transcription of DNA in a plant cell, can be operably linked to a sequence encoding a GMT-targeted ZFP as disclosed herein.

For the purpose of expression in source tissues of the plant, such as the leaf, seed, root or stem, it is preferred that the promoters utilized have relatively high expression in these specific tissues; thereby providing tissue-specific expression of a GMT-targeted ZFP. For this purpose, one may choose from a number of promoters for genes with tissue- or cell-specific or enhanced expression. Examples of such promoters reported in the literature include the chloroplast glutamine synthetase GS2 promoter from pea (Edwards et al., *Proc. Natl. Acad. Sci. (U.S.A.)* 87:3459-3463 (1990)), the chloroplast fructose-1,6-biphosphatase (FBPase) promoter from wheat (Lloyd et al., *Mol. Gen. Genet.* 225:209-216 (1991)), the nuclear photosynthetic ST-LS1 promoter from potato (Stockhaus et al., *EMBO J* 8:2445-2451 (1989)), the serine/threonine kinase (PAL) promoter and the glucoamylase (CHS) promoter from *Arabidopsis thaliana*. Also reported to be active in photosynthetically active tissues are the ribulose-1,5-bisphosphate carboxylase (RbcS) promoter from eastern larch (*Larix laricina*), the promoter for the cab gene, cab6, from pine (Yamamoto et al., *Plant Cell Physiol.* 35:773-778 (1994)), the promoter for the Cab-1 gene from wheat (Fejes et al., *Plant Mol. Biol.* 15:921-932 (1990)), the promoter for the CAB-1 gene from spinach (Lubberstedt et al., *Plant Physiol.* 104:997-1006 (1994)), the promoter for the cab1R gene from rice (Luan et al., *Plant Cell.* 4:971-981 (1992)), the pyruvate, orthophosphate dikinase (PPDK) promoter from corn (Matsuoka et al., *Proc. Natl. Acad. Sci. (U.S.A.)* 90: 9586-9590 (1993)), the promoter for the tobacco Lhcb1*2 gene (Cerdan et al., *Plant Mol. Biol.* 33:245-255 (1997)), the *Arabidopsis thaliana* SUC2 sucrose-H+ symporter promoter (Truernit et al., *Planta.* 196:564-570 (1995)) and the promoter for the thylakoid membrane proteins from spinach (psaD, psaF, psaE, PC, FNR, atpC, atpD, cab, rbcS). Other promoters for the chlorophyll a/b-binding proteins can also be utilized, such as the promoters for LhcB gene and PsbP gene from white mustard (Sinapis alba; Kretsch et al., *Plant Mol. Biol.* 28:219-229 (1995)).

For the purpose of expression in sink tissues of the plant, such as the tuber of the potato plant, the fruit of tomato, or the seed of corn, wheat, rice and barley, it is preferred that promoters utilized for expression of a ZFP-encoding sequence have relatively high expression in these specific tissues. A number of promoters for genes with tuber-specific or tuber-enhanced expression are known, including the class I patatin promoter (Bevan et al., *EMBO J.* 8:1899-1906 (1986); Jefferson et al., *Plant Mol. Biol.* 14:995-1006 (1990)), the promoter for the potato tuber ADPGPP genes, both the large and small subunits, the sucrose synthase promoter (Salanoubat and Belliard, *Gene* 60:47-56 (1987), Salanoubat and Belliard, *Gene* 84:181-185 (1989)), the promoter for the major tuber proteins including the 22 kd protein complexes and protease inhibitors (Hannapel, *Plant Physiol.* 101:703-704 (1993)), the promoter for the granule-bound starch synthase gene (GBSS) (Visser et al., *Plant Mol. Biol.* 17:691-699 (1991)) and other class I and II patatins promoters (Koster-Topfer et al., *Mol. Gen. Genet.* 219:390-396 (1989); Mignery et al., *Gene.* 62:27-44 (1988)).

Other promoters can also be used to express a polypeptide in specific tissues, such as seeds or fruits. In certain embodiments, the promoter used is a seed specific promoter. Examples of such promoters include the 5' regulatory regions from such genes as napin (Kridl et al., *Seed Sci. Res.* 1:209:219 (1991)), phaseolin (Bustos, et al., *Plant Cell*, 1(9):839-853 (1989)), soybean trypsin inhibitor (Riggs, et al., *Plant Cell* 1(6):609-621 (1989)), ACP (Baerson, et al., *Plant Mol. Biol.*, 22(2):255-267 (1993)), stearoyl-ACP desaturase (Slocombe, et al., *Plant Physiol.* 104(4):167-176 (1994)), soybean a' subunit of b-conglycinin (soy 7s, (Chen et al., *Proc. Natl. Acad. Sci.*, 83:8560-8564 (1986))), and oleosin (see, for example, Hong, et al., *Plant Mol. Biol.*, 34(3):549-555 (1997)). Further examples include the promoter for β-conglycinin (Chen et al., *Dev. Genet.* 10: 112-122 (1989)). Also included are the zeins, which are a group of storage proteins found in corn endosperm. Genomic clones for zein genes have been isolated (Pedersen et al., *Cell* 29:1015-1026 (1982), and Russell et al., *Transgenic Res.* 6(2):157-168) and the promoters from these clones, including the 15 kD, 16 kD, 19 kD, 22 kD, and 27 kD genes, could also be used. Other promoters known to function, for example, in corn include the promoters for the following genes: waxy, Brittle, Shrunken 2, Branching enzymes I and II, starch synthases, debranching enzymes, oleosins, glutelins and sucrose synthases. A particularly preferred promoter for corn endosperm expression is the promoter for the glutelin gene from rice, more particularly the Osgt-1 promoter (Zheng et al., *Mol. Cell Biol.* 13:5829-5842 (1993)). Examples of promoters suitable for expression in wheat include those promoters for the ADP glucose pyrosynthase (ADPGPP) subunits, the granule bound and other starch synthase, the branching and debranching enzymes, the embryogenesis-abundant proteins, the gliadins and the glutenins. Examples of such promoters in rice include those promoters for the ADPGPP subunits, the granule bound and other starch synthase, the branching enzymes, the debranching enzymes, sucrose synthases and the glutelins. A exemplary promoter is the promoter for rice glutelin, Osgt-1. Examples of such promoters for barley include those for the ADPGPP subunits, the granule bound and other starch synthase, the branching enzymes, the debranching enzymes, sucrose synthases, the hordeins, the embryo globulins and the aleurone specific proteins. A preferred promoter for expression in the seed is a napin promoter. Another preferred promoter for expression is an Arcelin5 promoter.

Root specific promoters may also be used. An example of such a promoter is the promoter for the acid chitinase gene (Samac et al., *Plant Mol. Biol.* 25:587-596 (1994)). Expression in root tissue can also be accomplished by utilizing the root specific subdomains of the CaMV 35S promoter that have been identified (Lam et al., *Proc. Natl. Acad. Sci. (U.S.A.)* 86:7890-7894 (1989)). Other root cell-specific promoters include those reported by Conkling et al. (Conkling et al., *Plant Physiol.* 93:1203-1211 (1990)).

Additional promoters that can be utilized are described, for example, in U.S. Pat. Nos. 5,378,619; 5,391,725; 5,428,147; 5,447,858; 5,608,144; 5,614,399; 5,633,441; 5,633,435; and 4,633,436. In addition, a tissue specific enhancer can be used (Fromm et al., *The Plant Cell* 1:977-984 (1989)).

In certain embodiments, the promoter used to direct expression of the nucleic acid of choice depends on the particular application. For example, a strong constitutive promoter can be used for expression and purification. In contrast, when a protein is to be used in vivo, either a constitutive or an inducible promoter is used, depending on the particular use of the protein. In addition, a weak promoter can be used, when low but sustained levels of protein are required. The promoter typically can also include elements that are responsive to transactivation, e.g., hypoxia response elements and small molecule control systems such as tet-regulated systems and the RU-486 system. See, e.g., Gossen et al. (1992) *Proc. Natl. Acad. Sci USA* 89:5547-5551; Oligino et al.(1998) *Gene Ther.* 5:491-496; Wang et al. (1997) *Gene Ther.* 4:432-441; Neering et al. (1996) *Blood* 88:1147-1155; and Rendahl et al. (1998) *Nat. Biotechnol.* 16:757-761.

Promoters suitable for use in plant expression systems include, but are not limited to, viral promoters such as the 35S RNA and 19S RNA promoters of cauliflower mosaic virus (CaMV) (Brisson et al. (1984) *Nature* 310:511-514, Example 1); the coat protein promoter of TMV (Takamatsu et al (1987) *EMBO J.* 6:307-311); plant promoters such as the small subunit of RUBISCO (Coruzzi et al (1984) *EMBO J.* 3:1671-1680; Broglie et al. (1984) *Science* 224:838-843; plant heat shock promoters, e.g., soybean hsp17.5-E or hsp17.3-B (Gurley et al. (1986) *Cell. Biol.* 6:559-565) may be used. Other examples of promoters that may be used in expression vectors comprising nucleotides encoding GMT-targeted ZFPs include the promoter for the small subunit of ribulose-1,5-bis-phosphate carboxylase; promoters from tumor-inducing plasmids of *Agrobacterium tumefaciens*, the nopaline synthase (NOS) and octopine synthase promoters; the RUBISCO promoter; bacterial T-DNA promoters such as mas and ocs promoters; or the figwort mosaic virus 35S promoter or others such as CaMV 19S (Lawton et al. (1987) *Plant Molecular Biology* 9:315-324), nos (Ebert et al. (1987) *Proc. Natl. Acad. Sci. USA* 84:5745-5749), Adh1 (Walker et al. (1987) *Proc. Natl Acad. Sci. USA* 84:6624-6628), sucrose synthase (Yang et al. (1990) *Proc. Natl. Acad. Sci. USA* 87:4144-4148), alpha-tubulin, ubiquitin, actin (Wang et al. (1992) *Mol. Cell. Biol.* 12:3399), cab (Sullivan et al. (1989) *Mol. Gen. Genet.* 215:431), PEPCase (Hudspeth et al. (1989) *Plant Molecular Biology* 12:579-589) or those associated with the R gene complex (Chandler et al. (1989) *The Plant Cell* 1:1175-1183). Further suitable promoters include the Z10 promoter from a gene encoding a 10 kD zein protein, a Z27 promoter from a gene encoding a 27 kD zein protein, inducible promoters, such as the light inducible promoter derived from the pea rbcS gene (Coruzzi et al. (1971) *EMBO J.* 3:1671) and the actin promoter from rice (McElroy et al. (1990) *The Plant Cell* 2:163-171); seed specific promoters, such as the phaseolin promoter from beans, may also be used (Sengupta-Gopalan et al. (1985) *Proc. Natl. Acad. Sci. USA.* 83:3320-3324). Other suitable plant promoters are known to those of skill in the art.

Furthermore, additional promoters can be employed as described herein as many, if not all, genes have promoter regions capable of regulating gene expression. Additional promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide pairs. In addition to promoter sequences, enhancer sequences can also influence the level of gene expression. Some isolated promoter sequences can provide for gene expression of heterologous DNAs, that is a DNA different from the native or homologous DNA.

Thus, novel tissue-specific promoter sequences may be employed. cDNA clones from a particular tissue are isolated and those clones that are expressed specifically in that tissue are identified, for example, using Northern blotting. Preferably, the gene isolated is not present in a high copy number, but is relatively abundant in specific tissues. The promoter and control elements of corresponding genomic clones can then be localized using techniques well known to those of skill in the art.

In certain embodiments, the GMT-targeted ZFP polynucleotide sequence is under the control of the cauliflower mosaic virus (CaMV) 35S promoter. The caulimorvirus family has provided a number of exemplary promoters for transgene expression in plants, in particular, the (CaMV) 35S promoter. (See, e.g., Kay et al. (1987) *Science* 236:1299.) Additional promoters from this family such as the figwort mosaic virus promoter, the Commelina yellow mottle virus promoter, and the rice tungro bacilliform virus promoter have been described in the art, and may also be used in the methods and compositions disclosed herein. (See, e.g., Sanger et al. (1990) *Plant Mol. Biol.* 14:433-443; Medberry et al. (1992) *Plant Cell* 4:195-192; Yin and Beachy (1995) *Plant J.* 7:969-980.)

The promoters may be modified, if desired, to affect their control characteristics. For example, the CaMV 35S promoter may be ligated to the portion of the RUBISCO gene that represses the expression of RUBISCO in the absence of light, to create a promoter that is active in leaves, but not in roots. The resulting chimeric promoter may be used as described herein. Constitutive plant promoters such as actin and ubiquitin, having general expression properties known in the art may be used to express GMT-targeted ZFPs. (See, e.g., McElroy et al. (1990) *Plant Cell* 2:163-171; Christensen et al. (1992) *Plant Mol. Biol.* 18:675-689.)

Additionally, depending on the desired tissue, expression can be targeted to the endosperm, aleurone layer, embryo (or its parts, such as scutellum and cotyledons), pericarp, stem, leaves, tubers, roots, etc. Examples of known tissue-specific promoters include the tuber-directed class I patatin promoter, the promoters associated with potato tuber ADPGPP genes, the soybean promoter of β-conglycinin (7S protein) which drives seed-directed transcription, and seed-directed promoters from the zein genes of maize endosperm. (See, e.g., Bevan et al., 1986, *Nucleic Acids Res.* 14: 4625-38; Muller et al., 1990, *Mol. Gen. Genet.* 224: 136-46; Bray, 1987, *Planta* 172: 364-370; Pedersen et al., 1982, *Cell* 29: 1015-26.) Additional seed-specific promoters include the phaseolin and napin promoters.

In addition to a promoter, an expression vector typically contains a transcription unit or expression cassette that contains additional elements required for the expression of the nucleic acid in host cells, either prokaryotic or eukaryotic. A typical expression cassette thus contains a promoter operably linked, e.g., to the nucleic acid sequence, and signals required, e.g., for efficient polyadenylation of the transcript, transcriptional termination, ribosome binding, and/or translation termination.

The particular expression vector used to transport the genetic information into the cell is selected with regard to the intended use of the resulting ZFP polypeptide, e.g., expression in plants.

In addition, the recombinant constructs can include plant-expressible selectable or screenable marker genes for isolating, identifying or tracking of plant cells transformed by these constructs. Selectable markers include, but are not limited to, genes that confer antibiotic resistances (e.g., resistance to kanamycin or hygromycin) or herbicide resistance (e.g., resistance to sulfonylurea, phosphinothricin, or glyphosate). Screenable markers include, but are not limited to, the genes encoding beta-glucuronidase (Jefferson (1987) *Plant Molec Biol. Rep* 5:387-405), luciferase (Ow et al. (1986) *Science* 234:856-859), and the B and C1 gene products that regulate anthocyanin pigmnent production (Goff et al. (1990) *EMBO J* 9:2517-2522).

Thus, included within the terms selectable or screenable marker genes are also genes which encode a "secretable marker" whose secretion can be detected as a means of identifying or selecting for transformed cells. Examples include markers that encode a secretable antigen that can be identified by antibody interaction, or even secretable enzymes that can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

With regard to selectable secretable markers, the use of a gene that encodes a polypeptide that becomes sequestered in the cell wall, and which polypeptide includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extensin, or hydroxyproline rich glycoprotein (HPRG). The use of the maize HPRG (Stiefel et al. (1990) *The Plant Cell* 2:785-793 1990) is preferred as this molecule is well characterized in terms of molecular biology, expression, and protein structure. However, any one of a variety of extensins and/or glycine-rich wall proteins (Keller et al. (1989) *EMBO J.* 8:1309-1314) can be modified by the addition of an antigenic site to create a screenable marker.

Possible selectable markers for use in connection with the present disclosure include, but are not limited to, a neo gene (Potrykus et al. (1985) *Mol. Gen. Genet.* 199:183-188) which codes for kanamycin resistance and can be selected for using kanamycin, G418, and the like; a bar gene which codes for bialaphos resistance; a gene which encodes an altered EPSP synthase protein (Hinchee et al. (1988) *Bio/Technology* 6:915-922) thus conferring glyphosate resistance; a nitrilase gene such as bxn from *Klebsiella ozaenae* which confers resistance to bromoxynil (Stalker et al. (1988) *Science* 242: 419-423); a mutant acetolactate synthase gene (ALS) which confers resistance to imidazolinone, sulfonylurea or other ALS-inhibiting chemicals (European Patent Application 154, 204, 1985); a DHFR gene which confers methotrexate resistance (Thillet et al. (1988) *J Biol. Chem.* 263:12500-12508); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0 218 571, 1987).

Illustrative embodiments of selectable marker genes capable of being used in systems to select transformants are genes that encode the enzyme phosphinothricin acetyltransferase, such as the bar gene from Streptomyces hygroscopicus or the pat gene from Streptomyces viridochromogenes (U.S. Pat. No. 5,550,318, which is incorporated by reference herein). The enzyme phosphinothricin acetyl transferase (PAT) inactivates the active ingredient in the herbicide bialaphos, phosphinothricin (PPT). PPT inhibits glutamine synthetase, (Murakami et al. (1986) *Mol Gen. Genet.* 205:42-50; Twell et al., (1989) *Plant Physiol.* 91:1270-1274) causing rapid accumulation of ammonia and cell death. The success in using this selective system in conjunction with monocots was particularly surprising because of the major difficulties that have been reported in transformation of cereals (Potrykus (1989) *Trends Biotech.* 7:269-273).

Screenable markers that may be employed include, but are not limited to, a beta-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al. (1988) In: Chromosome Structure and Function: Impact of New Concepts, 18th Stadler Genetics Symposium, Jp. P. Gustafson and R. Appels, eds. (New York: Plenum Press) pp. 263-282); a beta-lactamase gene (Sutcliffe (1978) *Proc. Natl. Acad. Sci. USA* 75:3737-3741), which encodes an enzyme for which various chromogenic substrates are known (e.g., PADAC, a chromogenic cephalosporin); a xylE gene (Zukowsky et al. (1983) *Proc. Natl. Acad. Sci. USA.* 80:1101) which encodes a catechol dioxygenase that can convert chromogenic catechols; an alpha-amylase gene (Ikuta et al. (1990) *Bio/technology* 8:241-242); a tyrosinase gene (Katz et al. (1983) *J. Gen. Microbiol.* 129 (Pt. 9) 2703-2714) which encodes an enzyme capable of oxidizing tyrosine to DOPA and dopaquinone which in turn condenses to form the easily detectable compound melanin; a beta-galactosidase gene, which encodes an enzyme for which there are chromogenic substrates; a luciferase (lux) gene (Ow et al. (1986) *Science* 234:856-859), which allows for bioluminescence detection; an aequorin gene (Prasher et al. (1985) *Biochem. Biophys. Res. Comm.* 126:1259-1268), which may be employed in calcium-sensitive bioluminescence detection; and a green fluorescent protein gene (Niedz et al (1995) *Plant Cell Reports* 14:403).

Genes from the maize R gene complex are contemplated to be particularly useful as screenable markers. The R gene complex in maize encodes a protein that acts to regulate the production of anthocyanin pigments in most seed and plant tissue. Maize strains can have one, or as many as four, R alleles which combine to regulate pigmentation in a developmental and tissue specific manner. A gene from the R gene complex is useful for maize transformation, because the expression of this gene in transformed cells does not harm the cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively any genotype of maize can be utilized if the C1 and R alleles are introduced together. Anthocyanin pigments can be used as markers in plants other than maize. See, for example, Lloyd et al. (1992) *Science* 258: 1773-1775. Hence, alleles of the maize R gene and the genes involved in maize anthhocyanin biosynthesis are useful in a wide variety of plants.

R gene regulatory regions can be employed in chimeric constructs in order to provide mechanisms for controlling the expression of chimeric genes. More diversity of phenotypic expression is known at the R locus than at any other locus (Coe et al. (1988) in Corn and Corn Improvement, eds. Sprague, G. F. & Dudley, J. W. (Am. Soc. Agron., Madison, Wis.), pp. 81-258). Regulatory regions obtained from regions 5' to the structural R gene can be used in directing the expression of genes involved in, e.g., insect resistance, drought resistance, herbicide tolerance or other protein coding regions. For the purposes of the present disclosure, any of the various R gene family members can be employed (e.g., P, S, Lc, etc.). However, a preferred member will generally be Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker is firefly luciferase, encoded by the lux gene. The presence of the lux gene in transformed cells can be detected using, for example, X-ray film, scintillation counting, fluorescent spectrophotometry, low-light video cameras, photon counting cameras or multiwell luminometry. This system can be developed for populational screening for bioluminescence, such as on tissue culture plates, or even for whole plant screening.

Elements of the present disclosure are exemplified through the use of particular marker genes. However in light of this disclosure, numerous other possible selectable and/or screenable marker genes will be apparent to those of skill in the art in addition to the one set forth herein. Therefore, it will be understood that the foregoing discussion is exemplary rather than exhaustive. In light of the techniques disclosed herein and the general recombinant techniques known in the art, it is possible to introduce any gene, including those encoding marker genes and/or GMT-targeted ZFPs, into a recipient cell to generate a transformed plant cell, e.g., a dicot or a monocot cell.

Other elements that are optionally included in expression vectors also include a replicon that functions in *E. coli* (or in a prokaryotic or eucaryotic host other than *E. coli*), a selective marker that functions in a prokaryotic or eucaryotic host, e.g., a gene encoding antibiotic resistance, to permit selection of cells that harbor recombinant plasmids, and unique restriction sites in nonessential regions of the vector to allow insertion of recombinant sequences.

Standard transfection methods can be used to produce bacterial, mammalian, yeast, insect, and other cell lines or, preferably, plants that express GMT-targeted zinc finger proteins, which can be purified, if desired, using standard techniques. See, e.g., Colley et al. (1989) *J. Biol. Chem.* 264:17619-17622; and *Guide to Protein Purification, in Methods in Enzymology*, vol. 182 (Deutscher, ed.) 1990. Transformation of non-plant eukaryotic cells and prokaryotic cells is performed according to standard techniques. See, e.g., Morrison (1977) *J. Bacteriol.* 132:349-351; Clark-Curtiss et al. (1983) in *Methods in Enzymology* 101:347-362 (Wu et al., eds), Sambrook, supra and Ausubel, supra.

Transformation systems for plants are also known. (See, e.g., Weissbach & Weissbach, *Methods for Plant Molecular Biology*, Academic Press, NY, Section VIII, pp. 421-463 (1988); Grierson & Corey, *Plant Molecular Biology*, 2d Ed., Blackie, London, Ch. 7-9 (1988)). For example, *Agrobacterium* is often successfully employed to introduce nucleic acids into plants. Such transformation preferably uses binary *Agrobacterium* T-DNA vectors which can be used to transform dicotyledonous plants, monocotyledonous plants and plant cells (Bevan (1984) *Nuc. Acid Res.* 12:8711-8721; Horsch et al. (1985) *Science* 227:1229-1231; Bevan et al. (1982) *Ann. Rev. Genet* 16:357-384; Rogers et al. (1986) *Methods Enzymol.* 118:627-641; Hemalsteen et al. (1984) *EMBO J* 3:3039-3041). In embodiments that utilize the *Agrobacterium* system for transforming plants, the recombinant DNA constructs typically comprise at least the right T-DNA border sequence flanking the DNA sequences to be transformed into the plant cell. In preferred embodiments, the sequences to be transferred are flanked by the right and left T-DNA border sequences. The design and construction of such T-DNA based transformation vectors are well known to those skilled in the art.

Other gene transfer and transformation methods include, but are not limited to, protoplast transformation through calcium-, polyethylene glycol (PEG)- or electroporation-mediated uptake of naked DNA (see Paszkowski et al. (1984) *EMBO J* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338: 274-276); electroporation of plant tissues (D'Halluin et al. (1992) Plant Cell 4:1495-1505); microinjection, silicon carbide mediated DNA uptake (Kaeppler et al. (1990) *Plant Cell Reporter* 9:415-418), microprojectile bombardment (see Klein et al. (1983) *Proc. Nat. Acad. Sci. USA* 85:4305-4309; and Gordon-Kamm et al. (1990) *Plant Cell* 2:603-618); direct gene transfer, in vitro protoplast transformation, plant virus-mediated transformation, liposome-mediated transformation, vacuum infiltration (Bechtold et al. (1998) *Methods Mol. Biol.* 82:259-266 (1998); Clough et al. (1998) *Plant J,* 16(6): 735-743; and Ye et al. (1999) *Plant J.* 19(3): 249-257) and ballistic particle acceleration. See, e.g., Paszkowski et al. (1984) *EMBO J.* 3:2717-2722; U.S. Pat. Nos. 4,684,611; 4,407,956; 4,536,475; Crossway et al., (1986) *Biotechniques* 4:320-334; Riggs et al (1986) *Proc. Natl. Acad. Sci USA* 83:5602-5606; Hinchee et al. (1988) *Biotechnology* 6:915-921; U.S. Pat. No. 4,945,050.

A wide variety of host cells, plants and plant cell systems can be used, including, but not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, canola) and plants used for experimental purposes (e.g., *Arabidopsis*).

GMT-targeted ZFPs and the resulting gene product(s) the ZFP modulates (GMT and downstream products such as tocopherol) can also be produced from seed by way of seed-based production techniques using, for example, canola (rape seed), corn, soybeans, rice and barley seed, and the GMT-targeted ZFP, and/or sequences encoding it, can be recovered during seed germination. See, e.g., PCT Publication Numbers WO 99/40210; WO 99/16890; WO 99/07206; U.S. Pat. No. 5,866,121; and U.S. Pat. No. 5,792,933; and all references cited therein.

B. Delivery of Polypeptides

In additional embodiments, GMT-targeted ZFPs or fusion proteins comprising GMT-targeted ZFPs are administered directly to target plant cells. In certain in vitro situations, the target cells are cultured in a medium containing a fusion protein comprising one or more functional domains fused to one or more of the GMT-targeted ZFPs described herein. An important factor in the administration of polypeptide compounds in plants is ensuring that the polypeptide has the ability to traverse a cell wall. However, proteins, viruses, toxins, ballistic methods and the like have the ability to translocate polypeptides across a plant cell wall.

For example, "plasmodesmata" is the term given to the structures involved in cell-to-cell transport of endogenous and viral proteins and ribonucleoprotein complexes (RNPCs) in plants. Examples of viruses which can be linked to a GMT-targeted plant zinc finger polypeptide (or fusion containing the same) for facilitating its uptake into plant cells (optionally via plasmodesmata) include tobacco mosaic virus (Oparka et al. (1997) *Plant J.* 12:781-789); rice phloem thioredoxin (Ishiwatari et al. (1998) *Planta* 205:12-22); potato virus X (Cruz et al. (1998) *Plant Cell* 10:495-510) and the like. Other suitable chemical and/or biochemical moieties that provide enhanced cellular uptake (such as, for example, membrane translocation peptides and signal peptides) can also be linked, either covalently or non-covalently, to the ZFPs. Toxin molecules also have the ability to transport polypeptides across cell walls.

Particle-mediated delivery techniques (e.g., ballistic injection) as described above regarding nucleic acids can also be used to introduce polypeptides into a plant cell.

Production and Characterization of Stable Transgenic Plants

Techniques for generating transgenic plants are known in the art (see, e.g., Swain W F (1991) *TIBTECH* 9: 107-109; Ma J K C et al. (1994) *Eur J Immunology* 24: 131-138; Hiatt A et al. (1992) *FEBS Letters* 307:71-75; Hein M B et al. (1991) *Biotechnology Progress* 7:455-461; Duering K (1990) *Plant Molecular Biology* 15: 281-294). Non-limiting examples of transformation procedures are described herein and include *agrobacterium*-mediated transformation, microinjection, particle bombardment, and vacuum infiltration.

Typically, after effecting delivery of a polynucleotide to recipient plant cells by any of the methods discussed above, successfully transformed cells are identified for further culturing and plant regeneration. As mentioned above, in order to improve the ability to identify transformants, one may desire to employ a selectable or screenable marker gene as, or in addition to, the expressible sequence. In this case, one would then generally assay the potentially transformed cell population by exposing the cells to a selective agent or agents, or one would screen the cells for the desired marker gene trait.

A. Selection

An exemplary embodiment of methods for identifying successfully transformed cells involves exposing the recipient cultures to a selective agent, such as a metabolic inhibitor, an antibiotic, herbicide or the like. Cells that have been transformed and have stably integrated a marker gene conferring resistance to the selective agent used, will grow and divide in culture. Sensitive cells will not be amenable to further culturing.

To use the bar-bialaphos or the EPSPS-glyphosate selective system, tissue is cultured for about 0-28 days on nonselective medium and subsequently transferred to medium containing from about 1-3 mg/l bialaphos or about 1-3 mM glyphosate, as appropriate. While ranges of about 1-3 mg/l bialaphos or about 1-3 mM glyphosate will typically be preferred, it is proposed that ranges of at least about 0.1-50 mg/l bialaphos or at least about 0.1 -50 mM glyphosate will find utility in the practice of the present disclosure. Tissue can be placed on any porous, inert, solid or semi-solid support, including but not limited to filters and solid culture medium. Bialaphos and glyphosate are provided as non-limiting examples of agents suitable for selection of transformants.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants. In a similar fashion, the introduction of the C1 and B genes will result in pigmented cells and/or tissues.

The enzyme luciferase is also useful as a screenable marker in the context of the present disclosure. In the presence of the substrate luciferin, cells expressing luciferase emit light that can be detected on photographic or x-ray film, in a luminometer (or liquid scintillation counter), by devices that enhance night vision, or by a highly light sensitive video camera, such as a photon counting camera. All of these assays are nondestructive and transformed cells can be cultured further following identification. The photon counting camera is especially valuable as it allows one to identify specific cells or groups of cells that are expressing luciferase and manipulate those in real time.

It is further contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective growth inhibition of transformants and nontransformants alike, thus causing the selection technique to be ineffective. Selection with a growth inhibiting compound, such as bialaphos or glyphosate at concentrations below those that cause 100% inhibition, followed by screening of growing tissue for expression of a screenable marker gene such as e.g. luciferase, would allow the recovery of transformants from cell or tissue types that are not amenable to selection alone. Combinations of selection and screening will enable the identification of transformants in a wider variety of cell and tissue types.

B. Regeneration and Seed Production

Cells that survive the exposure to the selective agent, or cells that have been scored positive in a screening assay, can be cultured in media that supports regeneration of plants, for example dicamba or 2,4-D, NAA, NAA+2,4-D and/or picloram. Tissue is preferably maintained on a basic medium with growth regulators (optionally agar) until sufficient tissue is available to begin plant regeneration efforts, or following repeated rounds of manual selection, until the morphology of the tissue is suitable for regeneration; then transferred to medium conducive to maturation of embryoids. Shoot development typically signals the time to transfer to medium lacking growth regulator.

The transformed cells, identified by selection or screening and cultured in an appropriate medium that supports regeneration, are then allowed to mature into plants. After the regenerating plants have reached the stage of shoot and root development, they can be transferred to a greenhouse for further growth and testing.

Mature plants are then obtained from cell lines that are known to express the GMT-targeted ZFP. If possible, the regenerated plants are self-pollinated. In addition, pollen obtained from the regenerated plants is crossed to seed grown plants of agronomically important inbred lines. In some cases, pollen from plants of these inbred lines is used to pollinate regenerated plants. The trait is genetically characterized by evaluating the segregation of the trait in first-generation and later generation progeny. The heritability and expression in plants of traits selected in tissue culture are of particular importance if the traits are to be commercially useful.

Regenerated plants can be repeatedly crossed to inbred plants in a process known as backcross conversion. When a sufficient number of crosses to the recurrent inbred parent have been completed in order to produce a product of the backcross conversion process that is substantially isogenic with the recurrent inbred parent except for the presence of the introduced polynucleotide sequence(s), the plant is self-pollinated at least once in order to produce a homozygous backcross converted inbred. Progeny of these plants are true breeding and the weight percentage of alpha tocopherol in a plant part, e.g., the seeds, is compared to the weight percentage of alpha tocopherol in the recurrent parent inbred, in the field under a range of environmental conditions. Methods of determining weight percentages are well known in the art.

Alternatively, seed from transformed monocot or dicot plants regenerated from transformed tissue cultures is grown in the field and self-pollinated to generate true breeding plants.

Seed from the fertile transgenic plants can then be evaluated for the presence and/or expression of GMT and/or alpha tocopherol. A substantial activation of the production of GMT is an increase in the activity of GMT per cell and/or an increase in the weight percent of GMT and/or alpha tocopherol, preferably at least 2-fold (or any integral value above 2-fold), more preferably at least 5-fold (or any integral value above 5-fold), even more preferably at least 20-fold (or any integral value above 20-fold) and even more preferably at least 100-fold (or any integral value above 100-fold) or more, as compared the levels normally present in a non-transformed or non-transgenic plant.

Once a transgenic plant (e.g., seed) expressing the GMT-targeted ZFP sequence and having an increase in GMT expression and/or alpha tocopherol levels is obtained, seeds can be used to develop true breeding plants. The true breeding plants are used to develop a line of plants exhibiting increased expression of GMT and/or higher alpha tocopherol levels.

C. Determination of Stably Transformed Plant Tissues

To confirm the presence of a ZFP as described herein within the regenerating plants, or seeds or progeny derived from the regenerated plant, a variety of assays can be performed. Such assays include, for example, molecular biological assays well known to those of skill in the art, such as Southern (DNA) and Northern (RNA) blotting, nuclease protection, PCR, RT-PCR and real-time PCR (e.g. Taqman®); biochemical assays, such as detecting the presence of a protein product, e.g., by immunological means (ELISAs and Western blots) or by enzymatic function; assays for the presence of a metabolite (e.g., α-, β- or γ-tocopherol); plant part assays, such as leaf, seed or root assays; and also, by analyzing the phenotype of the whole regenerated plant.

Whereas DNA analysis techniques may be conducted using DNA isolated from any part of a plant, RNA may only be expressed in particular cells or tissue types and hence it may be necessary to prepare RNA for analysis from particular tissues. PCR techniques can be used for detection and quantitation of RNA produced from introduced polynucleotide(s). For example, GMT mRNA can be detected by real-time PCR, e.g., TaqMan® analysis. In the use of PCR for analysis of RNA, it is first necessary to reverse transcribe RNA into DNA, using enzymes such as reverse transcriptase, and then through the use of conventional PCR techniques amplify the DNA (e.g., RT-PCR). In most instances PCR techniques, while useful, will not demonstrate integrity of the RNA product. Further information about the nature of the RNA product can be obtained by RNA ("Northern") blotting. This technique will demonstrate the presence of an RNA species and give information about the integrity of that RNA. The presence or absence of an RNA species can also be determined using dot or slot blot hybridizations.

Expression of GMT itself may also be evaluated by specifically identifying GMT, alpha tocopherol, or by evaluating the phenotypic changes brought about by their expression. Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Very frequently the expression of a gene product is determined by evaluating the phenotypic results of its expression. These assays also may take many forms including but not limited to analyzing changes in the chemical composition, morphology, or physiological properties of a plant, plant tissue or plant cell.

Thus, GMT-targeted ZFP (or fusion polypeptides comprising the GMT-targeted ZFPs described herein) can be used to modulate GMT expression in plant cells, thereby optimizing vitamin E content of the crop (e.g., by providing a higher percentage of alpha tocopherol). GMT-targeted ZFPs can be targeted to the coding region, regions outside of the GMT coding region and, in certain embodiments, to regions outside of known regulatory region(s) of the gene. In these embodiments, additional molecules, exogenous and/or endogenous, can optionally be used to facilitate repression or activation of gene expression. The additional molecules can also be fusion molecules, for example, fusions between a ZFP and a functional domain such as an activation or repression domain. See, for example, WO 0/41566.

Applications in the Production of Feed and Oil

Any of the plants or parts thereof, disclosed herein, can be processed to produce a feed, meal, protein, or oil preparation, including oil preparations high in total tocopherol content and oil preparations high in any one or more of each tocopherol component listed herein (e.g., α-, β- γ- or δ-tocopherol). A particularly preferred plant part for this purpose is a seed. In a preferred embodiment, the feed, meal, protein or oil preparation is designed for livestock animals or humans, or both. Methods to produce feed, meal, protein and oil preparations are known in the art. See, for example, U.S. Pat. Nos. 4,957,748; 5,100,679; 5,219,596; 5,936,069; 6,005,076; 6,146,669 and 6,156,227. In a preferred embodiment, the protein preparation is a high protein preparation. Such a high protein preparation preferably has a protein content of greater than 5% w/v (or any integral value greater than 5%), more preferably 10% w/v (or any integral value greater than 10%), and even more preferably 15% w/v (or any integral value greater than 15%). In a preferred oil preparation, the oil preparation is a high oil preparation with an oil content derived from a plant or part thereof, as disclosed herein, of greater than 5% w/v (or any integral value greater than 5%), more preferably 10% w/v (or any integral value greater than 10%), and even more preferably 15% w/v (or any integral value greater than 15%). In a preferred embodiment the oil preparation is a liquid and of a volume greater than 1, 5, 10 or 50 liters. The present disclosure provides for oil produced from plants as disclosed herein or generated by a method disclosed herein. Such an oil may exhibit enhanced oxidative stability. Also, such oil may be a minor or major component of any resultant product. Moreover, such oil may be blended with other oils. In a preferred embodiment, the oil produced according to the methods and compositions disclosed herein and/or from plants as disclosed herein constitutes greater than 0.5%, 1%, 5%, 10%, 25%, 50%, 75% or 90% by volume or weight of the oil component of any product. In another embodiment, the oil preparation may be blended and can constitute greater than 10%, 25%, 35%, 50% or 75% of the blend by volume. Oil produced from a plant as disclosed herein can be admixed with one or more organic solvents or petroleum distillates.

Additional Applications

Tocopherols are an important component of mammalian diets. Epidemiological evidence indicates that tocopherol supplementation can result in decreased risk for cardiovascular disease and cancer, can aid in immune function, and is associated with prevention or retardation of a number of degenerative disease processes in humans (Traber and Sies, *Annu. Rev. Nutr.* 16:321-347 (1996)). Tocopherol functions, in part, by stabilizing the lipid bilayer of biological membranes (Skrypin and Kagan, *Biochim. Biophys. Acta* 815:209 (1995); Kagan, *N.Y Acad. Sci.* p 121, (1989); Gomez-Femandez et al., *Ann. N.Y. Acad. Sci.* p 109 (1989)), reducing polyunsaturated fatty acid (PUFA) free radicals generated by lipid oxidation (Fukuzawa et al., *Lipids* 17: 511-513 (1982)), and scavenging oxygen free radicals, lipid peroxy radicals and singlet oxygen species (Diplock et al. *Ann. N Y Acad. Sci.* 570: 72 (1989); Fryer, *Plant Cell Environ.* 15(4):381-392 (1992)).

Tocopherols are primarily synthesized only by plants and certain other photosynthetic organisms, including cyanobacteria. As a result, mammalian dietary tocopherols are obtained almost exclusively from these sources. Plant tissues vary considerably in total tocopherol content and tocopherol composition, with α-tocopherol the predominant tocopherol species found in green, photosynthetic plant tissues. Leaf tissue can contain from 10-50 μg of total tocopherols per gram fresh weight, but most of the world's major staple crops (e.g., rice, maize, wheat, potato) produce low to extremely low levels of total tocopherols, of which only a small percentage is α-tocopherol (Hess, Vitamin E, α-tocopherol, *In Antioxidants in Higher Plants*, R. Alscher and J. Hess, Eds., CRC Press, Boca Raton. pp. 111-134 (1993)). Oil seed crops generally contain much higher levels of total tocopherols, but (x-tocopherol is present only as a minor component in most oilseeds (Taylor and Barnes, *Chemy Ind., October*:722-726 (1981)).

The recommended daily dietary intake of 15-30 mg of vitamin E is difficult to achieve from the average American diet. For example, it would take over 750 grams of spinach leaves in which α-tocopherol comprises 60% of total tocopherols, or 200-400 grams of soybean oil to satisfy this recommended daily vitamin E intake. While it is possible to augment the diet with supplements, most of these supplements contain primarily synthetic vitamin E, having six stereoisomers, whereas natural vitamin E is predominantly composed of only a single isomer. Furthermore, supplements tend to be relatively expensive, and the general population is disinclined to take vitamin supplements on a regular basis. Accordingly, consumption of plant foodstuffs, in which modulation of GMT expression has resulted in production of increased alpha tocopherol levels, will improve human health.

In addition to the health benefits of tocopherols, increased α-tocopherol levels in crops have been associated with enhanced stability and extended shelf life of plant products (Peterson, *Cereal-Chem.* 72(1):21-24 (1995); Ball, *Fat-soluble vitamin assays in food analysis. A comprehensive review*, London, Elsevier Science Publishers Ltd. (1988)). Further, tocopherol supplementation of swine, beef, and poultry feeds has been shown to significantly increase meat quality and extend the shelf life of post-processed meat products by retarding post-processing lipid oxidation, which contributes to the undesirable flavor components (Sante and Lacourt, *J. Sci. Food Agric.* 65(4):503-507 (1994); Buckley et al., *J. of Animal Science* 73:3122-3130 (1995)).

All references cited herein are hereby incorporated by reference in their entirety for all purposes.

The following examples are presented as illustrative of, but not limiting, the claimed subject matter.

EXAMPLES

Example 1

Production of Modified Plant Zinc Finger Binding Proteins

This example describes a strategy to select amino acid sequences for plant zinc finger backbones from among existing plant zinc finger sequences, and subsequent conceptual modification of the selected plant zinc finger amino acid sequences to optimize their DNA binding ability. Oligonucleotides used in the preparation of polynucleotides encoding proteins containing these zinc fingers in tandem array are then described.

A. Selection of Plant Zinc Finger Backbones

A search was conducted for plant zinc fingers whose backbone sequences (i.e., the portion of the zinc finger outside of the −1 through +6 portion of the recognition helix) resembled that of the SP-1 consensus sequence described by Berg (1992) *Proc. Natl. Acad. Sci. USA* 89:11,109-11,110. The sequences selected included the two conserved cysteine residues, a conserved basic residue (lysine or arginine) located two residues to the C-terminal side of the second (i.e. C-terminal) cysteine, a conserved phenylalanine residue located two residues to the C-terminal side of the basic residue, the two conserved histidine residues, and a conserved arginine residue located two residues to the C-terminal side of the first (i.e., N-terminal) conserved histidine. The amino acid sequences of these selected plant zinc finger backbones (compared to the SP-1 consensus sequence) are shown below, with conserved residues shown in bold and X referring to residues located at positions −1 through +6 in the recognition helix (which will differ among different proteins depending upon the target sequence):

```
SP-1 consensus:
    YKCPECGKSFSXXXXXXXXHQRTHTGEKP    (SEQ ID NO: 10)

F1:
KKKSKGHECPICFRVFKXXXXXXXHKRSHTGEKP  (SEQ ID NO: 11)

F2
    YKCTVCGKSFSXXXXXXXXHKRLHTGEKP    (SEQ ID NO: 12)

F3
    FSCNYCQRKFYXXXXXXXHVRIH         (SEQ ID NO: 13)
       -5  -1    5
```

The first finger (F1) was chosen because it contained a basic sequence N-terminal to the finger that is also found adjacent to the first finger of SP-1. The finger denoted F1 is a Petunia sequence, the F2 and F3 fingers are *Arabidopsis* sequences.

B. Modification of Plant Zinc Finger Backbones

Two of the three plant zinc fingers (F1 and F3, above) were modified so that their amino acid sequences more closely resembled the sequence of SP-1, as follows. (Note that the sequence of SP-1 is different from the sequence denoted "SP-1 consensus.") In F3, the Y residue at position −2 was converted to a. G, and the sequence QNKK (SEQ ID NO: 14) was added to the C-terminus of F3. The QNKK sequence is present C-terminal to the third finger of SP-1, and permits greater flexibility of that finger, compared to fingers 1 and 2, which are flanked by the helix-capping sequence T G E K/R K/P (SEQ ID NO: 15). Such flexibility can be beneficial when the third finger is modified to contain a non-$C_2H_2$ structure. Finally, several amino acids were removed from the N-terminus of F1. The resulting zinc finger backbones had the following sequences:

```
KSKGHECPICFRVFKXXXXXXXHKRSHTGEKP    (SEQ ID NO: 16)

YKCTVCGKSFSXXXXXXXHKRLHTGEKP     (SEQ ID NO: 17)

FSCNYCQRKFGXXXXXXXHVRIHQNKK      (SEQ ID NO: 18)
```

Amino acid residues denoted by X, present in the recognition portion of these zinc fingers, are designed or selected depending upon the desired target site, according to methods disclosed, for example, in U.S. Pat. No. 6,453,242 and WO 00/41566 (the disclosures of which are hereby incorporated by reference), and/or references cited supra.

C. Nucleic Acid Sequences Encoding Backbones for Modified Plant ZFPs

The following polynucleotide sequences are used for design of a three-finger plant ZFP that contains the F1, F2 and F3 backbones described above. Polynucleotides encoding multi-finger ZFPs are designed according to an overlapping oligonucleotide method as described in, for example, U.S. Pat. No. 6,453,242 and WO 00/41566. Oligonucleotides H1, H2 and H3 (below) comprise sequences corresponding to the reverse complement of the recognition helices of fingers 1-3 respectively; accordingly, nucleotides denoted by N will vary depending upon the desired amino acid sequences of the recognition helices, which, in turn, will depend upon the nucleotide sequence of the target site. Oligonucleotides PB1, PB2 and PB3 encode the beta-sheet portions of the zinc fingers, which are common to all constructs. Codons used frequently in *Arabidopsis* and *E. coli* were selected for use in these oligonucleotides.

```
H1:
5'-CTC ACC GGT GTG AGA ACG CTT GT-            (SEQ ID NO: 19)
G NNN NNN NNN NNN NNN NNN NNN CTT
GAA AAC ACG GAA-3'

H2:
5'-TTC ACC AGT ATG AAG ACG CTT AT-            (SEQ ID NO: 20)
G NNN NNN NNN NNN NNN NNN NNN AGA
AAA AGA CTT ACC-3'

H3:
5'-CTT CTT GTT CTG GTG GAT ACG CAC GT-        (SEQ ID NO: 21)
G NNN NNN NNN NNN NNN NNN NNN
ACC GAA CTT ACG CTG-3'

PB1:
5'-AAGTCTAAGGGTCACGAGTGCCCAATCTGCTTCCGTGTTTTCAAG-3'       (SEQ ID NO: 22)

PB2:
5'-TCTCACACCGGTGAGAAGCCATACAAGTGCACTGTTTGTGGTAAGTCTTTTTCT-3'   (SEQ ID NO: 23)

PB3:
5'-CTTCATACTGGTGAAAAGCCATTCTCTTGCAACTACTGCCAGCGTAAGTTCGGT-3'   (SEQ ID NO: 24)
```

Briefly, these six oligonucleotides were annealed and amplified by polymerase chain reaction. The initial amplification product was reamplified using primers that were complementary to the initial amplification product and that also contained 5' extensions containing restriction enzyme recognition sites, to facilitate cloning. The second amplification product was inserted into a vector containing, for example, one or more functional domains, nuclear localization sequences, and/or epitope tags. See, for example, U.S. Pat. No. 6,453,242 and WO 00/41566.

Example 2

Construction of Vectors for Expression of Modified Plant ZFPs

Figure 1B:
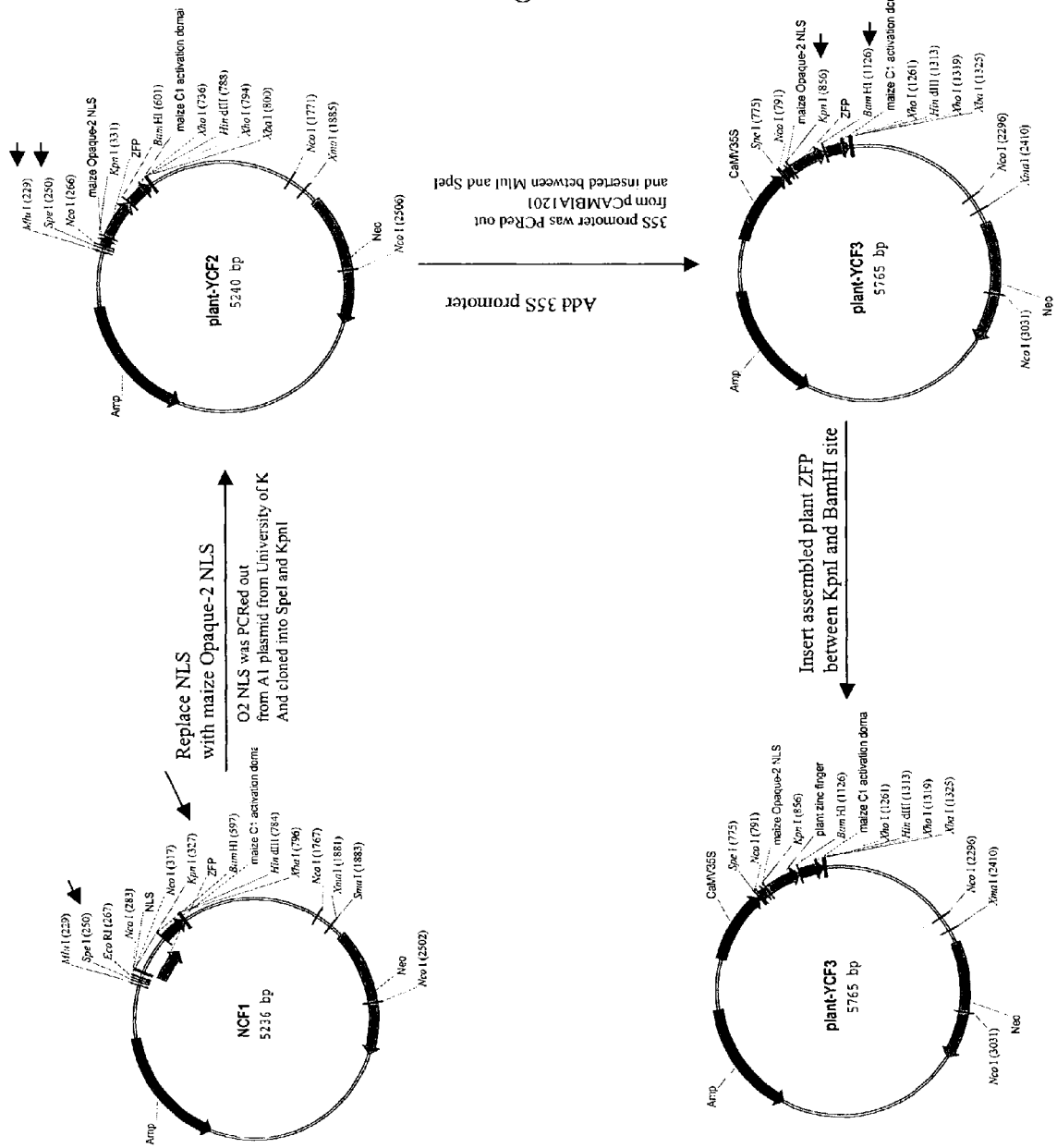

YCF3 was generated as shown schematically in FIG. 1. The starting construct was a plasmid containing a CMV promoter, a SV40 nuclear localization sequence (NLS), a ZFP DNA binding domain, a Herpesvirus VP16 transcriptional activation domain and a FLAG epitope tag (pSB5186-NVF). This construct was digested with SpeI to remove the CMV promoter. The larger fragment was gel-purified and self-ligated to make a plasmid termed GF1. GF1 was then digested with KpnI and HindIII, releasing sequences encoding the ZFP domain, the VP16 activation domain, and the FLAG epitope tag, then the larger fragment was ligated to a KpnI/HindIII fragment containing sequences encoding a ZFP binding domain and a VP16 activation domain, named GF2. This resulted in deletion of sequences encoding the FLAG tag from the construct.

GF2 was digested with BamHI and HindIII, releasing a small fragment encoding the VP16 activation domain, and the larger fragment was purified and ligated to a BamHI/HindIII digested PCR fragment containing the maize C1 activation domain (Goff et al. (1990) *EMBO J.* 9:2517-2522) (KpnI and HindIII sites were introduced into the PCR fragment through KpnI and HindIII site-containing primers) to generate NCF1. A PCR fragment containing a Maize Opaque-2 NLS was digested with SpeI/KpnI and ligated to the larger fragment from KpnI/SpeI digested NCF1 to produce YCF2. YCF2 was then digested with MluI and SpeI and the larger fragment was ligated to an MluI and SpeI digested PCR fragment containing the plant-derived CaMV 35S promoter (MluI and SpeI sites were introduced into the PCR fragment through MluI or SpeI site containing primers) to generate the YCF3 vector.

Sequences encoding GMT-targeted ZFP binding domains can be inserted, as KpnI/BamHI fragments, into KpnI/BamHI-digested YCF3 to generate constructs encoding ZFP-functional domain fusion proteins for modulation of gene expression in plant cells. For example, a series of *Arabidopsis* and *Brassica* GMT-ZFP domains, described in Examples 3 and 5 below, were inserted into KpnI/BamHI-digested YCF3 to generate expression vectors encoding GMT-ZFP-activation domain fusion polypeptides that enhance expression of plant (e.g., *Arabidopsis thaliana, Brassica*) GMT.

Example 3

Modified Plant ZFP Designs for Regulation of an *Arabidopsis thaliana* Gamma Tocopherol Methyltransferase (GMT) Gene GMT-targeted zinc finger proteins were designed to recognize various target sequences in the *Arabidopsis* GMT gene and upstream regions. The amino acid sequence of the GMT protein is disclosed at GenBank Accession Number AAD38271; and the mRNA sequence is disclosed at GenBank Accession No. AF104220. Sequences upstream of the GMT coding region were obtained from either the tair homepage (www.arabidopsis.com) or the NCBI sequence viewer at Reference No. At1G64970. Approximately 1.95 kbp of GMT upstream sequence is shown in FIG. 6. Table 1 shows the nucleotide sequences of the various GMT target sites, both within the gene and in the upstream region (see Example 11 for further details) and the amino acid sequences, of the −1 through +6 recognition regions of the zinc fingers, for a number of three-finger ZFPs that recognize these target sites. Sequences encoding these binding domains (AGMT ZFPs) were prepared as described in Example 1 and inserted into YCF3 as described in Example 2.

Example 4

Modulation of Expression of an *Arabidopsis thaliana* Gamma Tocopherol Methyltransferase (GMT) Gene

*Arabidopsis thaliana* protoplasts were prepared and transfected with plasmids encoding GMT-targeted ZFP-activation domain fusion polypeptides. Preparation of protoplasts and polyethylene glycol-mediated transfection were performed as described. Abel et al. (1994) *Plant Journal* 5:421-427. The different plasmids contained the GMT-targeted ZFP binding domains described in Table 1, inserted as KpnI/BamHI fragments into YCF3.

At 18 hours after transfection, RNA was isolated from transfected protoplasts, using an RNA extraction kit from Qiagen (Valencia, Calif.) according to the manufacturer's instructions. The RNA was then treated with DNase (Rnase-free), and analyzed for GMT mRNA content by real-time PCR (TaqMan®). Table 2 shows the sequences of the primers and probes used for TaqMan® analysis. Results for GMT mRNA levels were normalized to levels of 18S rRNA. These normalized results are shown in FIG. 2 as fold-activation of

TABLE 1

| ZFP# | Target | F1 | F2 | F3 |
|---|---|---|---|---|
| AGMT1 | GTGGACGAGT (SEQ ID NO: 25) | RSDNLAR (SEQ ID NO: 26) | DRSNLTR (SEQ ID NO: 27) | RSDALTR (SEQ ID NO: 28) |
| AGMT3 | TGGTGGGTGT (SEQ ID NO: 29) | RSDALTR (SEQ ID NO: 30) | RSDHLTT (SEQ ID NO: 31) | RSDHLTT (SEQ ID NO: 32) |
| AGMT4 | GAAGAGGATT (SEQ ID NO: 33) | QSSNLAR (SEQ ID NO: 34) | RSDNLAR (SEQ ID NO: 35) | QSGNLTR (SEQ ID NO: 36) |
| AGMT5 | GAGGAAGGGG (SEQ ID NO: 37) | RSDHLAR (SEQ ID NO: 38) | QSGNLAR (SEQ ID NO: 39) | RSDNLTR (SEQ ID NO: 40) |
| AGMT6 | TGGGTAGTC (SEQ ID NO: 41) | ERGTLAR (SEQ ID NO: 42) | QSGSLTR (SEQ ID NO: 43) | RSDHLTT (SEQ ID NO: 44) |
| AGMT7 | GGGGAAAGGG (SEQ ID NO: 45) | RSDHLTQ (SEQ ID NO: 46) | QSGNLAR (SEQ ID NO: 47) | RSDHLSR (SEQ ID NO: 48) |
| AGMT8 | GAAGAGGGTG (SEQ ID NO: 49) | QSSHLAR (SEQ ID NO: 50) | RSDNLAR (SEQ ID NO: 51) | QSGNLAR (SEQ ID NO: 52) |
| AGMT9 | GAGGAGGATG (SEQ ID NO: 53) | QSSNLQR (SEQ ID NO: 54) | RSDNALR (SEQ ID NO: 55) | RSDNLQR (SEQ ID NO: 56) |
| AGMT10 | GAGGAGGAGG (SEQ ID NO: 57) | RSDNALR (SEQ ID NO: 58) | RSDNLAR (SEQ ID NO: 59) | RSDNLTR (SEQ ID NO: 60) |
| AGMT11 | GTGGCGGCTG (SEQ ID NO: 61) | QSSDLRR (SEQ ID NO: 62) | RSDELQR (SEQ ID NO: 63) | RSDALTR (SEQ ID NO: 64) |
| AGMT12 | TGGGGAGAT (SEQ ID NO: 65) | QSSNLAR (SEQ ID NO: 66) | QSGHLQR (SEQ ID NO: 67) | RSDHLTT (SEQ ID NO: 68) |
| AGMT13 | GAGGAAGCT (SEQ ID NO: 69) | QSSDLRR (SEQ ID NO: 70) | QSGNLAR (SEQ ID NO: 71) | RSDNLTR (SEQ ID NO: 72) |
| AGMT14 | GCTTGTGGCT (SEQ ID NO: 73) | DRSHLTR (SEQ ID NO: 74) | TSGHLTT (SEQ ID NO: 75) | QSSDLTR (SEQ ID NO: 76) |
| AGMT15 | GTAGTGGATG (SEQ ID NO: 77) | QSSNLAR (SEQ ID NO: 78) | RSDALSR (SEQ ID NO: 79) | QSGSLTR (SEQ ID NO: 80) |
| AGMT16 | GTGTGGGATT (SEQ ID NO: 81) | QSSNLAR (SEQ ID NO: 82) | RSDHLTT (SEQ ID NO: 83) | RSDALTR (SEQ ID NO: 84) |

Figure 2:
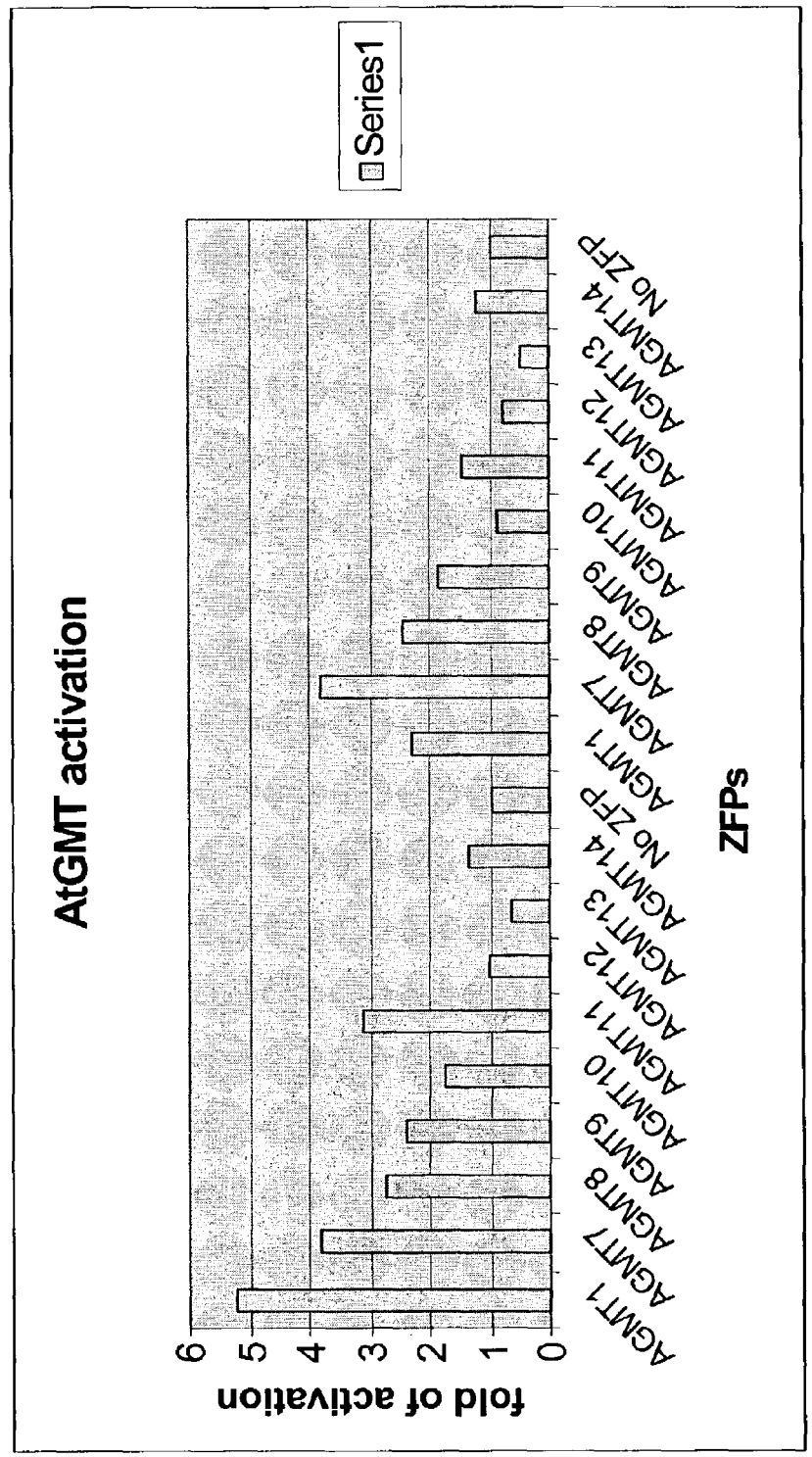
FIG. 2 shows the results of analysis of GMT mRNA in RNA isolated from *Arabidopsis thaliana* protoplasts transfected with constructs encoding fusion of a transcriptional activation domain with various *Arabidopsis* GMT-targeted plant ZFPs. Results are expressed as GMT mRNA normalized to 18S rRNA. AGMT numbers on the abscissa refer to the GMT-targeted plant ZFP binding domains shown in Table 1. Duplicate TaqMan® analyses are shown for each RNA sample.

GMT mRNA levels, compared to protoplasts transfected with carrier DNA (denoted "No ZFP" in FIG. 2). The results indicate that expression of the GMT gene was enhanced in protoplasts that were transfected with plasmids encoding fusions between a transcriptional activation domain and a GMT-targeted ZFP binding domain.

TABLE 2

| SEQUENCE | | |
|---|---|---|
| GMT forward primer | 5'-AATGATCTCGCGGCTGCT-3' | (SEQ ID NO: 85) |
| GMT reverse primer | 5'-GAATGGCTGATCCAACGCAT-3' | (SEQ ID NO: 86) |
| GMT probe | 5'-TCACTCGCTCATAAGGCTTCCTTCCAAGT-3' | (SEQ ID NO: 87) |
| 18S forward primer | 5'-TGCAACAAACCCCGACTTATG-3' | (SEQ ID NO: 88) |
| 18S reverse primer | 5'-CCCGCGTCGACCTTTTATC-3' | (SEQ ID NO: 89) |
| 18S probe | 5'-AATAAATGCGTCCCTT-3' | (SEQ ID NO: 90) |

Example 5

Modified Plant ZFP Designs for Regulation of a *Brassica napus* Gamma Tocopherol Methyltransferase (GMT) Gene GMT-targeted plant zinc finger proteins were designed to recognize various target sequences in the *Brassica napus* GMT gene (FIG. 7). See also WO 02/063022, the disclosure of which is hereby incorporated by reference for all purposes. Table 3 shows the nucleotide sequences of the various GMT target sites, and the amino acid sequences (−1 through +6 of the recognition region) of zinc fingers in a collection of three-finger ZFPs that recongnize the target sites (CGMT proteins). Sequences encoding these binding domains were prepared as described in Example 1 and inserted into YCF3 as described in Example 2.

Example 6

Modulation of Expression of a *Brassica napus* Gamma Tocopherol Methyltransferase (GMT) Gene

*Brassica nabus* protoplasts were prepared and transfected with plasmids encoding GMT-targeted ZFP-activation domain fusion polypeptides essentially as described in Example 4 except that the mannitol concentration was 0.55M (instead of 0.4M) and the concentration of protoplasts before transfection was $0.2 \times 10^6$ (instead of $1 \times 10^6$). The different plasmids contained the GMT-targeted ZFP binding domains described in Table 3, inserted as KpnI/BamnHI fragments into YCF3.

At 18 hours after transfection, RNA was isolated from transfected protoplasts, using an RNA extraction kit from Qiagen (Valencia, Calif.) according to the manufacturer's

TABLE 3

Figure 3:
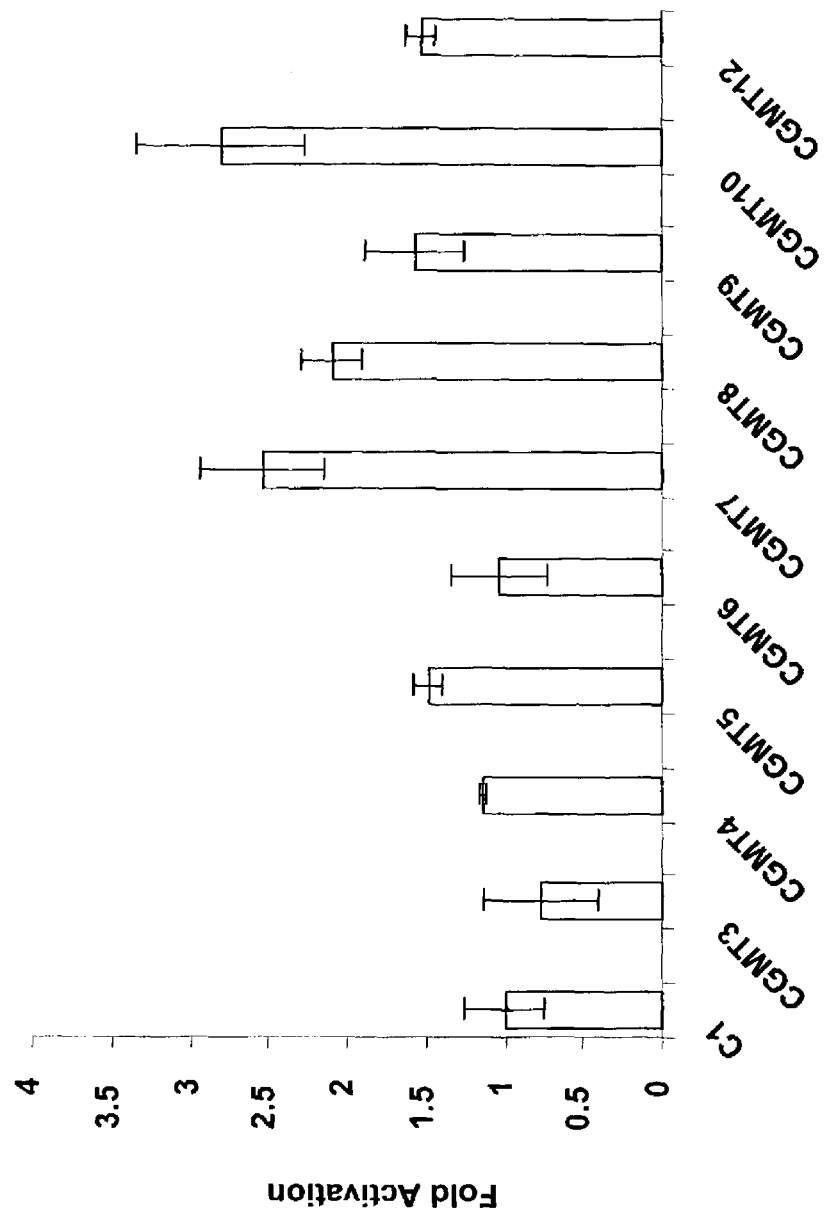
FIG. 3 shows the results of analysis of activation of GMT in *Brassica* protoplasts transfected with constructs encoding fusion of a transcriptional activation domain with various canola GMT-targeted plant ZFPs. RNA was isolated from *Brassica* protoplasts and results are expressed as fold activation of GMT mRNA as normalized to GAPDH RNA. Designations on the abscissa refer to the GMT-targeted plant ZFP binding domains shown in Table 3. C1 refers to an activation domain only.

| CGMT | Target | F1 | F2 | F3 |
|---|---|---|---|---|
| 3 | GATGCTGGT (SEQ ID NO: 91) | QSSHLAR (SEQ ID NO: 92) | QSSDLTR (SEQ ID NO: 93) | TSGNLTR (SEQ ID NO: 94) |
| 4 | GAGGAAGAT (SEQ ID NO: 95) | QSSNLAR (SEQ ID NO: 96) | QSGNLAR (SEQ ID NO: 97) | RSDNLTR (SEQ ID NO: 98) |
| 5 | GAAGAAGAG (SEQ ID NO: 99) | RSDNLAR (SEQ ID NO: 100) | QSGNLAR (SEQ ID NO: 101) | QSGNLAR (SEQ ID NO: 102) |
| 6 | GAGGTTGGA (SEQ ID NO: 103) | QSGHLAR (SEQ ID NO: 104) | TSGALTR (SEQ ID NO: 105) | RSDNLTR (SEQ ID NO: 106) |
| 7 | GATGATGAT (SEQ ID NO: 107) | QSSNLAR (SEQ ID NO: 108) | TSGNLTR (SEQ ID NO: 109) | TSGNLTR (SEQ ID NO: 110) |
| 8 | CGGGGAGAG (SEQ ID NO: 111) | RSSNLAR (SEQ ID NO: 112) | QSGHLQR (SEQ ID NO: 113) | RSDHLRE (SEQ ID NO: 114) |
| 9 | TAGTTGGAA (SEQ ID NO: 115) | QSGNLAR (SEQ ID NO: 116) | RSDALTT (SEQ ID NO: 117) | RSDNLTT (SEQ ID NO: 118) |
| 10 | GTAGAGGAC (SEQ ID NO: 119) | DRSNLTR (SEQ ID NO: 120) | RSDNLAR (SEQ ID NO: 121) | QSGSLTR (SEQ ID NO: 122) |
| 12 | GAGGTTGGC (SEQ ID NO: 123) | DRSHLTR (SEQ ID NO: 124) | TSGALTR (SEQ ID NO: 125) | RSDNLTR (SEQ ID NO: 126) | instructions. The RNA was then treated with DNase (RNase-free), and analyzed for GMT mRNA content by real-time PCR (TaqMan®). Table 4 shows the sequences of the primers and probe used for TaqMan® analysis. Results for GMT mRNA levels were normalized to levels of GAPDH mRNA. These normalized results are shown in FIG. 3 as fold-activation of GMT mRNA levels, compared to protoplasts transfected with DNA encoding an activation domain only (denoted, "C1" in FIG. 3). The results indicate that expression of the GMT gene was enhanced in canola (*Brassica*) protoplasts that were transfected with plasmids encoding fusions between a transcriptional activation domain and a GMT-targeted ZFP binding domain.

B. Transformation of *Arabidopsis thaliana*

Transformation was conducted essentially as described in Clough S J and Bent A F (1998) "Floral dip: a simplified method for *Agrobacterium*-mediated transformation of *Arabidopsis thaliana*" *Plant J.* 16:735-43. (See, also Bechtold, N., Ellis, J., and Pelletier, G. (1993) "In planta *Agrobacterium*-mediated gene transfer by infiltration of adult *Arabidopsis thaliana* plants" C. R. Acad. Sci. Paris, Life Sciences 316:1194-1199 and http://plantpath.wisc.edu/~afb/protocol.html, Jun. 11, 2001). Wild type *Arabidopsis* seedlings, Columbia ecotype, were grown under long days (16 hours light, 8 hours dark) at 22° C. in pots of Ready Earth soil less mixture covered with window screen material. When the

TABLE 4

| | SEQUENCE | |
|---|---|---|
| cGMT forward primer* | 5'-CAATGGAAAGCGGTGAGCATAT-3' | (SEQ ID NO: 127) |
| cGMT reverse primer | 5'-TCCTTCCTCCTGGAGCCG-3' | (SEQ ID NO: 128) |
| cGMT probe | 5'-CTGACAAGGCCAAGTTCGTGAAGGAATTG-3' | (SEQ ID NO: 129) |
| GAPDH forward primer | 5'-GATCATCAAGATTGTATCTGATC-3' | (SEQ ID NO: 130) |
| GAPDH reverse primer | 5'-CGGTTCCTTCGATAACTAAGTC-3' | (SEQ ID NO: 131) |
| GAPDH probe | 5'-CGGTTCCTTCGATAACTAAGTC-3' | (SEQ ID NO: 132) |

*"c" refers to canola

Example 7

Modulation of GMT Expression in Transgenic *Arabidopsis*

Transgenic *Arabidopsis* plants were prepared, and their GMT levels assayed, as follows.

A. *Agrobacterium* Preparation

*Agrobacterium* strain GV3101 was streaked on AB plates (1× AB salts (per liter, 1 g NH$_4$Cl; 300 mg MgSO$_4$; 150 mgKCl; 10 mg CaCl$_2$; 2.5 mg FeSO$_4$)+1× AB buffer (per liter, 3 g K$_2$HPO$_4$; 1.15g NaH$_2$PO$_4$; pH to 7.2)+0.2% glucose+15 g agar) and incubated at 30° C. for 2 days. A single colony was picked and used to inoculate 2 mL of liquid MG-LB medium (per liter, 10 g tryptone; 5 g yeast extract; 10 g mannitol; 1.9 g L-glutamic acid; 0.5 g KH$_2$PO$_4$; 0.2 g NaCl; 0.2 g MgSO$_4$.7H$_2$O, pH to 7.2). This culture was incubated overnight with shaking at 30° C.

The next morning, the 2 mL culture was used to inoculate 100 mL of liquid MG-LB medium and grown for 4 to 6 hours with shaking at 30° C. The culture was chilled on ice, transferred to a sterile centrifuge bottle and centrifuged at 4000×G at 4° C. for 5 minutes. The bacterial pellet was resuspended in 1 mL ALB medium (per liter, 10 g tryptone; 5 g yeast extract). 100 µL aliquots of the resuspended culture were placed into chilled 1.5 mL tubes and flash frozen in liquid nitrogen. The tubes were thawed on ice and 3 µL of the AGMT-ZFP plasmid DNA (AGMT5, AGMT6, AGMT7, AGMT8, AGMT 9 and AGMT 10) was mixed gently with the cells. The tubes were again flash frozen in liquid nitrogen and then allowed to thaw and incubate at 37° C. for 5 minutes. The cultures were then transferred to 2 mL of MG-LB medium and incubated with shaking for 3 hours at 30° C. After incubation, the cultures were pelleted by centrifugation, resuspend in 1 mL of 1× AB salts, and plated on AB minimal plates supplemented with 100 µg/mL kanamycin. The plates were incubated for 2 days at 30°. Single colonies were selected for transformation of *Arabidopsis thaliana* plants.

plants were approximately 4-6 weeks old, the primary flowering bolts were removed and the secondary bolts were allowed to emerge and grow until they were up to 10 cm long.

A single colony of transformed *Agrobacterium tumefaciens* containing each of the AGMT-ZFPs (see above) was grown in 2 mL of YEP (per liter, 10 g peptone; 10 g yeast extract; 5 g NaCl) plus 100 µg/mL kanamycin at 30° C. overnight. This 2 mL culture was used to inoculate a 500 mL culture of YEP plus 100 µg/mL kanamycin and again grown at 30° C. overnight. The resulting cultures were centrifuged at 5000×g at 4° C. for 15 minutes and the bacterial pellets were resuspended in 5% sucrose to an OD$_{600}$ of approximately 0.8. 0.05% Silwet L-77 (Sentre Chemical Company, Memphis, Tenn.) was added to the culture after resuspension. The plants were then dipped with a gentle agitation in the *Agrobacterium* solution for about 90 seconds. The pots were then placed in a tray under a plastic wrap cover to maintain high humidity for 16 to 24 hours. The plastic wrap was removed the next day and the plants were allowed to grow, mature and set seed. T0 seeds were collected and subjected to bialaphos selection.

C. Selection of Primary AGMT-ZFP Transformants of *Arabidopsis thaliana*

Each AGMT-ZFP vector contains the Bar gene which confers resistance to the herbicide bialaphos to use as a selection marker for transformation. T1 plants containing the AGMT-ZFPs were selected by resistance to the herbicide, as follows. See, also, Kobayashi et al. (1995) *Jpn J Genet* 70(3):409-422.

T0 seeds were sprinkled on top of Ready Earth soil-less mixture in 4" plastic pots and watered via subirrigation. The pots were then placed at 4° C. for vernalization. After 48 hours, the pots were removed from the cold and the seedlings were allowed to germinate and grow under longs days (16 hours light, 8 hours dark) at 22° C. After one week, the seedlings were sprayed until wet with a solution of 100 µg bialaphos plus 0.005% Silwet L-77. The plants were sprayed again 2 days later. After an additional week of growth, the T1 seedlings were apparent among the non-transformed plants as they grew green and healthy. The T1 seedlings were transferred to individual pots and allowed to grow until seed set.

For analysis of RNA abundance, leaves of 14-leaf T1 seedlings were harvested and ground in liquid nitrogen. Total RNA from the leaves was isolated using an RNeasy plant mini kit (Qiagen, Valencia, Calif.) according to the manufacturer's instructions. RNA analysis by real-time PCR (Taqman®) was performed in a 96-well format on an ABI 7700SDS instrument. Each RNA sample (25 ng total RNA) was combined with 0.3 μm of each primer, 0.1 μm probe, 5.5 mM $MgCl_2$, 0.3 mM each dNTP, 0.625 Units AmpliTaq Gold® polymerase, 6.25 Units reverse transcriptase and 5 Units of RNase inhibitor in Taqman Buffer A (Perkin Elmer). Reverse transcription was performed for 30 min. at 48° C. After denaturation for 10 min at 95° C., amplification reactions were conducted for 40 cycles of 95° C. for 15 sec. and 60° C. for 1 min. The primers and probes used for analysis of *Arabidopsis* GMT mRNA are shown in Table 2.

Figure 4:
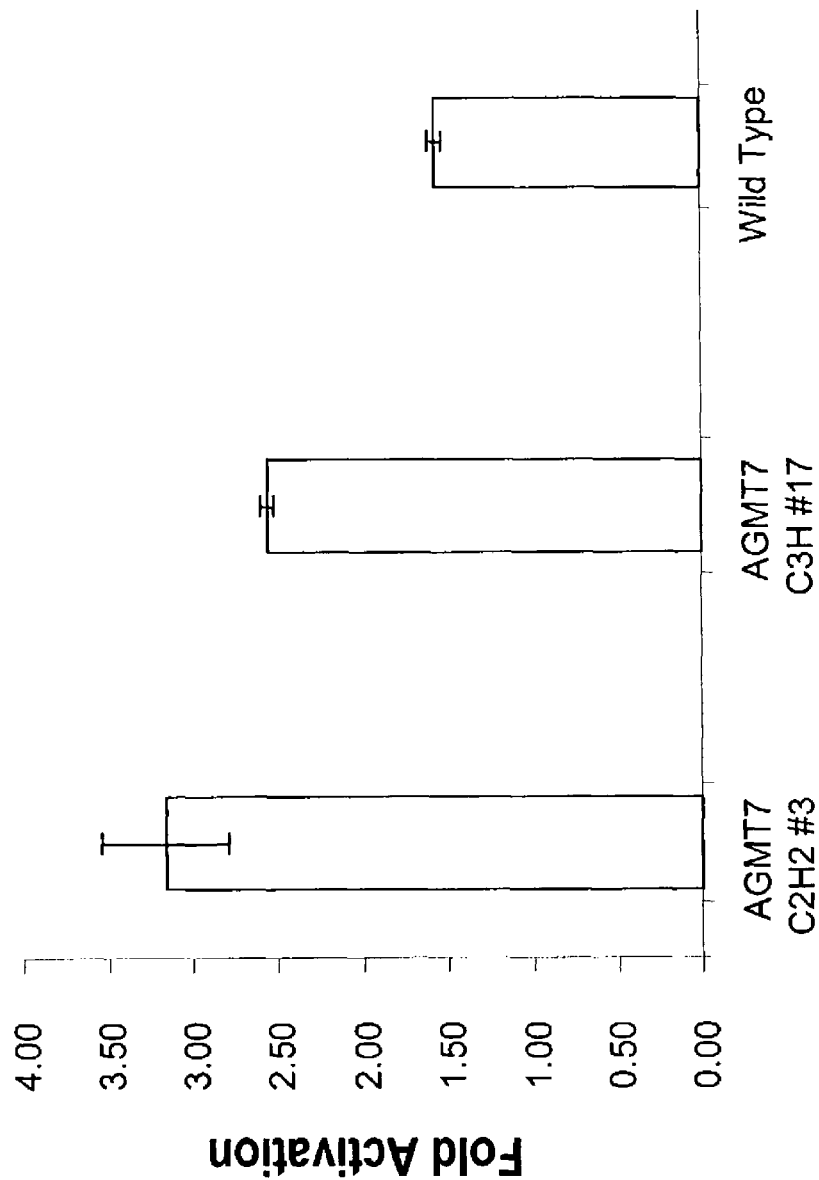
FIG. 4 shows the results of analysis of GMT mRNA in RNA isolated from transgenic *Arabidopsis thaliana* stably transformed with constructs encoding fusion of a transcriptional activation domain with an *Arabidopsis* GMT-targeted plant ZFP (AGMT-7). Results from individual plants are expressed as levels of GMT mRNA normalized to 18S rRNA. AGMT numbers on the abscissa refer to the GMT-targeted plant ZFP binding domains shown in Table 1 and include both canonical (C2H2) and non-canonical (C3H) recognition helices in a plant backbone. The average of duplicate TaqMan® analyses is shown for each RNA sample.
Figure 5:
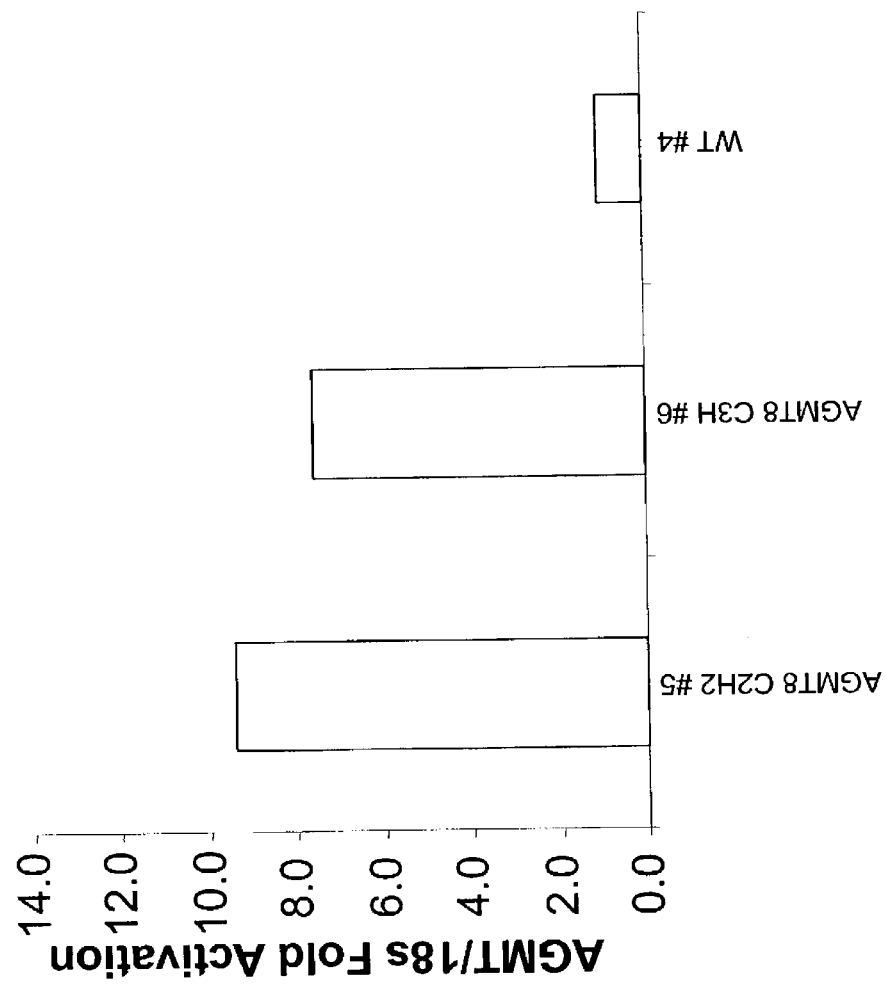
FIG. 5 shows the results of analysis of GMT mRNA in RNA isolated from transgenic *Arabidopsis thaliana* stably transformed with constructs encoding fusion of a transcriptional activation domain with an *Arabidopsis* GMT-targeted plant ZFP (AGMT-8). Results from individual plants are expressed as levels of GMT mRNA normalized to 18S rRNA. AGMT numbers on the abscissa refer to the GMT-targeted plant ZFP binding domains shown in Table 1 and include both canonical (C2H2) and non-canonical (C3H) recognition helices in a plant backbone. The average of duplicate TaqMan® analyses is shown for each RNA sample.

FIGS. 4 and 5 show the results of RNA analysis from these transgenic plants and demonstrate that GMT-targeted ZFPs can be used to create transgenic plants that overexpress GMT.

Example 8

Modulation of α-tocopherol Levels in Transgenic *Arabidopsis*

Constructs were prepared to direct expression of GMT-targeted zinc finger transcription factor sequences in Arabidopsis. The coding regions of AGMT 5, 6, 7, 8, 9, and 10 (see Example 3, Table 1) were removed from an intermediate plasmid by digestion with the restriction endonucleases NotI and HindIII and gel-purified using the "QIAquick Gel Extraction Kit" (QIAGEN Inc., Valencia, Calif.). These NotI/HindIII fragments also contained sequences encoding the C1 activation domain in frame with the ZFP-encoding sequences.

The napin promoter-containing binary vector pCGN9979 (See FIG. 8) was prepared by digesting with NotI and HindIII endonucleases. Enzymes were subsequently removed using "StrataClean Resin™" (Stratagene, La Jolla, Calif.) followed by "MicroSpin™S-400 HR Column" treatment (Pharmacia, Uppsala, Sweden). The ZFP insert was ligated into the NotI/HindIII-digested pCGN9979 vector. The resulting plasmids, containing genes encoding different GMT-targeted ZFPs in the plant binary transformation vector under the control of the napin embryo-specific promoter (Kridl et al., *Seed Sci. Res.* 1:209:219 (1991)), were labeled as follows: pMON67192 (encodes the AGMT7 ZFP), 67193 (encodes the AGMT8 ZFP), 67194 (encodes the AGMT9 ZFP), 67195 (encodes the AGMT10 ZFP), 67209 (encodes the AGMT5 ZFP) and 67248 (encodes the AGMT6 AFP).

Additionally, sequences encoding the AGMT7 ZFP (in frame with the C1 activation domain) were ligated into the 35S binary vector pCGN9977 (See FIG. 8), which was likewise previously prepared by digestion with NotI and HindIII endonucleases. The resulting plasmid, containing a gene encoding the AGMT7 ZFP in the plant binary transformation vector under the control of the 35S promoter (Lam et al., *Proc. Natl. Acad. Sci.* (*U.S.A*) 86:7890-7894 (1989)), was labeled pMON67203 (AGMT7).

The plant binary constructs described above were used in *Arabidopsis thaliana* plant transformation to direct the expression of ZFP coding sequences in transgenic *Arabidopsis* plants. Binary vector constructs were transformed into ABI strain *Agrobacterium* cells by the method of Holsters et al. *Mol. Gen. Genet.* 163:181-187 (1978). Transgenic *Arabidopsis thaliana* plants were obtained by *Agrobacterium*-mediated transformation as described by Valverkens et al., *Proc. Nat. Acad. Sci.* 85:5536-5540 (1988), Bent et al., *Science* 265:1856-1860 (1994), and Bechtold et al., *C. R. Acad. Sci., Life Sciences* 316:1194-1199 (1993). Transgenic plants were selected by sprinkling the transformed $T_1$ seeds directly onto soil and then vernalizing them at 4° C. in the absence of light for 4 days. The seeds were then transferred to 21° C., 16 hours light and sprayed with a 1:200 dilution of Finale (Basta) at 7 days and 14 days after seeding. Transformed plants were grown to maturity and the $T_2$ seed that was produced was analyzed for tocopherol content and composition according to the methods of Savidge et al. *Plant Physiology* 129: 321-332 (2002).

Results of the tocopherol analyses of T2 segregating seed are shown in Table 5. Tocopherol levels from transgenic plants harboring the 35S binary vector (pCGN9977) and the napin binary vector (pCGN9979) served as control values for these data. The average percent alpha-tocopherol in control seed was 1.0% (SD±0.19).

TABLE 5

| Pedigree | Construct | ZFP | Percent alpha-tocopherol | ng alpha toco./mg seed | ng gamma toco./mg seed | ng delta toco./mg seed | ng total toco./mg seed |
|---|---|---|---|---|---|---|---|
| 9977-AT00002:0002. | 9977 | none | 1.0 | 5.366834 | 498.8373 | 17.97528 | 522.1794 |
| 9977-AT00002:0001. | 9977 | none | 1.2 | 6.187854 | 510.304 | 19.11867 | 535.6105 |
| 9979-AT00002-11:@.0057. | 9979 | none | 1.5 | 7.300825 | 473.5709 | 16.29171 | 497.1635 |
| 9979-AT00002-11:@.0058. | 9979 | none | 1.2 | 6.165902 | 506.6412 | 17.27851 | 530.0856 |
| 9979-AT00002-11:@.0059. | 9979 | none | 1.2 | 6.299336 | 522.0054 | 19.33543 | 547.6401 |
| 9979-AT00002-11:@.0060. | 9979 | none | 1.1 | 5.874412 | 514.6812 | 17.77902 | 538.3346 |
| 9979-AT00002-11:@.0052. | 9979 | none | 1.2 | 6.043109 | 488.9328 | 19.50845 | 514.4843 |
| 9979-AT00002-11:@.0053. | 9979 | none | 0.9 | 4.926066 | 507.91 | 19.08846 | 531.9245 |
| 9979-AT00002-11:@.0054. | 9979 | none | 1.1 | 5.87757 | 520.9799 | 19.28981 | 546.1473 |
| 9979-AT00002-11:@.0061. | 9979 | none | 1.1 | 6.131828 | 516.0248 | 17.67938 | 539.836 |
| 9979-AT00002-11:@.0062. | 9979 | none | 1.2 | 6.331842 | 489.6971 | 17.92709 | 513.956 |
| 9979-AT00002-11:@.0056. | 9979 | none | 1.0 | 5.110125 | 505.1397 | 17.68305 | 527.9329 |
| 9979-AT00002-11:@.0064. | 9979 | none | 0.9 | 4.707543 | 506.9394 | 16.76739 | 528.4143 |
| 9979-AT00002-11:@.0063. | 9979 | none | 1.1 | 6.080769 | 513.3447 | 17.20391 | 536.6294 |
| 9979-AT00002-11:@.0068. | 9979 | none | 0.9 | 4.708477 | 509.9288 | 18.75534 | 533.3926 |
| 9979-AT00002-11:@.0067. | 9979 | none | 0.9 | 5.003342 | 520.3514 | 17.27921 | 542.634 |
| 9979-AT00002-51:@.0021. | 9979 | none | 0.9 | 4.974233 | 538.8947 | 21.96888 | 565.8378 |

TABLE 5-continued

| Pedigree | Construct | ZFP | Percent alpha-tocopherol | ng alpha toco./mg seed | ng gamma toco./mg seed | ng delta toco./mg seed | ng total toco./mg seed |
|---|---|---|---|---|---|---|---|
| 9979-AT00002-51:@.0022. | 9979 | none | 1.2 | 6.830187 | 540.8528 | 19.28383 | 566.9668 |
| 9979-AT00002-54:@.006. | 9979 | none | 0.9 | 4.813241 | 517.4411 | 17.35707 | 539.6115 |
| 9979-AT00002-54:@.007. | 9979 | none | 0.5 | 2.746544 | 519.757 | 19.46998 | 541.9735 |
| 9979-AT00002-11:@.0065. | 9979 | none | 0.7 | 3.704619 | 516.2277 | 17.43394 | 537.3662 |
| 9979-AT00002-11:@.0069. | 9979 | none | 0.7 | 3.859497 | 528.8631 | 16.55543 | 549.278 |
| 9979-AT00002-11:@.0072. | 9979 | none | 1.0 | 5.749024 | 542.3595 | 21.61421 | 569.7227 |
| 9979-AT00002-11:@.0073. | 9979 | none | 1.1 | 5.892664 | 525.9711 | 20.15092 | 552.0147 |
| 9979-AT00002-11:@.0074. | 9979 | none | 1.1 | 5.654187 | 510.5691 | 17.1232 | 533.3465 |
| 9979-AT00002-11:@.0075. | 9979 | none | 0.9 | 4.291789 | 485.0458 | 13.17424 | 502.5119 |
| 9979-AT00002-11:@.0076. | 9979 | none | 0.9 | 4.441188 | 470.5685 | 13.88574 | 488.8954 |
| 9979-AT00002-11:@.0077. | 9979 | none | 0.9 | 4.530983 | 470.2076 | 12.37014 | 487.1087 |
| 9979 | 9979 | none | 0.9 | 4.673195 | 478.74 | 21.83727 | 505.2505 |
| 9979 | 9979 | none | 0.8 | 4.046739 | 458.9283 | 23.29231 | 486.2674 |
| 67203-AT00002:0019. | 67203 | AGMT7 | 1.2 | 6.456146 | 518.0693 | 16.78881 | 541.3143 |
| 67203-AT00002:0006. | 67203 | AGMT7 | 1.2 | 6.821836 | 519.9235 | 19.25696 | 546.0023 |
| 67203-AT00002:0023. | 67203 | AGMT7 | 1.3 | 7.088371 | 536.5217 | 20.38964 | 563.9997 |
| 67203-AT00002:0021. | 67203 | AGMT7 | 1.3 | 7.30579 | 530.8464 | 20.61111 | 558.7633 |
| 67203-AT00002:0016. | 67203 | AGMT7 | 1.3 | 7.297616 | 528.2991 | 20.79472 | 556.3915 |
| 67203-AT00002:0007. | 67203 | AGMT7 | 1.3 | 7.480828 | 538.9235 | 21.46867 | 567.873 |
| 67203-AT00002:0011. | 67203 | AGMT7 | 1.3 | 7.448331 | 525.6754 | 19.92797 | 553.0517 |
| 67203-AT00002:0009. | 67203 | AGMT7 | 1.3 | 7.346842 | 517.1449 | 20.33798 | 544.8297 |
| 67203-AT00002:0015. | 67203 | AGMT7 | 1.4 | 7.847813 | 527.355 | 20.57655 | 555.7794 |
| 67203-AT00002:0014. | 67203 | AGMT7 | 1.4 | 7.545572 | 500.4691 | 20.13023 | 528.1449 |
| 67203-AT00002:0008. | 67203 | AGMT7 | 1.5 | 7.971544 | 519.5422 | 20.14195 | 547.6557 |
| 67203-AT00002:0012. | 67203 | AGMT7 | 1.5 | 8.057284 | 513.1941 | 18.02038 | 539.2718 |
| 67203-AT00002:0002. | 67203 | AGMT7 | 1.5 | 8.451939 | 535.8659 | 21.20712 | 565.5249 |
| 67203-AT00002:0010. | 67203 | AGMT7 | 1.6 | 8.783329 | 535.9021 | 21.74267 | 566.4281 |
| 67203-AT00002:0003. | 67203 | AGMT7 | 3.9 | 19.40358 | 468.0844 | 15.82054 | 503.3085 |
| 67203-AT00002:0022. | 67203 | AGMT7 | 4.0 | 19.36351 | 447.1754 | 14.84754 | 481.3865 |
| 67192-AT00002:0003. | 67192 | AGMT7 | 1.0 | 5.64092 | 521.0006 | 17.78871 | 544.4302 |
| 67192-AT00002:0004. | 67192 | AGMT7 | 1.3 | 6.973442 | 502.299 | 17.26257 | 526.535 |
| 67192-AT00002:0001. | 67192 | AGMT7 | 1.5 | 8.257101 | 510.8634 | 17.60309 | 536.7236 |
| 67192-AT00002:0012. | 67192 | AGMT7 | 2.2 | 11.11029 | 479.3307 | 19.46262 | 509.9036 |
| 67192-AT00002:0013. | 67192 | AGMT7 | 2.8 | 12.95365 | 427.0795 | 15.7201 | 455.7533 |
| 67192-AT00002:0011. | 67192 | AGMT7 | 3.1 | 14.69112 | 446.1682 | 20.25478 | 481.1141 |
| 67192-AT00002:0008. | 67192 | AGMT7 | 3.1 | 17.4513 | 519.9088 | 22.27846 | 559.6386 |
| 67192-AT00002:0006. | 67192 | AGMT7 | 3.4 | 15.75728 | 428.3939 | 14.52554 | 458.6767 |
| 67192-AT00002:0010. | 67192 | AGMT7 | 5.4 | 30.45396 | 513.2124 | 16.27228 | 559.9386 |
| 67192-AT00002:0002. | 67192 | AGMT7 | 9.0 | 45.79556 | 450.0719 | 13.52997 | 509.3974 |
| 67192-AT00002:0005. | 67192 | AGMT7 | 11.8 | 57.14258 | 417.5475 | 11.22179 | 485.9118 |
| 67192-AT00002:0007. | 67192 | AGMT7 | 12.8 | 54.63492 | 360.2564 | 11.42102 | 426.3124 |
| 67192-AT00002:0009. | 67192 | AGMT7 | 19.8 | 75.01104 | 294.1284 | 9.209545 | 378.349 |
| 67193-AT00002:0021. | 67193 | AGMT8 | 1.1 | 5.828819 | 491.6747 | 11.86887 | 509.3724 |
| 67193-AT00002:0013. | 67193 | AGMT8 | 1.4 | 6.829073 | 468.9173 | 10.41714 | 486.1635 |
| 67193-AT00002:0011. | 67193 | AGMT8 | 1.4 | 7.446827 | 506.0293 | 12.92017 | 526.3963 |
| 67193-AT00002:0010. | 67193 | AGMT8 | 1.4 | 7.634651 | 516.1219 | 11.81049 | 535.567 |
| 67193-AT00002:0027. | 67193 | AGMT8 | 1.4 | 7.516825 | 507.3381 | 12.26755 | 527.1225 |
| 67193-AT00002:0027. | 67193 | AGMT8 | 1.4 | 7.516825 | 507.3381 | 12.26755 | 527.1225 |
| 67193-AT00002:0029. | 67193 | AGMT8 | 1.5 | 8.087136 | 528.7185 | 20.51892 | 557.3245 |
| 67193-AT00002:0029. | 67193 | AGMT8 | 1.5 | 8.087136 | 528.7185 | 20.51892 | 557.3245 |
| 67193-AT00002:0028. | 67193 | AGMT8 | 1.5 | 8.039417 | 521.8643 | 20.03431 | 549.938 |
| 67193-AT00002:0028. | 67193 | AGMT8 | 1.5 | 8.039417 | 521.8643 | 20.03431 | 549.938 |
| 67193-AT00002-1:@. | 67193 | AGMT8 | 1.5 | 6.894725 | 448.0334 | 9.996367 | 464.9244 |
| 67193-AT00002:0015. | 67193 | AGMT8 | 1.5 | 9.545339 | 614.4004 | 15.75685 | 639.7025 |
| 67193-AT00002:0026. | 67193 | AGMT8 | 1.5 | 8.138147 | 517.786 | 13.32594 | 539.2501 |
| 67193-AT00002:0026. | 67193 | AGMT8 | 1.5 | 8.138147 | 517.786 | 13.32594 | 539.2501 |
| 67193-AT00002:0008. | 67193 | AGMT8 | 1.5 | 7.61878 | 483.1284 | 11.02061 | 501.7678 |
| 67193-AT00002:0025. | 67193 | AGMT8 | 1.5 | 7.695632 | 484.0676 | 11.77428 | 503.5375 |
| 67193-AT00002:0025. | 67193 | AGMT8 | 1.5 | 7.695632 | 484.0676 | 11.77428 | 503.5375 |
| 67193-AT00002:0018. | 67193 | AGMT8 | 1.5 | 8.216321 | 511.2826 | 14.7906 | 534.2895 |
| 67193-AT00002:0016. | 67193 | AGMT8 | 1.5 | 8.132132 | 507.8143 | 12.52671 | 528.4732 |
| 67193-AT00002:0022. | 67193 | AGMT8 | 1.5 | 7.517034 | 469.3582 | 11.06654 | 487.9418 |
| 67193-AT00002:0014. | 67193 | AGMT8 | 1.5 | 7.972343 | 495.1879 | 14.18323 | 517.3435 |
| 67193-AT00002:0005. | 67193 | AGMT8 | 1.5 | 7.188283 | 446.7586 | 10.37737 | 464.3242 |
| 67193-AT00002:0009. | 67193 | AGMT8 | 1.6 | 7.681328 | 474.3848 | 11.02567 | 493.0918 |
| 67193-AT00002:0024. | 67193 | AGMT8 | 1.6 | 7.66989 | 471.743 | 11.43526 | 490.8482 |
| 67193-AT00002:0024. | 67193 | AGMT8 | 1.6 | 7.66989 | 471.743 | 11.43526 | 490.8482 |
| 67193-AT00002:0007. | 67193 | AGMT8 | 1.6 | 6.818068 | 417.0578 | 8.51423 | 432.3901 |
| 67193-AT00002:0017. | 67193 | AGMT8 | 1.6 | 8.159261 | 484.3607 | 10.96223 | 503.4822 |
| 67193-AT00002:0023. | 67193 | AGMT8 | 1.7 | 7.821458 | 452.7247 | 11.43721 | 471.9833 |
| 67193-AT00002:0020. | 67193 | AGMT8 | 1.7 | 9.20318 | 511.9599 | 21.17125 | 542.3343 |
| 67193-AT00002:0006. | 67193 | AGMT8 | 1.7 | 8.554496 | 471.5054 | 11.34364 | 491.4035 |
| 67193-AT00002:0012. | 67193 | AGMT8 | 1.8 | 8.15091 | 446.5283 | 10.31871 | 464.9979 |
| 67193-AT00002:0002. | 67193 | AGMT8 | 1.8 | 7.645335 | 413.1175 | 9.669136 | 430.4319 |
| 67193-AT00002:0019. | 67193 | AGMT8 | 1.8 | 9.296898 | 500.9426 | 12.71749 | 522.957 |

TABLE 5-continued

| Pedigree | Construct | ZFP | Percent alpha-tocopherol | ng alpha toco./mg seed | ng gamma toco./mg seed | ng delta toco./mg seed | ng total toco./mg seed |
|---|---|---|---|---|---|---|---|
| 67193-AT00002:0003. | 67193 | AGMT8 | 2.1 | 8.504101 | 391.805 | 8.743615 | 409.0527 |
| 67193-AT00002:0004. | 67193 | AGMT8 | 2.1 | 8.191602 | 370.685 | 11.66403 | 390.5406 |
| 67194-AT00002:0012. | 67194 | AGMT9 | 1.8 | 10.79321 | 575.1213 | 27.90332 | 613.8178 |
| 67194-AT00002:0009. | 67194 | AGMT9 | 1.8 | 9.659837 | 513.1325 | 23.41763 | 546.21 |
| 67194-AT00002-4:@. | 67194 | AGMT9 | 2.1 | 11.89942 | 540.2132 | 26.34586 | 578.4585 |
| 67194-AT00002:0013. | 67194 | AGMT9 | 2.1 | 10.63811 | 470.8163 | 22.34907 | 503.8035 |
| 67194-AT00002:0010. | 67194 | AGMT9 | 2.2 | 10.43597 | 444.17 | 17.00089 | 471.6069 |
| 67194-AT00002-2:@. | 67194 | AGMT9 | 2.3 | 11.59268 | 468.6614 | 20.27799 | 500.5321 |
| 67194-AT00002-3:@. | 67194 | AGMT9 | 2.3 | 12.64086 | 503.6159 | 26.06139 | 542.3182 |
| 67194-AT00002:0007. | 67194 | AGMT9 | 2.3 | 11.52096 | 462.6215 | 19.35805 | 493.5005 |
| 67194-AT00002:0008. | 67194 | AGMT9 | 2.3 | 11.40906 | 456.6562 | 17.71749 | 485.7828 |
| 67194-AT00002:0005. | 67194 | AGMT9 | 2.5 | 10.59122 | 398.4139 | 13.00738 | 422.0126 |
| 67194-AT00002:0011. | 67194 | AGMT9 | 2.7 | 13.23345 | 453.3107 | 15.41229 | 481.9564 |
| 67194-AT00002:0006. | 67194 | AGMT9 | 3.2 | 14.70703 | 426.481 | 14.40909 | 455.5971 |
| 67195-AT00002-1:@. | 67195 | AGMT10 | 1.3 | 6.703724 | 504.704 | 18.21746 | 529.6252 |
| 67195-AT00002-3:@. | 67195 | AGMT10 | 1.3 | 6.852619 | 507.7522 | 17.42615 | 532.031 |
| 67195-AT00002:0020. | 67195 | AGMT10 | 1.3 | 6.727767 | 490.6688 | 15.16044 | 512.557 |
| 67195-AT00002-8:@. | 67195 | AGMTT0 | 1.5 | 8.017698 | 509.3505 | 18.36896 | 535.7372 |
| 67195-AT00002:0025. | 67195 | AGMT10 | 1.8 | 9.485004 | 505.4105 | 16.55682 | 531.4524 |
| 67195-AT00002-2:@. | 67195 | AGMT10 | 2.3 | 11.54356 | 482.6744 | 18.02384 | 512.2418 |
| 67195-AT00002-13:@. | 67195 | AGMT10 | 2.4 | 11.88921 | 465.6642 | 16.51018 | 494.0636 |
| 67195-AT00002-16:@. | 67195 | AGMTT0 | 2.5 | 13.18958 | 496.7596 | 18.0188 | 527.968 |
| 67195-AT00002-14:@. | 67195 | AGMT10 | 2.5 | 11.54534 | 434.1089 | 14.61205 | 460.2663 |
| 67195-AT00002:0018. | 67195 | AGMT10 | 2.6 | 11.24305 | 406.3564 | 12.44661 | 430.0461 |
| 67195-AT00002:0019. | 67195 | AGMT10 | 2.7 | 14.27686 | 488.258 | 19.83586 | 522.3707 |
| 67195-AT00002-7:@. | 67195 | AGMT10 | 2.8 | 14.21028 | 471.3492 | 16.58054 | 502.14 |
| 67195-AT00002:0022. | 67195 | AGMT10 | 3.0 | 15.63457 | 493.1855 | 16.35003 | 525.1701 |
| 67195-AT00002:0023. | 67195 | AGMT10 | 3.1 | 17.46871 | 518.8368 | 20.74723 | 557.0527 |
| 67195-AT00002:0024. | 67195 | AGMT10 | 3.3 | 15.33742 | 437.4806 | 14.05917 | 466.8772 |
| 67195-AT00002-12:@. | 67195 | AGMT10 | 3.4 | 18.0103 | 496.2832 | 18.82132 | 533.1148 |
| 67195-AT00002:0021. | 67195 | AGMT10 | 3.5 | 18.9232 | 506.1765 | 17.99567 | 543.0954 |
| 67195-AT00002-17:@. | 67195 | AGMT10 | 3.7 | 19.13428 | 487.4689 | 15.6879 | 522.291 |
| 67195-AT00002-4:@. | 67195 | AGMT10 | 3.7 | 16.40702 | 410.0247 | 15.61339 | 442.0451 |
| 67195-AT00002-5:@. | 67195 | AGMT10 | 4.2 | 20.74123 | 456.1185 | 17.22584 | 494.0856 |
| 67195-AT00002-9:@. | 67195 | AGMT10 | 4.5 | 21.42422 | 434.493 | 16.84467 | 472.7618 |
| 67195-AT00002-6:@. | 67195 | AGMT10 | 5.5 | 26.96608 | 449.9448 | 15.75884 | 492.6697 |
| 67209-AT00002:0009. | 67209 | AGMT5 | 1.3 | 6.523129 | 497.5241 | 16.87045 | 520.9177 |
| 67209-AT00002:0005. | 67209 | AGMT5 | 1.3 | 6.866733 | 506.6264 | 14.73554 | 528.2287 |
| 67209-AT00002:0001. | 67209 | AGMT5 | 1.3 | 6.854235 | 501.6383 | 18.06956 | 526.5621 |
| 67209-AT00002:0008. | 67209 | AGMT5 | 1.3 | 7.379161 | 524.0302 | 21.13477 | 552.5441 |
| 67209-AT00002:0006. | 67209 | AGMT5 | 1.5 | 7.85297 | 509.6949 | 17.61663 | 535.1645 |
| 67209-AT00002:0015. | 67209 | AGMT5 | 1.5 | 8.232466 | 510.8809 | 20.35555 | 539.4689 |
| 67209-AT00002:0012. | 67209 | AGMT5 | 1.5 | 7.882147 | 491.5553 | 15.63579 | 515.0732 |
| 67209-AT00002:0011. | 67209 | AGMT5 | 1.6 | 8.243328 | 498.6947 | 16.04594 | 522.984 |
| 67209-AT00002:0002. | 67209 | AGMT5 | 5.8 | 31.51494 | 491.2804 | 15.93072 | 538.7261 |
| 67209-AT00002:0010. | 67209 | AGMT5 | 5.9 | 31.71606 | 495.1827 | 14.92844 | 541.8272 |
| 67209-AT00002:0018. | 67209 | AGMT5 | 6.3 | 32.76043 | 471.9309 | 14.02284 | 518.7141 |
| 67209-AT00002:0007. | 67209 | AGMT5 | 6.5 | 34.37377 | 484.0701 | 14.41657 | 532.8605 |
| 67209-AT00002:0014. | 67209 | AGMT5 | 6.7 | 35.73441 | 484.6109 | 14.83528 | 535.1806 |
| 67209-AT00002:0004. | 67209 | AGMT5 | 6.9 | 33.38658 | 435.9932 | 12.33526 | 481.7151 |
| 67209-AT00002:0013. | 67209 | AGMT5 | 7.0 | 37.08117 | 478.9937 | 15.02489 | 531.0997 |
| 67209-AT00002:0016. | 67209 | AGMT5 | 7.4 | 37.04708 | 447.8279 | 13.15924 | 498.0342 |
| 67209-AT00002:0003. | 67209 | AGMT5 | 7.5 | 33.44907 | 399.4448 | 10.55172 | 443.4456 |
| 67209-AT00002:0017. | 67209 | AGMT5 | 8.8 | 36.30308 | 368.5792 | 9.282464 | 414.1648 |
| PMON67248 | 67248 | AGMT6 | 1.3 | 6.321132 | 456.4824 | 16.18991 | 478.9934 |
| PMON67248 | 67248 | AGMT6 | 1.3 | 6.660183 | 471.2561 | 22.48794 | 500.4042 |
| PMON67248 | 67248 | AGMT6 | 1.3 | 7.110155 | 504.2517 | 19.47217 | 530.834 |
| PMON67248 | 67248 | AGMT6 | 1.4 | 7.284769 | 485.4177 | 19.20365 | 511.9062 |
| PMON67248 | 67248 | AGMT6 | 1.5 | 7.975595 | 518.4006 | 20.57383 | 546.9501 |
| PMON67248 | 67248 | AGMT6 | 1.5 | 8.358604 | 523.6472 | 21.38442 | 553.3902 |
| PMON67248 | 67248 | AGMT6 | 1.6 | 8.227805 | 496.0041 | 20.27214 | 524.5041 |
| PMON67248 | 67248 | AGMT6 | 1.7 | 7.321649 | 414.7517 | 19.18408 | 441.2575 |
| PMON67248 | 67248 | AGMT6 | 1.8 | 8.639623 | 463.902 | 17.53926 | 490.0808 |
| PMON67248 | 67248 | AGMT6 | 2.0 | 7.833421 | 357.5244 | 19.34061 | 384.6984 |
| PMON67248 | 67248 | AGMT6 | 2.3 | 9.256798 | 378.4031 | 17.8021 | 405.462 |
| PMON67248 | 67248 | AGMT6 | 2.4 | 9.033592 | 355.1541 | 19.19918 | 383.3869 |
| PMON67248 | 67248 | AGMT6 | 2.6 | 10.575683 | 74.9089 | 16.74246 | 402.227 |

Figure 9:
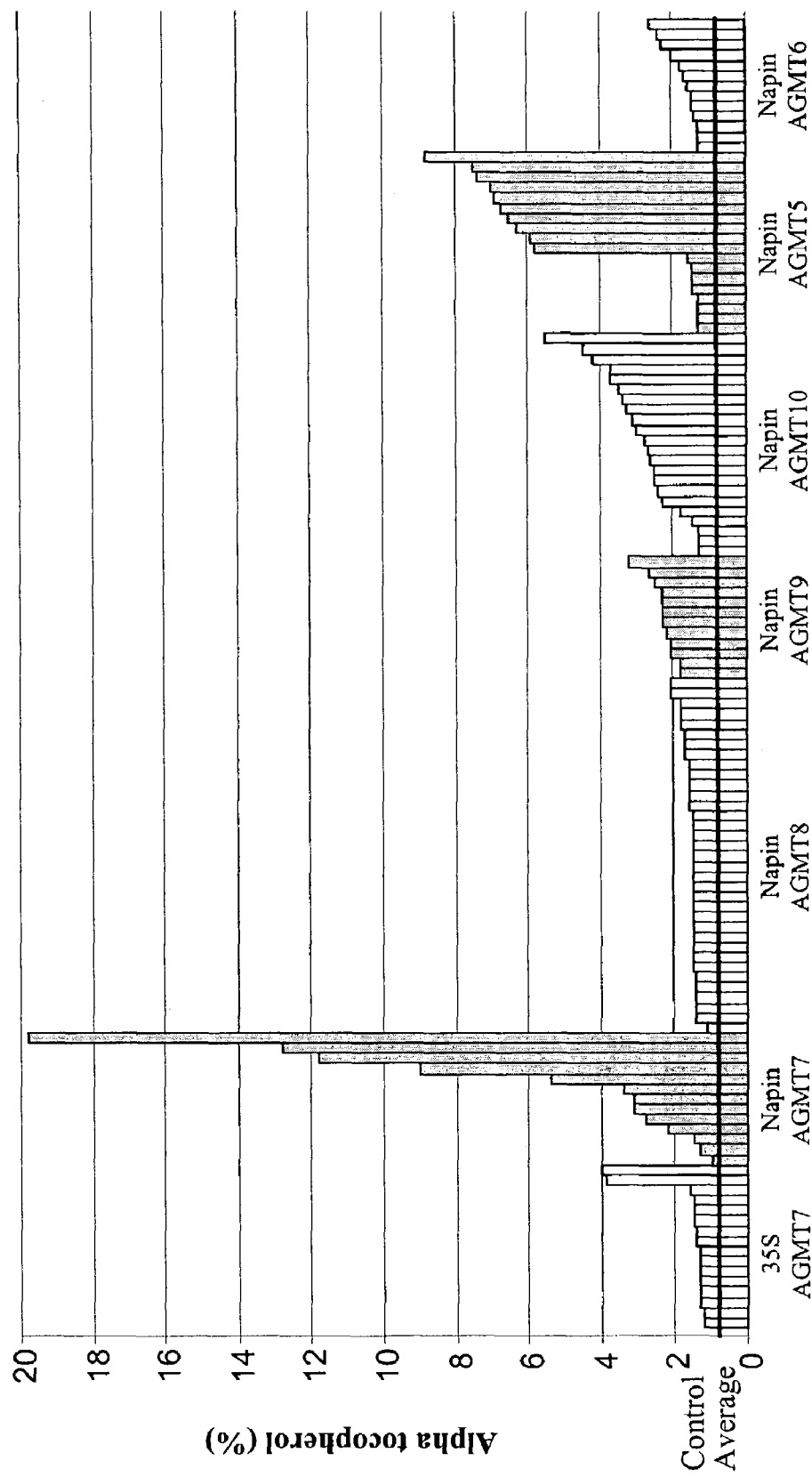
FIG. 9 shows alpha tocopherol levels in the T2 seed from individual transgenic *Arabidopsis* expressing different GMT-targeted zinc finger proteins.
Figure 10:
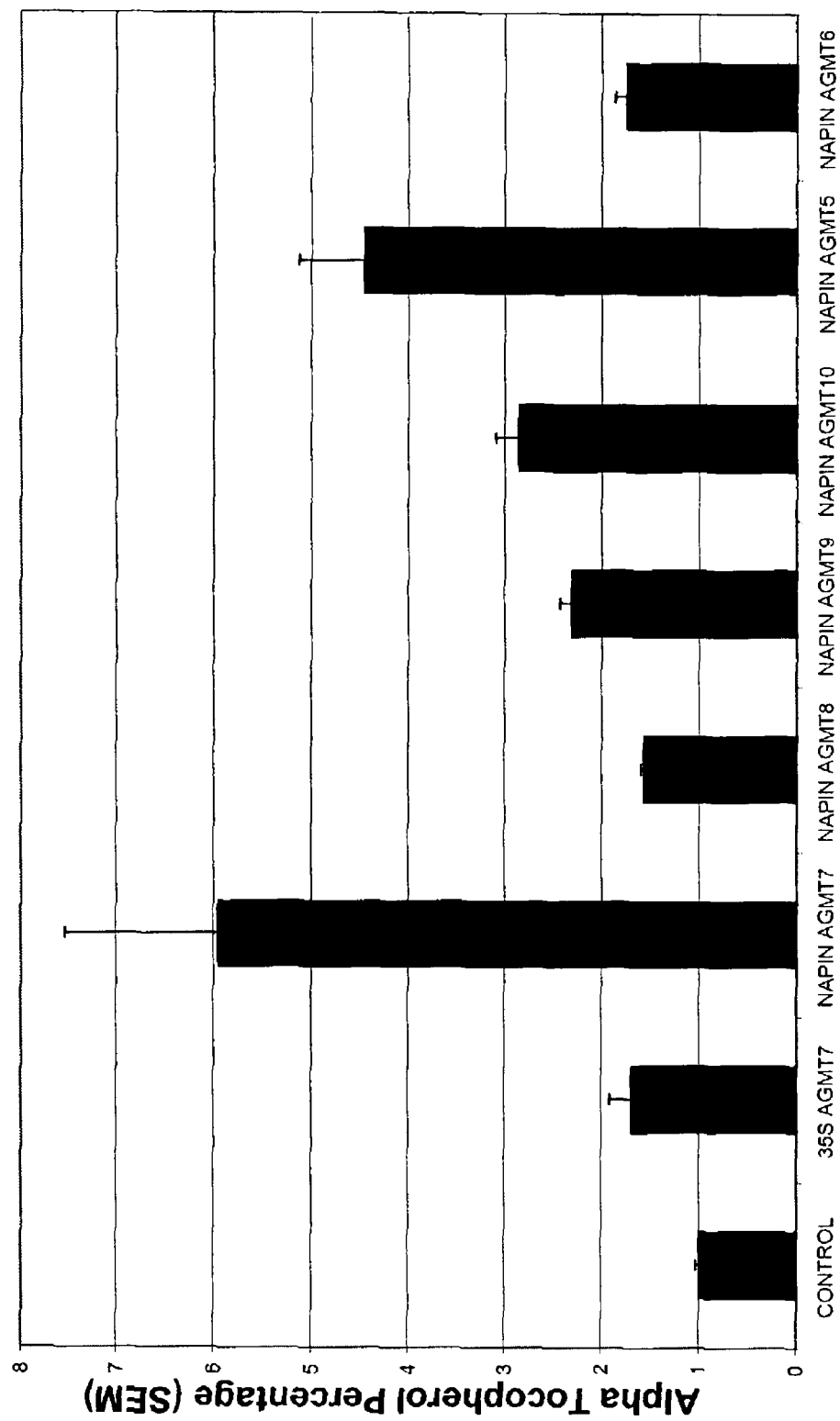
FIG. 10 shows mean (±SEM) seed alpha-tocopherol percentage in the T2 seed from *Arabidopsis thaliana* plants expressing zinc finger transcription factors designed to upregulate the expression of the endogenous GMT gene.

The results presented in Table 5 are presented graphically in FIG. 9, and summarized in Table 6 and FIG. 10. Taken together, these results indicate that transgenic plants comprising GMT-targeted ZFPs linked to an activation domain produce increased levels of α-tocopherol, compared to plants not containing GMT-targeted ZFPs.

Table 6

Summary of *Arabidopsis* T2 seed alpha tocopherol percentage data from transgenic plants expressing zinc finger transcription factors designed to upregulate the endogenous GMT gene

| ARABIDOPSIS SUMMARY | CONTROL | 35S AGMT7 | NAPIN AGMT7 | NAPIN AGMT8 | NAPIN AGMT9 | NAPIN AGMT10 | NAPIN AGMT5 | NAPIN AGMT6 |
|---|---|---|---|---|---|---|---|---|
| MEAN | 1.00 | 1.69 | 5.95 | 1.57 | 2.31 | 2.86 | 4.45 | 1.74 |
| SEM | 0.03 | 0.22 | 1.59 | 0.03 | 0.12 | 0.23 | 0.68 | 0.12 |
| N | 30 | 16 | 13 | 35 | 12 | 22 | 18 | 13 |

Example 9

Modulation of α-tocopherol Levels in T3 Seeds from Transgenic *Arabidopsis*

T2 seeds from the transgenic plants described in Example 8 were advanced to the next generation, and the resulting T3 seeds were analyzed for tocopherol content as described in Example 8. Results are shown in Table 7. The first 5 rows of the table provide information obtained from T3 seeds obtained from control plants transfected with the 9977 construct, a vector containing a 35S promoter but lacking sequences encoding a GMT-targeted ZFP (see Example 8). Lines 16-20 present data from T3 seeds obtained from plants transfected with the 9979 construct, a vector containing a napin promoter but lacking sequences encoding a GMT-targeted ZFP (see Example 8). For each transgenic line, the information in the table is provided as a series of entries which begins with data from R2 seed and is followed by R3/T3 data for the progeny of that R2 seed. For example, for R2 62703-3 (a vector encoding the AGMT7 ZFP under control of the 35S promoter, see Example 8), R2 values are shown in row 6 of Table 7, and the R3 progeny seed values are presented in the succeeding rows (rows 7-14 of Table 7).

TABLE 7

Tocopherol levels of T3 seeds in transgenic Arabidopsis

| Crop | Biotype | Serial Number | ng/mg:aT | ng/mg:gT | ng/mg:dT | total toco. | % alpha | Gen | Pedigree | Construct |
|---|---|---|---|---|---|---|---|---|---|---|
| AT | SEED | 69000358158 | 2 | 496 | 14 | 512 | 0.4 | R3 | 9977-AT00002:0002.0014. | 9977 |
| AT | SEED | 69000358247 | 2 | 486 | 12 | 500 | 0.4 | R3 | 9977-AT00002:0002.0011. | 9977 |
| AT | SEED | 69000358259 | 3 | 502 | 14 | 519 | 0.6 | R3 | 9977-AT00002:0002.0013. | 9977 |
| AT | SEED | 69000358146 | 4 | 479 | 12 | 495 | 0.8 | R3 | 9977-AT00002:0002.0015. | 9977 |
| AT | SEED | 69000358235 | 4 | 473 | 12 | 489 | 0.8 | R3 | 9977-AT00002:0002.0012. | 9977 |
| | | | | | | | 3.9 | R2 | 67203-3 | |
| AT | SEED | 69000358069 | 6 | 521 | 17 | 544 | 1.1 | R3 | 67203-AT00002:0003.0009. | 67203 |
| AT | SEED | 69000358273 | 6 | 463 | 11 | 480 | 1.3 | R3 | 67203-AT00002:0003.0004. | 67203 |
| AT | SEED | 69000358285 | 9 | 454 | 13 | 476 | 1.9 | R3 | 67203-AT00002:0003.0003. | 67203 |
| AT | SEED | 69000358297 | 9 | 455 | 10 | 474 | 1.9 | R3 | 67203-AT00002:0003.0002. | 67203 |
| AT | SEED | 69000358071 | 11 | 478 | 14 | 503 | 2.2 | R3 | 67203-AT00002:0003.0008. | 67203 |
| AT | SEED | 69000358057 | 11 | 471 | 13 | 495 | 2.2 | R3 | 67203-AT00002:0003.0010. | 67203 |
| AT | SEED | 69000358300 | 11 | 458 | 11 | 480 | 2.3 | R3 | 67203-AT00002:0003.0001. | 67203 |
| AT | SEED | 69000358261 | 12 | 440 | 11 | 463 | 2.6 | R3 | 67203-AT00002:0003.0005. | 67203 |
| AT | SEED | 69000358122 | 3 | 467 | 10 | 480 | 0.6 | R3 | 9979-AT00002-76:@.0011.0020. | 9979 |
| AT | SEED | 69000358312 | 4 | 490 | 13 | 507 | 0.8 | R3 | 9979-AT00002-76:@.0011.0023. | 9979 |
| AT | SEED | 69000358108 | 4 | 487 | 12 | 503 | 0.8 | R3 | 9979-AT00002-76:@.0011.0022. | 9979 |
| AT | SEED | 69000358110 | 5 | 482 | 14 | 501 | 1.0 | R3 | 9979-AT00002-76:.0011.0021. | 9979 |
| AT | SEED | 69000358134 | 6 | 481 | 12 | 499 | 1.2 | R3 | 9979-AT00002-76:@.0011.0019. | 9979 |
| | | | | | | | 9.0 | R2 | 67192-2 | |
| AT | SEED | 69000359009 | 34 | 422 | 8 | 464 | 7.3 | R3 | 67192-AT00002:0002.0006. | 67192 |
| AT | SEED | 69000357740 | 36 | 393 | 6 | 435 | 8.3 | R3 | 67192-AT00002:0002.0009. | 67192 |
| AT | SEED | 69000358564 | 40 | 415 | 9 | 464 | 8.6 | R3 | 67192-AT00002:0002.0002. | 67192 |
| AT | SEED | 69000357738 | 45 | 409 | 8 | 462 | 9.7 | R3 | 67192-AT00002:0002.0010. | 67192 |
| AT | SEED | 69000359011 | 47 | 421 | 9 | 477 | 9.9 | R3 | 67192-AT00002:0002.0007. | 67192 |
| AT | SEED | 69000358538 | 49 | 427 | 10 | 486 | 10.1 | R3 | 67192-AT00002:0002.0005. | 67192 |
| AT | SEED | 69000357752 | 50 | 434 | 9 | 493 | 10.1 | R3 | 67192-AT00002:0002.0008. | 67192 |
| AT | SEED | 69000358540 | 47 | 366 | 6 | 419 | 11.2 | R3 | 67192-AT00002:0002.0004. | 67192 |
| AT | SEED | 69000358576 | 52 | 399 | 9 | 460 | 11.3 | R3 | 67192-AT00002:0002.0001. | 67192 |
| AT | SEED | 69000358552 | 57 | 371 | 6 | 434 | 13.1 | R3 | 67192-AT00002:0002.0003. | 67192 |
| | | | | | | | 11.8 | R2 | 67192-5 | |
| AT | SEED | 69000358932 | 59 | 405 | 7 | 471 | 12.5 | R3 | 67192-AT00002:0005.0005. | 67192 |
| AT | SEED | 69000358956 | 62 | 414 | 8 | 484 | 12.8 | R3 | 67192-AT00002:0005.0007. | 67192 |
| AT | SEED | 69000359100 | 71 | 450 | 11 | 532 | 13.3 | R3 | 67192-AT00002:0005.0003. | 67192 |
| AT | SEED | 69000358944 | 64 | 391 | 7 | 462 | 13.9 | R3 | 67192-AT00002:0005.0006. | 67192 |
| AT | SEED | 69000358982 | 70 | 408 | 8 | 486 | 14.4 | R3 | 67192-AT00002:0005.0010. | 67192 |
| AT | SEED | 69000359097 | 74 | 406 | 8 | 488 | 15.2 | R3 | 67192-AT00002:0005.0002. | 67192 |
| AT | SEED | 69000359085 | 69 | 376 | 7 | 452 | 15.3 | R3 | 67192-AT00002:0005.0001. | 67192 |
| AT | SEED | 69000358968 | 72 | 389 | 7 | 468 | 15.4 | R3 | 67192-AT00002:0005.0008. | 67192 |
| AT | SEED | 69000358970 | 114 | 323 | 5 | 442 | 25.8 | R3 | 67192-A100002:0005.0009. | 67192 |
| | | | | | | | 12.8 | R2 | 67192-7 | |
| AT | SEED | 69000357699 | 23 | 447 | 14 | 484 | 4.8 | R3 | 67192-AT00002:0007.0004. | 67192 |
| AT | SEED | 69000359073 | 24 | 412 | 10 | 446 | 5.4 | R3 | 67192-AT00002:0007.0010. | 67192 |
| AT | SEED | 69000357714 | 26 | 417 | 11 | 454 | 5.7 | R3 | 67192-AT00002:0007.0002. | 67192 |
| AT | SEED | 69000359061 | 29 | 397 | 10 | 436 | 6.7 | R3 | 67192-AT00002:0007.0009. | 67192 |
| AT | SEED | 69000357702 | 31 | 397 | 13 | 441 | 7.0 | R3 | 67192-AT00002:0007.0003. | 67192 |
| AT | SEED | 69000357687 | 35 | 396 | 9 | 440 | 8.0 | R3 | 67192-AT00002:0007.0005. | 67192 |
| AT | SEED | 69000357726 | 40 | 404 | 10 | 454 | 8.8 | R3 | 67192-AT00002:0007.0001. | 67192 |
| AT | SEED | 69000358994 | 45 | 381 | 8 | 434 | 10.4 | R3 | 67192-AT00002:0007.0008. | 67192 |

TABLE 7-continued

Tocopherol levels of T3 seeds in transgenic Arabidopsis

| Crop | Biotype | Serial Number | ng/mg:aT | ng/mg:gT | ng/mg:dT | total toco. | % alpha | Gen | Pedigree | Construct |
|---|---|---|---|---|---|---|---|---|---|---|
| AT | SEED | 69000357675 | 50 | 402 | 10 | 462 | 10.8 | R3 | 67192-AT00002:0007.0006. | 67192 |
| AT | SEED | 69000357663 | 54 | 371 | 8 | 433 | 12.5 | R3 | 67192-AT00002:0007.0007. | 67192 |
|  |  |  |  |  |  |  | 19.8 | R2 | 67192-9 |  |
| AT | SEED | 69000358893 | 87 | 396 | 10 | 493 | 17.6 | R3 | 67192-AT00002:0009.0006. | 67192 |
| AT | SEED | 69000358754 | 78 | 300 | 5 | 383 | 20.4 | R3 | 67192-AT00002:0009.0010. | 67192 |
| AT | SEED | 69000358879 | 85 | 322 | 7 | 414 | 20.5 | R3 | 67192-AT00002:0009.0004. | 67192 |
| AT | SEED | 69000358881 | 82 | 304 | 6 | 392 | 20.9 | R3 | 67192-AT00002:0009.0005. | 67192 |
| AT | SEED | 69000358843 | 107 | 329 | 6 | 442 | 24.2 | R3 | 67192-AT00002:0009.0001. | 67192 |
| AT | SEED | 69000358920 | 112 | 339 | 8 | 459 | 24.4 | R3 | 67192-AT00002:0009.0009. | 67192 |
| AT | SEED | 69000358855 | 98 | 279 | 5 | 382 | 25.7 | R3 | 67192-AT00002:0009.0002. | 67192 |
| AT | SEED | 69000358867 | 121 | 332 | 7 | 460 | 26.3 | R3 | 67192-AT00002:0009.0003. | 67192 |
| AT | SEED | 69000358918 | 113 | 307 | 7 | 427 | 26.5 | R3 | 67192-AT00002:0009.0008. | 67192 |
| AT | SEED | 69000358906 | 115 | 308 | 5 | 428 | 26.9 | R3 | 67192-AT00002:0009.0007. | 67192 |
|  |  |  |  |  |  |  | 3.7 | R2 | 67195-17 |  |
| AT | SEED | 69000358425 | 8 | 469 | 13 | 490 | 1.6 | R3 | 67195-AT00002-17:@.0004. | 67195 |
| AT | SEED | 69000358437 | 10 | 429 | 10 | 449 | 2.2 | R3 | 67195-AT00002-17:@.0005. | 67195 |
| AT | SEED | 69000358627 | 11 | 429 | 9 | 449 | 2.4 | R3 | 67195-AT00002-17:@.0001. | 67195 |
| AT | SEED | 69000358639 | 10 | 390 | 7 | 407 | 2.5 | R3 | 67195-AT00002-17:@.0002. | 67195 |
| AT | SEED | 69000358449 | 11 | 417 | 9 | 437 | 2.5 | R3 | 67195-AT00002-17:@.0006. | 67195 |
| AT | SEED | 69000358766 | 12 | 419 | 8 | 439 | 2.7 | R3 | 67195-AT00002-17:@.0009. | 67195 |
| AT | SEED | 69000358778 | 13 | 382 | 8 | 403 | 3.2 | R3 | 67195-AT00002-17:@.0010. | 67195 |
| AT | SEED | 69000358831 | 14 | 409 | 9 | 432 | 3.2 | R3 | 67195-AT00002-17:@.0003. | 67195 |
| AT | SEED | 69000358451 | 24 | 467 | 9 | 500 | 4.8 | R3 | 67195-AT00002-17:@.0008. | 67195 |
|  |  |  |  |  |  |  | 4.2 | R2 | 67195-5 |  |
| AT | SEED | 69000358730 | 8 | 483 | 14 | 505 | 1.6 | R3 | 67195-AT00002-5:@.0006. | 67195 |
| AT | SEED | 69000358780 | 13 | 469 | 13 | 495 | 2.6 | R3 | 67195-AT00002-5:@.0001. | 67195 |
| AT | SEED | 69000358792 | 13 | 442 | 12 | 467 | 2.8 | R3 | 67195-AT00002-5:@.0002. | 67195 |
| AT | SEED | 69000358829 | 13 | 435 | 13 | 461 | 2.8 | R3 | 67195-AT00002-5:@.0005. | 67195 |
| AT | SEED | 69000358413 | 14 | 417 | 12 | 443 | 3.2 | R3 | 67195-AT00002-5:@.0010. | 67195 |
| AT | SEED | 69000358742 | 16 | 440 | 14 | 470 | 3.4 | R3 | 67195-AT00002-5:@.0007. | 67195 |
| AT | SEED | 69000358817 | 16 | 435 | 11 | 462 | 3.5 | R3 | 67195-AT00002-5:@.0004. | 67195 |
| AT | SEED | 69000358805 | 17 | 399 | 11 | 427 | 4.0 | R3 | 67195-AT00002-5:@.0003. | 67195 |
|  |  |  |  |  |  |  | 5.5 | R2 | 67195-6 |  |
| AT | SEED | 69000358691 | 16 | 427 | 9 | 452 | 3.5 | R3 | 67195-AT00002-6:@.0006. | 67195 |
| AT | SEED | 69000358716 | 19 | 455 | 10 | 484 | 3.9 | R3 | 67195-AT00002-6:@.0010. | 67195 |
| AT | SEED | 69000358677 | 19 | 441 | 8 | 468 | 4.1 | R3 | 67195-AT00002-6:@.0003. | 67195 |
| AT | SEED | 69000358653 | 20 | 446 | 9 | 475 | 4.2 | R3 | 67195-AT00002-6:@.0001. | 67195 |
| AT | SEED | 69000358665 | 23 | 445 | 9 | 477 | 4.8 | R3 | 67195-AT00002-6:@.0002. | 67195 |
| AT | SEED | 69000358704 | 21 | 401 | 8 | 430 | 4.9 | R3 | 67195-AT00002-6:@.0009. | 67195 |
| AT | SEED | 69000358689 | 21 | 400 | 8 | 429 | 4.9 | R3 | 67195-AT00002-6:@.0005. | 67195 |
|  |  |  |  |  |  |  | 4.5 | R2 | 67195-9 |  |
| AT | SEED | 69000358398 | 14 | 473 | 15 | 502 | 2.8 | R3 | 67195-AT00002-9:@.0002. | 67195 |
| AT | SEED | 69000358348 | 14 | 408 | 9 | 431 | 3.2 | R3 | 67195-AT00002-9:@.0007. | 67195 |
| AT | SEED | 69000358728 | 16 | 449 | 12 | 477 | 3.4 | R3 | 67195-AT00002-9:@.0008. | 67195 |
| AT | SEED | 69000358350 | 16 | 445 | 14 | 475 | 3.4 | R3 | 67195-AT00002-9:@.0006. | 67195 |
| AT | SEED | 69000358386 | 17 | 453 | 12 | 482 | 3.5 | R3 | 67195-AT00002-9:@.0003. | 67195 |
| AT | SEED | 69000358401 | 18 | 448 | 13 | 479 | 3.8 | R3 | 67195-AT00002-9:@.0001. | 67195 |
| AT | SEED | 69000358641 | 15 | 373 | 10 | 398 | 3.8 | R3 | 67195-AT00002-9:@.0010. | 67195 |
| AT | SEED | 69000358362 | 21 | 380 | 10 | 411 | 5.1 | R3 | 67195-AT00002-9:@.0005. | 67195 |
| AT | SEED | 69000358374 | 25 | 338 | 7 | 370 | 6.8 | R3 | 67195-AT00002-9:@.0004. | 67195 |
|  |  |  |  |  |  |  | 7.5 | R2 | 67209-3 |  |
| AT | SEED | 69000358007 | 28 | 456 | 10 | 494 | 5.7 | R3 | 67209-AT00002.0003.0005. | 67209 |
| AT | SEED | 69000358045 | 31 | 424 | 8 | 463 | 6.7 | R3 | 67209-AT00002.0003.0001. | 67209 |
| AT | SEED | 69000357889 | 32 | 428 | 9 | 469 | 6.8 | R3 | 67209-AT00002.0003.0008. | 67209 |
| AT | SEED | 69000358019 | 30 | 394 | 7 | 431 | 7.0 | R3 | 67209-AT00002.0003.0004. | 67209 |
| AT | SEED | 69000358223 | 36 | 456 | 10 | 502 | 7.2 | R3 | 67209-AT00002.0003.0009. | 67209 |
| AT | SEED | 69000358211 | 35 | 442 | 9 | 486 | 7.2 | R3 | 67209-AT00002.0003.0010. | 67209 |
| AT | SEED | 69000357980 | 33 | 413 | 7 | 453 | 7.3 | R3 | 67209-AT00002.0003.0007. | 67209 |
| AT | SEED | 69000357992 | 35 | 385 | 7 | 427 | 8.2 | R3 | 67209-AT00002.0003.0006. | 67209 |
| AT | SEED | 69000358033 | 40 | 410 | 8 | 458 | 8.7 | R3 | 67209-AT00002.0003.0002. | 67209 |
| AT | SEED | 69000358021 | 45 | 422 | 9 | 476 | 9.5 | R3 | 67209-AT00002.0003.0003. | 67209 |
|  |  |  |  |  |  |  | 7.0 | R2 | 67209-13 | 67209 |
| AT | SEED | 69000358588 | 26 | 476 | 11 | 513 | 5.1 | R3 | 67209-AT00002.0013.0010. | 67209 |
| AT | SEED | 69000359047 | 28 | 472 | 11 | 511 | 5.5 | R3 | 67209-AT00002.0013.0001. | 67209 |
| AT | SEED | 69000358463 | 29 | 462 | 9 | 500 | 5.8 | R3 | 67209-AT00002.0013.0006. | 67209 |
| AT | SEED | 69000359059 | 28 | 439 | 9 | 476 | 5.9 | R3 | 67209-AT00002.0013.0002. | 67209 |
| AT | SEED | 69000358590 | 31 | 463 | 11 | 505 | 6.1 | R3 | 67209-AT00002.0013.0009. | 67209 |
| AT | SEED | 69000358615 | 29 | 425 | 8 | 462 | 6.3 | R3 | 67209-AT00002.0013.0007. | 67209 |
| AT | SEED | 69000358603 | 31 | 438 | 10 | 479 | 6.5 | R3 | 67209-AT00002.0013.0008. | 67209 |
| AT | SEED | 69000358526 | 44 | 434 | 8 | 486 | 9.1 | R3 | 67209-AT00002.0013.0003. | 67209 |
| AT | SEED | 69000358324 | 45 | 370 | 6 | 421 | 10.7 | R3 | 67209-AT00002.0013.0005. | 67209 |
| AT | SEED | 69000358336 | 47 | 362 | 6 | 415 | 11.3 | R3 | 67209-AT00002.0013.0004. | 67209 |
|  |  |  |  |  |  |  | 7.4 | R2 | 67209-16 | 67209 |
| AT | SEED | 69000358514 | 24 | 460 | 9 | 493 | 4.9 | R3 | 67209-AT00002:0016.0001. | 67209 |
| AT | SEED | 69000358487 | 28 | 482 | 11 | 521 | 5.4 | R3 | 67209-AT00002:0016.0006. | 67209 |
| AT | SEED | 69000358499 | 28 | 472 | 11 | 511 | 5.5 | R3 | 67209-AT00002:0016.0005. | 67209 |

TABLE 7-continued

Tocopherol levels of T3 seeds in transgenic Arabidopsis

| Crop | Biotype | Serial Number | ng/mg:aT | ng/mg:gT | ng/mg:dT | total toco. | % alpha | Gen | Pedigree | Construct |
|---|---|---|---|---|---|---|---|---|---|---|
| AT | SEED | 69000358475 | 29 | 441 | 8 | 478 | 6.1 | R3 | 67209-AT00002:0016.0007. | 67209 |
| AT | SEED | 69000359035 | 33 | 466 | 9 | 508 | 6.5 | R3 | 67209-AT00002:0016.0010. | 67209 |
| AT | SEED | 69000358502 | 32 | 437 | 10 | 479 | 6.7 | R3 | 67209-AT00002:0016.0004. | 67209 |
| AT | SEED | 69000359023 | 36 | 434 | 9 | 479 | 7.5 | R3 | 67209-AT00002:0016.0008. | 67209 |
|  |  |  |  |  |  |  | 8.8 | R2 | 67209-17 | 67209 |
| AT | SEED | 69000357978 | 29 | 468 | 11 | 508 | 5.7 | R3 | 67209-AT00002:0017.0002. | 67209 |
| AT | SEED | 69000357942 | 31 | 479 | 11 | 521 | 6.0 | R3 | 67209-AT00002:0017.0005. | 67209 |
| AT | SEED | 69000357916 | 27 | 418 | 8 | 453 | 6.0 | R3 | 67209-AT00002:0017.0008. | 67209 |
| AT | SEED | 69000357966 | 31 | 467 | 10 | 508 | 6.1 | R3 | 67209-AT00002:0017.0003. | 67209 |
| AT | SEED | 69000358095 | 35 | 483 | 12 | 530 | 6.6 | R3 | 67209-AT00002:0017.0001. | 67209 |
| AT | SEED | 69000357891 | 36 | 487 | 11 | 534 | 6.7 | R3 | 67209-AT00002:0017.0010. | 67209 |
| AT | SEED | 69000357928 | 34 | 443 | 9 | 486 | 7.0 | R3 | 67209-AT00002:0017.0007. | 67209 |
| AT | SEED | 69000357930 | 36 | 465 | 9 | 510 | 7.1 | R3 | 67209-AT00002:0017.0006. | 67209 |
| AT | SEED | 69000357954 | 35 | 450 | 9 | 494 | 7.1 | R3 | 67209-AT00002:0017.0004. | 67209 |
| AT | SEED | 69000357904 | 38 | 448 | 9 | 495 | 7.7 | R3 | 67209-AT00002:0017.0009. | 67209 |

Figure 11:
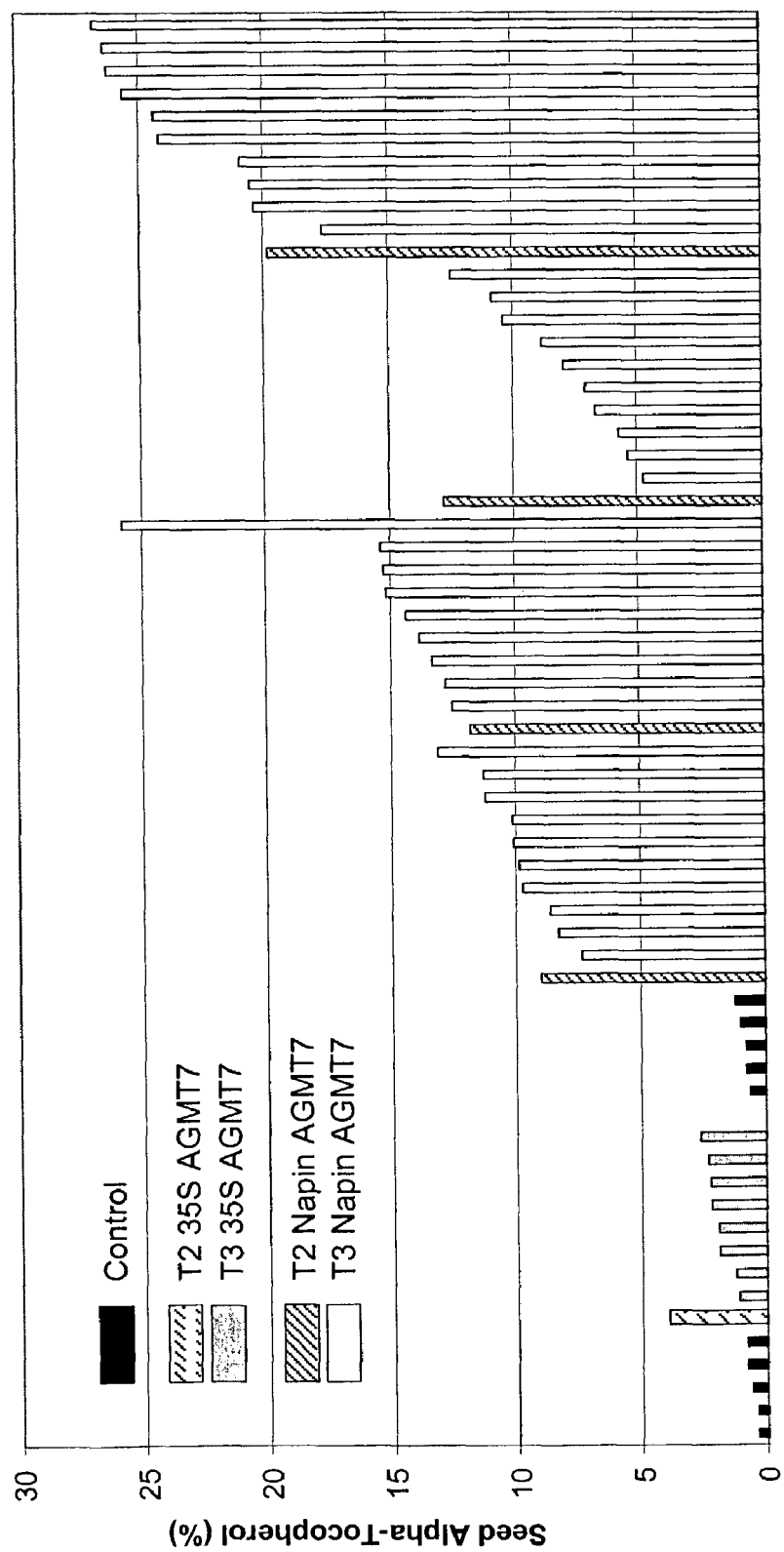
FIG. 11 shows alpha-tocopherol levels (as percent total tocopherols) in T3 seeds obtained from transgenic *Arabidopsis* transformed with the 67203 construct (which encodes the AGMT7 ZFP under the control of the 35S promoter), and in T3 seeds obtained from transgenic *Arabidopsis* transformed with the 67192 construct (which encodes the AGMT7 ZFP under the control of the napin promoter). Control plants were transformed with vectors containing either a 35S promoter (pCGN9977, leftmost 5 bars) or a napin promoter (pCGN9979, but lacking sequences encoding a ZFP.
Figure 12:
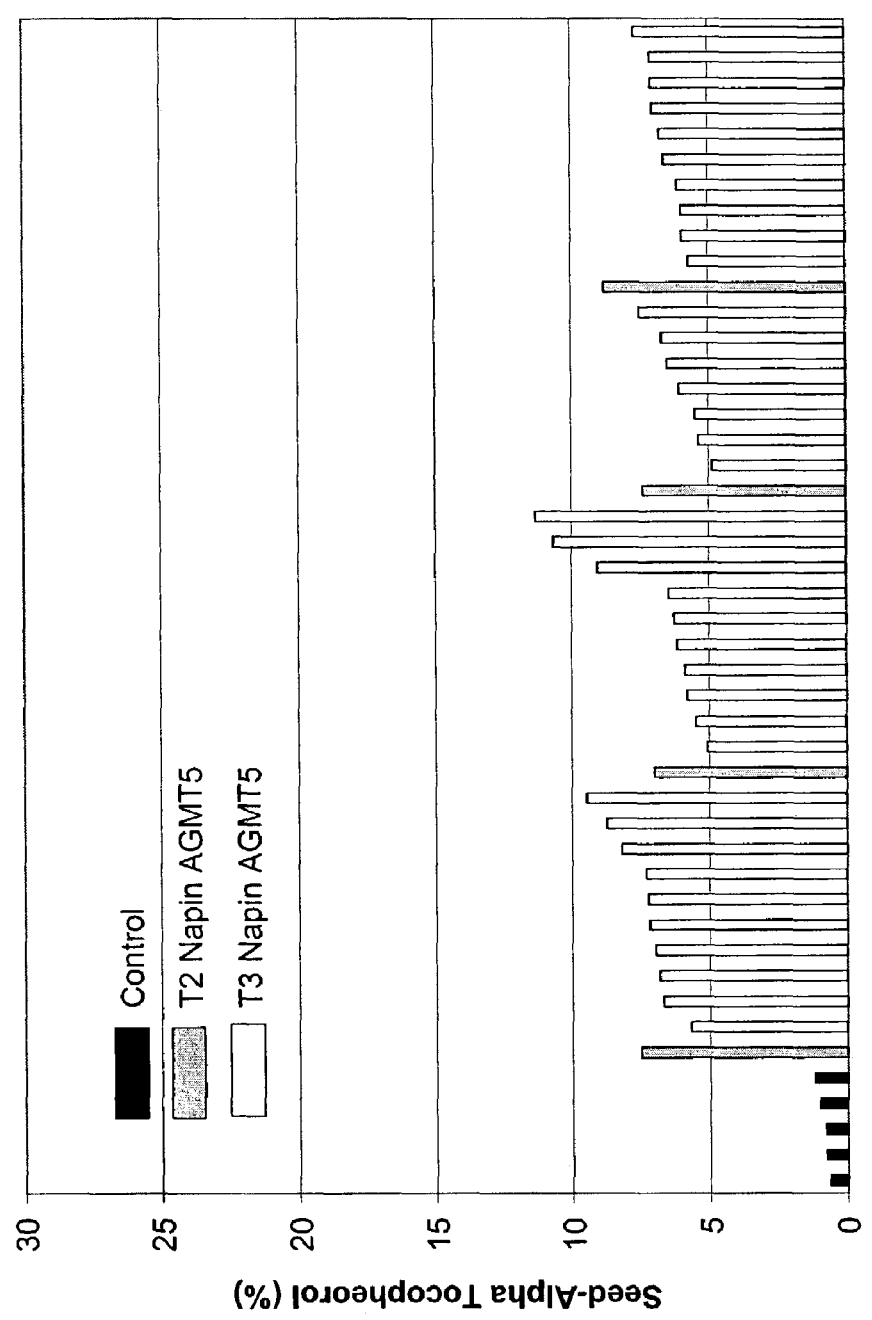
FIG. 12 shows alpha-tocopherol levels (as percent total tocopherols) in T3 seeds obtained from transgenic *Arabidopsis* transformed with the 67209 construct, which encodes the AGMT5 ZFP under the control of the napin promoter. Control plants were transformed with the pCGN9979 vector, which contains a napin promoter but lacks sequences encoding a ZFP.
Figure 13:
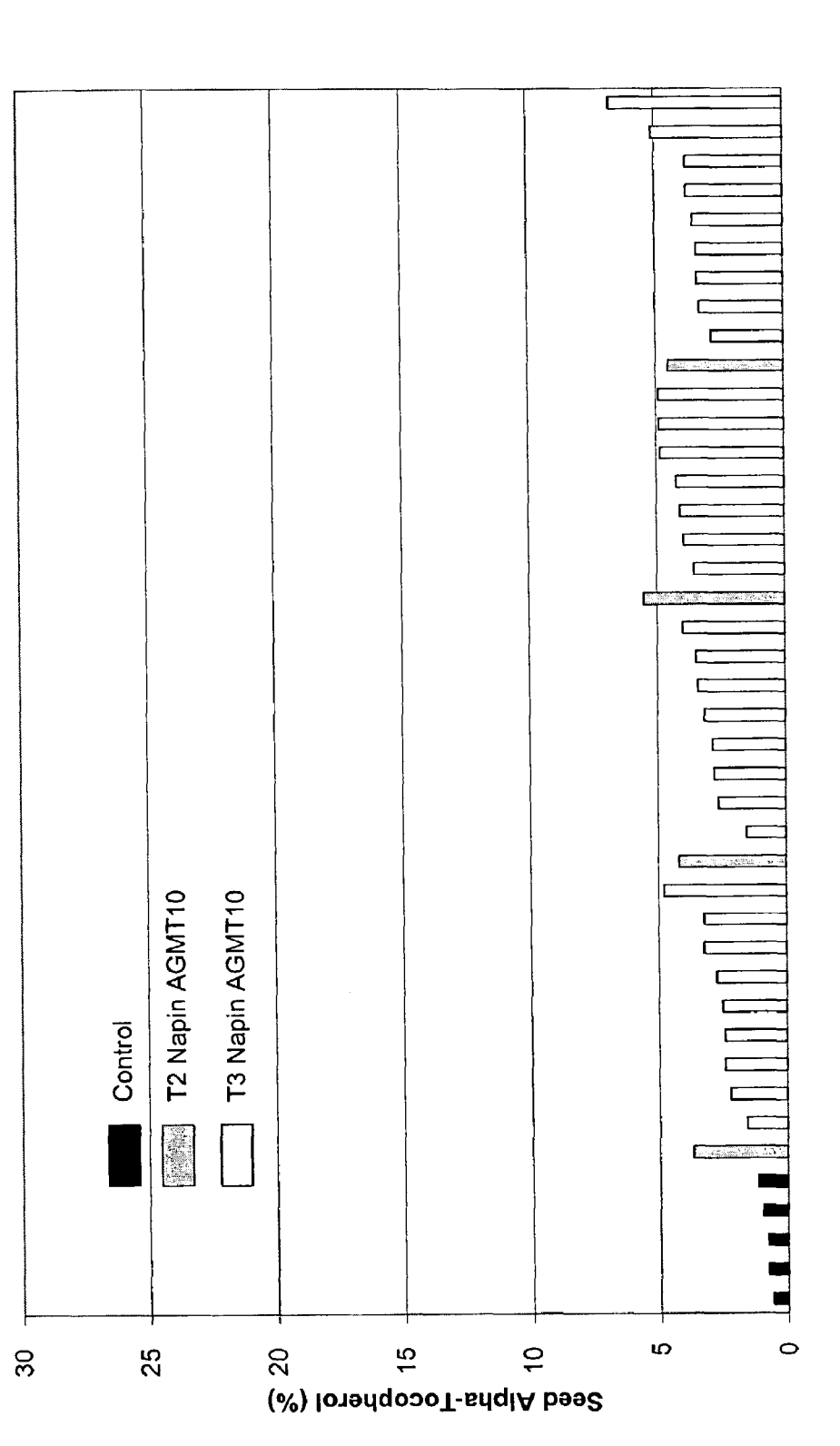
FIG. 13 shows alpha-tocopherol levels (as percent total tocopherols) in T3 seeds obtained from transgenic *Arabidopsis* transformed with the 67195 construct, which encodes the AGMT10 ZFP under the control of the napin promoter. Control plants were transformed with the pCGN9979 vector, which contains a napin promoter but lacks sequences encoding a ZFP.

Representative data obtained from the preceding table are presented graphically in FIG. 11 (for construct 67203 encoding the AGMT7 ZFP under the control of the 35S promoter and construct 67192 encoding the AGMT7 ZFP under the control of the napin promoter), FIG. 12 (for construct 67209 encoding the AGMT5 ZFP under the control of the napin promoter) and FIG. 13 (for construct 67195 encoding the AGMT10 ZFP under the control of the napin promoter). Taken together, the T3 data indicate that ZFP-induced increases in α-tocopherol levels are heritable in transgenic plants.

Example 10

Modulation of α-tocopherol Levels in Transgenic *Brassica* (Canola)

Constructs were prepared to direct expression of the zinc finger transcription factor sequences in *Brassica napus*. Plasmids containing the coding regions of CGMT 3, 4, 5, 6, 7, 8, 9, 10 and 12 (see Example 5, Table 3) were digested with the restriction endonucleases NotI and HindIII to liberate the ZFP insert, which was then gel-purified using the "QIAquick Gel Extraction Kit" (QIAGEN Inc., Valencia, Calif.). These NotI/HindIII fragments also contained sequences encoding the C1 activation domain in frame with the ZFP-encoding sequences.

Figure 14:
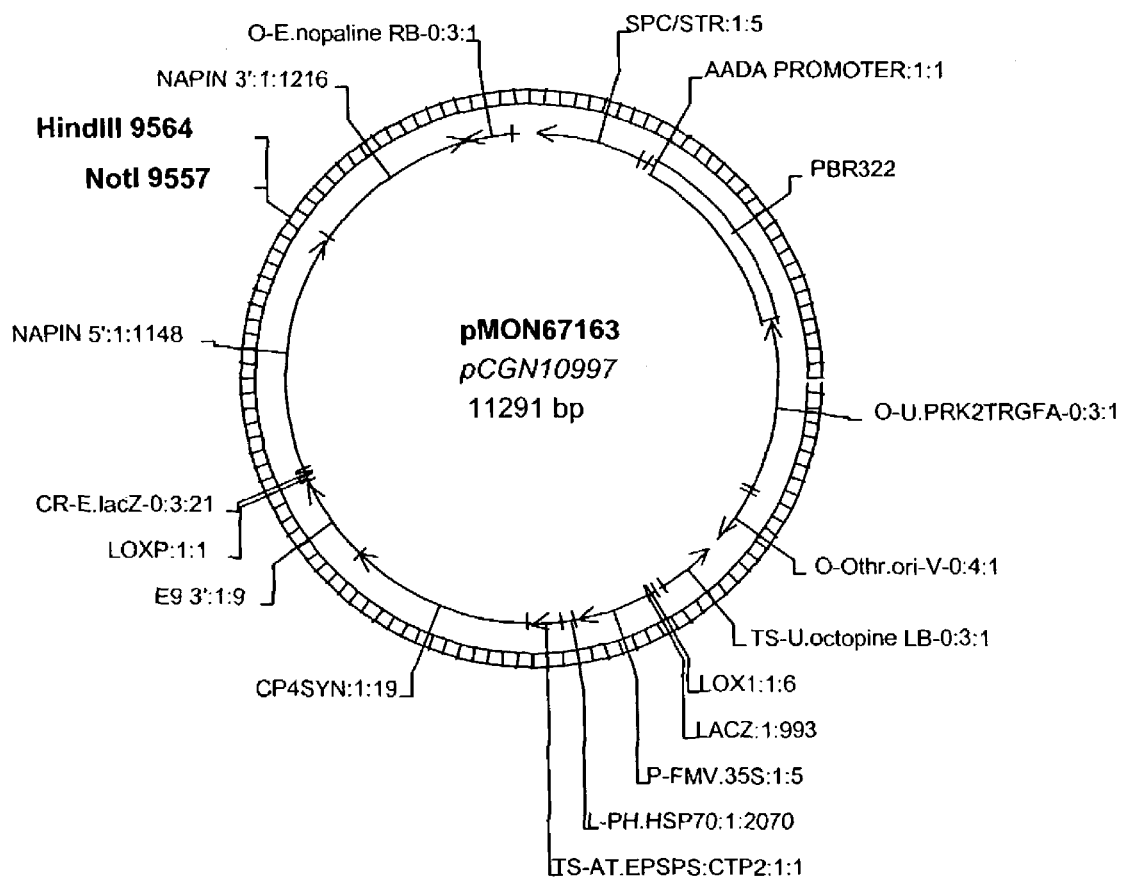
FIG. 14 shows a diagram of a vector used for the transformation of *Brassica napus* plants. ZFPs were cloned between the NotI and HindIII sites in the napin expression cassette.

The napin binary vector pCGN67163 (see FIG. 14) was prepared by digesting with NotI and HindIII endonucleases. Enzymes were subsequently removed using "StrataClean Resin™" (Stratagene, La Jolla, Calif.) followed by "MicroSpin™ S-400 HR Column" treatment (Pharmacia, Uppsala, Sweden). The ZFP-encoding insert was ligated into the pCGN67163 NotI/HindIII digested-vector. The resulting plasmids, containing genes encoding different GMT-targeted ZFPs in the plant binary transformation vector under the control of the napin embryo-specific promoter (Kridl et al., *Seed Sci. Res.* 1:209:219 (1991)), were labeled as follows: pMON67198 (encoding the CGMT4 ZFP), 67199 (encoding the CGMT5 ZFP), 67200 (encoding the CGMT6 ZFP), 67201 (encoding the CGMT8 ZFP), 67202 (encoding the CGMT12 ZFP), 67215 (encoding the CGMT3 ZFP), 67216 (encoding the CGMT7 ZFP), 67217 (encoding the CGMT9 ZFP), and 67218 (encoding the CGMT10 ZFP).

The plant binary constructs described above were used in *Brassica napus* (Ebony variety) plant transformation to direct the expression of the ZFPs in the embryo. Transgenic *Brassica* plants were obtained by *Agrobacterium*-mediated transformation as described by Radke et al. *Plant Cell Reports* 11: 499-505 (1992) and WO 00/61771. Transformed plants were grown to maturity and the R1 seed that was produced was analyzed for tocopherol content and composition as described in Example 8.

Results of the tocopherol analysis of Canola R1 segregating seed are shown in Table 8. Tocopherol levels from untransformed *Brassica napus* (Ebony variety) plants served as control values for these data. The average percent alpha-tocopherol in control seed was 39.9% (SD±8.2)

TABLE 8

| | | | ng tocopherol/mg seed | | | | |
|---|---|---|---|---|---|---|---|
| Pedigree | Construct | ZFP | % alpha | alpha | gamma | delta | ng total toco |
| SP30052:@. | CONTROL | none | 24.9 | 58.0 | 171.0 | 4.0 | 233.0 |
| SP30052:@. | CONTROL | none | 25.1 | 61.4 | 179.7 | 3.2 | 244.3 |
| SP30052:@. | CONTROL | none | 25.6 | 71.0 | 202.0 | 4.0 | 277.0 |
| SP30052:@. | CONTROL | none | 26.8 | 71.0 | 190.0 | 4.0 | 265.0 |
| SP30052:@. | CONTROL | none | 27.0 | 64.9 | 174.2 | 1.3 | 240.4 |
| SP30052:@. | CONTROL | none | 27.9 | 62.0 | 156.0 | 4.0 | 222.0 |
| SP30052:@. | CONTROL | none | 28.0 | 72.0 | 181.0 | 4.0 | 257.0 |
| SP30052:@. | CONTROL | none | 29.4 | 67.0 | 158.0 | 3.0 | 228.0 |
| SP30052:@. | CONTROL | none | 30.5 | 73.0 | 162.0 | 4.0 | 239.0 |
| SP30052:@. | CONTROL | none | 31.4 | 71.4 | 152.8 | 3.1 | 227.3 |
| SP30052:@. | CONTROL | none | 31.5 | 84.0 | 180.0 | 3.0 | 267.0 |
| SP30052:@. | CONTROL | none | 32.3 | 78.0 | 163.0 | 0.7 | 241.7 |
| SP30052:@. | CONTROL | none | 32.5 | 83.4 | 171.7 | 1.6 | 256.6 |
| SP30052:@. | CONTROL | none | 33.1 | 78.0 | 155.0 | 3.0 | 236.0 |
| SP30052:@. | CONTROL | none | 33.5 | 91.5 | 178.9 | 3.1 | 273.6 |

TABLE 8-continued

| Pedigree | Construct | ZFP | % alpha | ng tocopherol/mg seed | | | ng total toco |
| --- | --- | --- | --- | --- | --- | --- | --- |
| | | | | alpha | gamma | delta | |
| SP30052:@. | CONTROL | none | 33.5 | 78.0 | 152.0 | 3.0 | 233.0 |
| SP30052:@. | CONTROL | none | 34.3 | 89.2 | 167.8 | 3.2 | 260.2 |
| SP30052:@. | CONTROL | none | 34.3 | 71.0 | 134.0 | 2.0 | 207.0 |
| SP30052:@. | CONTROL | none | 34.5 | 90.3 | 166.6 | 4.8 | 261.7 |
| SP30052:@. | CONTROL | none | 35.1 | 81.0 | 147.0 | 3.0 | 231.0 |
| SP30052:@. | CONTROL | none | 35.3 | 76.0 | 136.0 | 3.0 | 215.0 |
| SP30052:@. | CONTROL | none | 36.1 | 97.0 | 168.0 | 4.0 | 269.0 |
| SP30052:@. | CONTROL | none | 36.1 | 99.4 | 171.9 | 4.1 | 275.4 |
| SP30052:@. | CONTROL | none | 36.1 | 123.9 | 213.1 | 5.9 | 342.9 |
| SP30052:@. | CONTROL | none | 36.4 | 94.0 | 161.5 | 2.5 | 257.9 |
| SP30052:@. | CONTROL | none | 36.5 | 88.0 | 150.5 | 3.0 | 241.5 |
| SP30052:@. | CONTROL | none | 36.9 | 121.0 | 201.0 | 6.0 | 328.0 |
| SP30052:@. | CONTROL | none | 37.4 | 55.0 | 91.1 | 0.9 | 147.0 |
| SP30052:@. | CONTROL | none | 37.6 | 108.0 | 175.9 | 3.4 | 287.3 |
| SP30052:@. | CONTROL | none | 38.6 | 81.0 | 126.0 | 3.0 | 210.0 |
| SP30052:@. | CONTROL | none | 39.4 | 99.0 | 148.0 | 4.0 | 251.0 |
| SP30052:@. | CONTROL | none | 39.9 | 105.0 | 154.0 | 4.0 | 263.0 |
| SP30052:@. | CONTROL | none | 40.4 | 102.7 | 150.2 | 1.6 | 254.5 |
| SP30052:@. | CONTROL | none | 40.5 | 105.0 | 149.0 | 5.0 | 259.0 |
| SP30052:@. | CONTROL | none | 40.8 | 122.0 | 174.9 | 2.1 | 299.1 |
| SP30052:@. | CONTROL | none | 41.0 | 111.2 | 157.3 | 2.7 | 271.2 |
| SP30052:@. | CONTROL | none | 41.6 | 101.7 | 141.9 | 0.9 | 244.5 |
| SP30052:@. | CONTROL | none | 41.7 | 74.4 | 101.8 | 2.0 | 178.1 |
| SP30052:@. | CONTROL | none | 41.9 | 144.6 | 193.0 | 7.2 | 344.8 |
| SP30052:@. | CONTROL | none | 42.1 | 114.7 | 153.1 | 4.5 | 272.4 |
| SP30052:@. | CONTROL | none | 42.7 | 114.0 | 149.0 | 4.0 | 267.0 |
| SP30052:@. | CONTROL | none | 42.8 | 145.7 | 188.2 | 6.2 | 340.1 |
| SP30052:@. | CONTROL | none | 43.7 | 113.8 | 143.4 | 3.3 | 260.5 |
| SP30052:@. | CONTROL | none | 43.8 | 112.6 | 142.0 | 2.3 | 256.8 |
| SP30052:@. | CONTROL | none | 43.9 | 94.0 | 117.0 | 3.0 | 214.0 |
| SP30052:@. | CONTROL | none | 44.0 | 138.0 | 171.4 | 4.5 | 313.9 |
| SP30052:@. | CONTROL | none | 44.6 | 95.0 | 116.0 | 2.0 | 213.0 |
| SP30052:@. | CONTROL | none | 44.6 | 116.0 | 140.0 | 4.0 | 260.0 |
| SP30052:@. | CONTROL | none | 45.4 | 108.0 | 126.3 | 3.3 | 237.6 |
| SP30052:@. | CONTROL | none | 45.6 | 114.1 | 132.3 | 3.9 | 250.2 |
| SP30052:@. | CONTROL | none | 45.7 | 111.0 | 129.0 | 3.0 | 243.0 |
| SP30052:@. | CONTROL | none | 45.8 | 116.0 | 134.0 | 3.0 | 253.0 |
| SP30052:@. | CONTROL | none | 46.4 | 98.6 | 113.0 | 0.9 | 212.5 |
| SP30052:@. | CONTROL | none | 46.4 | 104.0 | 118.0 | 2.0 | 224.0 |
| SP30052:@. | CONTROL | none | 47.2 | 116.0 | 127.0 | 3.0 | 246.0 |
| SP30052:@. | CONTROL | none | 48.3 | 127.9 | 133.9 | 3.0 | 264.8 |
| SP30052:@. | CONTROL | none | 50.0 | 147.7 | 144.6 | 3.3 | 295.6 |
| SP30052:@. | CONTROL | none | 50.2 | 146.0 | 141.5 | 3.6 | 291.1 |
| SP30052:@. | CONTROL | none | 50.2 | 139.0 | 134.0 | 4.0 | 277.0 |
| SP30052:@. | CONTROL | none | 52.3 | 139.0 | 124.0 | 3.0 | 266.0 |
| SP30052:@. | CONTROL | none | 54.3 | 152.0 | 125.0 | 3.0 | 280.0 |
| SP30052:@. | CONTROL | none | 54.6 | 148.0 | 120.0 | 3.0 | 271.0 |
| SP30052:@. | CONTROL | none | 56.0 | 147.3 | 113.9 | 1.9 | 263.1 |
| SP30052:@. | CONTROL | none | 56.8 | 156.0 | 116.3 | 2.3 | 274.6 |
| SP30052:@. | CONTROL | none | 57.8 | 115.0 | 82.0 | 2.0 | 199.0 |
| BN_G702:@. | 67198 | CGMT4 | 22.9 | 53.0 | 176.0 | 2.2 | 231.1 |
| BN_G656:@. | 67198 | CGMT4 | 28.6 | 69.0 | 169.4 | 2.6 | 241.0 |
| BN_G625:@. | 67198 | CGMT4 | 33.0 | 81.4 | 161.1 | 4.0 | 246.4 |
| BN_G655:@. | 67198 | CGMT4 | 35.6 | 86.1 | 151.1 | 4.7 | 241.9 |
| BN_G651:@. | 67198 | CGMT4 | 36.3 | 92.3 | 158.3 | 4.1 | 254.6 |
| BN_G687:@. | 67198 | CGMT4 | 37.8 | 71.4 | 115.4 | 2.1 | 188.8 |
| BN_G692:@. | 67198 | CGMT4 | 38.6 | 70.4 | 109.4 | 2.5 | 182.3 |
| BN_G680:@. | 67198 | CGMT4 | 42.5 | 90.9 | 117.7 | 5.3 | 213.9 |
| BN_G679:@. | 67198 | CGMT4 | 45.9 | 128.8 | 149.1 | 3.0 | 280.9 |
| BN_G653:@. | 67198 | CGMT4 | 49.0 | 114.9 | 115.0 | 4.8 | 234.7 |
| BN_G624:@. | 67198 | CGMT4 | 49.9 | 102.9 | 100.9 | 2.4 | 206.2 |
| BN_G650:@. | 67198 | CGMT4 | 50.0 | 87.6 | 84.9 | 2.6 | 175.1 |
| BN_G689:@. | 67198 | CGMT4 | 51.1 | 100.6 | 94.3 | 2.1 | 197.0 |
| BN_G652:@. | 67198 | CGMT4 | 53.3 | 121.9 | 104.6 | 2.3 | 228.8 |
| BN_G657:@. | 67198 | CGMT4 | 53.5 | 98.4 | 83.2 | 2.4 | 184.0 |
| BN_G691:@. | 67198 | CGMT4 | 54.3 | 115.6 | 93.5 | 3.9 | 213.0 |
| BN_G622:@. | 67198 | CGMT4 | 54.8 | 118.0 | 94.6 | 2.9 | 215.5 |
| BN_G688:@. | 67198 | CGMT4 | 55.9 | 104.1 | 80.8 | 1.4 | 186.3 |
| BN_G659:@. | 67198 | CGMT4 | 57.3 | 110.1 | 78.6 | 3.4 | 192.0 |
| BN_G654:@. | 67198 | CGMT4 | 58.6 | 113.2 | 76.6 | 3.4 | 193.3 |
| BN_G690:@. | 67198 | CGMT4 | 58.6 | 123.5 | 84.1 | 2.9 | 210.6 |
| BN_G623:@. | 67198 | CGMT4 | 58.7 | 126.2 | 86.1 | 2.7 | 215.0 |
| BN_G684:@. | 67198 | CGMT4 | 59.5 | 137.7 | 89.2 | 4.4 | 231.2 |
| BN_G660:@. | 67198 | CGMT4 | 60.8 | 117.8 | 74.0 | 2.0 | 193.8 |
| BN_G658:@. | 67198 | CGMT4 | 62.3 | 115.7 | 67.3 | 2.6 | 185.5 |
| BN_G626:@. | 67198 | CGMT4 | 62.3 | 138.3 | 81.1 | 2.4 | 221.8 |

TABLE 8-continued

| Pedigree | Construct | ZFP | % alpha | ng tocopherol/mg seed | | | ng total toco |
|---|---|---|---|---|---|---|---|
| | | | | alpha | gamma | delta | |
| BN_G685:@. | 67198 | CGMT4 | 63.7 | 132.2 | 73.0 | 2.3 | 207.5 |
| BN_G683:@. | 67198 | CGMT4 | 64.3 | 136.5 | 73.3 | 2.3 | 212.1 |
| BN_G686:@. | 67198 | CGMT4 | 65.6 | 128.7 | 66.5 | 1.1 | 196.3 |
| BN_G682:@. | 67198 | CGMT4 | 71.5 | 136.0 | 53.2 | 0.9 | 190.0 |
| BN_G681:@. | 67198 | CGMT4 | 73.4 | 141.5 | 49.2 | 2.0 | 192.7 |
| BN_G639:@. | 67199 | CGMT5 | 21.3 | 40.0 | 146.9 | 0.5 | 187.4 |
| BN_G636:@. | 67199 | CGMT5 | 24.0 | 52.4 | 164.6 | 1.4 | 218.4 |
| BN_G668:@. | 67199 | CGMT5 | 29.2 | 62.0 | 149.1 | 1.3 | 212.4 |
| BN_G637:@. | 67199 | CGMT5 | 29.6 | 58.9 | 138.8 | 1.3 | 199.0 |
| BN_G664:@. | 67199 | CGMT5 | 29.6 | 63.6 | 150.9 | 0.5 | 215.0 |
| BN_G631:@. | 67199 | CGMT5 | 29.9 | 59.0 | 137.1 | 1.2 | 197.2 |
| BN_G665:@. | 67199 | CGMT5 | 30.5 | 59.9 | 134.1 | 2.4 | 196.4 |
| BN_G705:@. | 67199 | CGMT5 | 31.5 | 68.8 | 148.6 | 0.8 | 218.2 |
| BN_G634:@. | 67199 | CGMT5 | 32.5 | 56.8 | 116.8 | 0.9 | 174.4 |
| BN_G661:@. | 67199 | CGMT5 | 33.0 | 70.4 | 141.4 | 1.2 | 213.0 |
| BN_G633:@. | 67199 | CGMT5 | 33.8 | 67.9 | 132.3 | 0.6 | 200.7 |
| BN_G630:@. | 67199 | CGMT5 | 34.7 | 73.1 | 137.3 | 0.4 | 210.9 |
| BN_G708:@. | 67199 | CGMT5 | 35.1 | 85.4 | 155.8 | 1.8 | 242.9 |
| BN_G663:@. | 67199 | CGMT5 | 35.5 | 73.3 | 132.1 | 0.9 | 206.3 |
| RN_G666:@. | 67199 | CGMT5 | 35.8 | 69.7 | 124.4 | 0.8 | 194.9 |
| BN_G704:@. | 67199 | CGMT5 | 35.9 | 82.3 | 145.4 | 1.7 | 229.3 |
| BN_G701:@. | 67199 | CGMT5 | 36.6 | 84.6 | 144.8 | 1.8 | 231.2 |
| BN_G706:@. | 67199 | CGMT5 | 36.9 | 83.1 | 138.6 | 3.4 | 225.2 |
| BN_G632:@. | 67199 | CGMT5 | 37.6 | 75.4 | 125.2 | 0.2 | 200.8 |
| BN_G627:@. | 67199 | CGMT5 | 38.7 | 80.3 | 126.7 | 0.7 | 207.7 |
| BN_G703:@. | 67199 | CGMT5 | 39.5 | 85.6 | 128.1 | 2.8 | 216.5 |
| BN_G629:@. | 67199 | CGMT5 | 40.2 | 92.9 | 136.1 | 2.3 | 231.3 |
| BN_G628:@. | 67199 | CGMT5 | 41.1 | 63.0 | 89.8 | 0.6 | 153.4 |
| BN_G707:@. | 67199 | CGMT5 | 44.9 | 104.2 | 126.9 | 1.2 | 232.3 |
| BN_G700:@. | 67199 | CGMT5 | 49.8 | 110.3 | 111.1 | 0.1 | 221.5 |
| BN_G638:@. | 67199 | CGMT5 | 50.2 | 98.1 | 97.3 | 0.0 | 195.4 |
| BN_G662:@. | 67199 | CGMT5 | 51.0 | 88.9 | 85.3 | 0.2 | 174.3 |
| BN_G667:@. | 67199 | CGMT5 | 68.0 | 125.2 | 58.6 | 0.2 | 184.1 |
| BN_G724:@. | 67200 | CGMT6 | 38.7 | 105.5 | 162.3 | 4.6 | 272.4 |
| BN_G641:@. | 67200 | CGMT6 | 48.5 | 183.3 | 186.9 | 7.4 | 377.6 |
| BN_G647:@. | 67200 | CGMT6 | 49.1 | 124.4 | 126.1 | 2.7 | 253.2 |
| BN_G669:@. | 67200 | CGMT6 | 49.5 | 143.7 | 140.2 | 6.4 | 290.4 |
| BN_G695:@. | 67200 | CGMT6 | 52.7 | 162.6 | 142.1 | 3.8 | 308.6 |
| BN_G671:@. | 67200 | CGMT6 | 55.3 | 159.4 | 123.8 | 5.0 | 288.2 |
| BN_G693:@. | 67200 | CGMT6 | 55.5 | 192.9 | 149.0 | 5.8 | 347.7 |
| BN_G648:@. | 67200 | CGMT6 | 56.9 | 147.8 | 107.4 | 4.6 | 259.8 |
| BN_G699:@. | 67200 | CGMT6 | 57.2 | 161.0 | 116.7 | 3.5 | 281.2 |
| BN_G698:@. | 67200 | CGMT6 | 58.3 | 131.1 | 90.9 | 3.0 | 225.0 |
| BN_G642:@. | 67200 | CGMT6 | 59.6 | 217.4 | 142.9 | 4.7 | 364.9 |
| BN_G644:@. | 67200 | CGMT6 | 60.4 | 185.0 | 115.6 | 5.6 | 306.1 |
| BN_G694:@. | 67200 | CGMT6 | 61.5 | 140.8 | 84.7 | 3.5 | 229.0 |
| BN_G696:@. | 67200 | CGMT6 | 63.8 | 162.6 | 89.5 | 2.8 | 254.9 |
| BN_G672:@. | 67200 | CGMT6 | 66.3 | 165.8 | 79.2 | 5.0 | 250.0 |
| BN_G645:@. | 67200 | CGMT6 | 66.8 | 152.3 | 71.9 | 3.7 | 227.9 |
| BN_G640:@. | 67200 | CGMT6 | 67.0 | 202.2 | 96.1 | 3.7 | 302.0 |
| BN_G646:@. | 67200 | CGMT6 | 69.6 | 193.5 | 81.1 | 3.3 | 277.9 |
| BN_G643:@. | 67200 | CGMT6 | 69.8 | 206.3 | 85.0 | 4.5 | 295.7 |
| BN_G649:@. | 67200 | CGMT6 | 72.1 | 136.2 | 52.8 | 0.0 | 189.0 |
| BN_G670:@. | 67200 | CGMT6 | 73.8 | 177.8 | 59.5 | 3.5 | 240.8 |
| BN_G674:@. | 67201 | CGMT8 | 22.5 | 60.9 | 205.8 | 4.3 | 271.1 |
| BN_G675:@. | 67201 | CGMT8 | 27.7 | 73.0 | 188.0 | 2.7 | 263.7 |
| BN_G729:@. | 67201 | CGMT8 | 33.5 | 92.0 | 179.0 | 4.0 | 275.0 |
| BN_G771:@. | 67201 | CGMT8 | 33.6 | 81.0 | 157.0 | 3.0 | 241.0 |
| BN_G752:@. | 67201 | CGMT8 | 34.8 | 93.4 | 172.0 | 3.3 | 268.7 |
| BN_G678:@. | 67201 | CGMT8 | 35.2 | 87.9 | 158.1 | 3.8 | 249.8 |
| BN_G753:@. | 67201 | CGMT8 | 35.8 | 101.6 | 177.4 | 4.8 | 283.8 |
| BN_G770:@. | 67201 | CGMT8 | 36.5 | 91.0 | 155.0 | 3.0 | 249.0 |
| BN_G772:@. | 67201 | CGMT8 | 36.7 | 93.1 | 156.9 | 3.9 | 254.0 |
| BN_G737:@. | 67201 | CGMT8 | 37.2 | 95.9 | 159.6 | 2.1 | 257.5 |
| BN_G749:@. | 67201 | CGMT8 | 37.8 | 83.6 | 135.5 | 2.3 | 221.3 |
| BN_G748:@. | 67201 | CGMT8 | 38.2 | 100.9 | 160.1 | 3.2 | 264.2 |
| BN_G730:@. | 67201 | CGMT8 | 39.2 | 85.3 | 130.3 | 2.1 | 217.7 |
| BN_G735:@. | 67201 | CGMT8 | 40.7 | 102.4 | 145.9 | 3.2 | 251.5 |
| BN_G733:@. | 67201 | CGMT8 | 41.7 | 105.6 | 144.7 | 2.7 | 253.0 |
| BN_G710:@. | 67201 | CGMT8 | 42.5 | 98.5 | 129.0 | 4.3 | 231.8 |
| BN_G750:@. | 67201 | CGMT8 | 43.2 | 113.0 | 144.4 | 3.9 | 261.3 |
| BN_G751:@. | 67201 | CGMT8 | 44.0 | 128.0 | 159.1 | 3.9 | 291.0 |
| BN_G755:@. | 67201 | CGMT8 | 46.9 | 155.2 | 171.5 | 4.2 | 330.9 |
| BN_G728:@. | 67201 | CGMT8 | 47.5 | 118.2 | 128.3 | 2.4 | 248.8 |
| BN_G746:@. | 67201 | CGMT8 | 48.6 | 112.8 | 117.7 | 1.6 | 232.1 |
| BN_G732:@. | 67201 | CGMT8 | 49.4 | 135.4 | 135.9 | 2.8 | 274.1 |

TABLE 8-continued

| Pedigree | Construct | ZFP | % alpha | ng tocopherol/mg seed | | | ng total toco |
|---|---|---|---|---|---|---|---|
| | | | | alpha | gamma | delta | |
| BN_G745:@. | 67201 | CGMT8 | 49.5 | 127.8 | 126.8 | 3.6 | 258.3 |
| BN_G709:@. | 67201 | CGMT8 | 50.7 | 117.8 | 110.9 | 3.6 | 232.3 |
| BN_G734:@. | 67201 | CGMT8 | 51.3 | 125.9 | 117.3 | 2.1 | 245.3 |
| BN_G676:@. | 67201 | CGMT8 | 55.2 | 163.4 | 130.6 | 2.0 | 296.0 |
| BN_G736:@. | 67201 | CGMT8 | 55.7 | 129.9 | 101.1 | 2.2 | 233.2 |
| BN_G677:@. | 67201 | CGMT8 | 57.1 | 149.8 | 110.0 | 2.7 | 262.6 |
| BN_G747:@. | 67201 | CGMT8 | 61.3 | 147.6 | 91.3 | 1.8 | 240.8 |
| BN_G718:@. | 67202 | CGMT12 | 46.4 | 107.3 | 121.1 | 3.0 | 231.4 |
| BN_G711:@. | 67202 | CGMT12 | 47.8 | 114.0 | 122.3 | 2.3 | 238.6 |
| BN_G781:@. | 67202 | CGMT12 | 50.2 | 103.0 | 100.0 | 2.0 | 205.0 |
| BN_G780:@. | 67202 | CGMT12 | 50.6 | 84.0 | 81.0 | 1.0 | 166.0 |
| BN_G773:@. | 67202 | CGMT12 | 55.1 | 119.0 | 95.0 | 2.0 | 216.0 |
| BN_G776:@. | 67202 | CGMT12 | 56.6 | 116.0 | 90.0 | 1.0 | 207.0 |
| BN_G784:@. | 67202 | CGMT12 | 56.8 | 129.0 | 96.0 | 2.0 | 227.0 |
| BN_G774:@. | 67202 | CGMT12 | 57.9 | 125.0 | 89.0 | 2.0 | 216.0 |
| BN_G757:@. | 67202 | CGMT12 | 58.2 | 139.0 | 97.0 | 3.0 | 239.0 |
| BN_G756:@. | 67202 | CGMTI2 | 60.2 | 151.0 | 97.0 | 3.0 | 251.0 |
| BN_G712:@. | 67202 | CGMT12 | 62.0 | 148.4 | 89.0 | 2.0 | 239.4 |
| BN_G775:@. | 67202 | CGMT12 | 62.8 | 142.0 | 82.0 | 2.0 | 226.0 |
| BN_G713:@. | 67202 | CGMT12 | 63.2 | 124.3 | 70.9 | 1.4 | 196.5 |
| BN_G782:@. | 67202 | CGMT12 | 64.1 | 123.0 | 68.0 | 1.0 | 192.0 |
| BN_G738:@. | 67202 | CGMT12 | 64.1 | 165.9 | 90.9 | 2.0 | 258.9 |
| BN_G779:@. | 67202 | CGMT12 | 65.2 | 150.0 | 78.0 | 2.0 | 230.0 |
| BN_G786:@. | 67202 | CGMT12 | 65.7 | 134.0 | 69.0 | 1.0 | 204.0 |
| BN_G783:@. | 67202 | CGMT12 | 68.2 | 137.0 | 63.0 | 1.0 | 201.0 |
| BN_G777:@. | 67202 | CGMT12 | 68.6 | 162.0 | 73.0 | 1.0 | 236.0 |
| BN_G717:@. | 67202 | CGMT12 | 69.9 | 164.2 | 69.8 | 0.9 | 234.9 |
| BN_G714:@. | 67202 | CGMT12 | 70.0 | 169.7 | 70.9 | 1.7 | 242.4 |
| BN_G716:@. | 67202 | CGMTI2 | 71.4 | 154.0 | 61.2 | 0.6 | 215.9 |
| BN_G715:@. | 67202 | CGMT12 | 72.2 | 172.5 | 64.8 | 1.6 | 239.0 |
| BN_G740:@. | 67202 | CGMT12 | 72.9 | 179.8 | 65.6 | 1.4 | 246.8 |
| BN_G742:@. | 67202 | CGMT12 | 73.2 | 153.0 | 55.0 | 1.0 | 209.0 |
| BN_G739:@. | 67202 | CGMT12 | 75.2 | 199.9 | 64.5 | 1.6 | 266.0 |
| BN_G719:@. | 67202 | CGMT12 | 78.3 | 179.1 | 48.9 | 0.7 | 228.6 |
| BN_G785:@. | 67202 | CGMT12 | 80.1 | 161.0 | 39.0 | 1.0 | 201.0 |
| BN_G741:@. | 67202 | CGMT12 | 84.3 | 201.2 | 36.0 | 1.4 | 238.5 |
| BN_G852:@. | 67215 | CGMT3 | 33.4 | 86.6 | 169.9 | 3.1 | 259.6 |
| BN_G789:@. | 67215 | CGMT3 | 36.3 | 83.8 | 143.8 | 3.2 | 230.9 |
| BN_G787:@. | 67215 | CGMT3 | 36.7 | 83.4 | 140.4 | 3.6 | 227.4 |
| BN_G791:@. | 67215 | CGMT3 | 37.9 | 86.0 | 138.5 | 2.2 | 226.6 |
| BN_G841:@. | 67215 | CGMT3 | 38.8 | 90.0 | 139.0 | 3.0 | 232.0 |
| BN_G820:@. | 67215 | CGMT3 | 39.3 | 103.0 | 155.0 | 4.0 | 262.0 |
| BN_G839:@. | 67215 | CGMT3 | 39.3 | 97.1 | 146.2 | 3.5 | 246.8 |
| BN_G856:@. | 67215 | CGMT3 | 40.7 | 93.7 | 133.5 | 3.1 | 230.3 |
| BN_G855:@. | 67215 | CGMT3 | 41.2 | 120.0 | 166.4 | 5.1 | 291.5 |
| BN_G819:@. | 67215 | CGMT3 | 41.9 | 112.0 | 151.0 | 4.0 | 267.0 |
| BN_G845:@. | 67215 | CGMT3 | 43.0 | 114.0 | 148.0 | 3.0 | 265.0 |
| BN_G846:@. | 67215 | CGMT3 | 43.5 | 105.0 | 134.0 | 2.4 | 241.4 |
| BN_G847:@. | 67215 | CGMT3 | 43.7 | 103.5 | 131.3 | 1.9 | 236.6 |
| BN_G851:@. | 67215 | CGMT3 | 43.9 | 100.6 | 125.8 | 2.6 | 229.0 |
| BN_G843:@. | 67215 | CGMT3 | 46.2 | 102.3 | 116.4 | 2.9 | 221.5 |
| BN_G850:@. | 67215 | CGMT3 | 46.2 | 114.3 | 130.7 | 2.4 | 247.4 |
| BN_G853:@. | 67215 | CGMT3 | 46.5 | 148.8 | 166.2 | 4.8 | 319.8 |
| BN_G842:@. | 67215 | CGMT3 | 47.1 | 124.0 | 136.0 | 3.0 | 263.0 |
| BN_G821:@. | 67215 | CGMT3 | 47.7 | 127.0 | 136.0 | 3.0 | 266.0 |
| BN_G849:@. | 67215 | CGMT3 | 48.4 | 108.3 | 112.8 | 2.8 | 223.9 |
| BN_G848:@. | 67215 | CGMT3 | 49.2 | 127.0 | 128.0 | 3.0 | 258.0 |
| BN_G840:@. | 67215 | CGMT3 | 50.6 | 118.0 | 112.0 | 3.0 | 233.0 |
| BN_G854:@. | 67215 | CGMT3 | 51.5 | 128.6 | 118.3 | 3.0 | 249.8 |
| BN_G793:@. | 67215 | CGMT3 | 52.6 | 122.3 | 108.3 | 2.1 | 232.7 |
| BN_G790:@. | 67215 | CGMT3 | 54.4 | 136.0 | 111.0 | 3.0 | 250.0 |
| BN_G858:@. | 67215 | CGMT3 | 54.5 | 140.0 | 114.0 | 3.0 | 256.9 |
| BN_G788:@. | 67215 | CGMT3 | 55.9 | 138.0 | 107.0 | 2.0 | 247.0 |
| BN_G844:@. | 67215 | CGMT3 | 60.4 | 160.2 | 103.1 | 1.9 | 265.2 |
| BN_G857:@. | 67215 | CGMT3 | 62.9 | 163.0 | 93.0 | 3.0 | 259.0 |
| BN_G792:@. | 67215 | CGMT3 | 63.9 | 164.0 | 89.8 | 2.8 | 256.7 |
| BN_G796:@. | 67216 | CGMT7 | 24.8 | 52.0 | 155.0 | 3.0 | 210.0 |
| BN_G823:@. | 67216 | CGMT7 | 25.4 | 47.0 | 136.0 | 2.0 | 185.0 |
| BN_G826:@. | 67216 | CGMT7 | 30.3 | 56.0 | 126.0 | 3.0 | 185.0 |
| BN_G825:@. | 67216 | CGMT7 | 30.8 | 66.0 | 144.0 | 4.0 | 214.0 |
| BN_G766:@. | 67216 | CGMT7 | 30.9 | 71.0 | 156.0 | 3.0 | 230.0 |
| BN_G822:@. | 67216 | CGMT7 | 32.7 | 65.0 | 131.0 | 3.0 | 199.0 |
| BN_G802:@. | 67216 | CGMT7 | 33.0 | 72.0 | 142.0 | 4.0 | 218.0 |
| BN_G800:@. | 67216 | CGMT7 | 34.4 | 72.0 | 133.0 | 4.0 | 209.0 |
| BN_G801:@. | 67216 | CGMT7 | 35.0 | 77.0 | 139.0 | 4.0 | 220.0 |
| BN_G798:@. | 67216 | CGMT7 | 35.0 | 69.0 | 125.0 | 3.0 | 197.0 |

TABLE 8-continued

| Pedigree | Construct | ZFP | % alpha | ng tocopherol/mg seed | | | ng total toco |
|---|---|---|---|---|---|---|---|
| | | | | alpha | gamma | delta | |
| BN_G795:@. | 67216 | CGMT7 | 36.7 | 80.0 | 133.0 | 5.0 | 218.0 |
| BN_G765:@. | 67216 | CGMT7 | 37.6 | 92.0 | 149.0 | 4.0 | 245.0 |
| BN_G824:@. | 67216 | CGMT7 | 39.7 | 89.0 | 132.0 | 3.0 | 224.0 |
| BN_G758:@. | 67216 | CGMT7 | 41.1 | 92.0 | 128.0 | 4.0 | 224.0 |
| BN_G799:@. | 67216 | CGMT7 | 41.7 | 95.0 | 129.0 | 4.0 | 228.0 |
| BN_G763:@. | 67216 | CGMT7 | 41.7 | 85.0 | 115.0 | 4.0 | 204.0 |
| BN_G794:@. | 67216 | CGMT7 | 41.7 | 78.0 | 106.0 | 3.0 | 187.0 |
| BN_G767:@. | 67216 | CGMT7 | 42.1 | 80.0 | 107.0 | 3.0 | 190.0 |
| BN_G768:@. | 67216 | CGMT7 | 43.2 | 82.0 | 105.0 | 3.0 | 190.0 |
| BN_G760:@. | 67216 | CGMT7 | 43.4 | 99.3 | 125.3 | 4.1 | 228.7 |
| BN_G759:@. | 67216 | CGMT7 | 44.2 | 99.4 | 122.7 | 2.9 | 225.0 |
| BN_G744:@. | 67216 | CGMT7 | 44.2 | 117.4 | 144.6 | 3.6 | 265.5 |
| BN_G804:@. | 67216 | CGMT7 | 45.8 | 98.0 | 112.0 | 4.0 | 214.0 |
| BN_G797:@. | 67216 | CGMT7 | 47.0 | 87.0 | 95.0 | 3.0 | 185.0 |
| BN_G762:@. | 67216 | CGMT7 | 48.4 | 106.0 | 110.0 | 3.0 | 219.0 |
| BN_G761:@. | 67216 | CGMT7 | 52.1 | 126.0 | 113.0 | 3.0 | 242.0 |
| BN_G743:@. | 67216 | CGMT7 | 52.4 | 119.9 | 106.3 | 2.5 | 228.6 |
| BN_G769:@. | 67216 | CGMT7 | 56.7 | 122.0 | 91.0 | 2.0 | 215.0 |
| BN_G890:@. | 67217 | CGMT9 | 33.3 | 94.0 | 183.8 | 4.0 | 281.7 |
| BN_G860:@. | 67217 | CGMT9 | 33.7 | 89.0 | 172.0 | 3.0 | 264.0 |
| BN_G885:@. | 67217 | CGMT9 | 34.9 | 84.1 | 154.2 | 2.9 | 241.2 |
| BN_G888:@. | 67217 | CGMT9 | 37.5 | 92.5 | 151.9 | 2.4 | 246.8 |
| BN_G859:@. | 67217 | CGMT9 | 37.7 | 90.2 | 146.5 | 2.6 | 239.3 |
| BN_G829:@. | 67217 | CGMT9 | 38.1 | 92.1 | 146.8 | 3.2 | 242.0 |
| BN_G863:@. | 67217 | CGMT9 | 42.6 | 88.9 | 116.6 | 3.0 | 208.5 |
| BN_G884:@. | 67217 | CGMT9 | 43.0 | 105.0 | 136.0 | 3.0 | 244.0 |
| BN_G864:@. | 67217 | CGMT9 | 43.5 | 89.5 | 113.4 | 2.7 | 205.6 |
| BN_G865:@. | 67217 | CGMT9 | 43.8 | 89.8 | 112.8 | 2.3 | 204.9 |
| BN_G881:@. | 67217 | CGMT9 | 45.0 | 118.0 | 141.0 | 3.0 | 262.0 |
| BN_G889:@. | 67217 | CGMT9 | 45.2 | 112.0 | 133.0 | 3.0 | 248.0 |
| BN_G887:@. | 67217 | CGMT9 | 45.4 | 99.0 | 117.0 | 2.0 | 218.0 |
| BN_G883 @. | 67217 | CGMT9 | 45.5 | 105.0 | 123.7 | 2.2 | 230.8 |
| BN_G891:@. | 67217 | CGMT9 | 45.6 | 119.0 | 139.7 | 2.1 | 260.8 |
| BN_G867:@. | 67217 | CGMT9 | 46.3 | 86.3 | 98.0 | 2.2 | 186.5 |
| BN_G828:@. | 67217 | CGMT9 | 46.4 | 110.8 | 125.6 | 2.4 | 238.8 |
| BN_G861:@. | 67217 | CGMT9 | 46.6 | 100.8 | 113.5 | 1.9 | 216.1 |
| BN_G830:@. | 67217 | CGMT9 | 48.0 | 128.4 | 136.5 | 2.5 | 267.5 |
| BN_G866:@. | 67217 | CGMT9 | 48.2 | 92.1 | 96.9 | 2.2 | 191.2 |
| BN_G806:@. | 67217 | CGMT9 | 48.5 | 119.7 | 123.8 | 3.5 | 246.9 |
| BN_G886:@. | 67217 | CGMT9 | 49.6 | 119.7 | 119.2 | 2.5 | 241.4 |
| BN_G879:@. | 67217 | CGMT9 | 49.8 | 112.5 | 111.0 | 2.3 | 225.7 |
| BN_G862:@. | 67217 | CGMT9 | 51.2 | 128.5 | 119.7 | 2.7 | 251.0 |
| BN_G892:@. | 67217 | CGMT9 | 53.4 | 125.0 | 107.0 | 2.0 | 234.0 |
| BN_G880:@. | 67217 | CGMT9 | 54.0 | 118.9 | 99.8 | 1.5 | 220.2 |
| BN_G827:@. | 67217 | CGMT9 | 54.8 | 131.0 | 106.0 | 2.0 | 239.0 |
| BN_G882:@. | 67217 | CGMT9 | 56.6 | 120.9 | 91.0 | 1.6 | 213.4 |
| BN_G805:@. | 67217 | CGMT9 | 57.5 | 127.5 | 92.5 | 1.8 | 221.8 |
| BN_G878:@. | 67217 | CGMT9 | 60.3 | 123.6 | 79.4 | 1.9 | 204.9 |
| BN_G810:@. | 67218 | CGMT10 | 38.0 | 86.7 | 139.0 | 2.3 | 228.0 |
| BN_G811:@. | 67218 | CGMT10 | 40.0 | 80.2 | 118.9 | 1.6 | 200.7 |
| BN_G869:@. | 67218 | CGMT10 | 40.0 | 73.8 | 109.4 | 1.4 | 184.6 |
| BN_G871:@. | 67218 | CGMT10 | 40.5 | 69.6 | 101.1 | 1.1 | 171.7 |
| BN_G874:@. | 67218 | CGMT10 | 41.3 | 91.6 | 127.9 | 2.2 | 221.8 |
| BN_G875:@. | 67218 | CGMT10 | 42.2 | 71.7 | 96.0 | 2.3 | 170.0 |
| BN_G835:@. | 67218 | CGMT10 | 43.9 | 93.4 | 117.7 | 1.5 | 212.6 |
| BN_G870:@. | 67218 | CGMT10 | 46.9 | 115.0 | 128.0 | 2.0 | 245.0 |
| BN_G807:@. | 67218 | CGMT10 | 47.4 | 82.8 | 90.4 | 1.2 | 174.5 |
| BN_G836:@. | 67218 | CGMT10 | 48.1 | 86.3 | 92.0 | 1.1 | 179.4 |
| BN_G808:@. | 67218 | CGMT10 | 49.7 | 97.6 | 97.3 | 1.4 | 196.3 |
| BN_G809:@. | 67218 | CGMT10 | 50.8 | 85.8 | 82.2 | 1.1 | 169.1 |
| BN_G832:@. | 67218 | CGMT10 | 51.0 | 85.2 | 80.9 | 1.0 | 167.1 |
| BN_G837:@. | 67218 | CGMT10 | 51.3 | 86.5 | 80.7 | 1.3 | 168.5 |
| BN_G868:@. | 67218 | CGMT10 | 52.0 | 97.6 | 89.3 | 0.8 | 187.7 |
| BN_G876:@. | 67218 | CGMT10 | 52.7 | 106.0 | 93.0 | 2.0 | 201.0 |
| BN_G818:@. | 67218 | CGMT10 | 53.3 | 99.4 | 85.4 | 1.6 | 186.4 |
| BN_G833:@. | 67218 | CGMT10 | 53.4 | 86.7 | 74.5 | 1.1 | 162.3 |
| BN_G814:@. | 67218 | CGMT10 | 57.2 | 118.5 | 88.0 | 0.5 | 207.0 |
| BN_G872:@. | 67218 | CGMT10 | 57.4 | 109.0 | 80.0 | 1.0 | 190.0 |
| BN_G817:@. | 67218 | CGMT10 | 58.0 | 112.4 | 80.2 | 1.1 | 193.8 |
| BN_G834:@. | 67218 | CGMT10 | 59.1 | 98.0 | 66.6 | 1.1 | 165.7 |
| BN_G838:@. | 67218 | CGMT10 | 59.4 | 117.0 | 79.0 | 1.0 | 197.0 |
| BN_G831:@. | 67218 | CGMT10 | 63.0 | 114.0 | 66.0 | 1.0 | 181.0 |
| BN_G816:@. | 67218 | CGMT10 | 64.3 | 194.0 | 104.6 | 3.4 | 301.9 |
| BN_G873:@. | 67218 | CGMT10 | 67.1 | 169.0 | 82.0 | 1.0 | 252.0 |
| BN_G815:@. | 67218 | CGMT10 | 68.1 | 111.2 | 50.8 | 1.3 | 163.3 |
| BN_G813:@. | 67218 | CGMT10 | 74.2 | 183.4 | 62.1 | 1.8 | 247.3 |

TABLE 8-continued

| | | | ng tocopherol/mg seed | | | | |
|---|---|---|---|---|---|---|---|
| Pedigree | Construct | ZFP | % alpha | alpha | gamma | delta | ng total toco |
| BN_G812:@. | 67218 | CGMT10 | 74.6 | 144.0 | 48.0 | 1.0 | 193.0 |
| BN_G877:@. | 67218 | CGMT10 | 80.1 | 113.0 | 27.0 | 1.0 | 141.0 |

Figure 15:
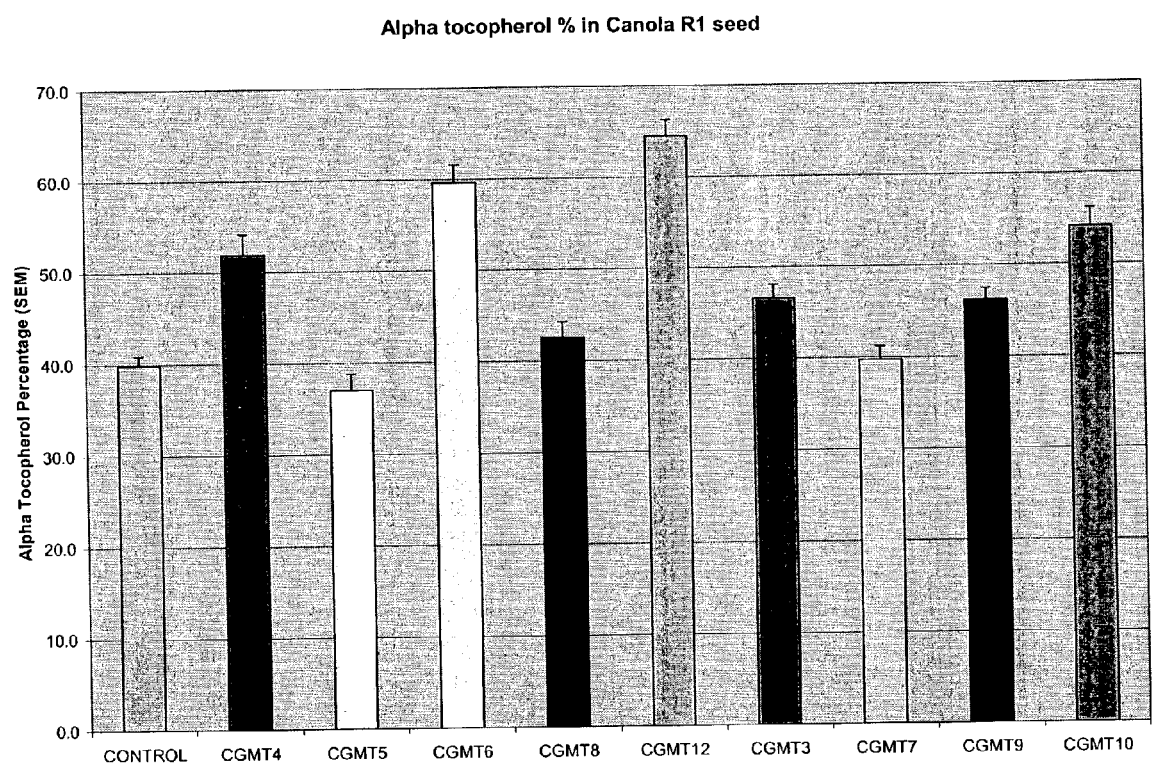
FIG. 15 shows mean (±SEM) seed alpha-tocopherol percentage in the R1 seed from *Brassica napus* plants expressing zinc finger transcription factors designed to upregulate the expression of the endogenous GMT gene under the control of the napin (embryo-specific) promoter.

The results presented in Table 8 are summarized in Table 9 and FIG. 15, and indicate that transgenic Canola (*Brassica*) comprising GMT-targeted ZFPs linked to an activation domain produce increased levels of α-tocopherol, compared to plants not containing GMT-targeted ZFPs.

TABLE 9

Summary of Canola R1 seed alpha-tocopherol percentage data from transgenic plants expressing zinc finger transcription factors designed to upregulate the endogenous GMT gene.

| CANOLA SUMMARY | CONTROL | CGMT4 | CGMT5 | CGMT6 | CGMT8 | CGMT12 | CGMT3 | CGMT7 | CGMT9 | CGMT10 |
|---|---|---|---|---|---|---|---|---|---|---|
| MEAN | 39.9 | 51.9 | 37.0 | 59.6 | 42.5 | 64.5 | 46.6 | 39.7 | 46.2 | 54.2 |
| SEM | 1.0 | 2.2 | 1.8 | 2.0 | 1.7 | 1.8 | 1.5 | 1.5 | 1.3 | 2.0 |
| N | 65 | 31 | 28 | 21 | 29 | 30 | 28 | 28 | 30 | 30 |

Example 11

Construction of the YCF4 Vector

YCF4 is a derivative of the YCF3 vector (see Example 2) which allows removal of sequences encoding the zinc finger and C1 activation domains as a NotI/HindIII fragment.

To generate YCF4, a primer containing a Not I site immediately downstream of a Spe I site (YCFnotI: GGGACT-TGACTAGTGCGGCCGCCACCATG) (SEQ ID No: 133) was designed. This primer was then used, in conjunction with the NVF1879rev primer (CGGGTTTAAACGGGC-CCTCTAGACTC) (SEQ ID No: 134) to amplify a 581 bp fragment (containing NLS-ZFP-C1) from YCF3. The amplified fragment was digested with Spe I and Hind III, and ligated to a longer fragment from a Spe I/Hind III digest of YCF3, to create YCF4.

Example 12

Modulation of GMT Gene Expression and Elevation of Seed α-tocopherol Levels in *Arabidopsis* using Engineered Transcription Factors In this example, synthetic zinc finger transcription factors (ZFP-TFs) were designed to upregulate the expression of the endogenous *Arabidopsis* γ-tocopherol methyltransferase (GMT) gene. This gene encodes the enzyme responsible for the conversion of γ-tocopherol to α-tocopherol, the tocopherol species with the highest vitamin E activity. A number of three-finger zinc finger protein (ZFP) DNA binding domains were constructed and proven to bind tightly to 9 bp DNA sequences located in either the promoter or coding region of the GMT gene. When these ZFPs were fused to a nuclear localization signal and the maize C1 activation domain, all but one upregulated the expression of the GMT gene in leaf protoplast transient assays. Seed-specific expression of these ZFP-TFs in transgenic *Arabidopsis* produced several lines with heritable elevations in seed α-tocopherol. These results demonstrate that engineered ZFP-TFs comprising plant-derived elements are capable of modulating the expression of endogenous genes and modulating levels of metabolites, in whole living plants.

Introduction

The tools of plant biotechnology allow the engineering of novel traits via introduction of foreign genes into plants and expression of these genes in a developmental or tissue specific manner using selected promoters. Desired traits can alternatively be obtained by regulating the expression of endogenous genes. One method to achieve this type of targeted gene regulation is through the use of engineered transcription factors. Transcription factors are trans-acting proteins that bind to specific cis-elements and regulate gene expression. Transcription factors are typically modular, consisting of a DNA-binding domain (DBD) and an effector domain (ED) that interacts with other regulatory proteins to either activate or repress transcription. Zinc finger proteins (ZFPs) are the most common DBDs in eukaryotes and over the past decade this motif has emerged as being particularly amenable to manipulations designed to achieve the specific recognition of a predetermined DNA sequence (see references 1-3 infra). Such designer ZFPs have been fused to different EDs to create hybrid zinc finger transcription factors (ZFP-TFs) that have been used successfully in the regulation of endogenous chromosomal genes in both animals (Rebar et al. (2002) *Nature Medicine* 8:1427-1432) and animal cell lines (references 4-9 infra) and more recently transgenic plants (10).

Figure 16:
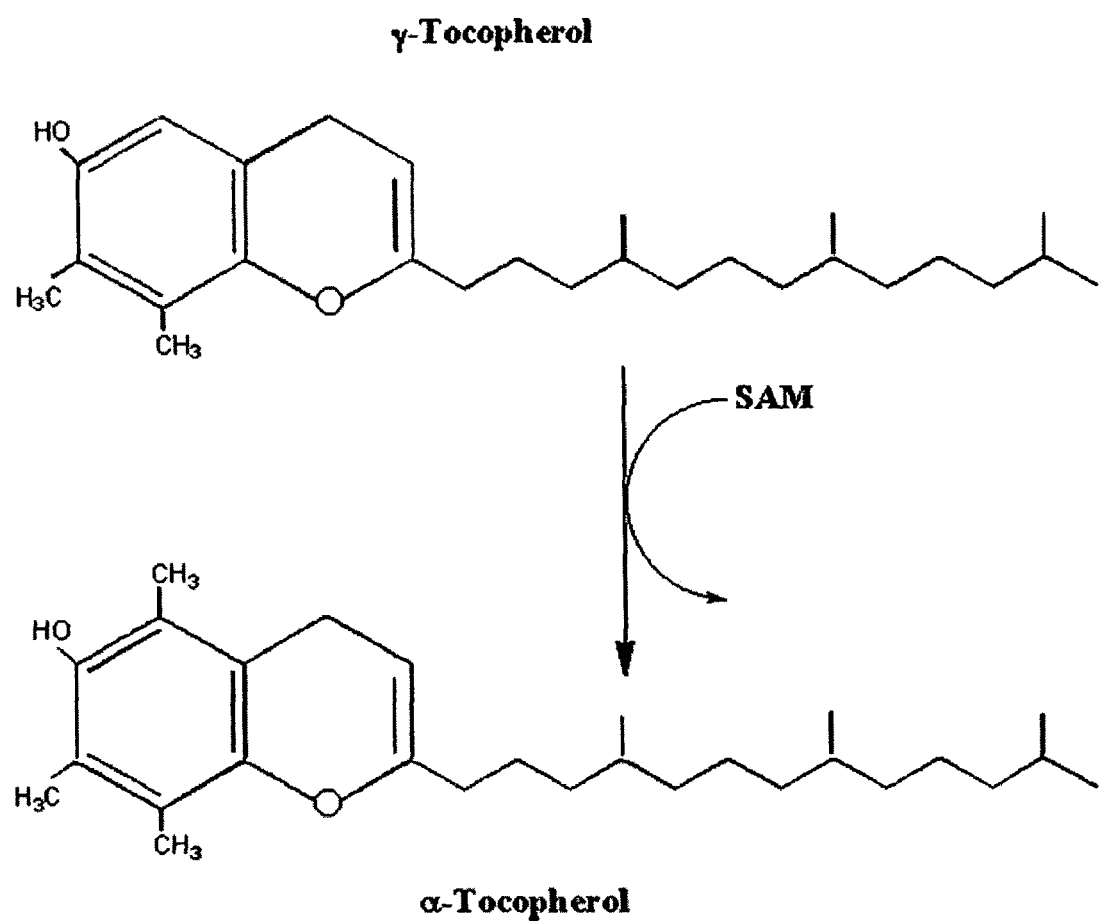
FIG. 16 shows the biosynthetic reaction catalyzed by γ-tocopherol metyltransferase (GMT). GMT adds a methyl group to ring carbon 5 of γ-tocopherol.

This example describes the production of exemplary ZFP-TFs comprising plant-derived DNA sequences that were engineered to activate the endogenous *Arabidopsis* γ-tocopherol methyltransferase (GMT) gene (GenBank Accession AF104220). GMT encodes the enzyme responsible for addition of a methyl group to ring carbon 5 of γ-tocopherol to form α-tocopherol (FIG. 16), the tocopherol isoform with the highest vitamin E activity (11). GMT is frequently limiting in seed tissue and, as a result, the tocopherol composition of seed from many plant species is made up predominately of γ-tocopherol (12). Transgenic overexpression of an *Arabidopsis* GMT cDNA was previously found to result in a greater than 85-fold increase in percent α-tocopherol relative to control seed, which translated into a nine-fold increase in the vitamin E activity of transgenic seed (13).

In this example, a number of three-finger ZFPs were designed to bind to target 9 bp sequences in the upstream and coding regions of the endogenous *Arabidopsis* GMT gene. Each of these ZFPs was fused to the maize opaque-2 nuclear localization signal (GenBank Accession M2941 1) and the maize C1 (GenBank Accession TVZMMB) activation ED (14, 15) to make ZFP-TFs. Expression of these ZFP-TFs in transgenic *Arabidopsis*, under the control of an embryo specific promoter (16), resulted in generation of several lines that had an elevated seed α-tocopherol percentage, with one line demonstrating a heritable 20-fold increase in percent α-tocopherol relative to control seed.

DNase I Hypersensitive Site Mapping of the *Arabidopsis* GMT Gene

Previous studies indicated that chromatin organization can be a determinant of ZFP-TF function within endogenous chromosomal loci. For example, the positioning of nucleosomes at endogenous loci can prevent the access of a DBD to its DNA binding site (18). Targeting ZFP-TFs to accessible regions of cellular chromatin can, in certain circumstances, increase their chances of successfully regulating the target gene (5, 7; see also WO 01/83751). Accordingly, DNase I hypersensitive site mapping was performed to locate accessible regions of the GMT gene. Given the impracticality of obtaining large quantities of *Arabidopsis* embryo tissue, leaf tissue was used for the hypersensitive site mapping of the GMT gene. This data was then utilized to infer potential accessible sites in the embryo. A previous study demonstrated that some DNase I hypersensitive sites, especially those near the transcription start site, are conserved between different tissues and cell types (7).

To map accessible regions in the *Arabidopsis* GMT gene, leaves from 3-4 week *Arabidopsis thaliana* (ecotype Columbia) grown on soil under a 16-hr-light/8-hr-dark cycle and 25° C. constant temperature were harvested, and intact nuclei were obtained and digested with increasing concentrations of DNase I (ref. 24). Hypersensitivity mapping was performed essentially as described (5). Briefly, DNA from DNase I-treated nuclei was isolated and digested to completion with Dra II, resolved on agarose gels and transferred to nylon membranes. These membranes were hybridized to an indirect end-labeled 500 bp probe derived from the genomic sequence located 1.5-2 kb upstream of the GMT transcription start site.

Figure 17:
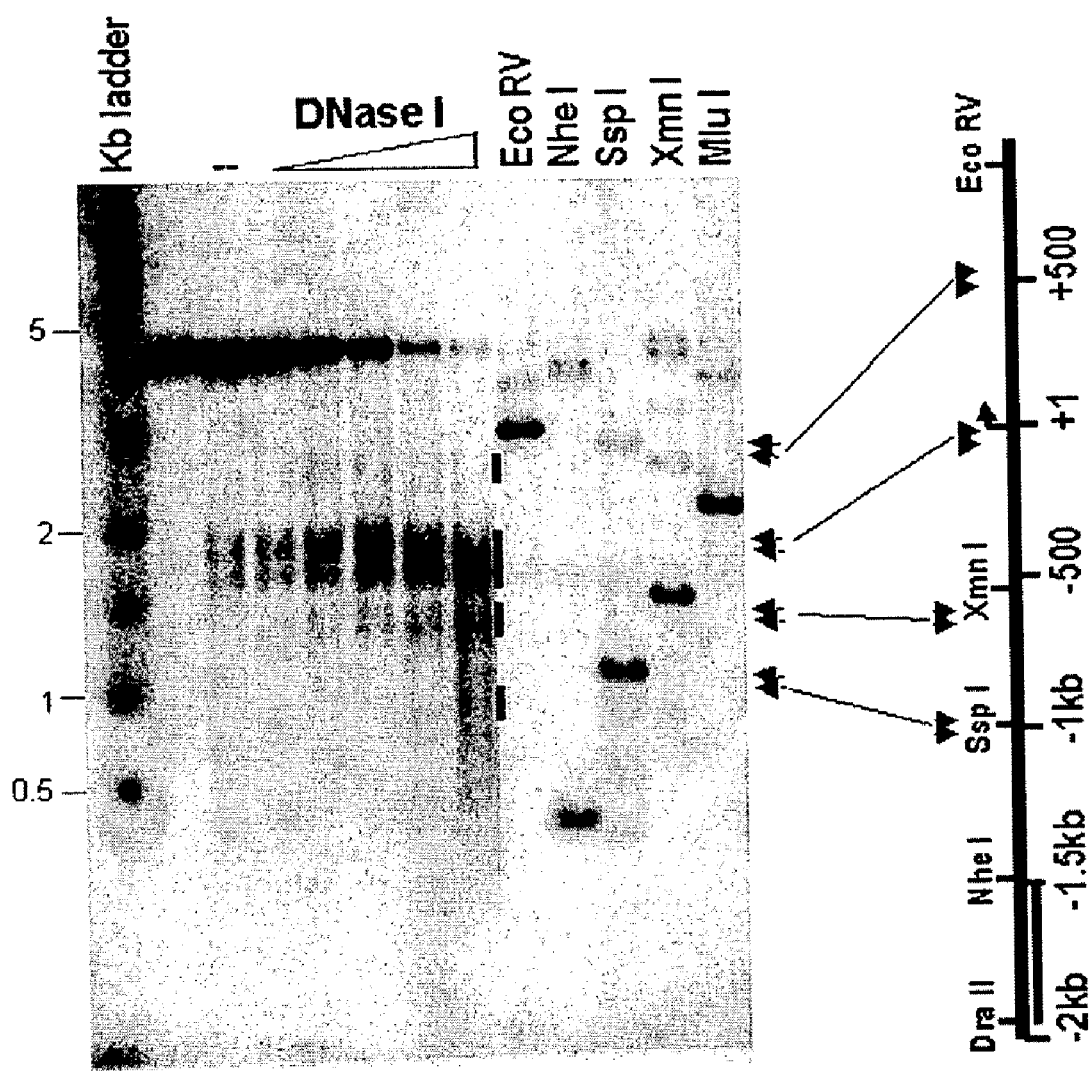
FIG. 17 shows the identification of DNase I hypersensitive sites in the *Arabidopsis* γ-tocopherol metyltransferase (GMT) gene. Nuclei from *Arabidopsis* leaves were digested with increasing concentrations of DNaseI or the indicated restriction enzymes. A 500 bp region of the genomic sequence located 1.5-2 kb upstream of the GMT transcription start site was used as a probe on a Southern blot of extracted nuclear DNA (left side of figure). The transcription start site (+1) of the GMT gene (represented on the right side of the figure) and the location of the probe (black line) are shown. Double arrows indicate the relationship of the observed hypersensitive sites to regions on the GMT gene.

The DNase I hypersensitive site mapping revealed four hypersensitive sites (FIG. 17). The most accessible, and therefore most easily detectable, hypersensitive site was a doublet centered at −140 bp upstream of the transcription start site, which encompassed the transcription start site and the 5' UTR. A second hypersensitive site was centered around −600 bp. This hypersensitive site was fairly narrow but had a high intensity. Two additional hypersensitive sites (at −1000 bp, +500 bp) were also detected.

Biochemical Characterization of ZFPs and Design of ZFP-TFs

Several target sites were selected, based on their positions relative to the DNase hypersensitive sites and their suitability as ZFP target sequences (see, e.g., U.S. Pat. No. 6,435,242). Locations of these target sites in the GMT gene, and their nucleotide sequences, are shown in FIG. 18. ZFPs were designed to bind to these target sequences, using design strategies disclosed, for example, in U.S. Pat. Nos. 6,007,988 and 6,453,242; WO 98/53058; WO 98/53059; WO 98/53060 and WO 00/41566 (but see below). The ZFPs were purified as fusions with the maltose-binding protein, and gel shift assays to determine binding specificity were performed as described previously (5, 7, 25), with the exception that an additional 150 mM NaCl was included in the binding reaction. See also U.S. Pat. No. 6,453,242 and WO 00/41566.

Although these ZFPs were assembled primarily using previous described methods (5, 7; see also U.S. Pat. No. 6,435, 242 and WO 00/41566), they were distinct from most previously reported synthetic ZFPs in two ways. Firstly, the backbone of these ZFPs was of plant origin, having been assembled from DNA fragments derived from several different plant ZFPs. See WO 02/57294. This unique zinc finger backbone had overall sequence similarities to human SP1, a natural ZFP (20). Secondly, for certain ZFPs, the first two fingers were canonical $C_2H_2$ fingers; while, in the third finger, the second conserved histidine and the two adjacent upstream amino acid residues were substituted with GlyGlyCys, making the third finger a $C_2HC$ type. See WO 02/57293. ZFPs with a plant backbone and one $C_2HC$ finger bound to their naked DNA target sequences with higher affinities and specificities than those previously-reported for synthetic ZFPs using a more conventional backbone (see 5, 7). The amino acid sequence of the recognition region (i.e., positions "−1" through "+6" with respect to the start of the α-helix of each finger) for each finger of each ZFP is shown in FIG. 18 ( the one-letter amino acid code is used). Gel mobility-shift analyses showed that the Kd value of these ZFPs for their naked DNA target sequence ranged from 0.0003 to 0.004 nM. As a comparison, the naturally-occurring ZFP SP1 exhibited a Kd of 0.055 nM for its target under the same gel shift conditions.

Figure 19:
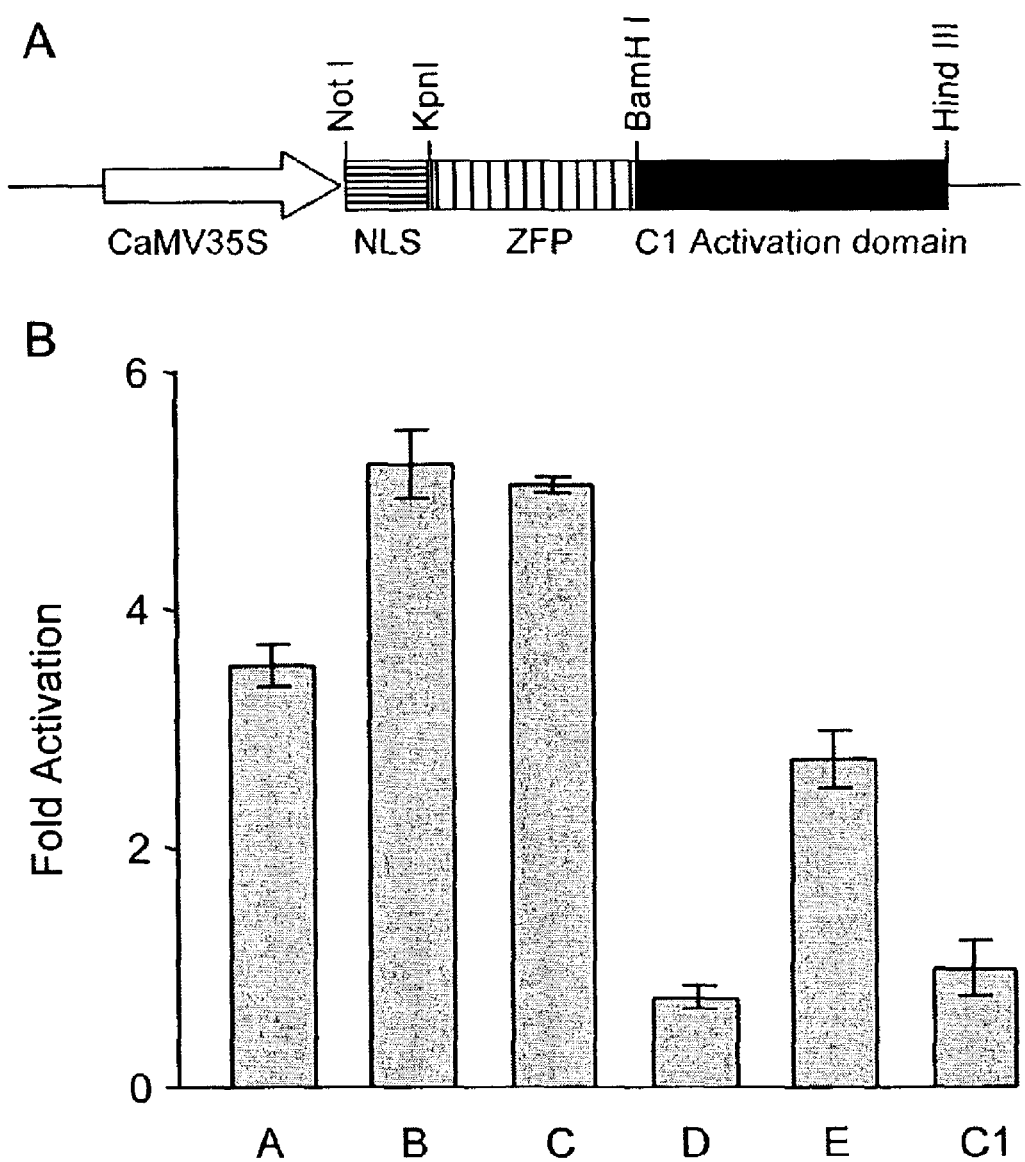
FIGS. 19A and 19B show the structure of vectors encoding GMT-targeted ZFP-TFs and shows transcriptional activation of the endogenous *Arabidopsis* γ-tocopherol methyltransferase (GMT) gene by ZFP-TFs in leaf protoplasts.

Translational fusions were made between the opaque-2 nuclear localization signal (NLS), the engineered ZFP binding domains, and the activation domain of C1, to generate the plant-derived ZFP-TFs (FIG. 19). Previous studies of C1, a transcriptional activator of genes encoding biosynthetic enzymes of the maize anthocyanin pigment pathway, demonstrated that the carboxy-terminal 100 amino acids were able to function as a transcriptional activator in maize, yeast and *Arabidopsis* (14, 15). A shortened C1 activation domain (60 carboxyl-terminal amino acids) was used here, as it was found to provide superior reporter gene activation in *Arabidopsis* leaf protoplast-based transient assays.

To construct the fusions, ZFP binding domains were subcloned into a plant ZFP expression vector, YCF4, generated from pcDNA3.1 (Invitrogen, Carlsbad, Calif.). YCF4 contains a CaMV35S promoter driving expression of the coding sequences from the maize opaque-2 nuclear localization signal (RKRKESNRESARRSRRSRYRKKV) (SEQ ID NO: 135) and 60 amino acids from the maize C1 activation domain (AGSSDDCSSAASVSLRVGSHDEPCFS-GDGDGDWMDDVRALASFLESDEDWLRC QTAGQLA) (SEQ ID NO: 136). All of the ZFP-TF expression vectors were constructed by subcloning the ZFP fragments into the KpnI and BamHI sites in YCF4 between the NLS and the C1-ED (FIG. 19). See Example 11 for additional information on the construction of YCF4.

Transcriptional Activation of the Endozenous *Arabidopsis* GMT Gene in Leaf Protoplasts Plasmids encoding each of the ZFP-TFs described above, cloned under the control of the constitutive 35S promoter (FIG. 19), were transiently transfected into *Arabidopsis* leaf protoplasts, and GMT mRNA levels were measured by quantitative real-time PCR analysis (TaqMan®).

Isolation and transformation of *Arabidopsis* leaf protoplasts were carried out as described (26) with the following modifications. Purified protoplasts were resuspended to a density of $5 \times 10^6$ protoplast/ml in a solution containing 400 mM mannitol, 15 mM $MgCl_2$ and 5 mM Mes-KOH at pH 5.6. Approximately $1.6 \times 10^6$ protoplasts (300 μl suspension) were added to a mixture of 50 μg ZFP-TF-encoding plasmid DNA in a 15 ml disposable conical tube and mixed well. PEG-CMS solution (400 mM mannitol, 100 mM $Ca(NO_3)_2$, 40% PEG3350) was immediately added to a final PEG concentration of 20% and the suspension was carefully mixed to a homogeneous phase. Following incubation at room temperature for 30 min, 10 ml of protoplast growth medium (400 mM sucrose, 4.4 g/L Murashige and Skoog salt and vitamin mixture (Gibco, Rockville, Md.), and 250 mg/L xylose) was added to the transfection mixture; it was then transferred to a 10 cm petri dish and incubated in the dark at 25° C. for 18-24 hours.

For quantitative RT-PCR analysis of mRNA abundance in protoplasts, total RNA from transfected *Arabidopsis* leaf protoplasts was isolated using the plant RNeasy kit (Qiagen, Valencia, Calif.). Real time PCR analysis was performed in a 96-well format on an ABI 7700 SDS machine (Perkin Elmer, Chicago, Ill.) and analyzed with SDS version 1.6.3 software. RNA samples (5 ng) were mixed with 0.3 µM each primer, 0.1 µM probe, 5.5 mM $MgCl_2$ and 0.3 mM each dNTP, 0.625 unit of AmpliTaq Gold RNA polymerase (Hoffman La-Roche, Inc.), 6.25 units of Multiscribe Reverse Transcriptase, and 5 units of RNase Inhibitor in TaqMan buffer A (Perkin Elmer). The reverse transcription was performed at 48° C. for 30 min. After denaturing at 95 C. for 10 min, PCR amplification reactions were conducted for 40 cycles at 95 C. for 15 s and at 60 C. for 1 min. The *Arabidopsis* GMT primer and probe set (AATGATCTCGCGGCTGCT, (SEQ ID NO: 85) GAATGCTGATTCCAACGCAT (SEQ ID NO: 86), FAM-TCACTCGCTCATAAGGCTTCCTTCCAAGT-TAMRA (SEQ ID NO: 87) ) were used to measure the *Arabidopsis* GMT expression levels. The GAPDH primer and probe set (GATCATCAAGATTGTATCTGATC (SEQ ID NO: 130), CGGTTCCTTCGATAACTAAGTC (SEQ ID NO: 131), FAM-CAATGCCTAGTTCCCCCCAGGGGAG-TAMRA (SEQ ID NO: 137) ) were used to monitor the internal control GAPDH mRNA.

Four of the ZFP-TFs tested increased GMT gene expression greater than two-fold, with ZFP-B, the most effective activator, giving a 5-fold increase (FIG. 19). A dose-response experiment, using the ZFP-B TF, verified that the level of activation was positively correlated with the amount of DNA used for transfection. Consistent with earlier studies showing that DNase I hypersensitivity is an indication of accessibility (7), the two ZFP-TFs targeted to DNase I hypersensitive sites (A and B) were found to be effective activators. Interestingly, ZFP-TFs targeted to sites outside of the DNase I hypersensitive sites were also capable of activating GMT transcription. These results are not entirely unforeseen as it has been previously shown that DNase I hypersensitive mapping is not sufficiently precise to reveal small stretches of accessible DNA (5).

Phenotypic Analysis of Transgenic Plants

Vectors were constructed in which sequences encoding ZFP-TFs were placed under the control of the napin embryo-specific promoter, and these vectors were stably transformed into *Arabidopsis*. Sequences encoding ZFP-TFs were subcloned downstream of the napin promoter (16) into NotI and HindIII sites of a plant transformation binary vector (pCGN9979, See Example 8 and FIG. 8). These vectors and their parent (lacking a ZFP-TF insert, used as a control) were electroporated into *Agrobacterium tumefaciens* strain ABI and grown under standard conditions (28), their structure was reconfirmed by restriction analysis, and they were transformed into *Arabidopsis* using the dipping method (29). Transgenic T1 plants (12-22 independent insertion events for each ZFP-TF) were grown to maturity and $T_2$ seed was analyzed for tocopherol content and composition (30). The four events with the highest seed α-tocopherol percentage from each of two ZFP-TFs (A and B) were advanced to the next generation and T3 seed from 10 individual T2 plants per event was analyzed for tocopherol content and composition.

Figure 20:
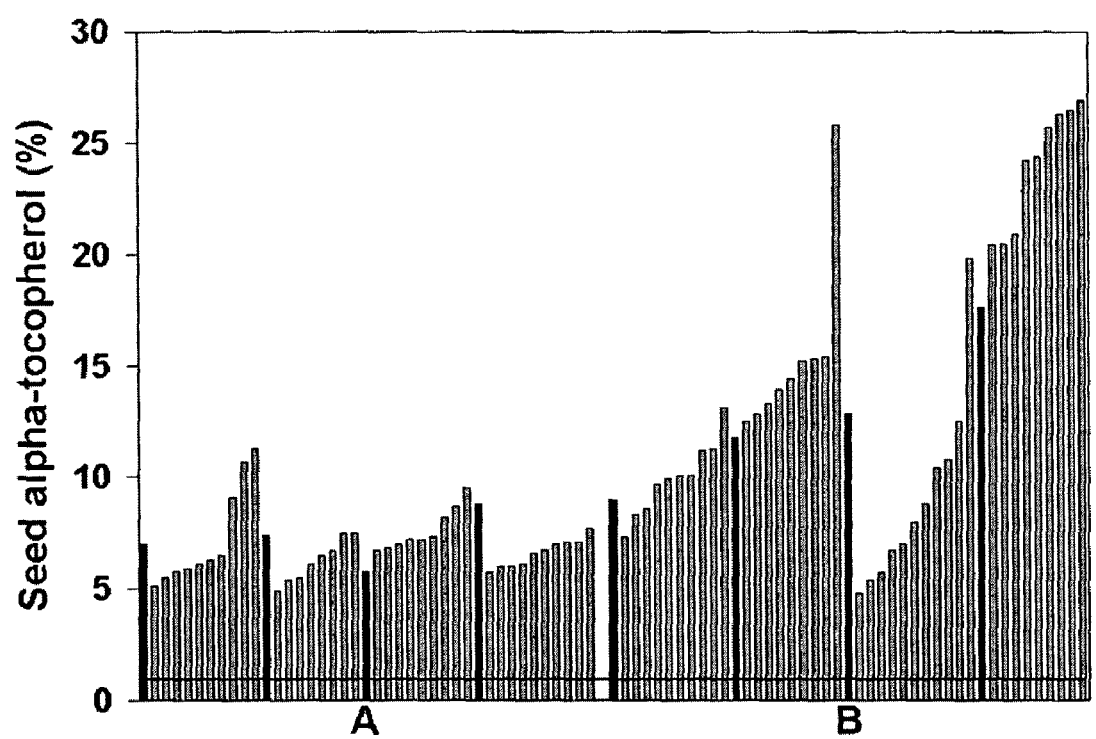
FIG. 20 shows analysis of alpha-tocopherol levels in T2 and T3 seed from selected transgenic *Arabidopsis* lines. Alpha-tocopherol levels were measured in seed from individual T1 (black bar) and several T2 (gray bars) transgenic *Arabidopsis* plants. The transgenic plants were derived from four independent transformation events with one of two zinc finger protein transcription factors (ZFP-A or ZFP-B, see FIG. 18) targeted to the endogenous γ-tocopherol methyltransferase gene. Alpha-tocopherol levels are presented as percent total seed tocopherol. Control value of 1.0 (black horizontal line; SEM 0.03) represents the average α-tocopherol percentage measured in control seed samples from 30 plants transformed with the parent binary vector (lacking a ZFP-TF insert).

Analysis of tocopherol composition (by HPLC) from transgenic lines (see Example 8 for methods) showed that segregating T2 seed contained as much as 19.8% α-tocopherol, compared to an average of 1% α-tocopherol in control seed (Table 10), while total tocopherol content was unchanged. Analysis of T3 seed from transgenic lines expressing either ZFP-TF A or B showed that the elevated α-tocopherol phenotype was heritable, with the highest α-tocopherol level recorded in T3 seed being 26.9% (FIG. 20, see also Example 9). Significantly, the two ZFP-TFs that were targeted to DNase I hypersensitive sites (A and B) provided the highest increase in seed α-tocopherol percentage. ZFPs C and E were effective activators in leaf, but not in seed, suggesting that these sites may not be accessible in the embryo. Because the GMT gene is normally poorly expressed in seed relative to the leaf it may therefore have a less accessible chromatin configuration in seed. Although it is apparent that the effectiveness of a particular ZFP-TF in one tissue does not guarantee its effectiveness in another, the finding that the two ZFP-TFs targeted to the major hypersensitive sites were effective in both leaf and seed tissue suggests that it is feasible to use DNaseI hypersensitivity mapping of a given gene in one tissue to predict accessible sites of that gene in another, more scarce, tissue type.

TABLE 10

Alpha-tocopherol percentage and frequency of zinc finger protein transcription factor (ZFP-TF) transgene expression in developing siliques from T1 transgenic Arabidopsis plants.

| CONSTRUCT | SEED α-TOCOPHEROL (%) | | | | | TRANGENE EXPRESSION | |
| --- | --- | --- | --- | --- | --- | --- | --- |
| | N | Mean | SEM | Min | Max | No. Expressing/No. assayed | % |
| CONTROL* | 30 | 1.0 | 0.03 | 0.5 | 1.5 | 0/17 | 0 |
| B | 18 | 4.5 | 0.68 | 1.3 | 8.8 | 7/13 | 54 |
| C | 13 | 6.0 | 1.59 | 1.0 | 19.8 | 4/7 | 57 |
| D | 35 | 1.6 | 0.03 | 1.1 | 2.1 | 16/16 | 100 |
| E | 12 | 2.3 | 0.12 | 1.8 | 3.2 | 12/12 | 100 |
| F | 22 | 2.9 | 0.23 | 1.3 | 5.5 | 14/17 | 82 |

*Controls were transformed with the parent binary vector (lacking a ZFP-TF insert).

Expression Analysis in Transgenic Plants

For TaqMan analysis of mRNA levels in developing *Arabidopsis* seed, total RNA was isolated from four developing siliques per plant. Total RNA was prepared using the SV Total RNA Isolation Kit (Promega, Madison, Wis.). RT-PCR was performed as described above, except that the assay consisted of 30 ng total RNA, 0.8 uM each primer, 0.15 uM probe, 10 units of Multiscribe Reverse Transcriptase, and 5 units of RNAse Inhibitor in 1× TaqMan Universal PCR Master Mix w/o AmpErase® (Perkin Elmer).

```
                                    (SEQ ID NO: 138)
(AATGATCTCGCGGCTGCT, (SEQ ID NO: 139)
GAATGGCTGCTGATCCAACGCAT, (SEQ ID NO: 140))
FAM- TCACTCGCTCATAAGGCTTCCTTCCAAGT-TAMRA (SEQ ID NO: 141)
(TGCCAGAACAAGAAGGGTGG, (SEQ ID NO: 142)
ATACCGACGCCGCCG, (SEQ ID NO: 143))
FAM-TCGTCCGACGACCCTGCGG-TAMRA;

(SEQ ID NO: 144)
(CGTCCCTGCCCTTTGTACAC, (SEQ ID NO: 145)
CGAACACTTCACCGGATCATT, (SEQ ID NO: 146))
VIC-CCGCCCGTCGCTCCTACCGAT-TAMRA; and (SEQ ID NO: 147)
(TGCCCCACCTTGAGACAAG, (SEQ ID NO: 148)
CTTGCTCTGGTTGGTGTTGCT, (SEQ ID NO: 149))
VIC-CCCTGGAATCTAACGGCCTTGGCA-TAMRA
``` were used to assay GMT, C1-ED, 18S RNA, and endogenous napin RNA respectively. For each RNA sample, 2 replicates were amplified in a one-step reaction and cycle threshold values were obtained. Relative values were calculated using the comparative Ct method (27).

Figure 21:
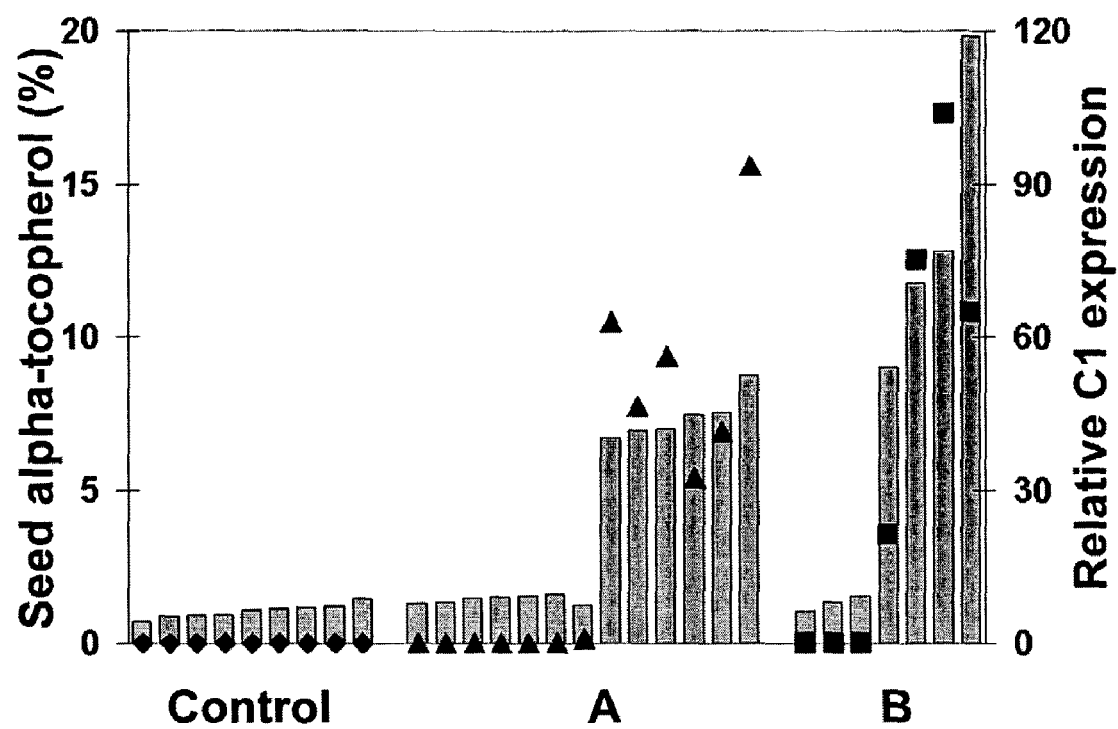
FIG. 21 shows analyses of α-tocopherol levels and levels of transgene expression in developing siliques from T1 transgenic *Arabidopsis* plants. de Alpha-tocopherol percentage was determined in T2 seeds (bars: expressed a percent of total seed tocopherol) and measured as described in Example 8. Measurement of C1-encoding mRNA was used to determine relative expression levels of transgenic ZFP-TFs in developing siliques containing T2 segregating seed from individual transgenic plants transformed with a binary vector containing no ZFP-TF (diamond), ZFP-TF A (triangles), or ZFP-TF B (squares) under the control of the napin embryo-specific promoter. Transgene expression data is normalized with 18S RNA and displayed as fold induction relative to the expression level of the weakest C1 expressor (arbitrarily set to a value of 1).

Quantitative RT-PCR analysis of RNA from developing siliques containing segregating T2 seed revealed concordance between the presence of the ZFP-TF transgene (as measured by C1-encoding mRNA) and an elevated level of seed α-tocopherol; however not all transgene expressors had elevated seed α-tocopherol (Table 10). The endogenous napin mRNA level was high in all samples, confirming that the developmental stage being assayed corresponded to the time when the napin-driven transgene was expected to be expressed. Twenty plants transformed with the two most effective ZFP-TFs in planta (A and B) and nine plants transformed with a control vector (binary transformation vector lacking a ZFP-TF insert) were selected for detailed analysis of the expression of the C1-ED and of endogenous GMT levels. Within these samples there was concordance between transgene expression and elevated α-tocopherol percentage in the seed, but no correlation between relative expression level of the ZFP-TF transgenes in developing siliques and percentage α-tocopherol in mature seed of the expressors (FIG. 21).

CONCLUSION

In this example, the vitamin E content of transgenic *Arabidopsis* seed was elevated by expressing ZFP-TFs designed to activate the endogenous GMT gene. The experimental approach incorporated information regarding the chromatin structure of the endogenous GMT locus and utilized plant-derived DNA sequences for the design of synthetic ZFP-TFs. ZFPs were designed to recognize 9 bp DNA sequences in the promoter or coding region of the GMT gene and all were found to bind with strong affinity to their target sequences in naked DNA. The ZFPs were then fused to a maize C1 activation domain, and four of these synthetic ZFP-TFs upregulated the expression of the endogenous GMT gene in a leaf protoplast assay system. It was further shown that these ZFP-TFs were able to alter seed tocopherol composition when expressed in transgenic plants, and can provide a greater than 20-fold increase in seed α-tocopherol percentage, in a heritable fashion. These results demonstrate that engineered ZFP-TFs can be used to target endogenous gene expression and increase the amount of product resulting from a specific step in a native biochemical pathway, thereby providing a powerful new method for modifying endogenous plant gene expression to achieve desired phenotypic alterations.

References Cited in Example 12

1. Pabo, C., Peisach, E. & Grant, R. Design and selection of novel $Cys_2His_2$ zinc finger proteins. *Annu. Rev. Biochem.* 70, 313-340 (2001).

2. Beerli, R. B. & Barbas, C. F., III. Engineering polydactyl zinc-finger transcription factors. *Nat. Biotech.* 20, 135-141 (2002).

3. Segal, D. J. & Barbas, C. F., III. Custom DNA-binding proteins come of age: polydactyl zinc-finger proteins. *Curr. Opin. Biotechnol.* 12, 632-637 (2001).

4. Beerli, R. R., Drier, B., & Barbas, C. F., III. Positive and negative regulation of endogenous genes by designed transcription factors. *Proc. Natl. Acad. Sci. USA* 97, 1495 -1500 (2000).

5. Zhang, L. et al. Synthetic zinc finger transcription factor action at an endogenous chromosomal site. *J. Biol. Chem.* 275, 33850-33860 (2000).

6. Dreier, B., Segal, D. J. & Barbas, C. F., III. Development of zinc finger domains for recognition of the 5'-ANN-3' family of DNA sequences and their use in the construction of artificial transcription factors. *J. Biol. Chem.* 276, 29466-29478 (2001).

7. Liu, P. -Q. et al. Regulation of an endogenous locus using a panel of designed zinc finger proteins targeted to accessible chromatin regions. *J. Biol. Chem.* 276, 11323-11334 (2001).

8. Ren, D., Collingwood, T. N., Rebar, E. J., Wolffe, A. P. & Camp, H. S. PPARgamma knockdown by engineered transcription factors: exogenous PPARgamma 2 but not PPARgamma 1 reactivates adipogenesis. *Genes Dev.* 16, 27-32 (2002).

9. Bartsevich, V. V. & Juliano, R. L. Regulation of the MDR1 gene by transcriptional repressors selected using peptide combinatorial libraries. *Mol Pharmacol* 58, 1-10. (2000).

10. Guan, X. et al. Heritable endogenous gene regulation in plants with designed polydactyl zinc finger transcription factors. *Proc Natl Acad Sci USA* 99, 13296-13301 (2002).

11. Bramley, P. M. et al. Vitamin E. *J Sci Food Agr* 80, 913-938 (2000).

12. Sheppard, A. J., Pennington, J. A.; Weihrauch, J. L. in Vitamin E in health and disease. (ed. Packer, J. F. L.) 9-31 (Marcel Dekker, New York, 1993).

13. Shintani, D. & Della-Penna, D. Elevating the vitamin E content of plants through metabolic engineering. *Science* 282, 2098-2100 (1998).

14. Guyer, D. et al. Activation of latent transgenes in *Arabidopsis* using a hybrid transcription factor. *Genet.* 149, 633-639 (1998).

15. Goff, S. A., Cone, K. C. & Fromm, M. E. Identification of functional domains in the maize transcriptional activator C1: comparison of wild-type and dominant inhibitor proteins. *Genes Dev.* 5, 298-309 (1991).

16. Kridl, J. et al. Isolation and characterization of an expressed napin gene from *Brassica napus. Seed Sci. Res.* 1, 209-219 (1991).

17. Ordiz, M. I., Barbas III, C. F. & Beachy, R. N. Regulation of transgene expression in plants with polydactyl zinc finger transcription factors. *Proc Natl Acad Sci USA* 99, 13290-13295 (2002).

18. Li, G., Chandrasekharan, M., Wolffe, A. & Hall, T. Chromatin structure and phaseolin gene regulation. *Plant Mol. Biol.* 46, 121-129 (2001).

19. Zinc finger proteins for DNA binding and gene regulation in plants. International Patent Application Publication WO 02/057294.

20. Cook, T., Gebelein, B. & Urrutia, R. Sp1 and its likes: biochemical and functional predictions for a growing family of zinc finger transcription factors. *Ann N Y Acad Sci* 880, 94-102. (1999).

21. Modified Zinc Finger Binding Proteins. International Patent Application Publication WO 02/057293.

22. Utley, R. T., Cote, J., Owen-Hughes, T. & Workman, J. L. SWI/SNF stimulates the formation of disparate activator-nucleosome complexes but is partially redundant with cooperative binding. *J. Biol. Chem.* 272, 12642-12649 (1997).

23. Huala, E. et al. The *Arabidopsis* Information Resource (TAIR): A comprehensive database and web-based information retrieval, analysis, and visualization system for a model plant. *Nucleic Acids Res.* 29, 102-105 (2001).

24. Li, G., Chandler, S., Wolffe, A. & Hall, T. Architectural specificity in chromatin structure at the TATA box in vivo: nucleosome displacement upon beta-phaseolin gene activation. *Proc Natl Acad Sci USA* 95, 4772-4777 (1998).

25. Desjarlais, J. R. & Berg, J. M. Use of a Zinc-Finger Consensus Sequence Framework and Specificity Rules to Design Specific DNA Binding Proteins. *Proc. Natl. Acad. Sci. USA* 90, 2256-2260. (1993).

26. Abel, S. & Theologis, A. Transient transformation of *Arabidopsis* leaf protoplasts: a versatile experimental system to study gene expression. *Plant J.* 5, 421-427 (1994).

27. PE_Applied_Biosytems. User Bulletin #2. Relative quantitation of gene expression. ABI prism 7700 sequence detections system. (The Perkin-Elmer Corporation, Chicago, Ill., 1997).

28. McBride, K. E., Schaaf, D. J., Daley, M. & Stalker, D. M. Controlled expression of plastid transgenes in plants based on a nuclear DNA-encoded and plastid-targeted T7 RNA polymerase. *Proc. Natl. Acad. Sci. USA* 91, 7301-7305 (1994).

29. Clough, S. & Bent, A. Floral dip: a simplified method for *Agrobacterium*-mediated transformation of *Arabidopsis thaliana. Plant J.* 16, 735-743 (1998).

30. Savidge, B. et al. Isolation and characterization of homogentisate phytyltransferase genes from Synechocystis PCC 6803 and Arabidopsis. *Plant Phys.* 129, 321-332 (2002).

Although the foregoing methods and compositions have been described in detail for purposes of clarity of understanding, certain modifications, as known to those of skill in the art, can be practiced within the scope of the appended claims. All publications and patent documents cited herein are hereby incorporated by reference in their entirety for all purposes to the same extent as if each were so individually denoted.

What is claimed is:

1. An isolated engineered zinc finger protein that specifically binds to a target site in a plant gamma-tocopherol methyl transferase (GMT) gene wherein the engineered zinc finger protein comprises at least 3 zinc finger domains designated F1, F2 and F3, and further wherein F1, F2 and F3 of the engineered zinc finger protein comprise the recognition helix regions sequences shown in a single row of Table 1 or Table 3.

2. The zinc finger protein of claim 1, wherein said protein modulates expression of GMT.

3. The zinc finger protein of claim 1 which, when present in plant cell, increases the amounts of vitamin E in the plant cell.

4. The zinc finger protein of claim 1, wherein the plant is a dicotyledenous plant.

5. The zinc finger protein of claim 4, wherein the dicot is *Brassica* or *Arabidopsis*.

6. The zinc finger protein of claim 1, wherein the ZFP comprises 3 component fingers that bind to the target site in the plant GMT gene.

7. A fusion polypeptide comprising the zinc finger protein according to claim 1 and at least one functional domain.

8. The fusion polypeptide of claim 7, wherein the functional domain is an activation domain.

9. An isolated polynucleotide encoding the protein of claim 1.

10. An expression vector comprising the isolated polynucleotide of claim 9.

11. The expression vector of claim 10, comprising a plant promoter.

12. The expression vector of claim 11, wherein the promoter is tissue specific.

13. The expression vector of claim 12, wherein the promoter is specific for seeds or leaves.

14. A plant cell comprising the isolated polynucleotide of claim 9.

15. A plant cell comprising the zinc finger protein according to claim 1.

16. A plant cell comprising the expression vector according to claim 10.

17. A transgenic plant comprising the isolated polynucleotide of claim 9.

18. A transgenic plant comprising the zinc finger protein according to claim 1.

19. A transgenic plant comprising the expression vector according to claim 10.

20. A method for modulating expression of GMT in a plant cell, the method comprising the step of contacting the cell with the zinc finger protein of claim 1.

21. A method for increasing the amounts of vitamin E present in a plant cell, the method comprising the step of contacting the plant cell with the zinc finger protein of claim 1.

22. A method for modulating expression of GMT in a plant cell, the method comprising the step of contacting the cell with the polynucleotide of claim 9.

23. A method for increasing the amounts of vitamin E present in a plant cell, the method comprising the step of contacting the cell with the polynucleotide of claim 9.

24. A method for modulating expression of GMT in a plant cell, the method comprising the step of contacting the cell with the expression vector of claim 10.

25. A method for increasing the amounts of vitamin E present in a plant cell, the method comprising the step of contacting the cell with the expression vector of claim 10.

26. A method for modulating the oil content of a seed, the method comprising constructing a transgenic plant according to claim 17 and obtaining seed therefrom.

27. The method of claim 26, wherein the modulation is increased α-tocopherol content, compared to a seed obtained from a non-transgenic plant.

28. A seed with altered oil content, wherein the seed is obtained from a transgenic plant according to claim 17 and comprises the polynucleotide, and wherein alteration is with respect to a seed obtained from a non-transgenic plant.

29. The seed of claim 28, wherein alteration in oil content comprises an increase in α-tocopherol content.

* * * * *